US008580277B2

(12) United States Patent
Yang et al.

(10) Patent No.: US 8,580,277 B2
(45) Date of Patent: Nov. 12, 2013

(54) INFLUENZA HEMAGGLUTININ AND NEURAMINIDASE VARIANTS

(75) Inventors: Chin-Fen Yang, San Jose, CA (US); George Kemble, Saratoga, CA (US); Kanta Subbaro, Washington, DC (US); Brian Murphy, Bethesda, MD (US)

(73) Assignee: Medimmune, LLC, Gaithersburg, MD (US)

( * ) Notice: Subject to any disclaimer, the term of this patent is extended or adjusted under 35 U.S.C. 154(b) by 0 days.

(21) Appl. No.: 13/077,488

(22) Filed: Mar. 31, 2011

(65) Prior Publication Data
US 2011/0182936 A1   Jul. 28, 2011

Related U.S. Application Data

(63) Continuation of application No. 11/836,413, filed on Aug. 9, 2007, now abandoned.

(60) Provisional application No. 60/821,832, filed on Aug. 9, 2006, provisional application No. 60/942,804, filed on Jun. 8, 2007.

(51) Int. Cl.
*A61K 39/145* (2006.01)
*C12N 7/01* (2006.01)

(52) U.S. Cl.
USPC .............. 424/206.1; 424/205.1; 424/209.1; 424/186.1; 435/235.1

(58) Field of Classification Search
None
See application file for complete search history.

(56) References Cited

U.S. PATENT DOCUMENTS

| | | | |
|---|---|---|---|
| 3,992,522 | A | 11/1976 | Chanock et al. |
| 4,071,618 | A | 1/1978 | Konobe et al. |
| 4,634,666 | A | 1/1987 | Engleman et al. |
| 4,659,569 | A | 4/1987 | Mitsuhashi et al. |
| 4,752,473 | A | 6/1988 | Nayak et al. |
| 5,166,057 | A | 11/1992 | Palese et al. |
| 5,665,362 | A | 9/1997 | Inglis et al. |
| 5,690,937 | A | 11/1997 | Parkin |
| 5,716,821 | A | 2/1998 | Wertz et al. |
| 5,756,341 | A | 5/1998 | Kistner et al. |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,922,326 | A | 7/1999 | Murphy |
| 6,001,634 | A | 12/1999 | Palese et al. |
| 6,033,886 | A | 3/2000 | Conzelmann |
| 6,090,391 | A | 7/2000 | Parkin |
| 6,146,642 | A | 11/2000 | Garcia-Sastre et al. |
| 6,146,873 | A | 11/2000 | Kistner |
| 6,168,943 | B1 | 1/2001 | Rose |
| 6,951,754 | B2 | 10/2005 | Hoffmann |
| 7,037,707 | B2 | 5/2006 | Webster et al. |
| 7,459,162 | B2 | 12/2008 | Yang et al. |
| 7,504,109 | B2 | 3/2009 | Yang et al. |
| 7,527,800 | B2 | 5/2009 | Yang et al. |
| 7,744,901 | B2 | 6/2010 | Yang et al. |
| 8,039,002 | B2 | 10/2011 | Yang et al. |
| 8,084,594 | B2 | 12/2011 | Gramer et al. |
| 2002/0119445 | A1 | 8/2002 | Parkin et al. |
| 2002/0164770 | A1 | 11/2002 | Hoffmann |
| 2003/0035814 | A1 | 2/2003 | Kawaoka |
| 2003/0147916 | A1 | 8/2003 | Ferko |
| 2004/0029251 | A1 | 2/2004 | Hoffman |
| 2004/0137013 | A1 | 7/2004 | Katinger |
| 2005/0042229 | A1 | 2/2005 | Yang |
| 2005/0266026 | A1 | 12/2005 | Hoffmann |
| 2008/0057081 | A1 | 3/2008 | Yang et al. |
| 2008/0069821 | A1 | 3/2008 | Yang et al. |
| 2009/0175898 | A1 | 7/2009 | Yang et al. |
| 2009/0175909 | A1 | 7/2009 | Yang et al. |
| 2010/0330118 | A1 | 12/2010 | Jin et al. |
| 2011/0052618 | A1 | 3/2011 | Yang et al. |
| 2011/0182936 | A1 | 7/2011 | Yang |
| 2012/0009215 | A1* | 1/2012 | Yang et al. ................ 424/206.1 |
| 2012/0034264 | A1 | 2/2012 | Yang et al. |

FOREIGN PATENT DOCUMENTS

| | | |
|---|---|---|
| EP | 0702085 | 3/1996 |
| EP | 0863202 | 9/1998 |
| EP | 0864645 | 9/1998 |
| EP | 0780475 | 6/1999 |
| EP | 1826269 | 8/2007 |
| JP | 2004-500842 | 1/2004 |
| WO | WO 91/03552 | 3/1991 |
| WO | WO 93/21306 | 10/1993 |
| WO | WO 96/10632 | 4/1996 |
| WO | WO 96/34625 | 11/1996 |
| WO | WO 97/06270 | 2/1997 |
| WO | WO 97/12032 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |

(Continued)

OTHER PUBLICATIONS

Extended European Search Report dated: May 16, 2012 in European Application No. 12159225 filed on: May 20, 2005.
Extended European Search Report dated: Oct. 11, 2012 in European Application No. 12172385 filed on: May 20, 2005.
Database EMBL [Online] E.B.I. Hinxton U.K., Jan. 15, 2008, Kaverin NV et al., "Hemagglutinin" XP002684322, Database Accession No. A8UDQ2.
Li et al., "Influenza A Virus (A/VietNam/1203/2004(H5N1) neuraminidase (NA) gene, complete cds" EMBL, Jul. 19, 2004, XP002544220 (ID AY651447).
Li et al., "Influenza A Virus (A/Viet Nam/1203/2004(H5N1) hemagglutinin (HA) gene, partial cds" EMBL, Jul. 19, 2004, XP002544221 (ID AY651334).

(Continued)

*Primary Examiner* — Michelle S Horning
(74) *Attorney, Agent, or Firm* — Grant Anderson LLP

(57) ABSTRACT

Polypeptides, polynucleotides, methods, compositions, and vaccines comprising (avian pandemic) influenza hemagglutinin and neuraminidase variants are provided.

20 Claims, 31 Drawing Sheets

(56) References Cited

FOREIGN PATENT DOCUMENTS

| WO | WO 00/53786 | 9/2000 |
|---|---|---|
| WO | WO 00/60050 | 10/2000 |
| WO | WO 01/83794 | 11/2001 |
| WO | WO 2005/116258 | 8/2005 |
| WO | WO 2005/116260 | 8/2005 |
| WO | WO 2008/021959 | 2/2008 |
| WO | WO 2010/093537 | 8/2010 |

OTHER PUBLICATIONS

Partial European Search Report dated: Oct. 11, 2012 in European Application No. 12174997 filed on: May 20, 2005.
Database EMBL [Online] E.B.I. Hinxton U.K., World Health Organization Global Influenza Program Surveillance: "Hemagglutinin," XP002684345, Database Accession No. Q4H2E2.
GeneBank Accession No. CAC84240.1, Apr. 15, 2005, "haemagglutinin" [Influenza A virus (A/duck/Hong Kong/182/77 (H6N9))].
Genebank Accessino No. AF250479.1, Jul. 25, 2000, Influenza A virus (A/Teal/Hong Kong/W312/97(H6N1)) segment 4 hemagglutinin (HA) gene, complete cds.
Genebank Accession No. CAC84982.1, Jan. 15, 2002, haemagglutinin [Influenza A virus (A/quail/Hong Kong/SF550/00(H6N1))].
Genebank Accession No. CAC84860.1, Apr. 15, 2005, haemagglutinin [Influenza A virus (A/chukka/Hong Kong/FY295/00(H6N1))].
Office Action mailed on: Sep. 27, 2012 in U.S. Appl. No. 13/230,203 published as: 2012/0009215 on Jan. 12, 2012.
Office Action mailed on: Mar. 14, 2012 in U.S. Appl. No. 13/230,203 published as: 2012/0009215 on Jan. 12, 2012.
Genebank Accession No. CAC84240.1 May 4, 2001 haemagglutinin [Influenza A virus (A/duck/Hong Kong/182/77 (H6N9)).
Office Action mailed on: Dec. 28, 2012 in U.S. Appl. No. 13/230,203 published as: 2012/0009215 on Jan. 12, 2012.
Office Action mailed on: Jan. 30, 2013 in U.S. Appl. No. 12/699,108, filed Feb. 3, 2010 and published as: 2010/0330118 on Dec. 30, 2010.
Extended European Search Report dated: Jan. 30, 2013 in European Application No. 12174997 filed on: May 20, 2005.
Wareing et al., "Preparation and characterization of attenuated cold-adapted influenza a reassortants derived from the A/Leningrad/134/17/57 donor strain," Vaccine 2002;20:2082-2090.
Ma et al., "Identification of H2N3 influenza A viruses from swine in the United States," PNAS, 2007; 104(52):20949-20954.
Sequence alignment of SEQ ID No. 5 in U.S. Appl. No. 12/699,108 with SEQ 10 No. 17 of US Patent No. 8,084,594 Gramer et al. Dec. 2007.
Sequence alignment of SEQ ID No. 6 in U.S. Appl. No. 12/699,108 UniProt database 10 No. A9YN70_91 NFA of Ma et al. 2007.
Attwood, T. The Babel of Bioinformatics, Science (2000) vol. 290, No. 5491, pp. 471-473.
Baker et al., Protein Structure Predication and Structural Genomics, Science (2001) vol. 294, No. 5540, pp. 93-96.
Banerjee and Barik. 1992.—Gene expression of vesicular stomatitis virus genome RNN. Virology. 188):417-28.
Baron and Barrett, 1997,—Rescue of Rinderpest Virus from Cloned eDNA, J. Virol. 71 :1265-1271.
Basler et al., 1999, "Mutation of Neuraminidase Cysteine Residues Yields Temperature—Sensitive Influenza Viruses", J. of Virology 73(10):8095-8103.
Beare et al., 1975, "Trials in Man with live Recombinants Made from AJPRI8/34 (HO N1) and Wild H3 N2 Influenza Viruses", Lancet 729-732.
Belshe et al., 1998, The efficacy of live attenuated, cold-adapted, trivalent, intranasal influenza virus vaccine in children: N Engl J Med 338:1405-12.
Belshe, 1995 "A Review of Attenuation of Influenza Viruses by Genetic manipulation", American Journal of Respiratory and Critical Care Medicine 152:S72-S75.
Bergmann, et al., 1995, "The relative amount of an influenza A virus segment present in the viral particle is not affected . . . ", J. of Gen. Virology, 76:3211-3215.
Boyce at al., 2000, "Safety and immunogenicity of adjuvanted and unadjuvanted subunit influenza vaccines administered intranasally 10 healthy adults", Vaccine 19:217-226.
Boyer et al., 1994, "Infectious transcripts and cDNA clones of RNA viruses", Virology. 198:415-26.
Brandt et al.. 2001, Molecular Determinants of Virulence, Cell Tropism, and Pathogenic Phenotype of Infectious Bursal Disease Virus•, Journal of Virology 75(24); 11974-11982.
Brigden and Elliott, 1996, Rescue of a Segmented Negative-Strand RNA Virus Entirely from Cloned Complementary DNAS•, Proc. Natl. Acad. Sci. USA 93:15400-15404.
Buchholz et al., 1999 "Generation of Bovine Resp. Syncytial Virus (BRSV) from cDNA: BRSV NS2 Is Not Essential for Virus Replication in Tissue Culture . . . " J. Virol. 73:251-259.
Bukreyev et al., 1996, "Recovery of infectious respiratory syncytial virus expressing an additional, foreign gene", J Viral. 70(10):6634-41.
Castrucci et al., 1995, "Reverse genetics system. For generation of an influenza A virus mutant containing a deletion of the carboxyl-terminal M2 ..", J Virol. 69(5):2725-28.
Chen et al., 1999, "Influenza A virus NS1 protein targets poly (A)-binding protein II of the cellular 3'-end processing machinery", EMBO 18: 2273-2283.
Clarke et al., 2000, "Rescue of mumps virus from cDNAJ", J Virol. 74 (10):4831-38.
Collins et al., 1996, "Parainfluenza Viruses", Fields Virology. Lippincott-Raven Publishers, Phi/a., pp. 1205-1241.
Collins et al., 1995, "Production of infectious human respiratory syncytial virus from cloned cDNA confirms an essential role . . . " PNAS 92: 11563-1567.
Collins et al.. 1991, "Rescue of Synthetic Analogs of Respiratory Syncytial Virus Genomic RNA and Effect of Truncations.", Proc. Nail. Acad. Sci. USA 88:9663-9667.
Conzelmann et al., 1994. "Rescue of synthetic genomic RNA analogs of rabies virus by plasmid-encoded proteins", J Virol. 68(2):713-19.
Conzelmann et al , 1998. "Nonsegmented negative-strand RNA viruses: genetics and manipulation of viral genomes", Annu Rev Genet. 32:123-162.
Conzelmann et al ., 1996. "Genetic engineering of animal RNA viruses", Trends Microbiol. 4(10):386-93.
Conzelmann. 1996. "Genetic manipulation of non-segmented negative-strand RNA viruses", J Gen Virol. 77 (Pt 3):381-89.
Cox, at al.; "Identification of Sequence Changes in the Cold-Adapted, Live Attenuated Influenza Vaccine Strain, A/Ann *Arbor/6/60* (H2N2)," Virology, 1988; 167: 554-567.
De and Banerjee, 1985. "Requirements and Functions of Vesicular Stomatitis Virus L . and NS Proteins in the Transcription ..", Biochem. & Biophys. Res. Commun. 126:40-49.
De and Banerjee, 1993. "Rescue of synthetic analogs of genome RNA of human parainfluenza virus type 3", Virology. 96:344-48.
De and Banerjee, 1994, "Reverse genetics of negative strand RNA viruses," Indian J Biochem & Biophys. 31:367-76.
De et al., "Complete sequence of a cDNA clone of the hemagglutinin gene of influenza AIChickenIScotiandI59 (H5Nl) virus: comparison with contemporary North American and European strains", Nucleic Acids Research, 1988. Vo!' 16, No. 9, pp. 4181-4182.
De et al., "Protection against virulent H5 avian influenza virus infection in chickens by an inactivated vaccine produced with recombinant vaccine virus", Jun. 1988, Vaccine, vol. 6, pp. 257-261.
De La Luna et al., 1995, "Influenza virus NS1 Protein Enhances the Rate of Translation Initiation of Viral mRNAs", J. of Virol. 69: 2427-2433.
De la Luna et al.. 1993. Influenza virus naked RNA can be expressed upon transfection into cells co-expressing the three subunits . . . n J. Gen.Virol. 74: 535-39.
Dimock et al., 1993, "Rescue of synthetic analogs of genomic RNA and replicative-intermed. RNA of human parainfluenza virus type 3,", J Virol. 67(5):2772-78.

(56) References Cited

OTHER PUBLICATIONS

Dreher and Hall, 1988, "Mutational Analysis of the Sequence and Structural Requirements in Brome Mosaic Virus RNA for Minus Strand Promoter Activity", J. Mol. Biol. 201 :31-40.

Dreher et at, 1984, "Mutant Viral RNAs Synthesized in vitro Show Altered Aminoacylation and Replicase Template Activities", Nature 311 :171-175.

Dunn et al., 1995, "Transcription of a recombinant bunyavirus RNA template by transiently expressed bunyavirus proteins", Virology, 211 :133-43.

Durbin et al., 1997, "Recovery of infectious Human Parainfluenza Virus Type 3 fram cDNA", Viral. 235:323-332.

Edwards et al., 1994. "A randomized controlled trial of cold adapted and inactivated vaccines for the prevention of influenza A disease", J Infect Dis 169:68-76.

Edwards, et al., "Saftey and immunogenicity of live attenuated cold adapted influenza B/Ann Arbor/1/86 reassortant virus vaccine in infants and children," J. Infect Dis. Apr. 1991; 163(4):740-745.

Egorov et al., 1998. "Transfectant Influenza A Viruses with Long Deletions in the NS1 Protein Grow Efficiently in Vero Cells", J. of Virology 72(8):6437-6441.

Elliot et al., 1997, Abstract # 96 10.sup.th International conference on Negative Strand Viruses.

Elliott et al., 1991, "Some highlights of virus research in 1990", J Gen Virol. 72:1761-79. Review.

Emerson and Yu, 1975, "Both NS and L Proteins are Required for in vitro RNA Synthesis by Vosicular Stomatitis Virus", J. Virol. 15:1348-1356.

Enami and Palese, 1991, "High-Efficiency Formation of Influenza Virus Transfectants", J. Virol. 65:2711-2713.

Enami et al., 1991, "An influenza virus containing nine different RNA segments", Virology. 185:291-98.

Enami et al, 2000. "Characterization of Influenza Virus NS1 Protein by Using a Novel Helper-Virus Free Reverse Genetic System", J. of Virology 74(12):5556-5561.

Enami et al., 1990, "Introduction of Site Specific Mutations into the Genome of Influenza Virus", Proc Nati Acad Sci USA 87: 3802-3805.

Fahey and Schooley, 1992, "Status of Immune-Based Therapies in HIV Infection and AIDS". Clin. Exp. Immunol. 88:1-5.

Flandorfar at al., 2003, •Chimeric Influenza A Viruses with a Functional Influenza B Virus Neuraminidase or Hemagglutinin, J. of Virology 77(17):9116-9123.

Flick, et al, "Promoter elements in the influenza vRNA terminal structure," RNA, 1996; 2(10):1046-1057.

Fodor et al., 1999, "Rescue of Influenza A Virus from Recombinant DNA", J. of Virology 73(11):9679-9682.

Fortes et al., 1994, "Influenza virus NS1 protein inhibits pre-mRNA splicing and blocks mRNA nucleocytoplasmic transport". EMBO J. 13: 704-712.

Fourchier et al., "Avian Influenza A Virus (H7N7) associated with Human conjunctivitus and a fatal case of acute respiratory distress syndrome," PNAS 2004, Feb. 3;101(5):1356-1361.

Furminger, "Vaccine Production", Textbook of Influenza, pp. 324-332; (1996).

Garcia-Sastre A, Palese P, 1993. "Genetic manipulation of negative-strand RNA virus genomes", Annu Rev Microbiol. 47:765-90.

Garcin et al., 1995. "A highly recombinogenic system for the recovery of infectious sendai paramyxovirus from cDNA: generation of a novel" EMBO J. 14: 6087-6094.

GeneBank Accession No. AY553802, Influenza A virus (A/little grebe/Thailand/Phichit-01/2004(H5N1) hemag-glutinin (HA) gene, partial cds. May 21, 2004.

Ghendon, "Cold-Adapted, Live Influenza Vaccines Developed in Russia," Textbook of Influenza, Chapter 29, pp. 391-399. 1998.

Goto et al., 1997. "Mutations Affecting the Sensitivity of the Influenza Virus Neuraminidase to 4-Guanidino-2,4-Dideoxy-2,3 Oehydro-N-Acetyineuraminic Acid", Virol. 238:265-27.

Govorkova, EA, et al., "African Green Monkey Kidney (Vero) Cells Provide an Alternative Host Cell," J. of Virology, Am. Soc. for Microbiology, Aug. 1996,70(8):5519-5524.

Grosfeld et al., 1995, RNA replication by respiratory syncytial virus (RSV) is directed by theN., P., and L proteins: transcription . . . J. Virol. 69(9):5677-5686.

Guan, Yi, et al., "Molecular Characterization of H9N2 Influenza Viruses: Were They the Donors of the "Internal". . . ?", Proc. Natl. Acad. Sci., U.S.A. Aug. 1999,96:9363-9367.

Hatada and Fukudo, 1992. "Binding of influenza A virus NS1 protein to dsRNA in vitro", J. of Gen. Virol. 73: 3325-3329.

He et al., 1997, "Recovery of Infectious SV5 from Cloned DNA and Expression of a Foreign Gene", Virol. 237:249-260.

Herlocher et al., "Sequence Comparisons of A1AA16/60 Influenza Viruses: Mutations Which May Contribute to Attenuation", Virus Research, 42:11-25; (1996).

Hoffman and Banerjee, 1997. "An Infectious Clone of Human Parainfluenza Virus Type 3", J. Virol. 71 :4272-4277.

Hoffman et al., "Eight-Plasmid Resue System for Influenza A Virus", International Congress Series, 1219:1007-1013; (2001).

Hoffman et al., 2002, "Rescue of influenza B virus from eight plasmids", PNAS 99: 11411-11416.

Hoffman et al.. "Ambisense" Approach for the Generation of Influenza A Virus: vRNA and mRNA Synthesis from One Template, Virology, 267:310-317; (2000).

Hoffman et al.. "Eight-Plasmid System for Rapid Generation of Influenza Virus Vaccines". Vaccine, 20:3165-3170; (2002).

Hoffmann et al., 2000 "Characterization of the Influenza A Virus Gene Pool in Avian Species in Southern China: Was H6N1 . . . ?" J. Virology, 74(14):6309-6315.

Hoffmann et al."Universal primer set for Ille full-length amplification of all influenza A viruses." Arch Virol. Dec. 2001;146 (12):2275-89).

Hoffmann et al., 2000, "A DNA transfection system for generation of influenza A virus from eight plasmids", PNAS 97(11):6108-6113.

Hoffmann et al..2000, "Unidirectional RNA polymerase 1-polymerase II transcription system for the generation of influenza A virus . . . ", J.I of Gen. Virology 81':2843-2847.

Hoffmann, Erich, "Aufbau eines RNA-Polymerase I-Vektorsystems zur gezielten Mutagenese von Influenza A Viren", "Generation of an RNA-Polymerase Vector Syst. for the Select. Mutagenesis ..,"Gieben 1997 (Doctoral Dissertation of Sch. of Nat. Sciences, Justus Uebig U. Gieben with translation).

Huang et al., 1990, "Determination of Influenza virus proteins required for genome replication", J Virol. 64(11 ):5669-73.

Kaplan et al., 1985. "In vitro Synthesis of Infectious Poliovirus RNA", Proc. Natl. Acad. Sci. USA 82:8424-8428.

Katinger et al., Attenuated Influenza Virus as a Vector for Mucosal Immunization against HIV-1A, Vaccines, pp. 315-319. (1997).

Kato et al., 1996, Initiation of Sendai Virus Multiplication from Transfected cDNA or RNA with Negative or Positive Sensen Genes to Cells 1:569-579.

Keitel, et al., "Live Cold-Adapted, Reassortant Influenza Vaccines (USA)," Textbook of Influenza, Chapter 28, pp. 373-390. 1998.

Kimura et al., 1992, "Transcription of a recombinant influenza virus RNA in cells that can express the influenza virus RNA polymerase . . . ", J Gen Viral. 73:1321-28.

Kobayashi et al., 1992, Reconstitution of influenza virus RNA polymerase from three subunits expressed using recombinant baculovirus system. Virus Res. 22:235-45.

Konarska et al., 1990, "Structure of RNAs replicated by the DNA-dependent T7 RNA polymerase", Cell. 63(3):609-18.

Krystal et at, 1986, "Expression of the Three Influenza Virus Polymerase Proteins in a Single Cell Allows Growth . . . ", Proc. Natl. Acad. Sci. USA 83:2709-2713.

Kunkel, 1985, "Rapid and Efficient Site-Specific Mutagenesis without Phenotypic Selection", Proc. Natl. Acad. Sci. USA 82:468-.

Lamb et al., 1996, Fundamental Virology 3.sup.rd ed. Chapters 20 and 21.

Lawson et al., 1995, "Recombinant vesicular stomatitis viruses from DNA", Proc Natl Acad Sci U S A.92:4477-81.

Levis et al., 1986, "Deletion Mapping of Sindbis Virus 01 RNAs Derived from cDNAs Defines the Sequences Essential for Replication and Packaging", Cell 44:137-145.

(56) References Cited

OTHER PUBLICATIONS

Li et al., 1999. Recombinant influenza A virus vaccines for the pathogenic human A/Hong Kong/97 (H5N1) viruses: J. of Infectious Diseases. 179:1132-1138.
Luytjes et al., 1989, "Amplification, Expression, and Packaging of a Foreign Gene by Influenza Virus", Cell 59:1107-1113.
Maassab et al., "Evaluation of a Cold-Recombinant Influenza Virus Vaccine in Ferrets", J. of Infectious Diseases, 146:780-790; (1982).
Maassab et al., "The Development of Live Attenuated Cold-adapted Influenza Virus Vaccine for Humans", Reviews in Medical Virology, 1999, vo!' 9, pp. 237-245.
Maassab. "Adaptation and growth characteristics of influenza virus at 25 degrees C", Nature, 213:612-614 (1967).
Martin et al., 1998, "Studies of the Binding Properties of Influenza Hemagglutinin Receptor-Site Mutants", Virology 241:101-111.
Mena et al., 1994, "Synthesis of biologically active influenza virus core proteins using a vaccinia virus-T7 RNA polymerase expression system", J Gen Virol. 75:2109-14.
Mena et at, 1996, Rescue of a Synthetic Chloramphenicol Acetyltransferase RNA into Influenza Virus-Like Particles Obtained from Recombinant Plasmids•, J. Virol. 70: 5016-5024.
Merten et al., •Production of influenza virus in Cell Cultures for Vaccine Preparation—, Novel Strategies in Design and Production of Vaccines, pp. 141-151; (1996).
Moyer et al., 1991, "Assembly and transcription of synthetic vesicular stomatitis virus nucleocapsids", J Virol. 65(5):2170-88.
Murphy & Coelingh, •Principles Underlying the Development and Use of live Attenuated Cold-Adapted Influenza A and B Virus Vaccines•, Viral Immunol. 15:295-323; (2002).
Muster et al., 1991, "An influenza A virus containing influenza B virus 5' and 3' noncoding regions on the neuraminidase gene ..:", Proc Nat! Acad Sci USA 88:5177-81.
Naito and Ishihama, 1976, "Function and Structure of RNA Polymerase from Vesicular Stomatitis Virus", J. Biol. Chern. 251:4307-4314.
Nakajima et at, 2003, "Restriction of Amino Acid Change in Influenza A Virus H3HA: Comparison of Amino Acid Changes Observed ..,", J. of Virology 77(18):10088-10098.
Nara et al.,1987, Simple, Rapid, Quantitative, Syncytium-Forming Micorassay for the Detection of Human Immunodeficiency . . . •, AIDS Res. Hum. Retroviruses 3:283-302.
Nemeroff et al., 1998. "Influenza Virus NS1 Protein Interacts with the Cellular 30 kDa Subunit of CPSF and Inhibits 3' End Formation ..". Mol. Cell 1:991-1000.
Neumann et al., "Reverse Genetics for the Control of Avian Influenza", Avian Diseases, 2003, vol. 47, pp. 882-887.
Neumann et al., 1994, "RNA Polymerase I-Mediated Expression of Influenza Viral RNA Molecules", Virol. 202:477-479.
Neumann et al., 1999, "Generation of Influenza A viruses entirely from cloned cDNAs", PNAS 96(16):9345-9350.
Neumann, et al., Genetic Engineering of Influenza and Other Negative-Strand RNA Viruses Containing Segmented Genomes,—Advances in Virus Research, 1999; 53; 265-300.
Nichol et al. 1999, "Effectiveness of live. attenuated Intranasal influenza virus vaccine in healthy, working adults: a randomized controlled trial", JAMA 282:137-44.
Palese et al. 1996, "Negative-Strand RNA Viruses: Genetic Engineering and Applications", Proc. Natl. Acad. Sci. USA 93.11354-11358.
Park et al., 1991, "Rescue of a Foreign Gene by Sendai Virus". Proc. Natl. Acad. Sci. USA 88:5537-5541.
Parkin et al., "Temperature Sensitive Mutants of Influenza A Virus Generated by Reverse Genetics . . . ". Virus Res., 46:31-44; (1996).
Parkin N. et al., Genetically Engineered live Attenuated Influenza A Virus Vaccine Candidates•, J. Viro!., pp. 2772-2778; (1997).
Pattnaik et al.. 1991. "Cells that express all five proteins of vesicular stomatitis virus from cloned cDNAs support replication .." Proc Nat! Acad Sci USA 88:1379-83.
Peeters et al.. 1999. "Rescue of Newcastle Disease Virus from Cloned cDNA: Evidence that Cleavability of the Fusion Protein . . .". J. Virol. 73:5001-5009.
Pekosz et al.. 1999. "Reverse genetics of negative-strand RNA viruses: closing the circle", Proc Natl Acad Sci USA. 96(16):8804-16.
Percy et al.. 1994. "Expression of a foreign protein by influenza A virus" J Virol 68(7):4486-92.
Perez, Daniel R. et al., 1998 "The Matrix 1 Protein of Influenza A Virus Inhibits the Transcriptase Activity of a Model . . . ", Article No. VY989318, Virology, 249:52-61.
Pleschka et al.. 1996. A Plasmid-Based Reverse Genetics System for I Influenza A Virus•. J. Virol. 70:4188-4192.
Qiu et. al., 1994, "The influenza virus NS1 protein is a poly(A)-binding protein that inhibits nuclear export of mRNAs containing poly(A)", J Virol. 68(4):2425-32.
Qui et al., 1995. "The influenza virus NS1 protein binds to a specific region in human U6 snRNA and inhibits U6-U2 and U6-U4 snRNA.. ". RNA Society 1:304-16.
Racaniello et al., 1981. "Cloned Poliovirus Complementary DNA is Infectious in Mammalian Cells," Science 214:916-919.
Radecke et al., "Reverse Genetics Meets the Nonsegmented Negative-Strand RNA Viruses," Medical Virology, vol. 7: 49-63 (1997).
Radecke et al., 1995. "Rescue of measles viruses from cloned DNA". EMBO J. 14(23):5773-84.
Roberts and Rose. 1998, "Recovery of Negative-Strand RNA Viruses from Plasmid DNAs: a Positive Approach Revitalizes a Negative Field", Virol. 247:1-6.
Rose 1996. " Positive Strands to the Rescue Again: A Segmented Negative-Strand Rna Virus Derived from Cloned . . . ".PNAS USA 94:14998-15000.
Schickli et al., 2001, "Plasmid-only rescue of influenza A virus vaccine candidates", Philos Trans Society of London Ser B 356:1965-1973.
Schlesinger. 1995. "RNA viruses as vectors for the expression of heterologous proteins", Mol Biotechnol. 3:155-65.
Schnell et al.. 1994, "Infectious Rabies Viruses from Cloned cDNA", EMBO J. 13:4195-4203.
Scholtissek, et al., "The Nucleoprotein as a Possible Major Factor in Determining Host Specificity of Influenza H3N2 Viruses," Virology, 1985; 147:287-294.
Seong et al., 1992, "A new method for reconstituting influenza polymerase and RNA in vitro: a study of the promoter elements for cRNA .. ". Virology 186:247-60.
Sidhu et at., 1995, "Rescue of synthetic measles virus minireplicons: measles genomic termini direct efficient expression . . . ", Virology. 208(2):800-07.
Snyder et al., "Four Viral Genes Independently Contribute to Attenuation of live Influenza A/Ann Arbor/6/60 (H2N2) Cold-Adapted . . . ", J. Virol., 62:488-95; (1988).
Subbarao et al, 1995, "Sequential addition of temperature-sensitive missense mutations into the PB2 gene of influenza A . . . ", J. of Virology 69(10):5969-5917.
Subbarao et al., The Attenuation Phenotype Conferred by the M Gene of the Influenza A/Ann Arbor/6/60 Cold-Adapted Virus (H2N2) on the . . . Virus Res., 25:37-50; (1992).
Szewczyk et al., 1988, •Purification. Thioredoxin Renaturation, and Reconstituted Activity of the Three Subunits of the III fluenza .. •• Proc. Nat!. Acad. Sci. USA 65:7907-7911.
Taylor et al., 1990, "Newcastle Disease Virus Fusion Protein Expressed in a Fowlpox Virus Recombinant Confers Protection in Chickens", J. Virol. 64:1441-1450.
Ward et al., 1988, "Direct Measurement of the Poliovirus RNA Polymerase Error Frequency in Vitro": J. Virol. 62:558-562.
Whelan et al., 1995, "Efficient recovery of infectious vesicular stomatitis virus entirely from cDNA clones", Proc.Natl.Acad.Sci. USA 92:8388-8392.
Xu et al., 1995 #AAB06964 (abstract only).
Xu et al., 1996, "Genetic Variation in Neuraminidase Genes of Influenza A (H3N2) Viruses", Virology 224:175-183.
Xu, Xiyan, et al., 1999 n Genetic Characterization of the Pathogenic Influenza A/Goose/Guangdong/1/96 (H5N1) Virus: . . . Article 10 viro. 1999.9820. Virology 261:15-19.
Yamanaka et al.. 1991, "In vivo analysis of the promoter structure of the influenza virus RNA genome using a transfection system . . . ," Proc Natl Acad Sci USA 88: 5369-5373.

(56) References Cited

OTHER PUBLICATIONS

Yu et al., 1995, "Functional cDNA clones of the human respiratory syncytial (RS) virus N, P, and L proteins support replication . . . ", J Virol. 69(4):2412-19.

Yusoff et al., 1987, "Nucleotide Sequence Analysis of the L Gene of Newcastle Disease Virus: Homologies with Sendi and Vesicular Stomatitis.", Nucleic Acids Res. 15:3961-76.

Zaghouani et al., 1992, "Cells Expressing an H Chain' to Gene Carrying a Viral T Cell Epitope Are Lysed by Specific Cytolytic T Cells", J. Immuno!. 148:3604-3609.

Zaghouani et al., 1991, "Induction of antibodies to the envelope protein of the human immunodeficiency virus by immunization ..", Proc. Natl. Acad Sci. USA 88:5645-5649.

Zhang and Air, 1994, "Expression of Functional Influenza Virus A Polymerase Proteins and Template from Cloned cDNAs .. ", Biochem. & Biophys. Res. Commun. 200:95-101.

Zhang et al., "Persistence of four related human immunodeficiency virus subtypes during the course of zidovudine therapy: relationship between virion RNA and proviral DNA." J. Virol. 1994; 68(1): 425-432.

Zobel et al., 1993, "RNA polymerase I catalyzed transcription of insert viral cDNA", Nucleic Acids Res. 21(16):3607-14.

Bender et al., 1999, "Characterization of the surface proteins of influenza A (H5N1) viruses ." Virology 254(1 ):1 15-23.

Database EMBL [Online] E.B.I. Hinxtoin U.K.; Nov. 1, 1999, Bender C et al: "Hemagglutinin (Fragment).", Database accession No. Q9WDG1.

Database EMBL [Online] E.B.I. Hinxton U.K.; May 1, 2000, Hiromoto Y et al: "Hemagglutinin (Fragment).", Database accession No. Q9QSJ8.

Database EMBL [Online] E.B.I. Hinxton U.K.; Nov. 1 1999, Bender C et al: "Hemagglutinin (Fragment).", Database accession No. Q9WDF7.

Development of a vaccine effective against avian influenza H5N1 infection in humans. RelevéÉpidémiologique Hebdomadaire / Section D'Hygiène Du Secrétariat De La Société Des Nations=Weekly Epidemiological Record / Health Section of the Secretariat of the League of Nations Jan. 23, 2004, vol. 79, No. 4, pp. 25-26.

Genbank Accession # AAW80717, hemagglutinin HA [Influenza A virus (ANiet Nam/1203/2004 (H5N 1 ))], published Feb. 9, 2005.

Genbank Accession# AAF74325, published Jun. 7, 2000.

GenBank Accession# AAW80723.1, published: Feb 9, 2005.

GenBank Accession# AF046080.1, published: May 17, 2005.

GenBank Accession# AF046097. 1, published , May 17, 2005.

GeneBank Accession# L20407.1 Influenza A Virus (A/Japan/305-/1957(H2N2)) hemag-glutinin (HA) gene, complete cds. [online] May 2, 2006 [retrieved Jul. 23, 2010]. Available on the internet, url: http://www.ncbi.nlm.nih.gov/nuccore/305154.

Genebank Accession No. AY651334, Li K S et al: "Influenza A virus (A/Viet Nam/1203/2004(H5N1)) hemagglutinin (HA) gene, partial cds." Jul. 19, 2004.

Genebank Accession No. AY651447, Li K S et al: "Influenza A virus (A/Viet Nam/1203/2004(H5N1)) neuraminidase (NA) gene, complete cds." Jul. 19, 2004.

Govorkova et al., "Lethality to ferrets of H5N1 influenza viruses isolated from humans and poultry in 2004" (Journal of Virology 79:2191-2198, Feb. 2005).

Ha et al., H5 avian and H9 swine influenza virus haemagglutinin structures: possible origin of influenza subtypes, 2002, The EMBO Journal, vol. 21, No. 5, pp. 865-875.

Hien et al., "Avian Influenza A (H5N1) in 10 Patients in Vietnam," The New England Journal of Medicine, vol. 350, No. 12, Mar. 18, 2004, pp. 1179-1188.

Hilleman Maurice R., 2000, "Vaccines in historic evolution and perspective: a narrative of vaccine discoveries", Vaccine 18: 1436-1447.

Hiromoto et al., "Evolutionary Characterization of the six internal genes of H5N1 human influenza A virus," Journal of General Virology, 81, pp. 1293-1303 (2000).

Hirst, M. et al., Emerg Infet Dis. Dec. 2004;10(12):2192-2195.

Hoffmann et al., 2005, "Role of specific hemaggluitnin amino acids in the immunogenicity. " PNAS USA 102 (36) 12915-20. Epub Aug. 23, 2005.

International Search Report and Written Opinion mailed on: Jul. 7, 2008 in International application No. PCT/US05/017733 filed on May 20, 2005 and published as WO/2005/116260 on Aug. 12, 2005.

International Search Report and Written Opinion mailed on: Oct. 25, 2006, in International application No. PCT/US05/017729 filed on May 20, 2005, and published as: WO/2005/0116258 on: Aug. 12, 2005.

International Search Report mailed on: Jul. 30, 2010, in International application No. PCT/US10/22970 filed on Feb. 3, 2010.

Jin et al., "Multiple amino acid residues confer temperature sensitivity to human influenza virus vaccine strains (FluMist) derived from cold adapted A/Ann Arbor/6/60," Virology 306 (2003) 18-24.

Kimura et al., 1993, "An in vivo study of the replication origin in the influenza virus complementary RNA", J Biochem (Tokyo) 113:88-92.

Li et al., "Genesis of a highly pathogenic and potentially pandemic H5N1 influenza virus in eastern Asia" Nature, Nature Publishing Group, London, UK, vol. 430, No. 6996, Jul. 8, 2004, pp. 209-213.

Office Action mailed Dec. 8, 2008 in U.S. Appl. No. 11/133,360, filed May 20, 2005, published as: US/2005/0287172 on: Dec. 29, 2005 and issued as US patent No. 7,527,800 on: May 5, 2009.

Office Action mailed Jun. 1, 2007 in U.S. Appl. No. 11/133,360, filed May 20, 2005, published as: US/2005/0287172 on: Dec. 29, 2005 and issued as US patent No. 7,527,800 on: May 5, 2009.

Office Action mailed Mar. 11, 2008 in U.S. Appl. No. 11/133,360, filed May 20, 2005, published as: US/2005/0287172 on: Dec. 29, 2005 and issued as US patent No. 7,527,800 on: May 5, 2009.

Office Action mailed on: Oct. 20, 2008 in U.S. Appl. No. 11/133,346, filed May 20, 2005, published as: US2006/0008473 on: Jan. 12, 2006 and issued as US patent No. 7,504,109 on: Mar. 17, 2009.

Office Action mailed on: May 6, 2008 in U.S. Appl. No. 11/133,346, filed May 20, 2005, published as: US2006/0008473 on: Jan. 12, 2006 and issued as US patent No. 7,504,109 on: Mar. 17, 2009.

Office Action mailed on: Oct. 15, 2007 in U.S. Appl. No. 11/133,346, filed May 20, 2005, published as: US2006/0008473 on: Jan. 12, 2006 and issued as US patent No. 7,504,109 on: Mar. 17, 2009.

Office Action mailed on: Apr. 20, 2007 in U.S. Appl. No. 11/133,346, filed May 20, 2005, published as: US2006/0008473 on: Jan. 12, 2006 and issued as US patent No. 7,504,109 on: Mar. 17, 2009.

Office Action mailed on: Jan. 29, 2010 in U.S. Appl. No. 12/354,085 published as: 2009/0136530 on May 28, 2009 and Issued as 7,744,901 on Jun. 29, 2010.

Office Action mailed on: Jun. 18, 2009 in U.S. Appl. No. 12/354,085, published as: 2009/0136530 on May 28, 2009 and Issued as 7,744,901 on Jun. 29, 2010.

Office Action mailed: Mar. 9, 2010 in U.S. Appl. No. 12/399,312, filed Mar. 6, 2009 and published as: 2009/0175909 on: Jul. 9, 2009 and Issued as: 7,981,429 on Jul. 19, 2011.

Office Action mailed: Nov. 26, 2010 in U.S. Appl. No. 12/399,312 filed Mar. 6, 2009 and published as: 2009/0175909 on: Jul. 9, 2009 and Issued as: 7,981,429 on Jul. 19, 2011

Office Action mailed: Mar. 10, 2011 in U.S. Appl. No. 12/399,312, filed Mar. 6, 2009 and published as: 2009/0175909 on: Jul. 9, 2009 and Issued as: 7,981,429 on Jul. 19, 2011.

Office Action mailed on: Jul. 12, 2011 in U.S. Appl. No. 12/769,304, filed Apr. 28, 2010 and published as: US-2011/0052618 on Mar. 3, 2011.

Office Action mailed: Jan. 27, 2012 in U.S. Appl. No. 13/161,938, filed Jun. 16, 2011 and published as: 2012/0034264 on: Feb. 9, 2012.

Office Action mailed on: Oct. 1, 2010 in U.S. Appl. No. 11/836,413, published as: 2008/0069821 on Mar. 20, 2008.

See SCORE Sequence Results 1, 16.rup (2007).

See SCORE Sequence Results 1, 2, 15.rup (2007).

Shortridge et al, 1998, "Characterization of H5N1 influenza viruse . . . " Virology 252(2):331-42.

Suarez et al., "Comparisons of Highly Virulent H5N1 Influenza A Viruses Isolated from Humans and Chickens from Hong Kong", Journal of Virology, vol. 72, No. 8 (1998), pp. 6678-6688.

(56) References Cited

OTHER PUBLICATIONS

Subbarao et al., Evaluation of a genetically modified Reassortant H5N1 Influenza A Virus vaccine Candidate generated by plasmid-based Reverse genetics, 2003, Virology, vol. 305 pp. 192-200.

Suguitan et al., 2006, "Live, attenuated influenza A H5N1 candidate vaccines . . . " PLoS Med. Sep. 2006; 3(9):e360.
Wareing et al., Vaccine 2005, vol. 23, Issue 31, pp. 4075-4081.
Wareing, J.M. et al., "Immunogenic and Isotope-Specific Responses to Russian and US Cold-Adapted Influenza A, Vaccine Donor . . . " J of Medical Virology (2001) 65:171-177.
Webby et al., 2004, "Responsiveness to a pandemic alert: use of reverse genetics for rapid development of influenza vaccines", Lancet 363: 1099-1103.
Zhou et al., "Rapid Evolution of H5N11 nfluenza Viruses in Chickens in Hong Kong," Journal of Virology, vol. 73, No. 4, pp. 3366-3374 (1999).
Zhou, et al., "Membrane-Anchored Incorporation of a Foreign Protein in Recombinant Influenza Virions", Article No. VY989169, Virology, 1998, vol. 246, pp. 83-94.
Office Action mailed on: Aug. 19, 2013 in U.S. Appl. No. 12/699,108, filed Feb. 3, 2010 and published as: 2010/0330118 on Dec. 30, 2010.

* cited by examiner

VN/1203/2004 wildtype HA:

CCT CAA AGA GAG AGA AGA AGA AAA AAG AGA    GGA TTA TTT
Pro Gln Arg Glu Arg Arg Arg Lys Lys Arg    Gly Leu Phe

Modified HA:

CCT CAA AGA GAG ACT    CGA    GGA TTA TTT
Pro Gln Arg Glu Thr    Arg    Gly Leu Phe

↓Site of cleavage of into HA1 and HA2 domains.

Residues that were mutagenized are underlined.

Fig 1

Virus isolation from swabs

| Virus | Mortality (dead/total) | Oropharyngeal | | Cloacal | | Antibody detected/ total |
|---|---|---|---|---|---|---|
| | | # shedding/ total | Mean $\log_{10}$ titer ($EID_{50}$) | # shedding/ total | Mean $\log_{10}$ titer ($EID_{50}$) | |
| 1997, 2003 and 2004 H5N1 wt | 8/8 | 8/8 | >6.3 | 8/8 | >4.5 | NA |
| 1997, 2003 and 2004 H5N1 ca | 0/8 | 0/8 | <0.9 | 0/8 | <0.9 | 0/8 |

Chickens were inoculated intranasally with $10^6$ $TCID_{50}$ of virus.

Fig 2

LD$_{50}$ in mice

| | |
|---|---|
| A/AA/6/60 ca | >10$^7$ TCID$_{50}$ |
| A/HK/491/97 | 10$^2$ TCID$_{50}$ |
| 1997 H5N1/AA ca | >10$^7$ TCID$_{50}$ |
| A/HK/213/2003 | 10$^6$ TCID$_{50}$ |
| 2003 H5N1/AA ca | >10$^7$ TCID$_{50}$ |
| A/Vietnam/1203/2004 | 10$^{0.4}$ TCID$_{50}$ |
| 2004 H5N1/AA ca | >10$^7$ TCID$_{50}$ |

Fig 3

| Tissue | Virus | Average fold difference in titer Over 3 days |
|---|---|---|
| LUNGS | A/AA/6/60 | 93 |
| | 1997 H5N1 | 501 |
| | 2003 H5N1 | 12 |
| | 2004 H5N1 | 430 |
| NASAL TURBINATES | A/AA/6/60 | 32 |
| | 1997 H5N1 | 185 |
| | 2003 H5N1 | none |
| | 2004 H5N1 | 100 |

$10^6$ $TCID_{50}$ of virus was administered intranasally and tissues were harvested on days 2, 3 or 4 post-infection. Virus titers are expressed as $\log_{10}$ $TCID_{50}$/g of tissue.

Fig 4

| Immunizing virus | Geometric mean serum HAI Ab titers against indicated virus | | |
|---|---|---|---|
| | 1997 wt | 2003 wt | 2004 wt |
| 2003 ca | 20 | 213.6 | 20 |
| 2003 wt | 20 | 394 | 20 |

An undetectable titer is assigned a value of 20

Fig 6

| Immunizing virus | Geometric mean serum neutralizing Ab titers against indicated virus | | |
|---|---|---|---|
| | 1997 wt | 2003 wt | 2004 wt |
| 2003 ca | 10 | 59.2 | 10 |
| 2003 wt | 10 | 93.3 | 10 |

An undetectable titer is assigned a value of 10

Fig 7

H5N1 1997 wt challenge

- 1997 ca
- 2003 ca
- 2004 ca

Mock immunized

H5N1 2004 wt challenge

- 1997 ca
- 2003 ca
- 2004 ca

Mock immunized

Days following administration of challenge virus

Fig 8

|  | Mean reduction in titer in lungs following | | | |
|---|---|---|---|---|
| Immunization | Homologous challenge | Heterologous H5N1 challenge | | |
| | | 1997 wt | 2003 wt | 2004 wt |
| 1997 ca | 2.5 | NA | 3.0 | 0.7 |
| 2003 ca | >5.8 | 2.3 | NA | 2.9 |
| 2004 ca | 2.0 | 1.4 | >5.7 | NA |

Fig 9

|  | Mean reduction in titer in NT following | | | |
|---|---|---|---|---|
| Immunization | Homologous challenge | Heterologous H5N1 challenge | | |
|  |  | 1997 wt | 2003 wt | 2004 wt |
| 1997 ca | 4.3 | NA | >1.2 | 2.6 |
| 2003 ca | >1.2 | 3.7 | NA | >3.3 |
| 2004 ca | 1.6 | 4.2 | >3.5 | NA |

A/Netherland/219/03 wildtype HA:
```
CCA AAG AGG AGG AGG AGA | GGC
Pro Lys Arg Arg Arg Arg ↓ Gly
```

Modified HAs:
```
CCA AAG GGG --- --- AGA    GGC
Pro Lys Gly         Arg    Gly    | Site of cleavage of into
                                  ↓ HA1 and HA2 domains.

CCA AAG ACT --- --- AGA    GGC
Pro Lys Thr         Arg    Gly

CCA AAG CCG --- --- AGA    GGC
Pro Lys Pro         Arg    Gly
```

Fig 14

| Immunizing virus | Doses | Geometric mean serum neutralizing Ab titers against indicated virus | | |
|---|---|---|---|---|
| | | 1997 wt | 2003 wt | 2004 wt |
| A/VN/2004 ca | 1 | 10 | 10 | 10 |
| | 2 | 160 | 528 | 388 |
| A/HK/2003 ca | 1 | 10 | 37 | 10 |
| | 2 | 19 | 1056 | 61 |

Fig 15

|  |  | Post Vaccination Sera (7 log$_{10}$PFU) HI Titer 32 days after dose 1 | | | |
| --- | --- | --- | --- | --- | --- |
|  |  | H6N9 A/Duck ca | H6N1 A/Teal ca | H6N2 A/Mallard ca | H1N1 A/New Cal ca |
| Test Antigen | Wt A/Duck | 13.5 | <8 | <8 | <8 |
|  | Wt A/Teal | <8 | 19.0 | <8 | <8 |
|  | Wt A/Mallard | <8 | <8 | 13.5 | <8 |
|  | Wt A/New Cal | <8 | <8 | <8 | 430.5 |

Fig 17

| Virus | Dosing schedule | Geometric mean neutralizing antibody titers achieved at indicated time post-infection[a] | | |
|---|---|---|---|---|
| | | d 0 | 4 weeks | 8 weeks |
| | d 0 | <10 | 80 | NA |
| H7N3 BC 04 ca | | | | |
| | d 0 | <10 | 87 | 403[b] |
| | d 0 and d 28 | <10 | 45 | 470 |
| | d 0 | <10 | 308 | NA |
| A/ck/BC/CN-6/04 | | | | |
| | d 0 | <10 | 320 | 941 |
| | d 0 and d 28 | <10 | 154 | 1701 |

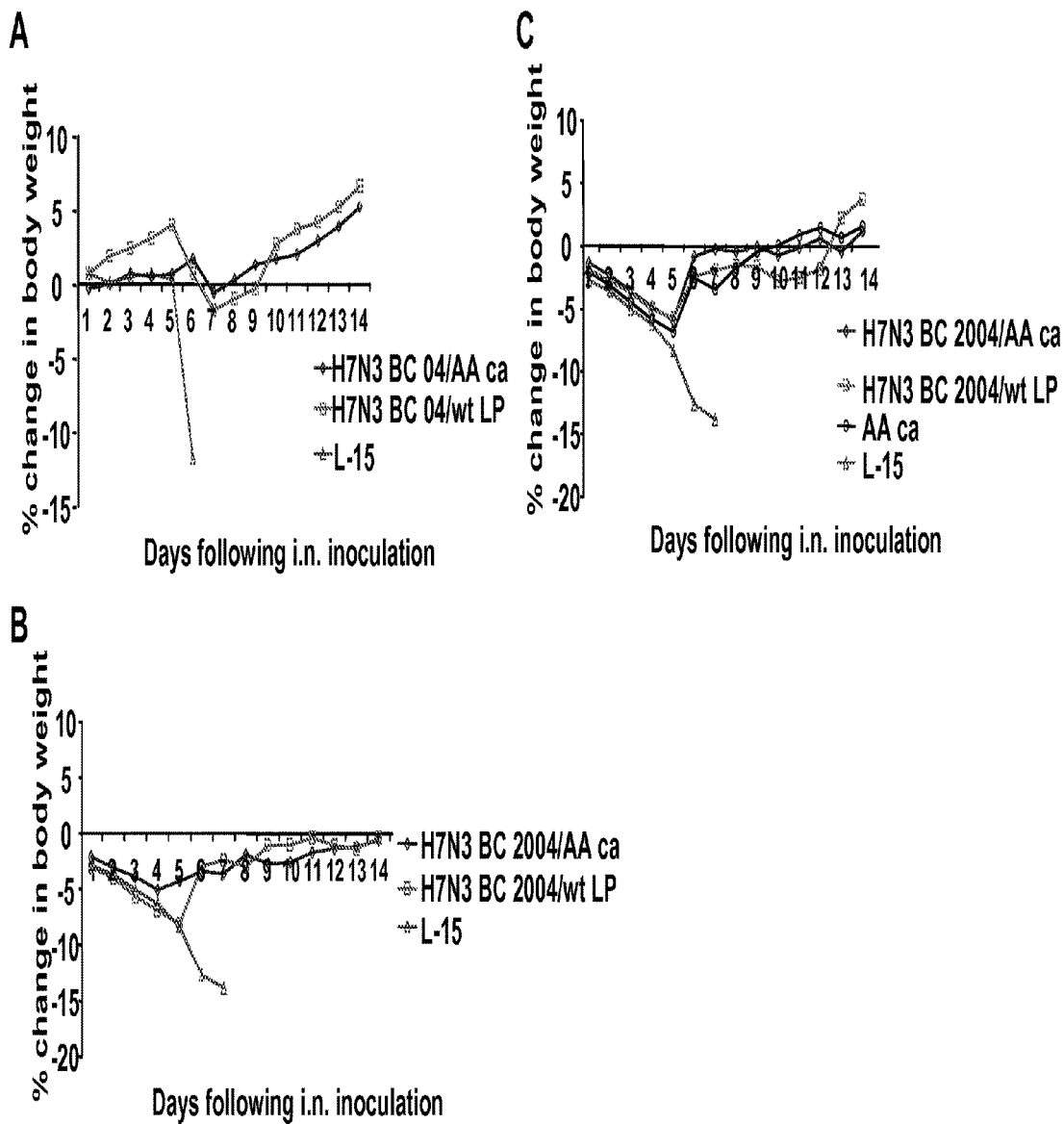
Fig 21 A-C

Challenge Virus

▨ G9 wt
⋯ HK/1073/99
▨ G9 wt
■ HK/2108/2003

⋯⋯⋯ Lower limit of detection study 1
— ⋅ — Lower limit of detection study 2

Fig 24 AB

| Vaccine Dose | N | No. Vaccine Virus Culture + (days) | Peak Titer Shed* ($\log_{10}TCID_{50}$/ mL) | No. Vaccine Virus PCR+ (days) |
|---|---|---|---|---|
| 1 | 26 | 2 (1) | 1.0 | 8 (1.1) |
| 2 | 24 | 0 | ≤0.6 | 2 (1.5) |

* Among those who shed virus

Fig 25

| Vaccine Dose | Sero-status | N | Mean HI titer, 1/log$_2$ Days After Dose | | | No. with 4-fold rise | % |
| --- | --- | --- | --- | --- | --- | --- | --- |
| | | | D0 | D28 | D42 | | |
| 1 | - | 26 | 1.7 | 2.6 | - - | 9 | 31 |
| 2 | - | 24 | 3.1 | 4.6 | 4.5 | 12 | 50 |
| Cumulative | | 24 | | | | 22 | 92 |

Fig 26

| Vaccine Dose | N | No. Nasal wash Culture + (days) | No. Nasal wash PCR+ (days) |
|---|---|---|---|
| 1 | 21 | 0 | 2 (2.0) |
| 2 | 18 | 0 | 3 (1.0) |

Vaccine virus was not detected by any method in throat swab specimens.

Fig 27

|  |  | Mean HI titer, $1/\log_2$ | | | |
| --- | --- | --- | --- | --- | --- |
|  |  | Days after dose | | | |
| Vaccine Dose | N | D0 | D28 | No. with 4-fold rise | % |
| 1 | 20 | 2.6 | 2.8 | 0 | 0 |
| 2 | 18 | 2.7 | 3.1 | 1 | 6 |
| Cumulative | 18 |  |  | 2 | 11 |

SEQUENCE LISTING

```
<160> NUMBER OF SEQ IDS NOS: 45

<210> SEQ ID NO 1
<211> LENGTH: 1767
<212> TYPE: DNA
<213> ORGANISM: Influenza A virus

<400> SEQUENCE: 1
agcaaaagca ggggttcaat ctgtcaaaat ggagaaaata gtgcttcttt ttgcaatagt    60
cagtcttgtt aaaagtgatc agatttgcat tggttaccat gcaaacaact cgacagagca   120
ggttgacaca ataatggaaa agaacgttac tgttacacat gcccaagaca tactggaaaa   180
```

| | | |
|---|---|---|
| gaaacacaac gggaagctct gcgatctaga tggagtgaag cctctaattt tgagagattg | 240 |
| tagcgtagct ggatggctcc tcggaaaccc aatgtgtgac gaattcatca atgtgccgga | 300 |
| atggtcttac atagtggaga aggccaatcc agtcaatgac ctctgttacc caggggattt | 360 |
| caatgactat gaagaattga acacctatt gagcagaata aaccattttg agaaaattca | 420 |
| gatcatcccc aaaagttctt ggtccagtca tgaagcctca ttaggggtga gctcagcatg | 480 |
| tccataccag ggaagtcct cctttttcag aaatgtggta tggcttatca aaagaacag | 540 |
| tacataccca acaataaaga ggagctacaa taataccaac caagaagatc ttttggtact | 600 |
| gtggggatt caccatccta atgatgcggc agagcagaca aagctctatc aaacccaac | 660 |
| cacctatatt tccgttggga catcaacact aaaccagaga ttggtaccaa aatagctac | 720 |
| tagatccaaa gtaaacgggc aaagtggaag gatggagttc ttctggacaa ttttaaagcc | 780 |
| gaatgatgca atcaacttcg agagtaatgg aaatttcatt gctccagaat atgcatacaa | 840 |
| aattgtcaag aaaggggact caacaattat gaaaagtgaa ttggaatatg gtaactgcaa | 900 |
| caccaagtgt caaactccaa tgggggcgat aaactctagc atgccattcc acaatataca | 960 |
| ccctctcacc attggggaat gccccaaata tgtgaaatca acagattag tccttgcgac | 1020 |
| tgggctcaga aatagccctc aaagagagac tcgaggatta tttggagcta tagcaggttt | 1080 |
| tatagaggga ggatggcagg gaatggtaga tggttggtat gggtaccacc atagcaatga | 1140 |
| gcaggggagt gggtacgctg cagacaaaga atccactcaa aaggcaatag atggagtcac | 1200 |
| caataaggtc aactcgatca ttgacaaaat gaacactcag tttgaggccg ttggaaggga | 1260 |
| atttaacaac ttagaaagga aatagagaa tttaaacaag aagatggaag acgggttcct | 1320 |
| agatgtctgg acttataatg ctgaacttct ggttctcatg gaaaatgaga gaactctaga | 1380 |
| cttcatgac tcaaatgtca agaaccttta cgacaaggtc cgactacagc ttagggataa | 1440 |
| tgcaaaggag ctgggtaacg gttgtttcga gttctatcat aaatgtgata atgaatgtat | 1500 |
| ggaaagtgta agaaatggaa cgtatgacta cccgcagtat tcagaagaag cgagactaaa | 1560 |
| aagagaggaa ataagtggag taaaattgga atcaatagga atttaccaaa tactgtcaat | 1620 |
| ttattctaca gtggcgagtt ccctagcact ggcaatcatg gtagctggtc tatccttatg | 1680 |
| gatgtgctcc aatgggtcgt tacaatgcag aatttgcatt taaatttgtg agttcagatt | 1740 |
| gtagttaaaa acacccttgt ttctact | 1767 |

<210> SEQ ID NO 2
<211> LENGTH: 1398
<212> TYPE: DNA
<213> ORGANISM: Influenza A virus

<400> SEQUENCE: 2

| | | |
|---|---|---|
| agcaaaagca ggagttcaaa atgaatccaa atcagaagat aataaccatc gggtcaatct | 60 |
| gtatggtaac tggaatagtt agcttaatgt tacaaattgg gaacatgatc tcaatatggg | 120 |
| tcagtcattc aattcacaca gggaatcaac accaatctga accaatcagc aatactaatt | 180 |
| ttcttactga gaaagctgtg gcttcagtaa aattagcggg caattcatct cttgtgcccca | 240 |
| ttaacggatg ggctgtatac agtaaggaca acagtataag gatcggttcc aagggggatg | 300 |
| tgtttgttat aagagagccg ttcatctcat gctcccactt ggaatgcaga actttctttt | 360 |
| tgactcaggg agccttgctg aatgacaagc actccaatgg gactgtcaaa gacagaagcc | 420 |
| ctcacagaac attaatgagt tgtcctgtgg gtgaggctcc ctccccatat aactcaaggt | 480 |
| ttgagtctgt tgcttggtca gcaagtgctt gccatgatgg caccagttgg ttgacgattg | 540 |

-continued

| | |
|---|---|
| gaatttctgg cccagacaat ggggctgtgg ctgtattgaa atacaatggc ataataacag | 600 |
| acactatcaa gagttggagg aacaacatac tgagaactca agagtctgaa tgtgcatgtg | 660 |
| taaatggctc ttgctttact gtaatgactg acggaccaag taatggtcag gcatcacata | 720 |
| agatcttcaa aatggaaaaa gggaaagtgg ttaaatcagt cgaattggat gctcctaatt | 780 |
| atcactatga ggaatgctcc tgttatccta atgccggaga aatcacatgt gtgtgcaggg | 840 |
| ataattggca tggctcaaat cggccatggg tatctttcaa tcaaaatttg gagtatcaaa | 900 |
| taggatatat atgcagtgga gttttcggag acaatccacg ccccaatgat ggaacaggta | 960 |
| gttgtggtcc ggtgtcctct aacggggcat atggggtaaa agggttttca tttaaatacg | 1020 |
| gcaatggtgt ctggatcggg agaaccaaaa gcactaattc caggagcggc tttgaaatga | 1080 |
| tttgggatcc aaatgggtgg actgaaacgg acagtagctt ttcagtgaaa caagatatcg | 1140 |
| tagcaataac tgattggtca ggatatagcg ggagttttgt ccagcatcca gaactgacag | 1200 |
| gactagattg cataagacct tgtttctggg ttgagttgat cagagggcgg cccaaagaga | 1260 |
| gcacaatttg gactagtggg agcagcatat ctttttgtgg tgtaaatagt gacactgtgg | 1320 |
| gttggtcttg gccagacggt gctgagttgc cattcaccat tgacaagtag tttgttcaaa | 1380 |
| aaactccttg tttctact | 1398 |

<210> SEQ ID NO 3
<211> LENGTH: 1767
<212> TYPE: DNA
<213> ORGANISM: Influenza A virus

<400> SEQUENCE: 3

| | |
|---|---|
| agcaaaagca ggggttcaat ctgtcaaaat ggagaaaata gtgcttcttt ttgcaatagt | 60 |
| cagtcttgtt aaaagtgatc agatttgcat tggttaccat gcaaacaact cgacagagca | 120 |
| ggttgacaca ataatggaaa agaacgttac tgttacacat gcccaagaca tactggaaaa | 180 |
| gacacacaac gggaagctct gcgatctaga tggagtgaag cctctaattt tgagagattg | 240 |
| tagtgtagct ggatggctcc tcggaaaccc aatgtgtgac gaattcatca atgtgccgga | 300 |
| atggtcttac atagtggaga aggccaatcc agccaatgac ctctgttacc cagggggattt | 360 |
| caacgactat gaagaattga aacacctatt gagcagaata aaccattttg agaaaattca | 420 |
| gatcatcccc aaaaattctt ggtccagtca tgaagcctca ttaggggtga gctcagcatg | 480 |
| tccataccaa ggaaagtcct cctttttcag gaatgtggta tggcttatca aaaagaacaa | 540 |
| tgcatacccca acaataaaga ggagctacaa taataccaac caagaagatc ttttggtatt | 600 |
| gtggggatt caccatccta atgatgcggc agagcagact aggctctatc aaaacccaac | 660 |
| cacctacatt tccgttggga catcaacact aaaccagaga ttggtaccaa aaatagctac | 720 |
| tagatccaaa gtaaacgggc aaaatggaag gatggagttc ttctggacaa ttttaaaacc | 780 |
| gaatgatgca atcaacttcg agagcaatgg aaatttcatt gctccagaat atgcatacaa | 840 |
| aattgtcaag aaaggggact cagcaattat gaaaagtgaa ttggaatatg gtaactgcaa | 900 |
| caccaagtgt caaactccaa tggggcgat aaactctagt atgccattcc acaatataca | 960 |
| ccctctcacc atcggggaat gccccaaata tgtgaaatca acagattag tccttgcgac | 1020 |
| tgggctcaga atagccctc aaagagagac tcgaggatta tttggagcta tagcaggttt | 1080 |
| tatagaggga ggatggcagg gaatggtaga tggttggtat gggtaccacc atagcaatga | 1140 |
| gcaggggagt gggtacgctg cagacaaaga atccactcaa aaggcaatag atggagtcac | 1200 |
| caataaggtc aactcgatca ttgacaaaat gaacactcag tttgaggccg ttggaaggga | 1260 |

```
atttaataac ttagaaagga gaatagagaa tttaaacaag aagatggaag acggattcct    1320
agatgtctgg acttataatg ctgaacttct ggttctcatg gaaaatgaga gaactctaga    1380
ctttcatgac tcaaatgtca agaacctttta cgacaaggtc cgactacagc ttagggataa   1440
tgcaaaggag ctgggtaacg gttgtttcga gttctatcac aaatgtgata atgaatgtat    1500
ggaaagtgta agaaacggaa cgtatgacta cccgcagtat tcagaagaag caagactaaa    1560
aagagaggaa ataagtggag taaaattgga gtcaatagga acttaccaaa tactgtcaat    1620
ttattctaca gtggcgagtt ccctagcact ggcaatcatg gtagctggtc tatctttatg    1680
gatgtgctcc aatgggtcgt tacaatgcag aatttgcatt taaatttgtg agttcagatt    1740
gtagttaaaa acacccttgt ttctact                                        1767

<210> SEQ ID NO 4
<211> LENGTH: 1458
<212> TYPE: DNA
<213> ORGANISM: Influenza A virus

<400> SEQUENCE: 4
agcaaaagca ggagttcaaa atgaatccaa atcagaagat aacaaccatt ggatcaatct     60
gtatggtaat tggaatagtt agcttgatgt tacaaattgg gaacataatc tcaatatggg    120
ttagtcattc aattcaaaca gggaatcaac accaggctga accatgcaat caaagcatta    180
ttacttatga aaacaacacc tgggtaaacc agacatatgt caacatcagc ataccaatt     240 ttcttactga gaaagctgtg gcttcagtaa cattagcggg caattcatct ctttgccccca    300 ttagtggatg ggctgtatac agtaaggaca acggtataag aatcggttcc aaggggatg     360 tgtttgttat aagagagccg ttcatctcat gctcccactt ggaatgcaga actttctttt    420
tgactcaggg agccttgctg aatgacaagc attctaatgg accgtcaaa gacagaagcc     480 ctcacagaac attaatgagt gtcccgtgg gtgaggctcc ttccccatac aactcgaggt     540 tgagtctgt tgcttggtcg gcaagtgctt gtcatgatgg cactagttgg ttgacaattg     600
gaatttctgg cccagacaat ggggctgtgg ctgtattgaa atacaatggc ataataacag    660
acactatcaa gagttggagg aacaacataa tgagaactca gagtctgaa tgtgcatgtg     720 taaatggctc ttgctttact gttatgactg atggaccaag taatgggcag gcttcataca    780
aaatcttcag aatagaaaaa gggaaagtag ttaaatcagc cgaattaaat gccccctaatt    840 atcactatga ggagtgctcc tgttatcctg atgctggaga aatcacatgt gtgtgcaggg    900
ataactggca tggctcaaat cggccatggg tatctttcaa tcaaaattg gagtatcgaa     960 taggatatat atgcagtgga gttttcggag acaatccacg ccccaatgat gggacaggca   1020
gttgtggtcc ggtgtccct aaaggggcat atggaataaa agggttctca tttaaatacg    1080
gcaatggtgt ttggatcggg agaaccaaaa gcactaattc caggagcggc tttgaaatga    1140
tttgggatcc aaatgatgg actggtacgg acagtaattt ttcagtaaag caagatattg    1200
tagctataac cgattggtca ggatatagcg ggagttttgt ccagcatcca gaactgacag    1260
gattagattg cataagacct tgtttctggg ttgagctaat cagagggcgg cccaaagaga   1320
gcacaatttg gactagtggg agcagcatat ccttttgtgg tgtaaatagt gacactgtgg   1380
gttggtcttg gccagacggt gctgagttgc cattcaccat tgacaagtag tttgttcaaa    1440
aaactccttg tttctact                                                 1458

<210> SEQ ID NO 5
<211> LENGTH: 1767
<212> TYPE: DNA
```

-continued

<213> ORGANISM: Influenza A virus

<400> SEQUENCE: 5

```
agcaaaagca ggggtataat ctgtcaaaat ggagaaaata gtgcttcttc ttgcaacagt 60
cagccttgtt aaaagtgacc agatttgcat tggttaccat gcaaacaact cgacagagca 120
agttgacaca ataatggaaa agaatgttac tgttacacat gcccaagaca tactggaaag 180
gacacacaac gggaagctct gcgatctaaa tggagtgaag cctctgattt tgagggattg 240
tagtgtagct ggatggctcc tcggaaaccc tatgtgtgac gaattcatca atgtgccgga 300
atggtcttac atagtggaga aggccagtcc agccaatgac ctctgttatc cagggaattt 360
caacgactat gaagaactga aacacctatt gagcagaata aaccattttg agaaaattca 420
gataatcccc aaaagttctt ggtccaatca tgatgcctca tcaggggtga gctcagcatg 480
tccatacctt gggaggtcct cctttttcag aaatgtggta tggcttatca aaaagaacag 540
tagctaccca acaataaaga ggagctacaa taataccaac caagaagatc ttttggtact 600
gtgggggatt caccatccta atgatgcggc agagcagaca aggctctatc aaaacccaac 660
cacctacatt tccgttggaa catcaacact gaaccagaga ttggttccag aaatagctac 720
tagacccaaa gtaaacgggc aaagtggaag aatggagttc ttctggacaa ttttaaagcc 780
gaatgatgcc atcaatttcg agagtaatgg aaatttcatt gctccagaat atgcatacaa 840
aattgtcaag aaaggggact caacaattat gaaaagtgaa ttggaatatg gtaactgcaa 900
caccaagtgt caaactccaa tgggggcaat aaactctagt atgccattcc acaacataca 960
cccctcacc atcggggaat gccccaaata tgtgaaatca aacagattag tccttgcaac 1020
tggactcaga aatacccctc aacgagagac gcgaggacta tttggagcta tagcaggttt 1080
tatagaggga ggatggcagg gaatggtaga tggttggtat gggtaccacc atagcaatga 1140
gcaggggagt ggatacgctg cagaccaaga atccacacaa aaggcaatag atggagtcac 1200
caataaggtc aactcgatca ttaacaaaat gaacactcag tttgaggccg ttggaaggga 1260
atttaataac ttggaaagga ggatagagaa tttaaacaag aaaatggaag acggattcct 1320
agatgtctgg acttacaatg ccgaacttct ggttctcatg gaaaatgaga gaactctaga 1380
ctttcatgac tcaaatgtca agaaccttta cgacaaggtc cgactacagc ttagggataa 1440
tgcaaaggag ctgggtaatg gttgtttcga attctatcac aaatgtgata acgaatgtat 1500
ggaaagtgta aaaaacggaa cgtatgacta cccgcagtat tcagaagaag caagactaaa 1560
cagagaggaa ataagtggag taaaattgga atcaatggga acttaccaaa tactgtcaat 1620
ttattcaaca gtggcgagtt ccctagcact ggcaatcatg gtagctggtc tatctttatg 1680
gatgtgctcc aatggatcgt tacaatgcag aatttgcatt taaatttgtg agttcagatt 1740
gtagttaaaa acacccttgt ttctact 1767

<210> SEQ ID NO 6
<211> LENGTH: 1401
<212> TYPE: DNA
<213> ORGANISM: Influenza A virus
<400> SEQUENCE: 6
agcaaaagca ggagtttaaa atgaatccaa atcagaagat aataaccatt ggatcaatct 60
gcatggtagt tgggataatc agcttgatgt tacaaattgg aaacacaata tcagtatggg 120
tcagccacat aattaaaact tggcacccaa accagcctga accatgcaac caaagcatca 180
atttttacac tgagcaggct gcagcttcag tgacattagc gggcaattcc tctctctgcc 240

-continued

| | |
|---|---|
| ctattagtgg atgggctata tacagcaagg acaatagtat aagaattggt tccaaagggg | 300 |
| atgtgtttgt tataagagaa ccattcatct catgctccca tttggaatgc agaaccfttt | 360 |
| tcttgaccca aggagcccta ttgaatgaca agcattctaa tgggaccgtc aaagacagga | 420 |
| gccctatag aactttaatg agctgtcctg ttggtgaggc ccttcccca tacaactcaa | 480 |
| ggtttgagtc tgttgcttgg tcagcaagtg cttgccatga tggcattagt tggctaacaa | 540 |
| ttggaatttc cggtccggat aatggggctg tggctgtgtt gaaatacaat ggcataataa | 600 |
| cagacaccat caagagttgg aggaacaaca cactgaggac gcaagagtct gaatgtgcat | 660 |
| gtgtgaatgg ttcttgtttt actgtaatga cagatggacc gagtaatgaa caggcctcat | 720 |
| acaagatttt caagatagaa aaggggaggg tagtcaaatc agttgagttg aacgccccta | 780 |
| attatcatta cgaggaatgc tcctgttatc ctgatgctgg cgaaatcaca tgtgtgtgca | 840 |
| gggataattg gcatggctcg aaccgaccat gggtgtcttt caatcagaat ctggagtatc | 900 |
| aaataggata tatatgcagt ggggttttcg gagacagtcc acgccccaat gatgggacag | 960 |
| gcagttgtgg tccagtgtct cttaacggag cgtatggagt aaaagggttt tcatttaaat | 1020 |
| acggcaatgg tgtttggatc gggagaacca aaagcactag ttccaggagc ggttttgaaa | 1080 |
| tgatttggga tccaaatggg tggaccgaaa cagacagtag cttctcgttg aagcaagaca | 1140 |
| tcatagcgat aactgattgg tcaggataca gcggagttt tattcaacat ccagaactga | 1200 |
| caggattaaa ttgcatgaga ccttgcttct gggttgaact aatcagaggg aggcccaaag | 1260 |
| agaaaacaat ctggactagt gggagcagta tatctttctg tggtgtaaat agtgacactg | 1320 |
| tgggttggtc ttggccagac ggtgctgagt tgccatacac cattgacaag tagtttgttc | 1380 |
| aaaaaactcc ttgtttctac t | 1401 |

<210> SEQ ID NO 7
<211> LENGTH: 1767
<212> TYPE: DNA
<213> ORGANISM: Influenza A virus

<400> SEQUENCE: 7

| | |
|---|---|
| agcaaaagca ggggtataat ctgtcaaaat ggagaaaata gtgcttcttc ttgcaacagt | 60 |
| cagccttgtt aaaagtgacc agatttgcat tggttaccat gcaaacaact cgacagagca | 120 |
| agttgacaca ataatggaaa agaatgttac tgttacacat gcccaagaca tactggaaag | 180 |
| gacacacaac gggaagctct gcgatctaaa tggagtgaag cctctgattt tgagggattg | 240 |
| tagtgtagct ggatggctcc tcggaaaccc tatgtgtgac gaattcatca atgtgccgga | 300 |
| atggtcttac atagtggaga aggccagtcc agccaatgac ctctgttatc cagggaattt | 360 |
| caacgactat gaagaactga aacacctatt gagcagaata aaccattttg agaaaattca | 420 |
| gataatcccc aaaagttctt ggtccaatca tgatgcctca tcagggtga gctcagcatg | 480 |
| tccataccttt ggaggtcct ccttttttcag aaatgtggta tggcttatca aaagaacag | 540 |
| tagctaccca acaataaaga ggagctacaa taataccaac caagaagatc ttttggtact | 600 |
| gtggggatt caccatccta tgatgcggc agagcagaca aggctctatc aaaacccaac | 660 |
| cacctacatt tccgttggaa catcaacact gaaccagaga ttggtttcag aaatagctac | 720 |
| tagacccaaa gtaaacggc aaagtggaag aatggagttc ttctggacaa tttaaagcc | 780 |
| gaatgatgcc atcaatttcg agagtaatgg aaatttcatt gctccagaat atgcatacaa | 840 |
| aattgtcaag aaaggggact caacaattat gaaaagtgaa ttggaatatg gtaactgcaa | 900 |
| caccaagtgt caaactccaa tggggggcaat aaactctagt atgccattcc acaacataca | 960 |

```
cccccctcacc atcggggaat gccccaaata tgtgaaatca acagattag tccttgcaac      1020 tggactcaga ataccccctc aacgagagac gcgaggacta tttggagcta tagcaggttt      1080
tatagaggga ggatggcagg gaatggtaga tggttggtat gggtaccacc atagcaatga      1140
gcaggggagt ggatacgctg cagaccaaga atccacacaa aaggcaatag atggagtcac      1200
caataaggtc aactcgatca ttaacaaaat gaacactcag tttgaggccg ttggaaggga      1260
atttaataac ttggaaagga ggatagaaa tttaaacaag aaaatggaag acggattcct      1320
agatgtctgg acttacaatg ccgaacttct ggttctcatg gaaaatgaga gaactctaga      1380 cttttcatgac tcaaatgtca agaaccttta cgacaaggtc cgactacagc ttagggataa      1440
tgcaaaggag ctgggtaatg gttgtttcga attctatcac aaatgtgata acgaatgtat      1500
ggaaagtgta aaaaacggaa cgtatgacta cccgcagtat tcagaagaag caagactaaa      1560
cagagaggaa ataagtggag taaaattgga atcaatggga acttaccaaa tactgtcaat      1620
ttattcaaca gtggcgagtt ccctagcact ggcaatcatg gtagctggtc tatctttatg      1680
gatgtgctcc aatggatcgt tacaatgcag aatttgcatt taaatttgtg agttcagatt      1740
gtagttaaaa acaccccttgt ttctact                                          1767

<210> SEQ ID NO 8
<211> LENGTH: 1401
<212> TYPE: DNA
<213> ORGANISM: Influenza A virus

<400> SEQUENCE: 8
agcaaaagca ggagtttaaa atgaatccaa atcagaagat aataaccatt ggatcaatct       60
gcatggtagt tgggataatc agcttgatgt tacaaattgg aaacacaata tcagtatggg      120
tcagccacat aattaaaact tggcacccaa accagcctga accatgcaac caaagcatca      180
atttttacac tgagcaggct gcagcttcag tgacattagc gggcaattcc tctctctgcc      240
ctattagtgg atgggctata tacagcaagg acaatagtat aagaattggt tccaaagggg      300
atgtgtttgt tataagagaa ccattcatct catgctccca tttggaatgc agaaccttt       360 tcttgaccca aggagcccta ttgaatgaca agcattctaa tgggaccgtc aaagacagga      420 gccctatag aactttaatg agctgtcctg ttggtgaggc cccttcccca tacaactcaa      480
ggtttgagtc tgttgcttgg tcagcaagtg cttgccatga tggcattagt tggctaacaa      540
ttggaatttc cggtccggat aatggggctg tggctgtgtt gaaatacaat ggcataataa      600
cagacaccat caagagttgg aggaacaaca cactgaggac gcaagagtct gaatgtgcat      660
gtgtgaatgg ttcttgtttt actgtaatga cagatggacc gagtaatgaa caggcctcat      720
acaagatttt caagatagaa aaggggaggg tagtcaaatc agttgagttg aacgccccta      780
attatcatta cgaggaatgc tcctgttatc ctgatgctgg cgaaatcaca tgtgtgtgca      840
gggataattg gcatgctcg aaccgaccat gggtgtcttt caatcagaat ctggagtatc      900
aaataggata tatatgcagt ggggttttcg gagacagtcc acgccccaat gatgggacag      960
gcagttgtgt tccagtgtct cttaacggag cgtatgagt aaaagggttt tcatttaaat      1020
acggcaatgg tgtttggatc gggagaacca aaagcactag ttccaggagc ggttttgaaa      1080
tgatttggga tccaaatggg tggaccgaaa cagacagtag cttctcgttg aagcaagaca      1140
tcatagcgat aactgattgg tcaggataca gcgggagttt tattcaacat ccagaactga      1200
caggattaaa ttgcatgaga ccttgcttct gggttgaact aatcagaggg aggcccaaag      1260
agaaaacaat ctggactagt gggagcagta tatctttctg tggtgtaaat agtgacactg      1320
```

| | | | | | |
|---|---|---|---|---|---|
| tgggttggtc | ttggccagac | ggtgctgagt | tgccatacac | cattgacaag | tagtttgttc | 1380 |
| aaaaaactcc | ttgtttctac | t | | | | 1401 |

<210> SEQ ID NO 9
<211> LENGTH: 1690
<212> TYPE: DNA
<213> ORGANISM: Influenza A virus

<400> SEQUENCE: 9

| | | | | | |
|---|---|---|---|---|---|
| ttaaccactc | aagatggaag | caataccact | aataactata | ctactagtag | taacagcaag | 60 |
| caatgcagac | aaaatctgca | tcggctacca | atcaacaaac | tccacagaaa | ccgtagacac | 120 |
| gctaacagaa | aacaatgttc | ctgtgacaca | tgccaaagaa | ttgctccaca | cagagcacaa | 180 |
| tgggatgctg | tgtgcaacaa | atctgggacg | tcctcttatt | ctagacactt | gcaccattga | 240 |
| aggactgatc | tatggcaacc | cttcttgtga | tctactgttg | ggaggaagag | aatggtccta | 300 |
| catcgtcgaa | agaccatcgg | ctgttaatgg | aatgtgttac | cccgggaatg | tagaaaacct | 360 |
| agaggaacta | aggtcatttt | ttagttctgc | tagttcctac | caaagaatcc | agatctttcc | 420 |
| agacacaatc | tggaatgtgt | cttacagtgg | aacaagcaaa | gcatgttcag | attcattcta | 480 |
| caggagcatg | agatggttga | ctcaaaagaa | caacgcttac | cctattcaag | acgcccaata | 540 |
| cacaaataat | agaggaaaga | gcattctttt | catgtggggc | ataaatcacc | cacctaccga | 600 |
| tactgcacag | acaaatctgt | acacaaggac | tgacacaaca | acaagtgtgg | caacagaaga | 660 |
| tataaatagg | accttcaaac | cagtgatagg | gccaaggccc | cttgtcaatg | gtctgcaggg | 720 |
| aagaattgat | tattattggt | cggtattgaa | accaggtcag | acattgcgag | taagatccaa | 780 |
| tgggaatcta | atcgctccat | ggtatgggca | cattctttca | ggagagagcc | acggaagaat | 840 |
| cctgaagact | gatttaaaca | gtggtagctg | tgtagtgcaa | tgtcaaacag | aaagaggtgg | 900 |
| cttaaatact | actttgccat | tccacaatgt | cagtaaatat | gcatttggaa | actgcccaaa | 960 |
| atatgttgga | gtaaagagtc | tcaaactggc | agttggtctg | aggaatgtgc | ctgctagatc | 1020 |
| aagtagagga | ctatttgggg | ccatagctgg | attcatagag | ggaggttggt | cagggctggt | 1080 |
| cgctggttgg | tatgggttcc | agcattcaaa | tgatcaaggg | gttggtatag | ctgcagatag | 1140 |
| agactcaact | caagggcaa | ttgacaaaat | aacgtccaaa | gtgaataata | tagtcgataa | 1200 |
| aatgaacaag | caatatgaaa | ttattgatca | tgaattcagc | gaggttgaaa | atagactcaa | 1260 |
| tatgatcaat | aataagattg | atgaccagat | acaagacata | tgggcatata | cgctgaatt | 1320 |
| gctagtgctg | cttgaaaacc | agaaaacact | cgatgagcat | gatgcgaatg | taaacaatct | 1380 |
| atataacaaa | gtgaagaggg | cactgggttc | caatgcaatg | gaagatggga | aggatgttt | 1440 |
| cgagctatac | cataaatgtg | atgatcagtg | catggagaca | attcggaacg | ggacctataa | 1500 |
| caggaggaag | tataagagg | aatcaagact | agaaagacag | aaaatagaag | gggtcaagct | 1560 |
| ggaatctgaa | ggaacttaca | aaatcctcac | catttattcg | actgtcgcct | catctcttgt | 1620 |
| gattgcaatg | gggtttgctg | ccttcttgtt | ctgggccatg | tccaatggat | cttgcagatg | 1680 |
| caacatttga | | | | | | 1690 |

<210> SEQ ID NO 10
<211> LENGTH: 1428
<212> TYPE: DNA
<213> ORGANISM: Influenza A virus

<400> SEQUENCE: 10

| | | | | | |
|---|---|---|---|---|---|
| aaatgaatcc | aaatcagaag | ataatagcaa | ttggctctgt | ttctctaact | attgcgacaa | 60 |

```
tatgcctcct catgcagatt gctatcttag caacgactat gacactacat ttcaagcaga    120
atgaatgcat caactcctcg aataatcaag tagtgccatg tgaaccaatc ataatagaaa    180
ggaacataac agagatagtg catttgaata gtactacctt agagaaggaa atttgtccta    240
aagtagcaga ctacaggaat tggtcaaaac cacaatgtca aatcacaggg ttcgctcctt    300
tctccaagga caattcaatt aggctctccg caggtggaga tatttgggtg acaagagaac    360
cttatgtatc gtgcggtctt ggtaaatgtt atcaatttgc acttgggcag ggaaccactt    420
tggagaacaa acactcaaac ggcacagcac atgatagaac tcctcataga acccttttaa    480
tgaatgagtt gggtgttccg tttcatttgg caaccaaaca agtgtgcata gcatggtcca    540
gctcaagctg ccatgatggg aaagcatggt tacatgtttg tgtcactggg gatgatagaa    600
atgcaacggc tagcatcatt tatgatggga tacttgttga cagtattggt tcatggtcta    660
aaaacatcct cagaactcag gagtcagaat gcgtttgcat caatggaacc tgtgcagtag    720
taatgactga tggaagtgca tcaggaaggg ctgacactag aatactattt attagagagg    780
ggaaaattgc acacattagc ccattgtcag gaagtgctca gcatgtggag gaatgctcct    840 gttaccccg atatccagaa gttagatgtg tttgcagaga caattggaag ggatccaata    900
ggcccgttct atatataaat atggcaaatt atagtattga ttccagttat gtgtgctcag    960
gacttgttgg cgacacacca agaaatgatg ataggtctag cagcagcaac tgcagagatc   1020
ctaataacga gagggggcc ccaggagtaa aagggtgggc ctttgacaat ggaaatgaca   1080 tttgatggg aagaacaatc aaaaaggatt cgcgctcagg ttatgagact ttcagggtca   1140
ttggtggttg gaccactgct aattccaagt cacagataaa tagacaagtc atagttgaca   1200
gtgataactc gtctgggtat tctggtatct tctctgttga aggcaaaagc tgcatcaaca   1260
ggtgttttta cgtggagttg ataagaggaa gaccaaagga gactagggtg tggtggactt   1320
caaatagcat cattgtattt tgtggaactt caggtaccta tggaacaggc tcatggcctg   1380
atggggcgaa tatcaatttc atgcctatat aagctttcgc aatttttag                1428
```

<210> SEQ ID NO 11
<211> LENGTH: 564
<212> TYPE: PRT
<213> ORGANISM: Influenza A virus

<400> SEQUENCE: 11

```
Met Glu Lys Ile Val Leu Leu Phe Ala Ile Val Ser Leu Val Lys Ser
 1               5                  10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140
```

```
Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
                180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
        210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Met Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
            355                 360                 365

Ser Asn Glu Gln Gly Ser Gly Tyr Ala Ala Asp Lys Glu Ser Thr Gln
        370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
        450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
                500                 505                 510

Glu Glu Ile Ser Gly Val Lys Leu Glu Ser Ile Gly Ile Tyr Gln Ile
            515                 520                 525

Leu Ser Ile Tyr Ser Thr Val Ala Ser Ser Leu Ala Leu Ala Ile Met
        530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 12
<211> LENGTH: 449
<212> TYPE: PRT
<213> ORGANISM: Influenza A virus

<400> SEQUENCE: 12

```
Met Asn Pro Asn Gln Lys Ile Ile Thr Ile Gly Ser Ile Cys Met Val
1               5                   10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
        35                  40                  45

Ile Ser Asn Thr Asn Phe Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asn Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
        355                 360                 365

Val Lys Gln Asp Ile Val Ala Ile Thr Asp Trp Ser Gly Tyr Ser Gly
    370                 375                 380
```

```
Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
            405                 410                 415

Trp Thr Ser Gly Ser Ser Ile Ser Phe Cys Gly Val Asn Ser Asp Thr
                420                 425                 430

Val Gly Trp Ser Trp Pro Asp Gly Ala Glu Leu Pro Phe Thr Ile Asp
        435                 440                 445

Lys

<210> SEQ ID NO 13
<211> LENGTH: 564
<212> TYPE: PRT
<213> ORGANISM: Influenza A virus

<400> SEQUENCE: 13

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asn Ser Trp Ser Ser His Glu Ala Ser
130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Asn Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
290                 295                 300
```

```
Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Thr Arg Gly Leu Phe Gly Ala Ile Ala Gly Phe Ile
        340                 345                 350

Glu Gly Gly Trp Gln Gly Met Val Asp Gly Trp Tyr Gly Tyr His His
    355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 14
<211> LENGTH: 469
<212> TYPE: PRT
<213> ORGANISM: Influenza A virus

<400> SEQUENCE: 14

Met Asn Pro Asn Gln Lys Ile Thr Thr Ile Gly Ser Ile Cys Met Val
1               5                   10                  15

Ile Gly Ile Val Ser Leu Met Leu Gln Ile Gly Asn Ile Ile Ser Ile
            20                  25                  30

Trp Val Ser His Ser Ile Gln Thr Gly Asn Gln His Gln Ala Glu Pro
        35                  40                  45

Cys Asn Gln Ser Ile Ile Thr Tyr Glu Asn Asn Thr Trp Val Asn Gln
    50                  55                  60

Thr Tyr Val Asn Ile Ser Asn Thr Asn Phe Leu Thr Glu Lys Ala Val
65                  70                  75                  80

Ala Ser Val Thr Leu Ala Gly Asn Ser Ser Leu Cys Pro Ile Ser Gly
                85                  90                  95

Trp Ala Val Tyr Ser Lys Asp Asn Gly Ile Arg Ile Gly Ser Lys Gly
            100                 105                 110

Asp Val Phe Val Ile Arg Glu Pro Phe Ile Ser Cys Ser His Leu Glu
```

```
            115                 120                 125
Cys Arg Thr Phe Phe Leu Thr Gln Gly Ala Leu Leu Asn Asp Lys His
130                 135                 140

Ser Asn Gly Thr Val Lys Asp Arg Ser Pro His Arg Thr Leu Met Ser
145                 150                 155                 160

Cys Pro Val Gly Glu Ala Pro Ser Pro Tyr Asn Ser Arg Phe Glu Ser
                165                 170                 175

Val Ala Trp Ser Ala Ser Ala Cys His Asp Gly Thr Ser Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Met
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Val Val Lys Ser Ala Glu Leu Asn Ala Pro
            260                 265                 270

Asn Tyr His Tyr Glu Glu Cys Ser Cys Tyr Pro Asp Ala Gly Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Arg Ile Gly Tyr Ile Cys Ser Gly
305                 310                 315                 320

Val Phe Gly Asp Asn Pro Arg Pro Asn Asp Gly Thr Gly Ser Cys Gly
                325                 330                 335

Pro Val Ser Pro Lys Gly Ala Tyr Gly Ile Lys Gly Phe Ser Phe Lys
            340                 345                 350

Tyr Gly Asn Gly Val Trp Ile Gly Arg Thr Lys Ser Thr Asn Ser Arg
        355                 360                 365

Ser Gly Phe Glu Met Ile Trp Asp Pro Asn Gly Trp Thr Gly Thr Asp
370                 375                 380

Ser Asn Phe Ser Val Lys Gln Asp Ile Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Ser Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 15
<211> LENGTH: 564
<212> TYPE: PRT
<213> ORGANISM: Influenza A virus

<400> SEQUENCE: 15

Met Glu Lys Ile Val Leu Leu Leu Ala Thr Val Ser Leu Val Lys Ser
1

-continued

```
               20                  25                  30
Asp Thr Ile Met Glu Lys Asn Val Thr Val Thr His Ala Gln Asp Ile
            35                  40                  45

Leu Glu Arg Thr His Asn Gly Lys Leu Cys Asp Leu Asn Gly Val Lys
 50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Ser Pro Ala Asn Asp Leu Cys Tyr Pro Gly Asn Phe Asn
             100                 105                 110

Asp Tyr Glu Glu Leu Lys His Leu Leu Ser Arg Ile Asn His Phe Glu
             115                 120                 125

Lys Ile Gln Ile Ile Pro Lys Ser Ser Trp Ser Asn His Asp Ala Ser
         130                 135                 140

Ser Gly Val Ser Ser Ala Cys Pro Tyr Leu Gly Arg Ser Ser Phe Phe
145                 150                 155                 160

Arg Asn Val Val Trp Leu Ile Lys Lys Asn Ser Ser Tyr Pro Thr Ile
                 165                 170                 175

Lys Arg Ser Tyr Asn Asn Thr Asn Gln Glu Asp Leu Leu Val Leu Trp
             180                 185                 190

Gly Ile His His Pro Asn Asp Ala Ala Glu Gln Thr Arg Leu Tyr Gln
             195                 200                 205

Asn Pro Thr Thr Tyr Ile Ser Val Gly Thr Ser Thr Leu Asn Gln Arg
         210                 215                 220

Leu Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                 245                 250                 255

Phe Glu Ser Asn Gly Asn Phe Ile Ala Pro Glu Tyr Ala Tyr Lys Ile
             260                 265                 270

Val Lys Lys Gly Asp Ser Thr Ile Met Lys Ser Glu Leu Glu Tyr Gly
             275                 280                 285

Asn Cys Asn Thr Lys Cys Gln Thr Pro Met Gly Ala Ile Asn Ser Ser
         290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                 325                 330                 335

Pro Gln Arg Glu Thr Arg Gly Leu Phe Gly Ala Ile Ala Gly Phe Ile
             340                 345                 350

Glu Gly Gly Trp Gln Gly Met Val Asp Gly Trp Tyr Gly Tyr His His
             355                 360                 365

Ser Asn Glu Gln Gly Ser Gly Tyr Ala Ala Asp Gln Glu Ser Thr Gln
         370                 375                 380

Lys Ala Ile Asp Gly Val Thr Asn Lys Val Asn Ser Ile Ile Asn Lys
385                 390                 395                 400

Met Asn Thr Gln Phe Glu Ala Val Gly Arg Glu Phe Asn Asn Leu Glu
                 405                 410                 415

Arg Arg Ile Glu Asn Leu Asn Lys Lys Met Glu Asp Gly Phe Leu Asp
             420                 425                 430

Val Trp Thr Tyr Asn Ala Glu Leu Leu Val Leu Met Glu Asn Glu Arg
             435                 440                 445
```

```
Thr Leu Asp Phe His Asp Ser Asn Val Lys Asn Leu Tyr Asp Lys Val
        450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Lys Asn
                485                 490                 495

Gly Thr Tyr Asp Tyr Pro Gln Tyr Ser Glu Glu Ala Arg Leu Asn Arg
                500                 505                 510

Glu Glu Ile Ser Gly Val Lys Leu Glu Ser Met Gly Thr Tyr Gln Ile
            515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 16
<211> LENGTH: 450
<212> TYPE: PRT
<213> ORGANISM: Influenza A virus

<400> SEQUENCE: 16

Met Asn Pro Asn Gln Lys Ile Ile Thr Ile Gly Ser Ile Cys Met Val
1               5                   10                  15

Val Gly Ile Ile Ser Leu Met Leu Gln Ile Gly Asn Thr Ile Ser Val
            20                  25                  30

Trp Val Ser His Ile Ile Lys Thr Trp His Pro Asn Gln Pro Glu Pro
        35                  40                  45

Cys Asn Gln Ser Ile Asn Phe Tyr Thr Glu Gln Ala Ala Ala Ser Val
    50                  55                  60

Thr Leu Ala Gly Asn Ser Ser Leu Cys Pro Ile Ser Gly Trp Ala Ile
65                  70                  75                  80

Tyr Ser Lys Asp Asn Ser Ile Arg Ile Gly Ser Lys Gly Asp Val Phe
                85                  90                  95

Val Ile Arg Glu Pro Phe Ile Ser Cys Ser His Leu Glu Cys Arg Thr
            100                 105                 110

Phe Phe Leu Thr Gln Gly Ala Leu Leu Asn Asp Lys His Ser Asn Gly
        115                 120                 125

Thr Val Lys Asp Arg Ser Pro Tyr Arg Thr Leu Met Ser Cys Pro Val
130                 135                 140

Gly Glu Ala Pro Ser Pro Tyr Asn Ser Arg Phe Glu Ser Val Ala Trp
145                 150                 155                 160

Ser Ala Ser Ala Cys His Asp Gly Ile Ser Trp Leu Thr Ile Gly Ile
                165                 170                 175

Ser Gly Pro Asp Asn Gly Ala Val Ala Val Leu Lys Tyr Asn Gly Ile
            180                 185                 190

Ile Thr Asp Thr Ile Lys Ser Trp Arg Asn Asn Thr Leu Arg Thr Gln
        195                 200                 205

Glu Ser Glu Cys Ala Cys Val Asn Gly Ser Cys Phe Thr Val Met Thr
210                 215                 220

Asp Gly Pro Ser Asn Glu Gln Ala Ser Tyr Lys Ile Phe Lys Ile Glu
225                 230                 235                 240

Lys Gly Arg Val Val Lys Ser Val Glu Leu Asn Ala Pro Asn Tyr His
                245                 250                 255

Tyr Glu Glu Cys Ser Cys Tyr Pro Asp Ala Gly Glu Ile Thr Cys Val
```

-continued

```
                260                 265                 270
Cys Arg Asp Asn Trp His Gly Ser Asn Arg Pro Trp Val Ser Phe Asn
        275                 280                 285

Gln Asn Leu Glu Tyr Gln Ile Gly Tyr Ile Cys Ser Gly Val Phe Gly
        290                 295                 300

Asp Ser Pro Arg Pro Asn Asp Gly Thr Gly Ser Cys Gly Pro Val Ser
305                 310                 315                 320

Leu Asn Gly Ala Tyr Gly Val Lys Gly Phe Ser Phe Lys Tyr Gly Asn
                325                 330                 335

Gly Val Trp Ile Gly Arg Thr Lys Ser Thr Ser Ser Arg Ser Gly Phe
            340                 345                 350

Glu Met Ile Trp Asp Pro Asn Gly Trp Thr Glu Thr Asp Ser Ser Phe
        355                 360                 365

Ser Leu Lys Gln Asp Ile Ile Ala Ile Thr Asp Trp Ser Gly Tyr Ser
        370                 375                 380

Gly Ser Phe Ile Gln His Pro Glu Leu Thr Gly Leu Asn Cys Met Arg
385                 390                 395                 400

Pro Cys Phe Trp Val Glu Leu Ile Arg Gly Arg Pro Lys Glu Lys Thr
                405                 410                 415

Ile Trp Thr Ser Gly Ser Ser Ile Ser Phe Cys Gly Val Asn Ser Asp
            420                 425                 430

Thr Val Gly Trp Ser Trp Pro Asp Gly Ala Glu Leu Pro Tyr Thr Ile
        435                 440                 445

Asp Lys
    450

<210> SEQ ID NO 17
<211> LENGTH: 564
<212> TYPE: PRT
<213> ORGANISM: Influenza A virus

<400> SEQUENCE: 17

Met Glu Lys Ile Val Leu Leu Leu Ala Thr Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Asp Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Asp Ala Ser
    130                 135                 140

Ser Gly Val Ser Ser Ala Cys Pro Tyr Leu Gly Arg Ser Ser Phe Phe
145                 150                 155                 160

Arg Asn Val Val Trp Leu Ile Lys Lys Asn Ser Ser Tyr Pro Thr Ile
                165                 170                 175

Lys Arg Ser Tyr Asn Asn Thr Asn Gln Glu Asp Leu Leu Val Leu Trp
```

```
                    180                 185                 190
Gly Ile His His Pro Asn Asp Ala Ala Glu Gln Thr Arg Leu Tyr Gln
            195                 200                 205
Asn Pro Thr Thr Tyr Ile Ser Val Gly Thr Ser Thr Leu Asn Gln Arg
        210                 215                 220
Leu Val Ser Glu Ile Ala Thr Arg Pro Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Thr Ile Met Lys Ser Glu Leu Glu Tyr Gly
        275                 280                 285
Asn Cys Asn Thr Lys Cys Gln Thr Pro Met Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Thr
                325                 330                 335
Pro Gln Arg Glu Thr Arg Gly Leu Phe Gly Ala Ile Ala Gly Phe Ile
            340                 345                 350
Glu Gly Gly Trp Gln Gly Met Val Asp Gly Trp Tyr Gly Tyr His His
        355                 360                 365
Ser Asn Glu Gln Gly Ser Gly Tyr Ala Ala Asp Gln Glu Ser Thr Gln
    370                 375                 380
Lys Ala Ile Asp Gly Val Thr Asn Lys Val Asn Ser Ile Ile Asn Lys
385                 390                 395                 400
Met Asn Thr Gln Phe Glu Ala Val Gly Arg Glu Phe Asn Asn Leu Glu
                405                 410                 415
Arg Arg Ile Glu Asn Leu Asn Lys Lys Met Glu Asp Gly Phe Leu Asp
            420                 425                 430
Val Trp Thr Tyr Asn Ala Glu Leu Leu Val Leu Met Glu Asn Glu Arg
        435                 440                 445
Thr Leu Asp Phe His Asp Ser Asn Val Lys Asn Leu Tyr Asp Lys Val
    450                 455                 460
Arg Leu Gln Leu Arg Asp Asn Ala Lys Glu Leu Gly Asn Gly Cys Phe
465                 470                 475                 480
Glu Phe Tyr His Lys Cys Asp Asn Glu Cys Met Glu Ser Val Lys Asn
                485                 490                 495
Gly Thr Tyr Asp Tyr Pro Gln Tyr Ser Glu Glu Ala Arg Leu Asn Arg
            500                 505                 510
Glu Glu Ile Ser Gly Val Lys Leu Glu Ser Met Gly Thr Tyr Gln Ile
        515                 520                 525
Leu Ser Ile Tyr Ser Thr Val Ala Ser Ser Leu Ala Leu Ala Ile Met
    530                 535                 540
Val Ala Gly Leu Ser Leu Trp Met Cys Ser Asn Gly Ser Leu Gln Cys
545                 550                 555                 560
Arg Ile Cys Ile

<210> SEQ ID NO 18
<211> LENGTH: 450
<212> TYPE: PRT
<213> ORGANISM: Influenza A virus

<400> SEQUENCE: 18
```

```
Met Asn Pro Asn Gln Lys Ile Ile Thr Ile Gly Ser Ile Cys Met Val
1               5                   10                  15

Val Gly Ile Ile Ser Leu Met Leu Gln Ile Gly Asn Thr Ile Ser Val
            20                  25                  30

Trp Val Ser His Ile Ile Lys Thr Trp His Pro Asn Gln Pro Glu Pro
        35                  40                  45

Cys Asn Gln Ser Ile Asn Phe Tyr Thr Glu Gln Ala Ala Ala Ser Val
    50                  55                  60

Thr Leu Ala Gly Asn Ser Ser Leu Cys Pro Ile Ser Gly Trp Ala Ile
65                  70                  75                  80

Tyr Ser Lys Asp Asn Ser Ile Arg Ile Gly Ser Lys Gly Asp Val Phe
                85                  90                  95

Val Ile Arg Glu Pro Phe Ile Ser Cys Ser His Leu Glu Cys Arg Thr
                100                 105                 110

Phe Phe Leu Thr Gln Gly Ala Leu Leu Asn Asp Lys His Ser Asn Gly
            115                 120                 125

Thr Val Lys Asp Arg Ser Pro Tyr Arg Thr Leu Met Ser Cys Pro Val
130                 135                 140

Gly Glu Ala Pro Ser Pro Tyr Asn Ser Arg Phe Glu Ser Val Ala Trp
145                 150                 155                 160

Ser Ala Ser Ala Cys His Asp Gly Ile Ser Trp Leu Thr Ile Gly Ile
                165                 170                 175

Ser Gly Pro Asp Asn Gly Ala Val Ala Val Leu Lys Tyr Asn Gly Ile
            180                 185                 190

Ile Thr Asp Thr Ile Lys Ser Trp Arg Asn Asn Thr Leu Arg Thr Gln
        195                 200                 205

Glu Ser Glu Cys Ala Cys Val Asn Gly Ser Cys Phe Thr Val Met Thr
    210                 215                 220

Asp Gly Pro Ser Asn Glu Gln Ala Ser Tyr Lys Ile Phe Lys Ile Glu
225                 230                 235                 240

Lys Gly Arg Val Val Lys Ser Val Glu Leu Asn Ala Pro Asn Tyr His
                245                 250                 255

Tyr Glu Glu Cys Ser Cys Tyr Pro Asp Ala Gly Glu Ile Thr Cys Val
                260                 265                 270

Cys Arg Asp Asn Trp His Gly Ser Asn Arg Pro Trp Val Ser Phe Asn
            275                 280                 285

Gln Asn Leu Glu Tyr Gln Ile Gly Tyr Ile Cys Ser Gly Val Phe Gly
        290                 295                 300

Asp Ser Pro Arg Pro Asn Asp Gly Thr Gly Ser Cys Gly Pro Val Ser
305                 310                 315                 320

Leu Asn Gly Ala Tyr Gly Val Lys Gly Phe Ser Phe Lys Tyr Gly Asn
                325                 330                 335

Gly Val Trp Ile Gly Arg Thr Lys Ser Thr Ser Ser Arg Ser Gly Phe
            340                 345                 350

Glu Met Ile Trp Asp Pro Asn Gly Trp Thr Glu Thr Asp Ser Ser Phe
        355                 360                 365

Ser Leu Lys Gln Asp Ile Ile Ala Ile Thr Asp Trp Ser Gly Tyr Ser
    370                 375                 380

Gly Ser Phe Ile Gln His Pro Glu Leu Thr Gly Leu Asn Cys Met Arg
385                 390                 395                 400

Pro Cys Phe Trp Val Glu Leu Ile Arg Gly Arg Pro Lys Glu Lys Thr
                405                 410                 415

Ile Trp Thr Ser Gly Ser Ser Ile Ser Phe Cys Gly Val Asn Ser Asp
```

```
                420                 425                 430
Thr Val Gly Trp Ser Trp Pro Asp Gly Ala Glu Leu Pro Tyr Thr Ile
        435                 440                 445
Asp Lys
    450

<210> SEQ ID NO 19
<211> LENGTH: 558
<212> TYPE: PRT
<213> ORGANISM: Influenza A virus

<400> SEQUENCE: 19

Met Glu Ala Ile Pro Leu Ile Thr Ile Leu Leu Val Val Thr Ala Ser
1               5                   10                  15

Asn Ala Asp Lys Ile Cys Ile Gly Tyr Gln Ser Thr Asn Ser Thr Glu
            20                  25                  30

Thr Val Asp Thr Leu Thr Glu Asn Asn Val Pro Val Thr His Ala Lys
        35                  40                  45

Glu Leu Leu His Thr Glu His Asn Gly Met Leu Cys Ala Thr Asn Leu
    50                  55                  60

Gly Arg Pro Leu Ile Leu Asp Thr Cys Thr Ile Glu Gly Leu Ile Tyr
65                  70                  75                  80

Gly Asn Pro Ser Cys Asp Leu Leu Leu Gly Gly Arg Glu Trp Ser Tyr
                85                  90                  95

Ile Val Glu Arg Pro Ser Ala Val Asn Gly Met Cys Tyr Pro Gly Asn
            100                 105                 110

Val Glu Asn Leu Glu Glu Leu Arg Ser Phe Phe Ser Ser Ala Ser Ser
        115                 120                 125

Tyr Gln Arg Ile Gln Ile Phe Pro Asp Thr Ile Trp Asn Val Ser Tyr
    130                 135                 140

Ser Gly Thr Ser Lys Ala Cys Ser Asp Ser Phe Tyr Arg Ser Met Arg
145                 150                 155                 160

Trp Leu Thr Gln Lys Asn Asn Ala Tyr Pro Ile Gln Asp Ala Gln Tyr
                165                 170                 175

Thr Asn Asn Arg Gly Lys Ser Ile Leu Phe Met Trp Gly Ile Asn His
            180                 185                 190

Pro Pro Thr Asp Thr Ala Gln Thr Asn Leu Tyr Thr Arg Thr Asp Thr
        195                 200                 205

Thr Thr Ser Val Ala Thr Glu Asp Ile Asn Arg Thr Phe Lys Pro Val
    210                 215                 220

Ile Gly Pro Arg Pro Leu Val Asn Gly Leu Gln Gly Arg Ile Asp Tyr
225                 230                 235                 240

Tyr Trp Ser Val Leu Lys Pro Gly Gln Thr Leu Arg Val Arg Ser Asn
                245                 250                 255

Gly Asn Leu Ile Ala Pro Trp Tyr Gly His Ile Leu Ser Gly Glu Ser
            260                 265                 270

His Gly Arg Ile Leu Lys Thr Asp Leu Asn Ser Gly Ser Cys Val Val
        275                 280                 285

Gln Cys Gln Thr Glu Arg Gly Gly Leu Asn Thr Thr Leu Pro Phe His
    290                 295                 300

Asn Val Ser Lys Tyr Ala Phe Gly Asn Cys Pro Lys Tyr Val Gly Val
305                 310                 315                 320

Lys Ser Leu Lys Leu Ala Val Gly Leu Arg Asn Val Pro Ala Arg Ser
                325                 330                 335

Ser Arg Gly Leu Phe Gly Ala Ile Ala Gly Phe Ile Glu Gly Gly Trp
```

```
                      340                 345                 350
Ser Gly Leu Val Ala Gly Trp Tyr Gly Phe Gln His Ser Asn Asp Gln
                355                 360                 365

Gly Val Gly Ile Ala Ala Asp Arg Asp Ser Thr Gln Arg Ala Ile Asp
            370                 375                 380

Lys Ile Thr Ser Lys Val Asn Asn Ile Val Asp Lys Met Asn Lys Gln
385                 390                 395                 400

Tyr Glu Ile Ile Asp His Glu Phe Ser Glu Val Glu Asn Arg Leu Asn
                405                 410                 415

Met Ile Asn Asn Lys Ile Asp Asp Gln Ile Gln Asp Ile Trp Ala Tyr
            420                 425                 430

Asn Ala Glu Leu Leu Val Leu Leu Glu Asn Gln Lys Thr Leu Asp Glu
                435                 440                 445

His Asp Ala Asn Val Asn Asn Leu Tyr Asn Lys Val Lys Arg Ala Leu
            450                 455                 460

Gly Ser Asn Ala Met Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asn
                485                 490                 495

Arg Arg Lys Tyr Lys Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
                515                 520                 525

Ser Thr Val Ala Ser Ser Leu Val Ile Ala Met Gly Phe Ala Ala Phe
            530                 535                 540

Leu Phe Trp Ala Met Ser Asn Gly Ser Cys Arg Cys Asn Ile
545                 550                 555

<210> SEQ ID NO 20
<211> LENGTH: 469
<212> TYPE: PRT
<213> ORGANISM: Influenza A virus

<400> SEQUENCE: 20

Met Asn Pro Asn Gln Lys Ile Ile Ala Ile Gly Ser Val Ser Leu Thr
1               5                   10                  15

Ile Ala Thr Ile Cys Leu Leu Met Gln Ile Ala Ile Leu Ala Thr Thr
            20                  25                  30

Met Thr Leu His Phe Lys Gln Asn Glu Cys Ile Asn Ser Ser Asn Asn
        35                  40                  45

Gln Val Val Pro Cys Glu Pro Ile Ile Ile Glu Arg Asn Ile Thr Glu
    50                  55                  60

Ile Val His Leu Asn Ser Thr Thr Leu Glu Lys Glu Ile Cys Pro Lys
65                  70                  75                  80

Val Ala Asp Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Gly Leu Gly Lys
        115                 120                 125

Cys Tyr Gln Phe Ala Leu Gly Gln Gly Thr Thr Leu Glu Asn Lys His
    130                 135                 140

Ser Asn Gly Thr Ala His Asp Arg Thr Pro His Arg Thr Leu Leu Met
145                 150                 155                 160

Asn Glu Leu Gly Val Pro Phe His Leu Ala Thr Lys Gln Val Cys Ile
```

|                | 165           |                | 170           |                | 175           |                |
|----------------|---------------|----------------|---------------|----------------|---------------|----------------|

Ala Trp Ser Ser Ser Cys His Asp Gly Lys Ala Trp Leu His Val
            180                 185                 190

Cys Val Thr Gly Asp Asp Arg Asn Ala Thr Ala Ser Ile Ile Tyr Asp
            195                 200                 205

Gly Ile Leu Val Asp Ser Ile Gly Ser Trp Ser Lys Asn Ile Leu Arg
            210                 215                 220

Thr Gln Glu Ser Glu Cys Val Cys Ile Asn Gly Thr Cys Ala Val Val
225                 230                 235                 240

Met Thr Asp Gly Ser Ala Ser Gly Arg Ala Asp Thr Arg Ile Leu Phe
            245                 250                 255

Ile Arg Glu Gly Lys Ile Ala His Ile Ser Pro Leu Ser Gly Ser Ala
            260                 265                 270

Gln His Val Glu Glu Cys Ser Cys Tyr Pro Arg Tyr Pro Glu Val Arg
            275                 280                 285

Cys Val Cys Arg Asp Asn Trp Lys Gly Ser Asn Arg Pro Val Leu Tyr
            290                 295                 300

Ile Asn Met Ala Asn Tyr Ser Ile Asp Ser Ser Tyr Val Cys Ser Gly
305                 310                 315                 320

Leu Val Gly Asp Thr Pro Arg Asn Asp Asp Arg Ser Ser Ser Ser Asn
            325                 330                 335

Cys Arg Asp Pro Asn Asn Glu Arg Gly Ala Pro Gly Val Lys Gly Trp
            340                 345                 350

Ala Phe Asp Asn Gly Asn Asp Ile Trp Met Gly Arg Thr Ile Lys Lys
            355                 360                 365

Asp Ser Arg Ser Gly Tyr Glu Thr Phe Arg Val Ile Gly Gly Trp Thr
            370                 375                 380

Thr Ala Asn Ser Lys Ser Gln Ile Asn Arg Gln Val Ile Val Asp Ser
385                 390                 395                 400

Asp Asn Ser Ser Gly Tyr Ser Gly Ile Phe Ser Val Glu Gly Lys Ser
            405                 410                 415

Cys Ile Asn Arg Cys Phe Tyr Val Glu Leu Ile Arg Gly Arg Pro Lys
            420                 425                 430

Glu Thr Arg Val Trp Trp Thr Ser Asn Ser Ile Ile Val Phe Cys Gly
            435                 440                 445

Thr Ser Gly Thr Tyr Gly Thr Gly Ser Trp Pro Asp Gly Ala Asn Ile
            450                 455                 460

Asn Phe Met Pro Ile
465

<210> SEQ ID NO 21
<211> LENGTH: 1737
<212> TYPE: DNA
<213> ORGANISM: Influenza A virus

<400> SEQUENCE: 21
agcaaaagca gggatacaa aatgaacact caaatcctgg tattcgctct ggtggcgagc      60
attccgacaa atgcagacaa gatctgcctt gggcatcatg ccgtgtcaaa cgggactaaa    120
gtaaacacat taactgagag aggagtggaa gtcgttaatg caactgaaac ggtggaacga    180
acaaacgttc ccaggatctg ctcaaaaggg aaaaggacag ttgacctcgg tcaatgtgga    240
cttctgggaa caatcactgg gccaccccaa tgtgaccaat cctagaatt ttcggccgac    300 ttaattattg agaggcgaga aggaagtgat gtctgttatc ctgggaaatt cgtgaatgaa    360
gaagctctga ggcaaattct cagagagtca ggcggaattg acaaggagac aatgggattc    420

| | |
|---|---|
| acctacagcg gaataagaac taatggaaca accagtgcat gtaggagatc aggatcttca | 480 |
| ttctatgcag agatgaaatg gctcctgtca acacagaca atgctgcttt cccgcaaatg | 540 |
| actaagtcat acaagaacac aaggaaagac ccagctctga taatatgggg gatccaccat | 600 |
| tccggatcaa ctacagaaca gaccaagcta tatgggagtg gaaacaaact gataacagtt | 660 |
| gggagttcta attaccaaca gtcctttgta ccgagtccag gagcgagacc acaagtgaat | 720 |
| ggccaatctg gaagaattga ctttcattgg ctgatactaa accctaatga cacggtcact | 780 |
| ttcagtttca atgggccctt catagctcca gaccgtgcaa gctttctgag agggaagtcc | 840 |
| atgggaattc agagtgaagt acaggttgat gccaattgtg aaggagattg ctatcatagt | 900 |
| ggagggacaa taataagtaa tttgccccttt cagaacataa atagcagggc agtaggaaaa | 960 |
| tgtccgagat atgttaagca agagagtctg ctgttggcaa caggaatgaa gaatgttccc | 1020 |
| gaaatcccaa agaggaggag agaggcctat ttggtgcta tagcgggttt cattgaaaat | 1080 |
| ggatgggaag gtttgattga tgggtggtat ggcttcaggc atcaaaatgc acaaggggag | 1140 |
| ggaactgctg cagattacaa aagcacccaa tcagcaattg atcaaataac agggaaatta | 1200 |
| aatcggctta tagaaaaaac taaccaacag tttgagttaa tagacaacga attcactgag | 1260 |
| gttgaaaggc aaattggcaa tgtgataaac tggaccagag attccatgac agaagtgtgg | 1320 |
| tcctataacg ctgaactctt agtagcaatg gagaatcagc acacaattga tctggccgac | 1380 |
| tcagaaatga acaaactgta cgaacgagtg aagagacaac tgagagaaa tgccgaagaa | 1440 |
| gatggcactg gttgcttcga aatatttcac aagtgtgatg acgactgcat ggccagtatt | 1500 |
| agaaacaaca cctatgatca cagcaagtac agggaagaag caatacaaaa tagaatacag | 1560 |
| attgacccag tcaaactaag cagcggctac aaagatgtga tactttggtt tagcttcggg | 1620 |
| gcatcatgtt tcatacttct ggccattgca atgggccttg tcttcatatg tgtgaagaat | 1680 |
| ggaaacatgc ggtgcactat ttgtatataa gtttggaaaa acacccttgt ttctact | 1737 |

<210> SEQ ID NO 22
<211> LENGTH: 1465
<212> TYPE: DNA
<213> ORGANISM: Influenza A virus

<400> SEQUENCE: 22

| | |
|---|---|
| agcaaaagca gggtgatcga gaatgaatcc aaatcagaaa ctatttgcat tatctggagt | 60 |
| ggcaatagca cttagtgtac tgaacttatt gataggaatc tcaaacgtcg gattgaacgt | 120 |
| atctctacat ctaaaggaaa aaggacccaa acaggaggag aatttaacat gcacgaccat | 180 |
| taatcaaaac aacactactg tagtagaaaa cacatatgta aataatacaa caataattac | 240 |
| caagggaact gatttgaaaa caccaagcta tctgctgttg aacaagagcc tgtgcaatgt | 300 |
| tgaagggtgg gtcgtgatag caaaagacaa tgcagtaaga tttgggggaaa gtgaacaaat | 360 |
| cattgttacc agggagccat atgtatcatg cgacccaaca ggatgcaaaa tgtatgcctt | 420 |
| gcaccaaggg actaccatta ggaacaaaca ttcaaatgga acgattcatg acagaacagc | 480 |
| tttcagaggt ctcatctcca ctccattggg cactccacca accgtaagta acagtgactt | 540 |
| tatgtgtgtt ggatggtcaa gcacaacttg ccatgatggg attgctagga tgactatctg | 600 |
| tatacaagga ataatgaca atgctacagc aacggtttat tacaacagaa ggctgaccac | 660 |
| taccattaag acctgggcca gaaacattct gaggactcaa gaatcagaat gtgtgtgcca | 720 |
| caatggcaca tgtgcagttg taatgaccga cggatcggct agtagtcaag cctatacaaa | 780 |
| agtaatgtat ttccacaagg gattagtagt taaggaggag gagttaaggg gatcagccag | 840 |

```
acatattgag gaatgctcct gttatggaca caatcaaaag gtgacctgtg tgtgcagaga      900
taactggcag ggagcaaaca ggcctattat agaaattgat atgagcacat tggagcacac      960
aagtagatac gtgtgcactg gaattctcac agacaccagc agacctgggg acaaatctag     1020
tggtgattgt tccaatccaa taactgggag tcccggcgtt ccgggagtga agggattcgg     1080
gtttctaaat ggggataaca catggcttgg taggaccatc agcccagat caagaagtgg      1140 attcgaaatg ttgaaaatac ctaatgcagg tactgatccc aattctagaa tagcagaacg     1200
acaggaaatt gtcgcaata caattggtc aggctattcc ggaagcttta ttgactattg       1260
gaatgataac agtgaatgct acaatccatg cttttacgta gagttaatta gaggaagacc     1320
cgaagaggct aaatacgtat ggtgggcaag taacagtcta attgccctat gtggaagccc     1380
attcccagtt gggtctggtt ccttccccga tggggcacaa atccaatact tttcgtaaaa     1440
tgcaaaaaaa ctccttgttt ctact                                          1465

<210> SEQ ID NO 23
<211> LENGTH: 1754
<212> TYPE: DNA
<213> ORGANISM: Influenza A virus

<400> SEQUENCE: 23
agcaaaagca ggggatacaa aatgaatact caaattttgg cattcattgc ttgtatgctg       60
attggaacta aaggagacaa aatatgtctt gggcaccatg ctgtggcaaa tgggacaaaa      120
gtgaacacac taacagagag gggaattgaa gtagtcaatg ccacggagac ggtgaaaact      180
gtaaatatta aaaaaatatg cactcaagga aaaaggccaa cagatctggg acaatgtgga      240
cttctaggaa ccctaatagg acctccccaa tgcgatcaat ttctggagtt tgacgctaat      300
ttgataattg aacgaagaga aggaaccgat gtgtgctatc ccgggaagtt cacaaatgaa      360
gaatcactga gcagatcct tcgagggtca ggaggaattg ataaagagtc aatgggtttc       420
acctatagtg gaataagaac caatgggggcg acgagtgcct gcagaagatc aggttcttct    480
ttctatgcgg agatgaagtg gttactgtcg aattcagaca atgcggcatt tccccaaatg      540
actaagtcgt ataggaatcc caggaacaaa ccagctctga taatctgggg agtgcatcac      600
tctggatcag ctactgagca gaccaaactc tatggaagtg gaaacaagtt gataacagta      660
ggaagctcga ataccagca atcattcact ccaagtccgg gagcacggcc acaagtgaat       720
ggacaatcag gaaggattga ttttcattgg ctactccttg accccaatga cacagtgacc      780
ttcactttca atggggcatt catagcccct gacagggcaa gtttctttag aggagaatcg      840
ctaggagtcc agagtgatgt tccttttggat tctggttgtg aagggggattg cttccacagt    900 gggggtacga tagtcagttc cctgccattc caaaacatca accctagaac agtggggaaa      960
tgccctcgat atgtcaaaca gacaagcctc cttttggcta caggaatgag aaacgtccca     1020
gagaacccca gcaggccta ccggaaacgg atgaccagag ccttttttgg agcgattgct      1080
ggattcatag agaatggatg ggaaggtctc atcgatggat ggtatggttt cagacatcaa     1140
aatgcacaag gagaaggaac tgcagctgac tacaaaagca cccaatctgc aatagatcag     1200
atcacaggca aattgaatcg tctgattgac aaaacaaacc agcagtttga actgatagac     1260
aatgaattca gtgagataga caacaaaatc gggaatgtca ttaactggac acgagactca     1320
atgactgagg tatggtcgta taatgctgag ctgttggtgg caatggagaa tcagcataca     1380
atagatcttg cagactcaga aatgaacaaa cttacgaac gcgtcagaaa acaactaagg      1440
gaaaatgctg aagaagatgg aactggatgc tttgagatat tccataagtg tgatgatcag     1500
```
tgtatggaga gcataaggaa caacacttat gaccataccc aatacaggac agagtcattg 1560
cagaatagaa tacagataga cccagtgaaa ttgagtagtg gatacaaaga cataatctta 1620
tggtttagct tcggggcatc atgttttctt cttctagcca ttgcaatggg attggttttc 1680
atttgcataa agaatggaaa catgcggtgc actatttgta tatagtttga gaaaaaaaca 1740
cccttgtttc tact 1754

<210> SEQ ID NO 24
<211> LENGTH: 1453
<212> TYPE: DNA
<213> ORGANISM: Influenza A virus

<400> SEQUENCE: 24
agcaaaagca ggtgcgagat gaatccgaat cagaagataa taacaatcgg ggtagtgaat 60
accactctgt caacaatagc ccttctcatt ggagtgggaa acttagtttt caacacagtc 120
atacatgaga aaataggaga ccatcaaata gtgacccatc caacaataat gacccctgaa 180
gtaccgaact gcagtgacac tataataaca tacaataaca ctgttataaa caacataaca 240
acaacaataa taactgaagc agaaaggcct ttcaagtctc cactaccgct gtgccccttc 300
agaggattct tccctttca caaggacaat gcaatacgac tgggtgaaaa caaagacgtc 360
atagtcacaa gggagcctta tgttagctgc gataatgaca actgctggtc ctttgctctc 420
gcacaaggag cattgctagg gactaaacat agcaatggga ccattaaaga cagaacacca 480
tataggtctc taattcgttt cccaatagga acagctccag tactaggaaa ttacaaagag 540
atatgcattg cttggtcgag cagcagttgc tttgacggga aagagtggat gcatgtgtgc 600
atgacaggga atgataatga tgcaagtgcc cagataatat atggaggaag aatgacagac 660
tccattaaat catggaggaa ggacatacta agaacccagg agtctgaatg tcaatgcatt 720
gacgggactt gtgttgttgc tgtcacagat ggccctgctg ctaatagtgc agatcacagg 780
gtttactgga tacgggaggg aagaataata aagtatgaaa atgttcccaa aacaaagata 840
caacacttag aagaatgttc ctgctatgtg gacattgatg tttactgtat atgtagggac 900
aattggaagg gctctaacag accttggatg agaatcaaca acgagactat actggaaaca 960
ggatatgtat gtagtaaatt tcactcagac acccccaggc cagctgaccc ttcaataatg 1020
tcatgtgact ccccaagcaa tgtcaatgga ggacccggag tgaaggggtt tggtttcaaa 1080
gctggcaatg atgtatggtt aggtagaaca gtgtcaacta gtggtagatc gggctttgaa 1140
attatcaaag ttacagaagg gtggatcaac tctcctaacc atgtcaaatc aattacacaa 1200
acactagtgt ccaacaatga ctggtcaggc tattcaggta gcttcattgt caaagccaag 1260
gactgttttc agccctgttt ttatgttgag cttatacgag ggaggcccaa caagaatgat 1320
gacgtctctt ggacaagtaa tagtatagtt actttctgtg gactagacaa tgaacctgga 1380
tcgggaaatt ggccagatgg ttctaacatt gggtttatgc ccaagtaata gaaaaaagca 1440
ccttgtttct act 1453

<210> SEQ ID NO 25
<211> LENGTH: 1733
<212> TYPE: DNA
<213> ORGANISM: Influenza A virus

<400> SEQUENCE: 25
agcgaaagca ggggatacaa aatgaatact caaattttgg cattcattgc ttgtatgctg 60
attggaacta aaggagacaa aatatgtctt gggcaccatg ctgtggcaaa tgggacaaaa 120

-continued

```
gtgaacacac taacagagag gggaattgaa gtagtcaatg ccacgagac ggtggaaact     180 gtaaatatta agaaaatatg cactcaagga aaaaggccaa cagatctggg acaatgtgga    240
cttctaggaa ccctaatagg acctccccaa tgcgatcaat ttctggagtt tgacgctaat    300
ttgataattg aacgaagaga aggaaccgat gtgtgctatc ccgggaagtt cacaaatgaa    360
gaatcactga gcagatcct tcagggtca ggaggaattg ataaagagtc aatgggtttc      420
acctatagtg gaataagaac caatggggcg acgagtgcct gcagaagatc aggttcttct   480
ttctatgcgg agatgaagtg gttactgtcg aattcagaca atgcggcatt tccccaaatg   540
actaagtcgt ataggaatcc caggaacaaa ccagctctga taatctgggg agtgcatcac   600
tctggatcag ctactgagca gaccaaactc tatggaagtg aaacaagtt gataacagta    660 ggaagctcga ataccagca atcattcact ccaagtccgg gagcacggcc acaagtgaat    720
ggacaatcag gaaggattga ttttcattgg ctactccttg accccaatga cacagtgacc   780
ttcactttca atggggcatt catagcccct gacagggcaa gtttctttag aggagaatcg   840
ctaggagtcc agagtgatgt tcctttggat tctggttgtg aaggggattg cttccacagt   900
gggggtacga tagtcagttc cctgccattc caaaacatca accctagaac agtggggaaa   960
tgccctcgat atgtcaaaca gacaagcctc cttttggcta caggaatgag aaacgtccca  1020
gagaccccca gaccagagg cctttttgga gcgattgctg gattcataga gaatggatgg    1080
gaaggtctca tcgatggatg gtatggttc agacatcaaa atgcacaagg agaaggaact    1140
gcagctgact acaaaagcac ccaatctgca atagatcaga tcacaggcaa attgaatcgt   1200
ctgattgaca aaacaaacca gcagtttgaa ctgatagaca atgaattcag tgagatagaa   1260
caacaaatcg gaatgtcat taactggaca cgagactcaa tgactgaggt atggtcgtat    1320
aatgctgagc tgttggtggc aatggagaat cagcatacaa tagatcttgc agactcagaa   1380
atgaacaaac tttacgaacg cgtcagaaaa caactaaggg aaaatgctga agaagatgga   1440
actggatgct ttgagatatt ccataagtgt gatgatcagt gtatggagag cataaggaac   1500
aacacttatg accataccca atacaggaca gagtcattgc agaatagaat acagatagac   1560
ccagtgaaat tgagtagtgg atacaaagac ataatcttat ggtttagctt cggggcatca   1620
tgttttcttc ttctagccat tgcaatggga ttggttttca tttgcataaa gaatggaaac   1680
atgcggtgca ctatttgtat atagtttgag aaaaaaacac ccttgtttct act           1733
```

```
<210> SEQ ID NO 26
<211> LENGTH: 1453
<212> TYPE: DNA
<213> ORGANISM: Influenza A virus

<400> SEQUENCE: 26
agcaaaagca ggtgcgagat gaatccgaat cagaagataa taacaatcgg ggtagtgaat   60
accactctgt caacaatagc ccttctcatt ggagtgggaa acttagtttt caacacagtc    120
atacatgaga aaataggaga ccatcaaata gtgacccatc aacaataat gaccctgaa    180 gtaccgaact gcagtgacac tataataaca tacaataaca ctgttataaa caacataaca    240
acaacaataa taactgaagc agaaaggcct tcaagtctc cactaccgct gtgccccttc    300
agaggattct tccttttca aaggacaat gcaatacgac tgggtgaaaa caagacgtc     360 atagtcacaa gggagcctta tgttagctgc gataatgaca actgctggtc ctttgctctc   420
gcacaaggag cattgctagg gactaaacat agcaatggga ccattaaaga cagaacacca   480
tataggtctc taattcgttt cccaatagga acagctccag tactaggaaa ttacaaagag   540
```

-continued

```
atatgcattg cttggtcgag cagcagttgc tttgacggga aagagtggat gcatgtgtgc   600
atgacaggga atgataatga tgcaagtgcc cagataatat atggaggaag aatgacagac   660
tccattaaat catggaggaa ggacatacta agaacccagg agtctgaatg tcaatgcatt   720
gacgggactt gtgttgttgc tgtcacagat ggccctgctg ctaatagtgc agatcacagg   780
gtttactgga tacggaggg aagaataata aagtatgaaa atgttcccaa aacaaagata   840
caacacttag aagaatgttc ctgctatgtg gacattgatg tttactgtat atgtagggac   900
aattggaagg gctctaacag accttggatg agaatcaaca acgagactat actggaaaca   960
ggatatgtat gtagtaaatt tcactcagac accccaggc cagctgaccc ttcaataatg  1020
tcatgtgact ccccaagcaa tgtcaatgga ggacccggag tgaagggtt tggtttcaaa  1080 gctggcaatg atgtatggtt aggtagaaca gtgtcaacta gtggtagatc gggcttgaa  1140 attatcaaag ttacagaagg gtggatcaac tctcctaacc atgtcaaatc aattacacaa  1200
acactagtgt ccaacaatga ctggtcaggc tattcaggta gcttcattgt caaagccaag  1260
gactgttttc agccctgttt ttatgttgag cttatacgag ggaggcccaa caagaatgat  1320
gacgtctctt ggacaagtaa tagtatagtt actttctgtg gactagacaa tgaacctgga  1380
tcgggaaatt ggccagatgg ttctaacatt gggtttatgc ccaagtaata gaaaaaagca  1440
ccttgtttct act                                                     1453
```

<210> SEQ ID NO 27
<211> LENGTH: 562
<212> TYPE: PRT
<213> ORGANISM: Influenza A virus

<400> SEQUENCE: 27

```
Met Asn Thr Gln Ile Leu Val Phe Ala Leu Val Ala Ser Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Val Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Thr Met Gly Phe Thr Tyr Ser Gly Ile Arg Thr Asn Gly Thr Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
            180                 185                 190

His Ser Gly Ser Thr Thr Glu Gln Thr Lys Leu Tyr Gly Ser Gly Asn
        195                 200                 205
```

```
Lys Leu Ile Thr Val Gly Ser Ser Asn Tyr Gln Gln Ser Phe Val Pro
    210                 215                 220

Ser Pro Gly Ala Arg Pro Gln Val Asn Gly Gln Ser Gly Arg Ile Asp
225                 230                 235                 240

Phe His Trp Leu Ile Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Glu Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro
                325                 330                 335

Lys Arg Arg Arg Arg Gly Leu Phe Gly Ala Ile Ala Gly Phe Ile Glu
            340                 345                 350

Asn Gly Trp Glu Gly Leu Ile Asp Gly Trp Tyr Gly Phe Arg His Gln
        355                 360                 365

Asn Ala Gln Gly Glu Gly Thr Ala Ala Asp Tyr Lys Ser Thr Gln Ser
    370                 375                 380

Ala Ile Asp Gln Ile Thr Gly Lys Leu Asn Arg Leu Ile Glu Lys Thr
385                 390                 395                 400

Asn Gln Gln Phe Glu Leu Ile Asp Asn Glu Phe Thr Glu Val Glu Arg
                405                 410                 415

Gln Ile Gly Asn Val Ile Asn Trp Thr Arg Asp Ser Met Thr Glu Val
            420                 425                 430

Trp Ser Tyr Asn Ala Glu Leu Leu Val Ala Met Glu Asn Gln His Thr
        435                 440                 445

Ile Asp Leu Ala Asp Ser Glu Met Asn Lys Leu Tyr Glu Arg Val Lys
    450                 455                 460

Arg Gln Leu Arg Glu Asn Ala Glu Glu Asp Gly Thr Gly Cys Phe Glu
465                 470                 475                 480

Ile Phe His Lys Cys Asp Asp Asp Cys Met Ala Ser Ile Arg Asn Asn
                485                 490                 495

Thr Tyr Asp His Ser Lys Tyr Arg Glu Glu Ala Ile Gln Asn Arg Ile
            500                 505                 510

Gln Ile Asp Pro Val Lys Leu Ser Ser Gly Tyr Lys Asp Val Ile Leu
        515                 520                 525

Trp Phe Ser Phe Gly Ala Ser Cys Phe Ile Leu Leu Ala Ile Ala Met
    530                 535                 540

Gly Leu Val Phe Ile Cys Val Lys Asn Gly Asn Met Arg Cys Thr Ile
545                 550                 555                 560

Cys Ile

<210> SEQ ID NO 28
<211> LENGTH: 471
<212> TYPE: PRT
<213> ORGANISM: Influenza A virus

<400> SEQUENCE: 28

Met Asn Pro Asn Gln Lys Leu Phe Ala Leu Ser Gly Val Ala Ile Ala
1               5                   10                  15

Leu Ser Val Leu Asn Leu Leu Ile Gly Ile Ser Asn Val Gly Leu Asn
```

-continued

```
                      20                  25                  30
Val Ser Leu His Leu Lys Glu Lys Gly Pro Lys Gln Glu Glu Asn Leu
         35                  40                  45

Thr Cys Thr Thr Ile Asn Gln Asn Asn Thr Thr Val Val Glu Asn Thr
     50                  55                  60

Tyr Val Asn Asn Thr Thr Ile Ile Thr Lys Gly Thr Asp Leu Lys Thr
 65                  70                  75                  80

Pro Ser Tyr Leu Leu Leu Asn Lys Ser Leu Cys Asn Val Glu Gly Trp
                 85                  90                  95

Val Val Ile Ala Lys Asp Asn Ala Val Arg Phe Gly Glu Ser Glu Gln
                100                 105                 110

Ile Ile Val Thr Arg Glu Pro Tyr Val Ser Cys Asp Pro Thr Gly Cys
            115                 120                 125

Lys Met Tyr Ala Leu His Gln Gly Thr Thr Ile Arg Asn Lys His Ser
        130                 135                 140

Asn Gly Thr Ile His Asp Arg Thr Ala Phe Arg Gly Leu Ile Ser Thr
145                 150                 155                 160

Pro Leu Gly Thr Pro Pro Thr Val Ser Asn Ser Asp Phe Met Cys Val
                165                 170                 175

Gly Trp Ser Ser Thr Cys His Asp Gly Ile Ala Arg Met Thr Ile
                180                 185                 190

Cys Ile Gln Gly Asn Asn Asp Asn Ala Thr Ala Thr Val Tyr Tyr Asn
                195                 200                 205

Arg Arg Leu Thr Thr Thr Ile Lys Thr Trp Ala Arg Asn Ile Leu Arg
            210                 215                 220

Thr Gln Glu Ser Glu Cys Val Cys His Asn Gly Thr Cys Ala Val Val
225                 230                 235                 240

Met Thr Asp Gly Ser Ala Ser Ser Gln Ala Tyr Thr Lys Val Met Tyr
                245                 250                 255

Phe His Lys Gly Leu Val Val Lys Glu Glu Leu Arg Gly Ser Ala
                260                 265                 270

Arg His Ile Glu Glu Cys Ser Cys Tyr Gly His Asn Gln Lys Val Thr
            275                 280                 285

Cys Val Cys Arg Asp Asn Trp Gln Gly Ala Asn Arg Pro Ile Ile Glu
        290                 295                 300

Ile Asp Met Ser Thr Leu Glu His Thr Ser Arg Tyr Val Cys Thr Gly
305                 310                 315                 320

Ile Leu Thr Asp Thr Ser Arg Pro Gly Asp Lys Ser Ser Gly Asp Cys
                325                 330                 335

Ser Asn Pro Ile Thr Gly Ser Pro Gly Val Pro Gly Val Lys Gly Phe
                340                 345                 350

Gly Phe Leu Asn Gly Asp Asn Thr Trp Leu Gly Arg Thr Ile Ser Pro
            355                 360                 365

Arg Ser Arg Ser Gly Phe Glu Met Leu Lys Ile Pro Asn Ala Gly Thr
        370                 375                 380

Asp Pro Asn Ser Arg Ile Ala Glu Arg Gln Glu Ile Val Asp Asn Asn
385                 390                 395                 400

Asn Trp Ser Gly Tyr Ser Gly Ser Phe Ile Asp Tyr Trp Asn Asp Asn
                405                 410                 415

Ser Glu Cys Tyr Asn Pro Cys Phe Tyr Val Glu Leu Ile Arg Gly Arg
                420                 425                 430

Pro Glu Glu Ala Lys Tyr Val Trp Trp Ala Ser Asn Ser Leu Ile Ala
            435                 440                 445
```

Leu Cys Gly Ser Pro Phe Pro Val Gly Ser Gly Ser Phe Pro Asp Gly
    450                 455                 460

Ala Gln Ile Gln Tyr Phe Ser
465                 470

<210> SEQ ID NO 29
<211> LENGTH: 567
<212> TYPE: PRT
<213> ORGANISM: Influenza A virus

<400> SEQUENCE: 29

Met Asn Thr Gln Ile Leu Ala Phe Ile Ala Cys Met Leu Ile Gly Thr
1               5                   10                  15

Lys Gly Asp Lys Ile Cys Leu Gly His His Ala Val Ala Asn Gly Thr
            20                  25                  30

Lys Val Asn Thr Leu Thr Glu Arg Gly Ile Glu Val Asn Ala Thr
        35                  40                  45

Glu Thr Val Glu Thr Val Asn Ile Lys Lys Ile Cys Thr Gln Gly Lys
    50                  55                  60

Arg Pro Thr Asp Leu Gly Gln Cys Gly Leu Leu Gly Thr Leu Ile Gly
65                  70                  75                  80

Pro Pro Gln Cys Asp Gln Phe Leu Glu Phe Asp Ala Asn Leu Ile Ile
                85                  90                  95

Glu Arg Arg Glu Gly Thr Asp Val Cys Tyr Pro Gly Lys Phe Thr Asn
            100                 105                 110

Glu Glu Ser Leu Arg Gln Ile Leu Arg Gly Ser Gly Ile Asp Lys
        115                 120                 125

Glu Ser Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Ile Trp Gly Val His
            180                 185                 190

His Ser Gly Ser Ala Thr Glu Gln Thr Lys Leu Tyr Gly Ser Gly Asn
        195                 200                 205

Lys Leu Ile Thr Val Gly Ser Ser Lys Tyr Gln Gln Ser Phe Thr Pro
    210                 215                 220

Ser Pro Gly Ala Arg Pro Gln Val Asn Gly Gln Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Asp Arg Ala Ser Phe Phe Arg Gly Glu
            260                 265                 270

Ser Leu Gly Val Gln Ser Asp Val Pro Leu Asp Ser Cys Glu Gly
        275                 280                 285

Asp Cys Phe His Ser Gly Gly Thr Ile Val Ser Ser Leu Pro Phe Gln
    290                 295                 300

Asn Ile Asn Pro Arg Thr Val Gly Lys Cys Pro Arg Tyr Val Lys Gln
305                 310                 315                 320

Thr Ser Leu Leu Leu Ala Thr Gly Met Arg Asn Val Pro Glu Asn Pro
                325                 330                 335

Lys Gln Ala Tyr Arg Lys Arg Met Thr Arg Gly Leu Phe Gly Ala Ile
            340                 345                 350

```
Ala Gly Phe Ile Glu Asn Gly Trp Glu Gly Leu Ile Asp Gly Trp Tyr
        355                 360                 365

Gly Phe Arg His Gln Asn Ala Gln Gly Glu Gly Thr Ala Ala Asp Tyr
    370                 375                 380

Lys Ser Thr Gln Ser Ala Ile Asp Gln Ile Thr Gly Lys Leu Asn Arg
385                 390                 395                 400

Leu Ile Asp Lys Thr Asn Gln Gln Phe Glu Leu Ile Asp Asn Glu Phe
            405                 410                 415

Ser Glu Ile Glu Gln Gln Ile Gly Asn Val Ile Asn Trp Thr Arg Asp
                420                 425                 430

Ser Met Thr Glu Val Trp Ser Tyr Asn Ala Glu Leu Leu Val Ala Met
            435                 440                 445

Glu Asn Gln His Thr Ile Asp Leu Ala Asp Ser Glu Met Asn Lys Leu
        450                 455                 460

Tyr Glu Arg Val Arg Lys Gln Leu Arg Glu Asn Ala Glu Glu Asp Gly
465                 470                 475                 480

Thr Gly Cys Phe Glu Ile Phe His Lys Cys Asp Asp Gln Cys Met Glu
                485                 490                 495

Ser Ile Arg Asn Asn Thr Tyr Asp His Thr Gln Tyr Arg Thr Glu Ser
                500                 505                 510

Leu Gln Asn Arg Ile Gln Ile Asp Pro Val Lys Leu Ser Ser Gly Tyr
            515                 520                 525

Lys Asp Ile Ile Leu Trp Phe Ser Phe Gly Ala Ser Cys Phe Leu Leu
530                 535                 540

Leu Ala Ile Ala Met Gly Leu Val Phe Ile Cys Ile Lys Asn Gly Asn
545                 550                 555                 560

Met Arg Cys Thr Ile Cys Ile
                565

<210> SEQ ID NO 30
<211> LENGTH: 469
<212> TYPE: PRT
<213> ORGANISM: Influenza A virus

<400> SEQUENCE: 30

Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Val Phe Asn
            20                  25                  30

Thr Val Ile His Glu Lys Ile Gly Asp His Gln Ile Val Thr His Pro
        35                  40                  45

Thr Ile Met Thr Pro Glu Val Pro Asn Cys Ser Asp Thr Ile Ile Thr
    50                  55                  60

Tyr Asn Asn Thr Val Ile Asn Asn Ile Thr Thr Ile Ile Thr Glu
65                  70                  75                  80

Ala Glu Arg Pro Phe Lys Ser Pro Leu Pro Leu Cys Pro Phe Arg Gly
                85                  90                  95

Phe Phe Pro Phe His Lys Asp Asn Ala Ile Arg Leu Gly Glu Asn Lys
            100                 105                 110

Asp Val Ile Val Thr Arg Glu Pro Tyr Val Ser Cys Asp Asn Asp Asn
        115                 120                 125

Cys Trp Ser Phe Ala Leu Ala Gln Gly Ala Leu Leu Gly Thr Lys His
    130                 135                 140

Ser Asn Gly Thr Ile Lys Asp Arg Thr Pro Tyr Arg Ser Leu Ile Arg
145                 150                 155                 160
```

-continued

```
Phe Pro Ile Gly Thr Ala Pro Val Leu Gly Asn Tyr Lys Glu Ile Cys
            165                 170                 175

Ile Ala Trp Ser Ser Ser Cys Phe Asp Gly Lys Glu Trp Met His
        180                 185                 190

Val Cys Met Thr Gly Asn Asp Asn Asp Ala Ser Ala Gln Ile Ile Tyr
        195                 200                 205

Gly Gly Arg Met Thr Asp Ser Ile Lys Ser Trp Arg Lys Asp Ile Leu
        210                 215                 220

Arg Thr Gln Glu Ser Glu Cys Gln Cys Ile Asp Gly Thr Cys Val Val
225                 230                 235                 240

Ala Val Thr Asp Gly Pro Ala Ala Asn Ser Ala Asp His Arg Val Tyr
            245                 250                 255

Trp Ile Arg Glu Gly Arg Ile Ile Lys Tyr Glu Asn Val Pro Lys Thr
        260                 265                 270

Lys Ile Gln His Leu Glu Glu Cys Ser Cys Tyr Val Asp Ile Asp Val
        275                 280                 285

Tyr Cys Ile Cys Arg Asp Asn Trp Lys Gly Ser Asn Arg Pro Trp Met
        290                 295                 300

Arg Ile Asn Asn Glu Thr Ile Leu Glu Thr Gly Tyr Val Cys Ser Lys
305                 310                 315                 320

Phe His Ser Asp Thr Pro Arg Pro Ala Asp Pro Ser Ile Met Ser Cys
            325                 330                 335

Asp Ser Pro Ser Asn Val Asn Gly Gly Pro Gly Val Lys Gly Phe Gly
        340                 345                 350

Phe Lys Ala Gly Asn Asp Val Trp Leu Gly Arg Thr Val Ser Thr Ser
        355                 360                 365

Gly Arg Ser Gly Phe Glu Ile Ile Lys Val Thr Glu Gly Trp Ile Asn
        370                 375                 380

Ser Pro Asn His Val Lys Ser Ile Thr Gln Thr Leu Val Ser Asn Asn
385                 390                 395                 400

Asp Trp Ser Gly Tyr Ser Gly Ser Phe Ile Val Lys Ala Lys Asp Cys
            405                 410                 415

Phe Gln Pro Cys Phe Tyr Val Glu Leu Ile Arg Gly Arg Pro Asn Lys
        420                 425                 430

Asn Asp Asp Val Ser Trp Thr Ser Asn Ser Ile Val Thr Phe Cys Gly
        435                 440                 445

Leu Asp Asn Glu Pro Gly Ser Gly Asn Trp Pro Asp Gly Ser Asn Ile
450                 455                 460

Gly Phe Met Pro Lys
465

<210> SEQ ID NO 31
<211> LENGTH: 560
<212> TYPE: PRT
<213> ORGANISM: Influenza A virus

<400> SEQUENCE: 31

Met Asn Thr Gln Ile Leu Ala Phe Ile Ala Cys Met Leu Ile Gly Thr
1               5                   10                  15

Lys Gly Asp Lys Ile Cys Leu Gly His His Ala Val Ala Asn Gly Thr
            20                  25                  30

Lys Val Asn Thr Leu Thr Glu Arg Gly Ile Glu Val Val Asn Ala Thr
        35                  40                  45

Glu Thr Val Glu Thr Val Asn Ile Lys Lys Ile Cys Thr Gln Gly Lys
    50                  55                  60
```

-continued

```
Arg Pro Thr Asp Leu Gly Gln Cys Gly Leu Leu Gly Thr Leu Ile Gly
 65                  70                  75                  80

Pro Pro Gln Cys Asp Gln Phe Leu Glu Phe Asp Ala Asn Leu Ile Ile
                 85                  90                  95

Glu Arg Arg Glu Gly Thr Asp Val Cys Tyr Pro Gly Lys Phe Thr Asn
            100                 105                 110

Glu Glu Ser Leu Arg Gln Ile Leu Arg Gly Ser Gly Ile Asp Lys
        115                 120                 125

Glu Ser Met Gly Phe Thr Tyr Ser Gly Ile Arg Thr Asn Gly Ala Thr
    130                 135                 140

Ser Ala Cys Arg Arg Ser Gly Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Ile Trp Gly Val His
                180                 185                 190

His Ser Gly Ser Ala Thr Glu Gln Thr Lys Leu Tyr Gly Ser Gly Asn
            195                 200                 205

Lys Leu Ile Thr Val Gly Ser Ser Lys Tyr Gln Gln Ser Phe Thr Pro
210                 215                 220

Ser Pro Gly Ala Arg Pro Gln Val Asn Gly Gln Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Asp Arg Ala Ser Phe Phe Arg Gly Glu
                260                 265                 270

Ser Leu Gly Val Gln Ser Asp Val Pro Leu Asp Ser Gly Cys Glu Gly
            275                 280                 285

Asp Cys Phe His Ser Gly Gly Thr Ile Val Ser Ser Leu Pro Phe Gln
        290                 295                 300

Asn Ile Asn Pro Arg Thr Val Gly Lys Cys Pro Arg Tyr Val Lys Gln
305                 310                 315                 320

Thr Ser Leu Leu Leu Ala Thr Gly Met Arg Asn Val Pro Glu Asn Pro
                325                 330                 335

Lys Thr Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
        370                 375                 380

Asp Gln Ile Thr Gly Lys Leu Asn Arg Leu Ile Asp Lys Thr Asn Gln
385                 390                 395                 400

Gln Phe Glu Leu Ile Asp Asn Glu Phe Ser Glu Ile Glu Gln Gln Ile
                405                 410                 415

Gly Asn Val Ile Asn Trp Thr Arg Asp Ser Met Thr Glu Val Trp Ser
                420                 425                 430

Tyr Asn Ala Glu Leu Leu Val Ala Met Glu Asn Gln His Thr Ile Asp
            435                 440                 445

Leu Ala Asp Ser Glu Met Asn Lys Leu Tyr Glu Arg Val Arg Lys Gln
450                 455                 460

Leu Arg Glu Asn Ala Glu Glu Asp Gly Thr Gly Cys Phe Glu Ile Phe
465                 470                 475                 480

His Lys Cys Asp Asp Gln Cys Met Glu Ser Ile Arg Asn Asn Thr Tyr
                485                 490                 495
```

Asp His Thr Gln Tyr Arg Thr Glu Ser Leu Gln Asn Arg Ile Gln Ile
                500                 505                 510

Asp Pro Val Lys Leu Ser Ser Gly Tyr Lys Asp Ile Ile Leu Trp Phe
                515                 520                 525

Ser Phe Gly Ala Ser Cys Phe Leu Leu Leu Ala Ile Ala Met Gly Leu
                530                 535                 540

Val Phe Ile Cys Ile Lys Asn Gly Asn Met Arg Cys Thr Ile Cys Ile
545                 550                 555                 560

<210> SEQ ID NO 32
<211> LENGTH: 469
<212> TYPE: PRT
<213> ORGANISM: Influenza A virus

<400> SEQUENCE: 32

Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Val Phe Asn
                20                  25                  30

Thr Val Ile His Glu Lys Ile Gly Asp His Gln Ile Val Thr His Pro
            35                  40                  45

Thr Ile Met Thr Pro Glu Val Pro Asn Cys Ser Asp Thr Ile Ile Thr
        50                  55                  60

Tyr Asn Asn Thr Val Ile Asn Asn Ile Thr Thr Ile Ile Thr Glu
65                  70                  75                  80

Ala Glu Arg Pro Phe Lys Ser Pro Leu Pro Cys Pro Phe Arg Gly
                85                  90                  95

Phe Phe Pro Phe His Lys Asp Asn Ala Ile Arg Leu Gly Glu Asn Lys
                100                 105                 110

Asp Val Ile Val Thr Arg Glu Pro Tyr Val Ser Cys Asp Asn Asp Asn
            115                 120                 125

Cys Trp Ser Phe Ala Leu Ala Gln Gly Ala Leu Leu Gly Thr Lys His
        130                 135                 140

Ser Asn Gly Thr Ile Lys Asp Arg Thr Pro Tyr Arg Ser Leu Ile Arg
145                 150                 155                 160

Phe Pro Ile Gly Thr Ala Pro Val Leu Gly Asn Tyr Lys Glu Ile Cys
                165                 170                 175

Ile Ala Trp Ser Ser Ser Ser Cys Phe Asp Gly Lys Glu Trp Met His
                180                 185                 190

Val Cys Met Thr Gly Asn Asp Asn Asp Ala Ser Ala Gln Ile Ile Tyr
            195                 200                 205

Gly Gly Arg Met Thr Asp Ser Ile Lys Ser Trp Arg Lys Asp Ile Leu
        210                 215                 220

Arg Thr Gln Glu Ser Glu Cys Gln Cys Ile Asp Gly Thr Cys Val Val
225                 230                 235                 240

Ala Val Thr Asp Gly Pro Ala Ala Asn Ser Ala Asp His Arg Val Tyr
                245                 250                 255

Trp Ile Arg Glu Gly Arg Ile Ile Lys Tyr Glu Asn Val Pro Lys Thr
                260                 265                 270

Lys Ile Gln His Leu Glu Glu Cys Ser Cys Tyr Val Asp Ile Asp Val
            275                 280                 285

Tyr Cys Ile Cys Arg Asp Asn Trp Lys Gly Ser Asn Arg Pro Trp Met
        290                 295                 300

Arg Ile Asn Asn Glu Thr Ile Leu Glu Thr Gly Tyr Val Cys Ser Lys
305                 310                 315                 320

```
Phe His Ser Asp Thr Pro Arg Pro Ala Asp Pro Ser Ile Met Ser Cys
                325                 330                 335

Asp Ser Pro Ser Asn Val Asn Gly Gly Pro Gly Val Lys Gly Phe Gly
            340                 345                 350

Phe Lys Ala Gly Asn Asp Val Trp Leu Gly Arg Thr Val Ser Thr Ser
        355                 360                 365

Gly Arg Ser Gly Phe Glu Ile Ile Lys Val Thr Glu Gly Trp Ile Asn
    370                 375                 380

Ser Pro Asn His Val Lys Ser Ile Thr Gln Thr Leu Val Ser Asn Asn
385                 390                 395                 400

Asp Trp Ser Gly Tyr Ser Gly Ser Phe Ile Val Lys Ala Lys Asp Cys
                405                 410                 415

Phe Gln Pro Cys Phe Tyr Val Glu Leu Ile Arg Gly Arg Pro Asn Lys
            420                 425                 430

Asn Asp Asp Val Ser Trp Thr Ser Asn Ser Ile Val Thr Phe Cys Gly
        435                 440                 445

Leu Asp Asn Glu Pro Gly Ser Gly Asn Trp Pro Asp Gly Ser Asn Ile
    450                 455                 460

Gly Phe Met Pro Lys
465

<210> SEQ ID NO 33
<211> LENGTH: 1743
<212> TYPE: DNA
<213> ORGANISM: Influenza A virus

<400> SEQUENCE: 33
agcaaaagca ggggaaaatg attgcagtca ttataatagc ggtactggca acggccggaa      60
aatcagacaa gatctgcatt gggtatcatg ccaacaattc aacaacacaa gtggatacga     120
tacttgagaa gaatgtaacc gtcacacact cagttgaatt gctggagaac caaaagaag      180 aaagattctg caagatcttg aacaaggccc ctctcgattt aagaggatgt accatagagg     240
gttggatctt ggggaatccc caatgcgacc tattgcttgg tgatcaaagc tggtcatata     300
tagtggaaag acctacagct caaaatggga tctgctaccc aggaattttg aatgaagtag     360
aagaactgaa ggcacttatt ggatcaggag aaagagtgga gagatttgaa atgtttccca     420
aaagtacatg ggcaggagta gacaccagca gtggggtaac aaaggcttgc ccttatacta     480
gtggttcgtc tttctacaga aacctcctat ggataataaa aaccaagtcc gcagcatatc     540
cagtaattaa gggaacctac aataacactg gaagccagcc aatcctctat ttctggggtg     600
tgcaccatcc tcctgacacc aatgagcaaa acactttgta tggctctggt gatcgatatg     660
tcaggatggg aactgaaagc atgaattttg ccaagagccc agaaattgcg gcaaggcctg     720
ctgtgaatgg tcaaagaggc agaattgatt attactggtc tgttttaaag ccgggggaaa     780
ccttgaatgt ggaatctaat ggaaatctaa tcgcccccttg gtatgcatac aaatttgtca     840
gcaccaatag taaggagcc gtcttcaagt caaatttacc aatcgagaac tgtgatgcca     900
catgccagac tattgcagga gtcttaagaa ccaataaaac atttcagaat gtaagccctc     960
tgtggatagg agaatgcccc aaatatgtga aagtgaaag tttgagggctt gcaactggac    1020 taagaaatat tccacagatt gagactagag acttttcgg agctatcgca gggtttattg    1080
aaggaggatg gactgaaatg ataggatggt ggtatggcta tcaccatgaa aattctcaag    1140
gctcagggta tgcggcagac agagaaagca ctcaaagggc tatagacgga attacaaata    1200
aggtcaattc cattatagac aaaatgaaca cacaattcga agctatagac cacgaattct    1260
```

```
caaatttgga gagaagaatt gacagtctga acaaaagaat ggaagatgga tttctggacg    1320
tttggacata caatgctgaa ctgttggttc ttcttgaaaa cgaaaggaca ctagacctac    1380
atgacgcgaa tgtgaagaac ctgtatgaaa aggtcaaatc acaactacgg acaatgcta    1440 atgatctagg aaatggatgc tttgaatttt ggcataagtg tgacaatgaa tgcatagagt    1500
ctgtcaaaaa tggtacctat gactatccca aatatcagga tgaaagcaaa ttgaacaggc    1560
aggaaataga atcggtgaag ctggagaacc ttggtgtgta tcaaatcctc gccatttata    1620
gtacggtatc gagcagtcta gtcttggtag ggctgattat agcaatgggt ctttggatgt    1680
gttcaaatgg ttcaatgcaa tgcaggatat gtatataatt aagaaaaaca cccttgttct    1740
act                                                                 1743

<210> SEQ ID NO 34
<211> LENGTH: 1460
<212> TYPE: DNA
<213> ORGANISM: Influenza A virus

<400> SEQUENCE: 34
agcaaaagca gggtcaagat gaatccaaat cagaagattc tatgcacatc tgctactgcc     60
attgcaatag cacaattgc tgtattaata ggaatagcaa acctgggttt gaacatagga    120
ctacacctga aaccgagctg caactgctcc aaccctcctc tgaaacaac aaatgtaagc    180 caaacaataa taaacaatta ctacaatgaa acaaatgtta cccaaataag taacacaaac    240
attcaacata tggggggaac cgaaaaggac ttcaacaatc tgactaaagg ctctgcaca    300 ataaattcat ggcatatatt cggaaaggac aatgctataa gaataggggga gaactctgat    360 gttttagtca agagagagcc atatgttttct tgtgatccag atgaatgcag attctatgct    420
ctcagccaag gaacaacaat acggggaaag cactcaaatg gaacaataca cgatagatcc    480
caataccgtg ctttagtgag ctggcctttta tcatcaccac ccactgtgta caataccaga    540
gtagaatgca ttggatggtc cagtacaagc tgccatgatg ggaaagcacg aatgtctata    600
tgtgtctcag gtcccaacaa caatgcatca gcagtgattt ggtacaaagg cggcctatc    660 acggaaatca atacgtgggc ccgaaacata ttgagaaccc aagaatctga gtgtgtatgc    720
cacaatggaa tatgtccagt agtgttcact gacggttctg ccaccggtcc agcagaaact    780
aggatatact atttcaaaga ggggaaaatc ctcaaatggg agccactaac tggaaccgcc    840
aagcacattg aagaatgctc ttgctatggg aaagactcag aaataacgtg cacatgtaga    900
gacaattggc aaggctcgaa tagaccagta atacaaataa ccccacaat gatgactcac    960 actagtcaat acatatgcag ccctgtcctc acagacaatc cacgcccaa tgaccccacg   1020 gtaggcaagt gtaatgatcc ttatccagga aacaacaata atggagtcaa aggattctca   1080
tatttagatg gtgacaatac atggctagga agaacgataa gcacagcctc taggtctggg   1140
tatgaaatgc tgaaagtgcc taatgcattg acagatgata gatcaaaacc tactcaaggt   1200
cagacaattg tattaaacac agactggagt ggttacagtg ggtctttcat tgattactgg   1260
gcaaaagggg agtgctatag agcatgcttc tacgttgagc tgatccgtgg aaggccaaaa   1320
gaggacaaag tgtggtggac cagtaatagt atagtgtcga tgtgttccag cacagagttc   1380 cttgacaat ggaactggcc agatgggggct aaaatagagt acttcctcta agatgtagaa   1440
aaaagaccct tgtttctact                                               1460

<210> SEQ ID NO 35
<211> LENGTH: 1747
```

```
<212> TYPE: DNA
<213> ORGANISM: Influenza A virus

<400> SEQUENCE: 35
agcaaaagca ggggaaaatg attgcaatca ttgtaatagc aatactggca gcagccggaa      60
aatcagacaa gatctgcatt gggtatcatg ccaacaattc aacaacacag gtagatacga     120
tacttgagaa gaatgtgact gtcacacact caattgaatt gctggaaaat cagaaggaag     180
aaagattctg caagatattg aacaaggccc ctctcgactt aagggaatgt accatagagg     240
gttggatctt ggggaatccc caatgcgacc tattgcttgg tgatcaaagc tggtcataca     300
ttgtggaaag acctactgct caaaacggga tctgctaccc aggaaccttg aatgaggtag     360
aagaactgag ggcacttatt ggatcaggag aaagggtaga gagatttgag atgtttcccc     420
aaagcacctg gcaaggagtt gacaccaaca gtggaacaac aagatcctgc ccttattcta     480
ctggtgatcc gtcttctac agaaacctcc tatggataat aaaaaccaag acagcagaat     540
atccagtaat taagggaatt tacaacaaca ctggaaccca gccaatcctc tatttctggg     600
gtgtgcatca tcctcctaac accgacgagc aagatactct gtatggctct ggtgatcgat     660
acgttagaat gggaactgaa agcatgaatt ttgccaagag tccggaaatt gcggcaaggc     720
ctgctgtgaa tggacaaaga ggcagaattg attattattg gtcggttta aaaccagggg     780
aaaaccttga tgtggaatct aatggaaatc taatcgcccc ttggtatgca acaaatttg     840
tcaacacaaa tagtaaagga gccgtcttca ggtcagattt accaatcgag aactgcgatg     900
ccacatgcca gactattgca ggggttctaa ggaccaataa acatttcag aatgtgagtc     960
ccctgtggat aggagaatgt cccaaatacg tgaaaagtga aagtctgagg cttgcaactg    1020
gactaagaaa tgttccacag attgaaacta gaggactctt cggagctatt gcagggttta    1080
ttgaaggagg atggactggg atgatagatg gtggtatgg ctatcaccat gaaaattctc    1140
aagggtcagg atatgcagcg gacagagaaa gcactcaaaa ggctgtaaac agaattacaa    1200
ataaggtcaa ttccatcatc aacaaaatga acacacaatt tgaagctgtc gatcacgaat    1260
tttcaaatct ggagaggaga atcgacaatc tgaacaaaag aatgcaagat ggatttctgg    1320
atgtttggac atacaatgct gaactgttgg ttcttcttga aaacgaaaga acactagaca    1380
tgcatgacgc aaatgtgaag aacctacatg aaaaggtcaa atcacaacta agggacaatg    1440
ctaacgatct agggaatggt tgctttgaat tttggcataa gtgtgacaat gaatgcatag    1500
agtctgtcaa aaatggtaca tatgactatc ccaaatacca gactgaaagc aaattaaaca    1560
ggctaaaaat agaatcagta aagctagaga accttggtgt gtatcaaatt cttgccattt    1620
atagtacggt atcgagcagc ctagtgttgg tagggctgat catggcaatg ggtcttggga    1680
tgtgttcaaa tggttcaatg cagtgcaatg tgtgtatatg attaagaaaa acacccttgt    1740
ttctact                                                              1747

<210> SEQ ID NO 36
<211> LENGTH: 1401
<212> TYPE: DNA
<213> ORGANISM: Influenza A virus

<400> SEQUENCE: 36
agcaaaagca ggagtttaac atgaatccaa atcagaagat aataaccatt gggtcaatct      60
gtatggtagt tggaataatc agcttgatgt tacaaattgg aaacataata tcaatatggg     120
ttagccacat aattcagact gggcatccaa accagcctgg ccatgcaat caaagcatca     180
atttttacac tgagcaggct gcagcttcag tgacattagc gggtaattcc tctctctgcc     240
```

```
ctattagtgg atgggctata tacagtaaag acaatagtat aagaattggt tccaaagggg      300
atgtgtttgt tatgagagaa ccattcgttt catgctccca tttggaatgc agaaccttt       360 tcttgactca aggagcccta ttgaatgaca agcattctaa tgggaccgtt aaagacagaa      420
gcccctatag aactttaatg agctgtcctg ttggtgaggc tccttcccca tacaactcaa      480
ggtttgagtc tgttgcttgg tcagcaagtg cttgccatga tggcattagt tggctaacaa      540
ttggaatttc cggtccggat aatggggctg tggctgtgtt gaaatacaat ggcataataa      600
cagacaccat caagagttgg aggaacaaca tactgaggac acaagagtct gaatgtgcat      660
gtgtgaatgg ttcttgtttt actgtaatga cagatggacc gagtaatgaa caggcctcat      720
acaagatttt caagatagag aaggggaaag tagtcaaatc agttgagttg aacgcccta      780 attatcatta cgaggaatgc tcctgttatc ctgatgctgg cgaaatcaca tgtgtgtgca      840
gggataattg gcatggctcg aaccgaccgt gggtgtcttt caatcagaat ctggagtatc      900
aaataggata tatgtgcagt gggggttttcg agacagtcc acgcccccaat gatggaacag      960 gcagttgcgg tccagtgtct cttaacggag agtatggagt aaaagggttt tcatttaagt     1020
acggtgatgg tgtttggatc gggagaacca aaagcactag ttccaggagc gggtttgaaa     1080
tgatttggga tccaaatggg tggaccgaaa cagatagtaa cttctcattg aagcaagaca     1140
tcatagcaat aactgattgg tcaggataca gcgggagttt tgtccaacat ccagaactga     1200
caggattaaa ttgcatgagg ccttgcttct gggttgaact aatcagaggg aggcccaaag     1260
agaaaacaat ctggactagt gggagcagta tatctttctg tggtgtaaat agtgacactg     1320
tgggttggtc ttggccagac ggtgctgagg tgccattcac cattgacaag tagtttgttc     1380
aaaaaactcc ttgtttctac t                                               1401

<210> SEQ ID NO 37
<211> LENGTH: 1745
<212> TYPE: DNA
<213> ORGANISM: Influenza A virus

<400> SEQUENCE: 37
agcaaaagca ggggaaaatg attgcaatca taatacttgc aatagtggtc tctaccagca       60
agtcagacag gatctgcatt ggttaccatg caaacaactc gacaacacaa gtggacacaa      120
tattagagaa gaatgtgaca gtgacacact cagtggagct cctagaaaac cagaaggaga      180
atagattctg cagagtcttg aataaagcgc cactggatct aatggactgc accactgagg      240
gttggatcct tggaaacccc cgatgtgata acttactcgg tgatcaaagt tggtcataca      300
tagtagagag gcctgatgcc caaaatggga tatgttaccc aggggtattg aaggagacgg      360
aagagctgaa agcactcatt gggtctatag atagcataca aagatttgaa atgtttccca      420
agagcacgtg gaccggggta gatactaata gcggagttac gagcgcttgc ccctacaatg      480
gtgaatcttc cttttacagg aatctgttgt ggataataaa aataagatct gatccgtact      540
cattgatcaa ggggacatat accaatacag gctctcagcc aatcttatat ttctggggtg      600
tgcaccatcc tccagatgaa gttgagcaag ctaacttgta tggaattggt acccggtatg      660
ttaggatggg aactgaaagt atgaattttg ccaaggtcc tgaaatagca ggcagaccac      720
ctgcgaatgg gcaacgagga agaattgatt attattggtc tgtgttgaag ccaggagaaa      780
ccttgaatgt ggaatccaat ggaaatttaa tagctccttg gtatgcttac aagttcacta      840
gttccagaaa caagggagct attttcaaat cagaccttcc aattgagaat tgtgatgctg      900
tctgtcaaac tttagctgga gcaataaata caaacaaaac cttccaaaat attagtccag      960
```

```
tctggattgg agaatgcccc aaatatgtta aaagtaagag cctaaaacta gcaactggtc   1020
tgagaaatgt tccacaggca gaaacaagag gattgtttgg agcaatagct gggtttatag   1080
aaggaggatg gacaggtatg gtagacggat ggtacggata ccaccatgaa aattcacagg   1140
ggtctggtta tgcagcagat aaagaaagca ctcagaaagc aatagacggg atcaccaata   1200
aagtcaattc aatcattgac aaaatgaaca cacaatttga ggcagtagag catgagttct   1260
caagtctcga aggagaata ggcaatctga acaaagaat ggaagatgga tttttagacg    1320
tgtggacata caatgctgaa cttctggttc tactggaaaa tgagaggact ttggacatgc   1380
atgatgctaa tgtaaagaat ctacatgaaa aggtgaaatc acaattaagg gataatgcaa   1440
aggatttggg taatgggtgt tttgaatttt ggcacaaatg cgacaatgaa tgcatcaact   1500
cagttaaaaa tggcacatat gactacccaa agtaccagga agagagcaga cttaataggc   1560
aggaaataaa atcagtgatg ctggaaaatc tgggagtata ccaaatcctt gctatttata   1620
gtacggtatc gagcagtctg gttttggtgg gactgatcat tgccatgggt ctttggatgt   1680
gctcaaatgg ctcaatgcaa tgcaagatat gtatataatt agaaaaaaac acccttgttt   1740
ctact                                                                1745

<210> SEQ ID NO 38
<211> LENGTH: 1467
<212> TYPE: DNA
<213> ORGANISM: Influenza A virus

<400> SEQUENCE: 38
agcaaaagca ggagtgaaaa tgaatccaaa tcagaggata ataacaattg gatccgtctc     60
tctaactatt gcaacagtgt gtttcctcat gcagattgcc atcctagcaa cgactgtgac   120
actgcatttc aaacaaaatg aatgcagcat tcccgcaaac aaccaagtaa cgccatgtga   180
accaatagta atagagagga cataacaga gatagtgtat ttgaataata ctaccataga   240
aaaagagatt tgtcctgaag tagtagaata caggaattgg tcaaaaccgc aatgtcaaat   300
tacagggttt gctcctttct ccaaggacaa ctcaattcgg cttttctgctg gtggggacat   360 ttggataaca agagaacctt atgtgtcatg cgaccccagt aaatgttatc aatttgcact   420
cgggcagggg accacgctgg acaacaaaca ctcaaatggc acaatacatg atagaatccc   480
tcatcggacc cttttgatga atgaattggg tgttccgttt catttgggaa ccaaacaagt   540
gtgcatagca tggtccagct caagctgtca tgatgggaaa gcatggttgc acgtttgtgt   600
cactggggat gatagaaatg caactgctag tttcatttat gatgggatgc ttattgacag   660
tattggttcc tggtctcaaa atatcctcag gactcaggag tcagaatgcg tttgtatcag   720
tggaacttgt acagtagtaa tgactgatgg aagtgcatca ggaagggcag acactagaat   780
actattcatt agagagggga aaattgtcca cattagtcca ttgtcaggaa gtgctcagca   840
tgtagaggaa tgttcttgtt atccccggta cccaaacgtc agatgtgtct gcagagacaa   900
ctggaagggc tctaataggc ccgttataga tataaatatg gcagattata gcattgactc   960
aagttatgtg tgctcaggac ttgttggaga cacaccaagg aacgatgata gctctagcag   1020
cagcaactgc agggatccta ataatgagag agggaaccca ggagtgaaag gtgggccctt   1080
tgataatgga aatgatgtgt ggatgggaag aacaatcagt aaagattcgc gctcaggcta   1140
tgagaccttc aaggtcattg gtggttgggc cattgctaat tccaagtcac agaccaatag   1200
acaagtcata gttgataata caactggtc tggttattct ggtattttct ctgttgaaag   1260
caaaggctgc atcaataggt gttttttatgt ggagttgata agaggaaggc cacaggagac   1320
```

```
tagagtatgg tggacctcaa acagtattgt cgtattttgt ggcacttcag ggacatatgg    1380
aacaggctca tggcctgatg gggcgaatat cgatttcatg cctatataag ctttcgcaat    1440
tttagaaaaa aactccttgt ttctact                                        1467

<210> SEQ ID NO 39
<211> LENGTH: 566
<212> TYPE: PRT
<213> ORGANISM: Influenza A virus

<400> SEQUENCE: 39

Met Ile Ala Val Ile Ile Ala Val Leu Ala Thr Ala Gly Lys Ser
1               5                   10                  15

Asp Lys Ile Cys Ile Gly Tyr His Ala Asn Asn Ser Thr Thr Gln Val
            20                  25                  30

Asp Thr Ile Leu Glu Lys Asn Val Thr Val Thr His Ser Val Glu Leu
        35                  40                  45

Leu Glu Asn Gln Lys Glu Glu Arg Phe Cys Lys Ile Leu Asn Lys Ala
    50                  55                  60

Pro Leu Asp Leu Arg Gly Cys Thr Ile Glu Gly Trp Ile Leu Gly Asn
65                  70                  75                  80

Pro Gln Cys Asp Leu Leu Leu Gly Asp Gln Ser Trp Ser Tyr Ile Val
                85                  90                  95

Glu Arg Pro Thr Ala Gln Asn Gly Ile Cys Tyr Pro Gly Ile Leu Asn
            100                 105                 110

Glu Val Glu Glu Leu Lys Ala Leu Ile Gly Ser Gly Glu Arg Val Glu
        115                 120                 125

Arg Phe Glu Met Phe Pro Lys Ser Thr Trp Ala Gly Val Asp Thr Ser
    130                 135                 140

Ser Gly Val Thr Lys Ala Cys Pro Tyr Thr Ser Gly Ser Ser Phe Tyr
145                 150                 155                 160

Arg Asn Leu Leu Trp Ile Ile Lys Thr Lys Ser Ala Ala Tyr Pro Val
                165                 170                 175

Ile Lys Gly Thr Tyr Asn Asn Thr Gly Ser Gln Pro Ile Leu Tyr Phe
            180                 185                 190

Trp Gly Val His His Pro Pro Asp Thr Asn Glu Gln Asn Thr Leu Tyr
        195                 200                 205

Gly Ser Gly Asp Arg Tyr Val Arg Met Gly Thr Glu Ser Met Asn Phe
    210                 215                 220

Ala Lys Ser Pro Glu Ile Ala Ala Arg Pro Val Asn Gly Gln Arg
225                 230                 235                 240

Gly Arg Ile Asp Tyr Tyr Trp Ser Val Leu Lys Pro Gly Glu Thr Leu
                245                 250                 255

Asn Val Glu Ser Asn Gly Asn Leu Ile Ala Pro Trp Tyr Ala Tyr Lys
            260                 265                 270

Phe Val Ser Thr Asn Ser Lys Gly Ala Val Phe Lys Ser Asn Leu Pro
        275                 280                 285

Ile Glu Asn Cys Asp Ala Thr Cys Gln Thr Ile Ala Gly Val Leu Arg
    290                 295                 300

Thr Asn Lys Thr Phe Gln Asn Val Ser Pro Leu Trp Ile Gly Glu Cys
305                 310                 315                 320

Pro Lys Tyr Val Lys Ser Glu Ser Leu Arg Leu Ala Thr Gly Leu Arg
                325                 330                 335

Asn Ile Pro Gln Ile Glu Thr Arg Gly Leu Phe Gly Ala Ile Ala Gly
            340                 345                 350
```

-continued

Phe Ile Glu Gly Gly Trp Thr Gly Met Ile Asp Gly Trp Tyr Gly Tyr
            355                 360                 365

His His Glu Asn Ser Gln Gly Ser Gly Tyr Ala Ala Asp Arg Glu Ser
        370                 375                 380

Thr Gln Arg Ala Ile Asp Gly Ile Thr Asn Lys Val Asn Ser Ile Ile
385                 390                 395                 400

Asp Lys Met Asn Thr Gln Phe Glu Ala Ile Asp His Glu Phe Ser Asn
                405                 410                 415

Leu Glu Arg Arg Ile Asp Ser Leu Asn Lys Arg Met Glu Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Leu His Asp Ala Asn Val Lys Asn Leu Tyr Glu
    450                 455                 460

Lys Val Lys Ser Gln Leu Arg Asp Asn Ala Asn Asp Leu Gly Asn Gly
465                 470                 475                 480

Cys Phe Glu Phe Trp His Lys Cys Asp Asn Glu Cys Ile Glu Ser Val
                485                 490                 495

Lys Asn Gly Thr Tyr Asp Tyr Pro Lys Tyr Gln Asp Glu Ser Lys Leu
            500                 505                 510

Asn Arg Gln Glu Ile Glu Ser Val Lys Leu Glu Asn Leu Gly Val Tyr
        515                 520                 525

Gln Ile Leu Ala Ile Tyr Ser Thr Val Ser Ser Ser Leu Val Leu Val
    530                 535                 540

Gly Leu Ile Ile Ala Met Gly Leu Trp Met Cys Ser Asn Gly Ser Met
545                 550                 555                 560

Gln Cys Arg Ile Cys Ile
                565

<210> SEQ ID NO 40
<211> LENGTH: 470
<212> TYPE: PRT
<213> ORGANISM: Influenza A virus

<400> SEQUENCE: 40

Met Asn Pro Asn Gln Lys Ile Leu Cys Thr Ser Ala Thr Ala Ile Ala
1               5                   10                  15

Ile Gly Thr Ile Ala Val Leu Ile Gly Ile Ala Asn Leu Gly Leu Asn
            20                  25                  30

Ile Gly Leu His Leu Lys Pro Ser Cys Asn Cys Ser Asn Pro Pro Pro
        35                  40                  45

Glu Thr Thr Asn Val Ser Gln Thr Ile Ile Asn Asn Tyr Tyr Asn Glu
    50                  55                  60

Thr Asn Val Thr Gln Ile Ser Asn Thr Asn Ile Gln His Met Gly Gly
65                  70                  75                  80

Thr Glu Lys Asp Phe Asn Asn Leu Thr Lys Gly Leu Cys Thr Ile Asn
                85                  90                  95

Ser Trp His Ile Phe Gly Lys Asp Asn Ala Ile Arg Ile Gly Glu Asn
            100                 105                 110

Ser Asp Val Leu Val Thr Arg Glu Pro Tyr Val Ser Cys Asp Pro Asp
        115                 120                 125

Glu Cys Arg Phe Tyr Ala Leu Ser Gln Gly Thr Thr Ile Arg Gly Lys
    130                 135                 140

His Ser Asn Gly Thr Ile His Asp Arg Ser Gln Tyr Arg Ala Leu Val
145                 150                 155                 160

Ser Trp Pro Leu Ser Ser Pro Thr Val Tyr Asn Thr Arg Val Glu
                165                 170                 175

Cys Ile Gly Trp Ser Ser Thr Ser Cys His Asp Gly Lys Ala Arg Met
            180                 185                 190

Ser Ile Cys Val Ser Gly Pro Asn Asn Asn Ala Ser Ala Val Ile Trp
        195                 200                 205

Tyr Lys Gly Arg Pro Ile Thr Glu Ile Asn Thr Trp Ala Arg Asn Ile
    210                 215                 220

Leu Arg Thr Gln Glu Ser Glu Cys Val Cys His Asn Gly Ile Cys Pro
225                 230                 235                 240

Val Val Phe Thr Asp Gly Ser Ala Thr Gly Pro Ala Glu Thr Arg Ile
                245                 250                 255

Tyr Tyr Phe Lys Glu Gly Lys Ile Leu Lys Trp Glu Pro Leu Thr Gly
            260                 265                 270

Thr Ala Lys His Ile Glu Glu Cys Ser Cys Tyr Gly Lys Asp Ser Glu
        275                 280                 285

Ile Thr Cys Thr Cys Arg Asp Asn Trp Gln Gly Ser Asn Arg Pro Val
    290                 295                 300

Ile Gln Ile Asn Pro Thr Met Met Thr His Thr Ser Gln Tyr Ile Cys
305                 310                 315                 320

Ser Pro Val Leu Thr Asp Asn Pro Arg Pro Asn Asp Pro Thr Val Gly
                325                 330                 335

Lys Cys Asn Asp Pro Tyr Pro Gly Asn Asn Asn Asn Gly Val Lys Gly
            340                 345                 350

Phe Ser Tyr Leu Asp Gly Asp Asn Thr Trp Leu Gly Arg Thr Ile Ser
        355                 360                 365

Thr Ala Ser Arg Ser Gly Tyr Glu Met Leu Lys Val Pro Asn Ala Leu
    370                 375                 380

Thr Asp Asp Arg Ser Lys Pro Thr Gln Gly Gln Thr Ile Val Leu Asn
385                 390                 395                 400

Thr Asp Trp Ser Gly Tyr Ser Gly Ser Phe Ile Asp Tyr Trp Ala Lys
                405                 410                 415

Gly Glu Cys Tyr Arg Ala Cys Phe Tyr Val Glu Leu Ile Arg Gly Arg
            420                 425                 430

Pro Lys Glu Asp Lys Val Trp Trp Thr Ser Asn Ser Ile Val Ser Met
        435                 440                 445

Cys Ser Ser Thr Glu Phe Leu Gly Gln Trp Asn Trp Pro Asp Gly Ala
    450                 455                 460

Lys Ile Glu Tyr Phe Leu
465                 470

<210> SEQ ID NO 41
<211> LENGTH: 567
<212> TYPE: PRT
<213> ORGANISM: Influenza A virus

<400> SEQUENCE: 41

Met Ile Ala Ile Ile Val Ile Ala Ile Leu Ala Ala Ala Gly Lys Ser
1               5                   10                  15

Asp Lys Ile Cys Ile Gly Tyr His Ala Asn Asn Ser Thr Thr Gln Val
            20                  25                  30

Asp Thr Ile Leu Glu Lys Asn Val Thr Val Thr His Ser Ile Glu Leu
        35                  40                  45

Leu Glu Asn Gln Lys Glu Glu Arg Phe Cys Lys Ile Leu Asn Lys Ala
    50                  55                  60

```
Pro Leu Asp Leu Arg Glu Cys Thr Ile Glu Gly Trp Ile Leu Gly Asn
 65                  70                  75                  80

Pro Gln Cys Asp Leu Leu Gly Asp Gln Ser Trp Ser Tyr Ile Val
                 85                  90                  95

Glu Arg Pro Thr Ala Gln Asn Gly Ile Cys Tyr Pro Gly Thr Leu Asn
                100                 105                 110

Glu Val Glu Glu Leu Arg Ala Leu Ile Gly Ser Gly Glu Arg Val Glu
            115                 120                 125

Arg Phe Glu Met Phe Pro Gln Ser Thr Trp Gln Gly Val Asp Thr Asn
        130                 135                 140

Ser Gly Thr Thr Arg Ser Cys Pro Tyr Ser Thr Gly Asp Pro Ser Phe
145                 150                 155                 160

Tyr Arg Asn Leu Leu Trp Ile Ile Lys Thr Lys Thr Ala Glu Tyr Pro
                165                 170                 175

Val Ile Lys Gly Ile Tyr Asn Asn Thr Gly Thr Gln Pro Ile Leu Tyr
            180                 185                 190

Phe Trp Gly Val His His Pro Pro Asn Thr Asp Glu Gln Asp Thr Leu
        195                 200                 205

Tyr Gly Ser Gly Asp Arg Tyr Val Arg Met Gly Thr Glu Ser Met Asn
210                 215                 220

Phe Ala Lys Ser Pro Glu Ile Ala Ala Arg Pro Ala Val Asn Gly Gln
225                 230                 235                 240

Arg Gly Arg Ile Asp Tyr Tyr Trp Ser Val Leu Lys Pro Gly Glu Thr
                245                 250                 255

Leu Asn Val Glu Ser Asn Gly Asn Leu Ile Ala Pro Trp Tyr Ala Tyr
            260                 265                 270

Lys Phe Val Asn Thr Asn Ser Lys Gly Ala Val Phe Arg Ser Asp Leu
        275                 280                 285

Pro Ile Glu Asn Cys Asp Ala Thr Cys Gln Thr Ile Ala Gly Val Leu
290                 295                 300

Arg Thr Asn Lys Thr Phe Gln Asn Val Ser Pro Leu Trp Ile Gly Glu
305                 310                 315                 320

Cys Pro Lys Tyr Val Lys Ser Glu Ser Leu Arg Leu Ala Thr Gly Leu
                325                 330                 335

Arg Asn Val Pro Gln Ile Glu Thr Arg Gly Leu Phe Gly Ala Ile Ala
            340                 345                 350

Gly Phe Ile Glu Gly Gly Trp Thr Gly Met Ile Asp Gly Trp Tyr Gly
        355                 360                 365

Tyr His His Glu Asn Ser Gln Gly Ser Gly Tyr Ala Ala Asp Arg Glu
370                 375                 380

Ser Thr Gln Lys Ala Val Asn Arg Ile Thr Asn Lys Val Asn Ser Ile
385                 390                 395                 400

Ile Asn Lys Met Asn Thr Gln Phe Glu Ala Val Asp His Glu Phe Ser
                405                 410                 415

Asn Leu Glu Arg Arg Ile Asp Asn Leu Asn Lys Arg Met Gln Asp Gly
            420                 425                 430

Phe Leu Asp Val Trp Thr Tyr Asn Ala Glu Leu Leu Val Leu Leu Glu
        435                 440                 445

Asn Glu Arg Thr Leu Asp Met His Asp Ala Asn Val Lys Asn Leu His
450                 455                 460

Glu Lys Val Lys Ser Gln Leu Arg Asp Asn Ala Asn Asp Leu Gly Asn
465                 470                 475                 480

Gly Cys Phe Glu Phe Trp His Lys Cys Asp Asn Glu Cys Ile Glu Ser
```

```
                      485                 490                 495
Val Lys Asn Gly Thr Tyr Asp Tyr Pro Lys Tyr Gln Thr Glu Ser Lys
                500                 505                 510

Leu Asn Arg Leu Lys Ile Glu Ser Val Lys Leu Glu Asn Leu Gly Val
            515                 520                 525

Tyr Gln Ile Leu Ala Ile Tyr Ser Thr Val Ser Ser Ser Leu Val Leu
        530                 535                 540

Val Gly Leu Ile Met Ala Met Gly Leu Trp Met Cys Ser Asn Gly Ser
545                 550                 555                 560

Met Gln Cys Asn Val Cys Ile
                565

<210> SEQ ID NO 42
<211> LENGTH: 450
<212> TYPE: PRT
<213> ORGANISM: Influenza A virus

<400> SEQUENCE: 42

Met Asn Pro Asn Gln Lys Ile Ile Thr Ile Gly Ser Ile Cys Met Val
1               5                   10                  15

Val Gly Ile Ile Ser Leu Met Leu Gln Ile Gly Asn Ile Ile Ser Ile
            20                  25                  30

Trp Val Ser His Ile Ile Gln Thr Gly His Pro Asn Gln Pro Gly Pro
        35                  40                  45

Cys Asn Gln Ser Ile Asn Phe Tyr Thr Glu Gln Ala Ala Ala Ser Val
    50                  55                  60

Thr Leu Ala Gly Asn Ser Ser Leu Cys Pro Ile Ser Gly Trp Ala Ile
65                  70                  75                  80

Tyr Ser Lys Asp Asn Ser Ile Arg Ile Gly Ser Lys Gly Asp Val Phe
                85                  90                  95

Val Met Arg Glu Pro Phe Val Ser Cys Ser His Leu Glu Cys Arg Thr
            100                 105                 110

Phe Phe Leu Thr Gln Gly Ala Leu Leu Asn Asp Lys His Ser Asn Gly
        115                 120                 125

Thr Val Lys Asp Arg Ser Pro Tyr Arg Thr Leu Met Ser Cys Pro Val
    130                 135                 140

Gly Glu Ala Pro Ser Pro Tyr Asn Ser Arg Phe Glu Ser Val Ala Trp
145                 150                 155                 160

Ser Ala Ser Ala Cys His Asp Gly Ile Ser Trp Leu Thr Ile Gly Ile
                165                 170                 175

Ser Gly Pro Asp Asn Gly Ala Val Ala Val Leu Lys Tyr Asn Gly Ile
            180                 185                 190

Ile Thr Asp Thr Ile Lys Ser Trp Arg Asn Asn Ile Leu Arg Thr Gln
        195                 200                 205

Glu Ser Glu Cys Ala Cys Val Asn Gly Ser Cys Phe Thr Val Met Thr
    210                 215                 220

Asp Gly Pro Ser Asn Glu Gln Ala Ser Tyr Lys Ile Phe Lys Ile Glu
225                 230                 235                 240

Lys Gly Lys Val Val Lys Ser Val Glu Leu Asn Ala Pro Asn Tyr His
                245                 250                 255

Tyr Glu Glu Cys Ser Cys Tyr Pro Asp Ala Gly Glu Ile Thr Cys Val
            260                 265                 270

Cys Arg Asp Asn Trp His Gly Ser Asn Arg Pro Trp Val Ser Phe Asn
        275                 280                 285

Gln Asn Leu Glu Tyr Gln Ile Gly Tyr Ile Cys Ser Gly Val Phe Gly
```

```
                   290                 295                 300
Asp Ser Pro Arg Pro Asn Asp Gly Thr Gly Ser Cys Gly Pro Val Ser
305                 310                 315                 320

Leu Asn Gly Glu Tyr Gly Val Lys Gly Phe Ser Phe Lys Tyr Gly Asp
                325                 330                 335

Gly Val Trp Ile Gly Arg Thr Lys Ser Thr Ser Arg Ser Gly Phe
            340                 345                 350

Glu Met Ile Trp Asp Pro Asn Gly Trp Thr Glu Thr Asp Ser Asn Phe
            355                 360                 365

Ser Leu Lys Gln Asp Ile Ile Ala Ile Thr Asp Trp Ser Gly Tyr Ser
        370                 375                 380

Gly Ser Phe Val Gln His Pro Glu Leu Thr Gly Leu Asn Cys Met Arg
385                 390                 395                 400

Pro Cys Phe Trp Val Glu Leu Ile Arg Gly Arg Pro Lys Glu Lys Thr
                405                 410                 415

Ile Trp Thr Ser Gly Ser Ser Ile Ser Phe Cys Gly Val Asn Ser Asp
                420                 425                 430

Thr Val Gly Trp Ser Trp Pro Asp Gly Ala Glu Val Pro Phe Thr Ile
            435                 440                 445

Asp Lys
    450

<210> SEQ ID NO 43
<211> LENGTH: 566
<212> TYPE: PRT
<213> ORGANISM: Influenza A virus

<400> SEQUENCE: 43

Met Ile Ala Ile Ile Ile Leu Ala Ile Val Val Ser Thr Ser Lys Ser
1               5                   10                  15

Asp Arg Ile Cys Ile Gly Tyr His Ala Asn Asn Ser Thr Thr Gln Val
            20                  25                  30

Asp Thr Ile Leu Glu Lys Asn Val Thr Val Thr His Ser Val Glu Leu
        35                  40                  45

Leu Glu Asn Gln Lys Glu Asn Arg Phe Cys Arg Val Leu Asn Lys Ala
    50                  55                  60

Pro Leu Asp Leu Met Asp Cys Thr Thr Glu Gly Trp Ile Leu Gly Asn
65                  70                  75                  80

Pro Arg Cys Asp Asn Leu Leu Gly Asp Gln Ser Trp Ser Tyr Ile Val
                85                  90                  95

Glu Arg Pro Asp Ala Gln Asn Gly Ile Cys Tyr Pro Gly Val Leu Lys
            100                 105                 110

Glu Thr Glu Glu Leu Lys Ala Leu Ile Gly Ser Ile Asp Ser Ile Gln
        115                 120                 125

Arg Phe Glu Met Phe Pro Lys Ser Thr Trp Thr Gly Val Asp Thr Asn
    130                 135                 140

Ser Gly Val Thr Ser Ala Cys Pro Tyr Asn Gly Glu Ser Ser Phe Tyr
145                 150                 155                 160

Arg Asn Leu Leu Trp Ile Ile Lys Ile Arg Ser Asp Pro Tyr Ser Leu
                165                 170                 175

Ile Lys Gly Thr Tyr Thr Asn Thr Gly Ser Gln Pro Ile Leu Tyr Phe
            180                 185                 190

Trp Gly Val His His Pro Pro Asp Glu Val Glu Gln Ala Asn Leu Tyr
        195                 200                 205

Gly Ile Gly Thr Arg Tyr Val Arg Met Gly Thr Glu Ser Met Asn Phe
```

```
                210             215               220
Ala Lys Gly Pro Glu Ile Ala Gly Arg Pro Ala Asn Gly Gln Arg
225                 230                 235                 240

Gly Arg Ile Asp Tyr Tyr Trp Ser Val Leu Lys Pro Gly Glu Thr Leu
                245                 250                 255

Asn Val Glu Ser Asn Gly Asn Leu Ile Ala Pro Trp Tyr Ala Tyr Lys
                260                 265                 270

Phe Thr Ser Ser Arg Asn Lys Gly Ala Ile Phe Lys Ser Asp Leu Pro
                275                 280                 285

Ile Glu Asn Cys Asp Ala Val Cys Gln Thr Leu Ala Gly Ala Ile Asn
                290                 295                 300

Thr Asn Lys Thr Phe Gln Asn Ile Ser Pro Val Trp Ile Gly Glu Cys
305                 310                 315                 320

Pro Lys Tyr Val Lys Ser Lys Ser Leu Lys Leu Ala Thr Gly Leu Arg
                325                 330                 335

Asn Val Pro Gln Ala Glu Thr Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His His Glu Asn Ser Gln Gly Ser Gly Tyr Ala Ala Asp Lys Glu Ser
                370                 375                 380

Thr Gln Lys Ala Ile Asp Gly Ile Thr Asn Lys Val Asn Ser Ile Ile
385                 390                 395                 400

Asp Lys Met Asn Thr Gln Phe Glu Ala Val Glu His Glu Phe Ser Ser
                405                 410                 415

Leu Glu Arg Arg Ile Gly Asn Leu Asn Lys Arg Met Glu Asp Gly Phe
                420                 425                 430

Leu Asp Val Trp Thr Tyr Asn Ala Glu Leu Leu Val Leu Leu Glu Asn
                435                 440                 445

Glu Arg Thr Leu Asp Met His Asp Ala Asn Val Lys Asn Leu His Glu
                450                 455                 460

Lys Val Lys Ser Gln Leu Arg Asp Asn Ala Lys Asp Leu Gly Asn Gly
465                 470                 475                 480

Cys Phe Glu Phe Trp His Lys Cys Asp Asn Glu Cys Ile Asn Ser Val
                485                 490                 495

Lys Asn Gly Thr Tyr Asp Tyr Pro Lys Tyr Gln Glu Glu Ser Arg Leu
                500                 505                 510

Asn Arg Gln Glu Ile Lys Ser Val Met Leu Glu Asn Leu Gly Val Tyr
                515                 520                 525

Gln Ile Leu Ala Ile Tyr Ser Thr Val Ser Ser Ser Leu Val Leu Val
                530                 535                 540

Gly Leu Ile Ile Ala Met Gly Leu Trp Met Cys Ser Asn Gly Ser Met
545                 550                 555                 560

Gln Cys Lys Ile Cys Ile
                565

<210> SEQ ID NO 44
<211> LENGTH: 469
<212> TYPE: PRT
<213> ORGANISM: Influenza A virus

<400> SEQUENCE: 44

Met Asn Pro Asn Gln Arg Ile Ile Thr Ile Gly Ser Val Ser Leu Thr
1               5                   10                  15

Ile Ala Thr Val Cys Phe Leu Met Gln Ile Ala Ile Leu Ala Thr Thr
```

```
                     20                  25                  30
Val Thr Leu His Phe Lys Gln Asn Glu Cys Ser Ile Pro Ala Asn Asn
             35                  40                  45

Gln Val Thr Pro Cys Glu Pro Ile Val Ile Glu Arg Asn Ile Thr Glu
             50                  55                  60

Ile Val Tyr Leu Asn Asn Thr Thr Ile Glu Lys Glu Ile Cys Pro Glu
 65                  70                  75                  80

Val Val Glu Tyr Arg Asn Trp Ser Lys Pro Gln Cys Gln Ile Thr Gly
                     85                  90                  95

Phe Ala Pro Phe Ser Lys Asp Asn Ser Ile Arg Leu Ser Ala Gly Gly
                 100                 105                 110

Asp Ile Trp Ile Thr Arg Glu Pro Tyr Val Ser Cys Asp Pro Ser Lys
             115                 120                 125

Cys Tyr Gln Phe Ala Leu Gly Gln Gly Thr Thr Leu Asp Asn Lys His
             130                 135                 140

Ser Asn Gly Thr Ile His Asp Arg Ile Pro His Arg Thr Leu Leu Met
145                 150                 155                 160

Asn Glu Leu Gly Val Pro Phe His Leu Gly Thr Lys Gln Val Cys Ile
                 165                 170                 175

Ala Trp Ser Ser Ser Cys His Asp Gly Lys Ala Trp Leu His Val
                 180                 185                 190

Cys Val Thr Gly Asp Asp Arg Asn Ala Thr Ala Ser Phe Ile Tyr Asp
             195                 200                 205

Gly Met Leu Ile Asp Ser Ile Gly Ser Trp Ser Gln Asn Ile Leu Arg
         210                 215                 220

Thr Gln Glu Ser Glu Cys Val Cys Ile Ser Gly Thr Cys Thr Val Val
225                 230                 235                 240

Met Thr Asp Gly Ser Ala Ser Gly Arg Ala Asp Thr Arg Ile Leu Phe
                 245                 250                 255

Ile Arg Glu Gly Lys Ile Val His Ile Ser Pro Leu Ser Gly Ser Ala
             260                 265                 270

Gln His Val Glu Glu Cys Ser Cys Tyr Pro Arg Tyr Pro Asn Val Arg
             275                 280                 285

Cys Val Cys Arg Asp Asn Trp Lys Gly Ser Asn Arg Pro Val Ile Asp
             290                 295                 300

Ile Asn Met Ala Asp Tyr Ser Ile Asp Ser Ser Tyr Val Cys Ser Gly
305                 310                 315                 320

Leu Val Gly Asp Thr Pro Arg Asn Asp Asp Ser Ser Ser Ser Ser Asn
                 325                 330                 335

Cys Arg Asp Pro Asn Asn Glu Arg Gly Asn Pro Gly Val Lys Gly Trp
             340                 345                 350

Ala Phe Asp Asn Gly Asn Asp Val Trp Met Gly Arg Thr Ile Ser Lys
             355                 360                 365

Asp Ser Arg Ser Gly Tyr Glu Thr Phe Lys Val Ile Gly Gly Trp Ala
         370                 375                 380

Ile Ala Asn Ser Lys Ser Gln Thr Asn Arg Gln Val Ile Val Asp Asn
385                 390                 395                 400

Asn Asn Trp Ser Gly Tyr Ser Gly Ile Phe Ser Val Glu Ser Lys Gly
                 405                 410                 415

Cys Ile Asn Arg Cys Phe Tyr Val Glu Leu Ile Arg Gly Arg Pro Gln
             420                 425                 430

Glu Thr Arg Val Trp Trp Thr Ser Asn Ser Ile Val Phe Cys Gly
             435                 440                 445
```

```
Thr Ser Gly Thr Tyr Gly Thr Gly Ser Trp Pro Asp Gly Ala Asn Ile
    450                 455                 460

Asp Phe Met Pro Ile
465

<210> SEQ ID NO 45
<211> LENGTH: 1464
<212> TYPE: DNA
<213> ORGANISM: Influenza A virus

<400> SEQUENCE: 45
agcaaaagca gggtgatcga gaatgaatcc aaatcagaaa ctatttgcat tatctggagt      60
ggcaatagca cttagtgtac tgaacttatt gataggaatc tcaaacgtcg gattgaacgt     120
atctctacat ctaaaggaaa aaggacccaa acaggaggag aatttaacat gcacgaccat     180
taatcaaaac aacactactg tagtagaaaa cacatatgta aataatacaa caataattac     240
caagggaact gatttgaaaa caccaagcta tctgctgttg aacaagagcc tgtgcaatgt     300
tgaagggtgg gtcgtgatag caaaagacaa tgcagtaaga tttggggaaa gtgaacaaat     360
cattgttacc agggagccat atgtatcatg cgacccaaca ggatgcaaaa tgtatgcctt     420
gcaccaaggg actaccatta ggaacaaaca ttcaaatgga acgattcatg acagaacagc     480
tttcagaggt ctcatctcca ctccattggg cactccacca accgtaagta acagtgactt     540
tatgtgtgtt ggatggtcaa gcacaacttg ccatgatggg attgctagga tgactatctg     600
tatacaagga ataatgaca atgctacagc aacggtttat acaacagaa ggctgaccac     660 taccattaag acctgggcca gaaacattct gaggactcaa gaatcagaat gtgtgtgcca     720
caatggcaca tgtgcagttg taatgaccga cggatcggct agtagtcaag cctatacaaa     780
agtaatgtat ttccacaagg gattagtagt taaggaggag gagttaaggg gatcagccag     840
acatattgag gaatgctcct gttatggaca caatcaaaag gtgacctgtg tgtgcagaga     900
taactggcag ggagcaaaca ggcctattat agaaattgat atgagcacat ggagcacac     960 aagtagatac gtgtgcactg gaattctcac agacaccagc agacctgggg acaaatctag    1020
tggtgattgt tccaatccaa taactgggag tcccggcgtt ccgggagtga agggattcgg    1080
gtttctaaat ggggataaca catggcttgg taggaccatc agccccagat caagaagtgg    1140
attcgaaatg ttgaaaatac ctaatgcagg tactgatccc aattctagaa tagcagaacg    1200
acaggaaatt gtcgacaata caattggtc aggctattcc ggaagcttta ttgactattg    1260
gaatgataac agtgaatgct acaatccatg cttttacgta gagttaatta gaggaagacc    1320
cgaagaggct aaatacgtat ggtgggcaag taacagtcta attgccctat gtggaagccc    1380
attcccagtt gggtctggtt ccttccccga tggggcacaa atccaatact tttcgtaaaa    1440
tgcaaaaaca cccttgtttc tact                                            1464
```

INFLUENZA HEMAGGLUTININ AND NEURAMINIDASE VARIANTS

CROSS REFERENCE TO RELATED APPLICATIONS

This patent application is a continuation of U.S. patent application Ser. No. 11/836,413 filed on Aug. 9, 2007 entitled INFLUENZA HEMAGGLUTININ AND NEURAMINIDASE VARIANTS, naming Chin-Fen Yang, George Kemble, Kanta Subbaro and Brian Murphy as inventors, now abandoned, which claims the benefit under 35 U.S.C. §119 (e) of U.S. Provisional Application No. 60/821,832 filed Aug. 9, 2006 entitled INFLUENZA HEMAGGLUTININ AND NEURAMINIDASE VARIANTS, naming Chin-Fen Yang, George Kemble, Kanta Subbaro and Brian Murphy as inventors and U.S. Provisional Application No. 60/942,804, filed Jun. 8, 2007 entitled INFLUENZA HEMAGGLUTININ AND NEURAMINIDASE VARIANTS, naming Chin-Fen Yang, George Kemble, Kanta Subbaro and Brian Murphy as inventors. The entirety of each of these patent applications is incorporated herein by reference.

BACKGROUND OF THE INVENTION

Vaccines against various and evolving strains of influenza are important from a community health stand point, as well as commercially, since each year numerous individuals are infected with different strains and types of influenza virus. Infants, the elderly, those without adequate health care and immuno-compromised persons are at special risk of death from such infections. Compounding the problem of influenza infections is that novel influenza strains evolve readily and can spread amongst various species, thereby necessitating the continuous production of new vaccines.

Numerous vaccines capable of producing a protective immune response specific for such different and influenza viruses/virus strains have been produced for over 50 years and include whole virus vaccines, split virus vaccines, surface antigen vaccines and live attenuated virus vaccines. However, while appropriate formulations of any of these vaccine types are capable of producing a systemic immune response, live attenuated virus vaccines have the advantage of also being able to stimulate local mucosal immunity in the respiratory tract. Considerable work in the production of influenza viruses, and fragments thereof, for production of vaccines has been done by the present inventors and co-workers; see, e.g., U.S. Application Nos. 60/420,708, filed Oct. 23, 2002; 60/574,117, filed May 24, 2004; 10/423,828, filed Apr. 25, 2003; 60/578,962, filed Jun. 12, 2004; and 10/870,690 filed Jun. 16, 2004, the disclosure of which is incorporated by reference herein.

Because of the continual emergence (or re-emergence) of different influenza strains, new influenza vaccines are continually desired. Such vaccines typically are created using antigenic moieties of the newly emergent virus strains, thus, polypeptides and polynucleotides of novel, newly emergent, or newly re-emergent virus strains (especially sequences of antigenic genes) are highly desirable.

The present invention provides new and/or newly isolated influenza hemagglutinin and neuraminidase variants that are capable of use in production of numerous types of vaccines as well as in research, diagnostics, etc. Numerous other benefits will become apparent upon review of the following.

SUMMARY OF THE INVENTION

In some aspects herein, the invention comprises an isolated or recombinant polypeptide that is selected from: any one of the polypeptides encoded by SEQ ID NO:1 through SEQ ID NO:10 or SEQ ID NO:21 through SEQ ID NO:26 or SEQ ID NO:33 through SEQ ID NO:38; any one of the polypeptides of SEQ ID NO:11 through SEQ ID NO:20 or SEQ ID NO:27 through SEQ ID NO:32 or SEQ ID NO:39 through SEQ ID NO:44; only the open reading frame encoding the polypeptides of SEQ ID NO:11 through SEQ ID NO:20 or SEQ ID NO:27 through SEQ ID NO:32 or SEQ ID NO:39 through SEQ ID NO:44; any alternative (e.g., the mature form without the signal peptide, or without the 5' and 3' sequences outside of the open reading frame, or the sequences as expressed on the surface of a virus (e.g., influenza)) form of the polypeptides of SEQ ID NO:11-20 or SEQ ID NO:27-32 or SEQ ID NO:39-44; any polypeptide that is encoded by a polynucleotide sequence which hybridizes under highly stringent conditions over substantially the entire length of a polynucleotide sequence of SEQ ID NO:1 through SEQ ID NO:10 or SEQ ID NO:21 through SEQ ID NO:26, SEQ ID NO:33-38, or SEQ ID NO:45; any polypeptide that is encoded by a polynucleotide sequence which hybridizes under highly stringent conditions to a polynucleotide sequence of SEQ ID NO:1 through SEQ ID NO:10 or SEQ ID NO:21 through SEQ ID NO:26 or SEQ ID NO:33 through SEQ ID NO:38, or SEQ ID NO:45; and, a fragment of any of the above wherein the sequence comprises a hemagglutinin or neuraminidase polypeptide, or a fragment of a hemagglutinin or neuraminidase polypeptide, preferably where the fragments generate an antibody that specifically binds a full length polypeptide of the invention. In various embodiments, the isolated or recombinant polypeptides of the invention are substantially identical to about 300 contiguous amino acid residues of any of the above polypeptides. In yet other embodiments, the invention comprises isolated or recombinant polypeptides, that comprise an amino acid sequence that is substantially identical over at least about 350 amino acids; over at least about 400 amino acids; over at least about 450 amino acids; over at least about 500 amino acids; over at least about 520 amino acids; over at least about 550 amino acids; over at least about 559 amino acids; over at least about 565 amino acids; or over at least about 566 amino acids contiguous of any of the above polypeptides. In some embodiments, the polypeptide sequence (e.g., as listed in "SEQUENCES" herein) comprises less than 565, 559, etc amino acids. In such embodiments, the shorter listed polypeptides optionally comprise less than 565, 559, etc. amino acids. In yet other embodiments, the polypeptides of the invention optionally comprise fusion proteins, proteins with a leader sequence, a precursor polypeptide, proteins with a secretion signal or a localization signal, or proteins with an epitope tag, an E-tag, or a His epitope tag. In still other embodiments, the invention comprises a polypeptide comprising a sequence having at least 85%, at least 90%, at least 93%, at least 95%, at least 98%, at least 98.5%, at least 99%, at least 99.2%, at least 99.4%, at least 99.6%, at least 99.8%, or at least 99.9% sequence identity to at least one polypeptide listed above. The hemagglutinin sequences of the invention can comprise both those sequences with unmodified and modified polybasic cleavage sites (thereby allowing growth of the viruses in eggs). The hemagglutinin polypeptide sequences of SEQ ID NOS:11, 13, 15, 17, 19, 27, 29, 31, 39, 41, or 43 comprise the endogenous amino terminal signal peptide sequences, however, the hemagglutinin polypeptide sequences of the invention also include the mature (amino terminal signal peptide cleaved) form of the hemagglutinin polypeptides. The cleavage sites of any hemagglutinin polypeptide sequence of any influenza strain can be routinely measured or predicted using any number of methods in the art.

In other aspects, the invention comprises a composition with one or more polypeptide listed above, or fragments thereof. The invention also includes polypeptides that are specifically bound by a polyclonal antisera raised against at least 1 antigen that comprises at least one amino acid sequence described above, or a fragment thereof. Such antibodies specific for the polypeptides described above are also features of the invention. The polypeptides of the invention are optionally immunogenic.

The invention also encompasses immunogenic compositions comprising an immunologically effective amount of one or more of any of the polypeptides described above as well as methods for stimulating the immune system of an individual to produce a protective immune response against influenza virus by administering to the individual an immunologically effective amount of any of the above polypeptides in a physiologically acceptable carrier.

Additionally, the invention includes recombinant influenza virus that comprises one or more of the polypeptides or polynucleotides above, in addition to immunogenic compositions comprising an immunologically effective amount of such recombinant influenza virus. Methods for stimulating the immune system of an individual to produce a protective immune response against influenza virus, through administering an immunologically effective amount of such recombinant influenza virus in a physiologically acceptable carrier are also part of the invention.

In other aspects, the invention comprises an isolated or recombinant nucleic acid that is selected from: any one of the polynucleotide sequences SEQ ID NO:1 through SEQ ID NO:10 or SEQ ID NO:21 through SEQ ID NO:26 or SEQ ID NO:33 through SEQ ID NO:38, or SEQ ID NO:45 (or complementary sequences thereof), any one of the polynucleotide sequences encoding a polypeptide of SEQ ID NO:11 through SEQ ID NO:20 or SEQ ID NO:27 through SEQ ID NO:32 or SEQ ID NO:39 through SEQ ID NO:44 (or complementary polynucleotide sequences thereof), a polynucleotide sequence which hybridizes under highly stringent conditions over substantially the entire length of any of the above polynucleotide sequences, and a polynucleotide sequence comprising all or a fragment of any of such polynucleotide sequences wherein the sequence preferably encodes a hemagglutinin or neuraminidase polypeptide or a fragment of a hemagglutinin or neuraminidase polypeptide. The invention also includes an isolated or recombinant nucleic acid that encodes an amino acid sequence which is substantially identical over at least about 300 amino acids of any polypeptide encoded by the above nucleic acids, or over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids of any polypeptide encoded by the above nucleic acids. Again, in situations wherein the amino acid is less than, e.g., 566, 565, 559, etc. in length (e.g., see, "SEQUENCES") then it should be understood that the length is optionally less than 566, 565, 559, etc. The invention also includes any of the above nucleic acids that comprise a polynucleotide encoding a hemagglutinin or neuraminidase polypeptide, or one or more fragments of one or more hemagglutinin or neuraminidase polypeptide. Other aspects of the invention include isolated or recombinant nucleic acids that encode a polypeptide (optionally a hemagglutinin or neuraminidase polypeptide) whose sequence has at least 98% identity, at least 98.5% identity, at least 99% identity, at least 99.2% identity, at least 99.4% identity, at least 99.6% identity, at least 99.8% identity, or at least 99.9% identity to at least one of the above described polynucleotides. The invention also includes isolated or recombinant nucleic acids encoding a polypeptide of hemagglutinin or neuraminidase produced by mutating or recombining one or more above described polynucleotide sequences. The polynucleotide sequences of the invention can optionally comprise one or more of, e.g., a leader sequence, a precursor sequence, or an epitope tag sequence or the like, and can optionally encode a fusion protein (e.g., with one or more additional nucleic acid sequences).

In yet other embodiments, the invention comprises a composition of matter having two or more above described nucleic acids (e.g., a library comprising at least about 2, 5, 10, 50 or more nucleic acids). Such compositions can optionally be produced by cleaving one or more above described nucleic acid (e.g., mechanically, chemically, enzymatically with a restriction endonuclease/RNAse/DNAse, etc.). Other compositions of the invention include, e.g., compositions produced by incubating one or more above described nucleic acid in the presence of deoxyribonucleotide triphosphates and a thermostable nucleic acid polymerase.

The invention also encompasses cells comprising at least one of the above described nucleic acids, or a cleaved or amplified fragment or product thereof. Such cells can optionally express a polypeptide encoded by such nucleic acid. Other embodiments of the invention include vectors (e.g., plasmids, cosmids, phage, viruses, virus fragments, etc.) comprising any of above described nucleic acids. Such vectors can optionally comprise an expression vector. Preferred expression vectors of the invention include, but are not limited to, vectors comprising pol I promoter and terminator sequences or vectors using both the pol I and pol II promoters "the polI/polII promoter system" (e.g., Zobel et al., Nucl. Acids Res. 1993, 21:3607; US20020164770; Neumann et al., Proc. Natl. Acad. Sci. USA 1999, 96:9345; Fodor et al., J. Virol. 1999, 73:9679; and US20030035814). Cells transduced by such vectors are also within the current invention.

In some embodiments, the invention encompasses a virus (e.g., an influenza virus) comprising one or more above described nucleic acids (e.g., encoding hemagglutinin and/or neuraminidase), or one or more fragments thereof. Immunogenic compositions comprising such virus are also part of the current invention. Such viruses can comprises a reassortment virus such as a 6:2 reassortment virus (e.g., comprising 6 genes encoding regions from one or more donor virus and 2 genes encoding regions from one or more above described nucleotide sequence (or one or more fragment thereof) which can optionally comprise hemagglutinin and/or neuraminidase). Reassortment viruses (optionally live viruses) of the invention can include donor viruses that are one or more of, e.g., cold-sensitive, cold-adapted, or an attenuated. For example, reassortment viruses can comprise e.g., A/Ann Arbor/6/60, PR8, etc. Reassortment viruses of the invention may alternatively exclude A/Ann Arbor/6/60. One preferred embodiment of the invention is a reassortant influenza virus, wherein the virus is a 6:2 reassortment influenza virus and comprises 6 gene encoding regions from A/Ann Arbor/6/60 and 2 gene encoding regions that encode a polypeptide selected from the group consisting of: the polypeptides of SEQ ID NOS:11-20, SEQ ID NOS:27-32, and SEQ ID NOS: 39-44. In an alternative embodiment, a reassortant influenza virus of the invention includes a 6:2 reassortment influenza virus, wherein said virus comprises 6 gene encoding regions from one or more donor viruses other than A/Ann Arbor/6/60 and 2 gene encoding regions that encode a polypeptide selected from the group consisting of: the polypeptides of SEQ ID NOS:11-20, SEQ ID NOS:27-32, and SEQ ID NOS:

39-44. In another alternative embodiment, a reassortant influenza virus of the invention includes a 6:2 reassortment influenza virus, wherein said virus comprises 6 gene encoding regions from one or more donor viruses other than A/Ann Arbor/6/60 and 2 gene encoding regions, wherein the 2 gene encoding regions are HA or NA polypeptides from any pandemic influenza strain. Methods of producing recombinant influenza virus through culturing a host cell harboring an influenza virus in a suitable culture medium under conditions permitting expression of nucleic acid and, isolating the recombinant influenza virus from one or more of the host cell or the medium are also part of the invention.

In other embodiments herein, the invention comprises immunogenic compositions having an immunologically effective amount of any of the above described recombinant influenza virus. Other embodiments include methods for stimulating the immune system of an individual to produce a protective immune response against influenza virus by administering to the individual an immunologically effective amount of any of the recombinant influenza virus described above (optionally in a physiologically effective carrier).

Other aspects of the invention include methods of producing an isolated or recombinant polypeptide by culturing any host cell above, in a suitable culture medium under conditions permitting expression of nucleic acid and, isolating the polypeptide from one or more of the host cells or the medium in which is the cells are grown.

Immunogenic compositions are also features of the invention. For example, immunogenic compositions comprising one or more of any of the polypeptides and/or nucleic acids described above and, optionally, an excipient such as a pharmaceutically acceptable excipient or one or more pharmaceutically acceptable administration component. Immunogenic compositions of the invention can also comprise any one or more above described virus as well (e.g., along with one or more pharmaceutically acceptable administration component).

Methods of producing immunogenic responses in a subject through administration of an effective amount of any of the above viruses (or immunogenic compositions) to a subject are also within the current invention. Additionally, methods of prophylactic or therapeutic treatment of a viral infection (e.g., viral influenza) in a subject through administration of any one or more above described virus (or immunogenic compositions) in an amount effective to produce an immunogenic response against the viral infection are also part of the current invention. Subjects for such treatment can include mammals (e.g., humans). Such methods can also comprise in vivo administration to the subject as well as in vitro or ex vivo administration to one or more cells of the subject. Additionally, such methods can also comprise administration of a composition of the virus and a pharmaceutically acceptable excipient that are administered to the subject in an amount effect to prophylactically or therapeutically treat the viral infection.

In other aspects the invention includes compositions of matter comprising nucleic acid sequences encoding hemagglutinin and/or neuraminidase polypeptides of one or more pandemic influenza strain and nucleic acid sequences encoding one or more polypeptide of A/Ann Arbor/6/60. Additionally, the invention includes compositions of matter comprising nucleic acid sequences encoding hemagglutinin and/or neuraminidase polypeptides of one or more pandemic influenza strain and nucleic acid sequences encoding one or more polypeptide of PR8 or A/Ann Arbor/6/60. Such sequences can include those listed in the "SEQUENCES" herein. Additionally, preferred embodiments of the invention include compositions of matter comprising sequences encoding hemagglutinin and/or neuraminidase of one or more pandemic influenza strain and nucleic acid sequences encoding a selected backbone strain in a 6:2 reassortment. Such compositions preferably include sequences encoding the hemagglutinin and neuraminidase selected from the "SEQUENCES" herein and a backbone strain, wherein the backbone strain is PR8 or A/Ann Arbor/6/60. The invention also includes such compositions as described above wherein the hemagglutinin comprises a modified polybasic cleavage site. The invention also includes live attenuated influenza vaccine comprising such above compositions.

These and other objects and features of the invention will become more fully apparent when the following detailed description is read in conjunction with the accompanying figures and appendix.

BRIEF DESCRIPTION OF THE DRAWINGS

FIG. 1: Shows modifications engineered into the HA gene of VN/1203/2004 to remove the polybasic cleavage site.

FIG. 2: Displays results showing that intranasally administered H5N1 ca reassortant viruses do not replicate in chickens.

FIG. 3: Illustrates that the H5N1/AA ca vaccine candidates are not lethal to mice.

FIG. 4: Illustrates that the 1997 and 2004 H5N1 ca reassortant viruses are restricted in replication in mice.

FIG. 6: Shows the serum HAI Ab titers elicited in mice following a single i.n. dose of vaccine.

FIG. 7: Shows serum neutralizing Ab titers elicited in mice following a single i.n. dose of vaccine.

FIG. 8: Illustrates that H5N1 ca reassortant viruses protect mice from lethal challenges with 50, 500 or 5000 $LD_{50}$ of wild-type H5N1 viruses.

FIG. 9: Illustrates the efficacy of protection from pulmonary replication of homologous and heterologous H5N1 challenge viruses in mice.

FIG. 10: Illustrates the efficacy of protection from replication of homologous and heterologous H5N1 challenge viruses in the upper respiratory tract of mice.

FIG. 11: Illustrates the efficacy of protection conferred by 2004 H5N1 ca vaccine against high dose ($10_5 TCID_{50}$) challenge with homologous or heterologous H5N1 wt viruses in mice.

FIG. 14: Shows modifications that can be engineered into the HA gene of A/Netherland/219/03 HA to remove the polybasic cleavage site.

FIG. 15: H5N1 ca vaccines elicit serum neutralizing antibody titers in mice. Sera were collected before (prebleed) and 28 days following each dose of vaccine; an undetectable titer is assigned a value of 10.

FIG. 17: Immunogenicity of H6 ca vaccines in ferrets.

FIG. 20: H7N3 BC 2004 ca is immunogenic in mice. a: Reciprocal geometric mean of serum neutralizing antibody titers against ck/BC/CN-6/04 wt. b: p<0.05 (Mann-Whitney U-test) compared to neutralization titers at 28 days post-infection.

FIG. 21(a)-21(i): H7N3 BC 04 ca is efficacious against lethal challenge with H7 viruses in mice. Efficacy against a lethal challenge of 50 $LD_{50}$ A/ck/BC/CN-7/04: four weeks following immunization with a single dose (a), eight weeks following immunization with a single dose (b), or eight weeks following immunization with 2 doses (2 doses administered at 4 weeks apart) (c). Efficacy against a lethal challenge of 50 $LD_{50}$ A/NL/219/03: four weeks following immunization with a single dose (d), eight weeks following immunization with a single dose (e), or eight weeks following immunization with 2 doses (2 doses administered at 4 weeks apart) (f). Efficacy against a lethal challenge of 50 $LD_{50}$ A/tk/Eng/63: four weeks following immunization with a single dose (g), eight weeks following immunization with a single dose (h), or eight weeks following immunization with 2 doses (2 doses administered at 4 weeks apart) (i).

FIGS. 22(a) and (b): H7N3 BC 04 ca vaccine is efficacious in mice. Virus titer was measured at 8 weeks in (a) nasal turbinates and (b) lungs.

FIGS. 24(a) and (b): Efficacy of the H9N2 ca vaccine in mice.

FIG. 25: Replication of H9N2 G9/AA ca is highly restricted in healthy adults.

FIG. 26: HI antibody responses to $10^{7.0}$ $TCID_{50}$ of H9N2 G9/AA ca in healthy adults.

FIG. 27: Replication of H5N1 VN2004 A/AA ca is highly restricted in healthy adults.

FIG. 28: HI antibody responses to $10^{6.7}$ $TCID_{50}$ of VN2004 A/AA ca in healthy adults.

DETAILED DESCRIPTION

Figure 5:
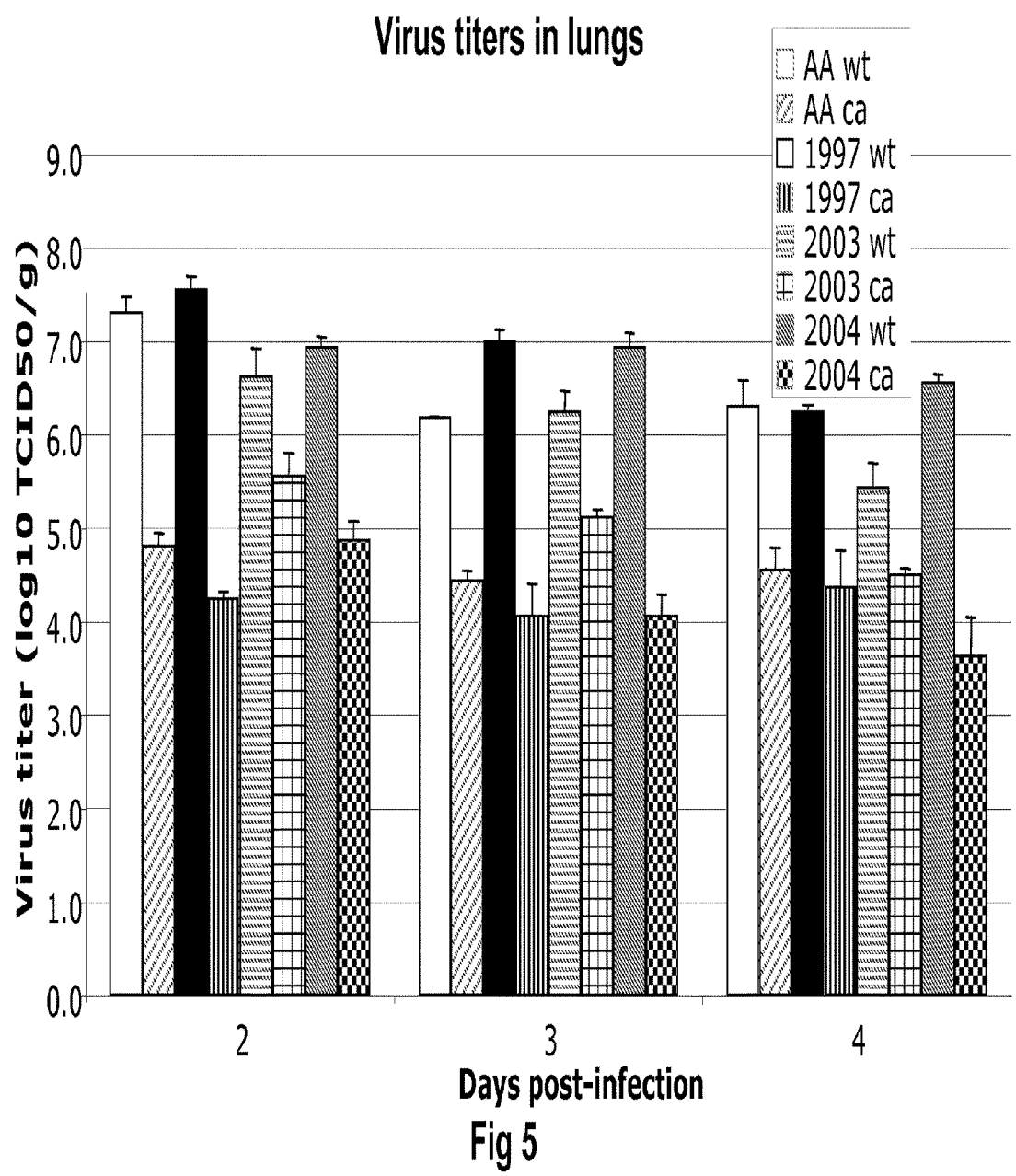
FIG. 5: Illustrates that the reassortant H5N1/AA ca influenza viruses are restricted in replication in lungs of mice.

The present invention includes polypeptide and polynucleotide sequences of influenza hemagglutinin and neuraminidase as well as vectors, compositions and the like comprising such sequences and methods of their use. Additional features of the invention are described in more detail herein.

DEFINITIONS

Unless defined otherwise, all technical and scientific terms used herein have the same meaning as commonly understood by one of ordinary skill in the art to which the invention pertains. The following definitions supplement those in the art and are directed to the current application and are not necessarily to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a virus" includes a plurality of viruses; reference to "a host cell" includes mixtures of host cells, and the like.

An "amino acid sequence" is a polymer of amino acid residues (a protein, polypeptide, etc.) or a character string representing an amino acid polymer, depending on context.

The terms "nucleic acid," "polynucleotide," "polynucleotide sequence" and "nucleic acid sequence" refer to single-stranded or double-stranded deoxyribonucleotide or ribonucleotide polymers, chimeras or analogues thereof, or a character string representing such, depending on context. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences in addition to the sequence explicitly indicated. From any specified polynucleotide sequence, either the given nucleic acid or the complementary polynucleotide sequence (e.g., the complementary nucleic acid) can be determined.

The term "nucleic acid" or "polynucleotide" also encompasses any physical string of monomer units that can be corresponded to a string of nucleotides, including a polymer of nucleotides (e.g., a typical DNA or RNA polymer), PNAs, modified oligonucleotides (e.g., oligonucleotides comprising bases that are not typical to biological RNA or DNA in solution, such as 2'-O-methylated oligonucleotides), and the like. A nucleic acid can be e.g., single-stranded or double-stranded.

A "subsequence" is any portion of an entire sequence, up to and including the complete sequence. Typically, a subsequence comprises less than the full-length sequence. A "unique subsequence" is a subsequence that is not found in any previously determined influenza polynucleotide or polypeptide sequence.

The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described herein.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type, or types.

"Expression of a gene" or "expression of a nucleic acid" means transcription of DNA into RNA (optionally including modification of the RNA, e.g., splicing), translation of RNA into a polypeptide (possibly including subsequent modification of the polypeptide, e.g., post-translational modification), or both transcription and translation, as indicated by the context.

An "open reading frame" or "ORF" is a possible translational reading frame of DNA or RNA (e.g., of a gene), which is capable of being translated into a polypeptide. That is, the reading frame is not interrupted by stop codons. However, it should be noted that the term ORF does not necessarily indicate that the polynucleotide is, in fact, translated into a polypeptide.

The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids.

An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

A "polypeptide" is a polymer comprising two or more amino acid residues (e.g., a peptide or a protein). The polymer can optionally comprise modifications such as glycosylation or the like. The amino acid residues of the polypeptide can be natural or non-natural and can be unsubstituted, unmodified, substituted or modified.

In the context of the invention, the term "isolated" refers to a biological material, such as a virus, a nucleic acid or a protein, which is substantially free from components that normally accompany or interact with it in its naturally occurring environment. The isolated biological material optionally comprises additional material not found with the biological material in its natural environment, e.g., a cell or wild-type virus. For example, if the material is in its natural environment, such as a cell, the material can have been placed at a location in the cell (e.g., genome or genetic element) not native to such material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

The term "chimeric" or "chimera," when referring to a virus, indicates that the virus includes genetic and/or polypeptide components derived from more than one parental viral strain or source. Similarly, the term "chimeric" or "chimera," when referring to a viral protein, indicates that the protein includes polypeptide components (i.e., amino acid subsequences) derived from more than one parental viral strain or source.

The term "recombinant" indicates that the material (e.g., a nucleic acid or protein) has been artificially or synthetically (non-naturally) altered by human intervention. The alteration can be performed on the material within, or removed from, its natural environment or state. Specifically, e.g., an influenza virus is recombinant when it is produced by the expression of a recombinant nucleic acid. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus", e.g., a recombinant influenza virus, is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding a hemagglutinin or neuraminidase of the invention. A 6:2 reassortant includes 6 genomic segments, most commonly the 6 internal genes from a first parental virus, and two complementary segments, e.g., hemagglutinin and neuraminidase, from a different parental virus.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction." In the context of the invention a variety of methods can be employed to introduce nucleic acids into cells, including electroporation, calcium phosphate precipitation, lipid mediated transfection (lipofection), etc.

The term "host cell" means a cell that contains a heterologous nucleic acid, such as a vector, and supports the replication and/or expression of the nucleic acid. Host cells can be prokaryotic cells such as E. coli, or eukaryotic cells such as yeast, insect, amphibian, avian or mammalian cells, including human cells. Exemplary host cells can include, e.g., Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells), etc.

An "immunologically effective amount" of influenza virus is an amount sufficient to enhance an individual's (e.g., a human's) own immune response against a subsequent exposure to influenza virus. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against influenza virus refers to an immune response exhibited by an individual (e.g., a human) that is protective against disease when the individual is subsequently exposed to and/or infected with such influenza virus. In some instances, the influenza virus (e.g., naturally circulating) can still cause infection, but it cannot cause a serious infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1999), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include, e.g., polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Influenza Virus

The polypeptides and polynucleotides of the invention, e.g., SEQ ID NO: 1-45, are variants of influenza HA and NA sequences. In general, influenza viruses are made up of an internal ribonucleoprotein core containing a segmented single-stranded RNA genome and an outer lipoprotein envelope lined by a matrix protein. The genome of influenza viruses is composed of eight segments of linear (−) strand ribonucleic acid (RNA), encoding the immunogenic hemagglutinin (HA) and neuraminidase (NA) proteins, and six internal core polypeptides: the nucleocapsid nucleoprotein (NP); matrix proteins (M); non-structural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB 1, PB2, and PA).

Influenza is commonly grouped into influenza A and influenza B categories. Influenza A and influenza B viruses each contain eight segments of single stranded RNA with negative polarity. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants. The eight genome segments of influenza B encode 11 proteins. The three largest genes code for components of the RNA polymerase, PB 1, PB2 and PA. Segment 4 encodes the HA protein. Segment 5 encodes NP. Segment 6 encodes the NA protein and the NB protein. Both proteins, NB and NA, are translated from overlapping reading frames of a bicistronic mRNA. Segment 7 of influenza B also encodes two proteins: M1 and BM2. The smallest segment encodes two products: NS1 is translated from the full length RNA, while NS2 is translated from a spliced mRNA variant.

Influenza Virus Vaccines

The sequences, compositions and methods herein are primarily, but not solely, concerned with production of influenza viruses for vaccines. Historically, influenza virus vaccines have primarily been produced in embryonated hen eggs using strains of virus selected or based on empirical predictions of relevant strains. More recently, reassortant viruses have been produced that incorporate selected hemagglutinin and/or neuraminidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines). Thus, it will be appreciated that HA and NA sequences (e.g., SEQ ID NO: 1-45) are quite useful in constructing influenza vaccines. The current invention includes viruses/vaccines comprising HA and/or NA sequences of pandemic influenza strains (including wherein the HA sequences comprise modified polybasic cleavage sites such as the modifications described herein); and including wherein the viruses/vaccines comprise a ca backbone such as A/AA/6/60 or the backbone of PR8.

Attempts at producing recombinant and reassortant vaccines in cell culture have been hampered by the inability of some of the strains approved for vaccine production to grow efficiently under standard cell culture conditions. However, prior work by the inventors and their coworkers provided a vector system, and methods for producing recombinant and reassortant viruses in culture, thus, making it possible to rapidly produce vaccines corresponding to one or many selected antigenic strains of virus, e.g., either A or B strains, various subtypes or substrains, etc., e.g., comprising the HA and/or NA sequences herein. See, Multi-Plasmid System for the production of Influenza virus, U.S. Application No. 60/420,708, filed Oct. 23, 2002, U.S. application Ser. No. 10/423,828, filed Apr. 25, 2003 and U.S. Application 60/574,117 filed May 24, 2004. Typically, the cultures are maintained in a system, such as a cell culture incubator, under controlled humidity and $CO_2$, at constant temperature using a temperature regulator, such as a thermostat to insure that the temperature does not exceed 35° C. Reassortant influenza viruses can be readily obtained by introducing a subset of vectors corresponding to genomic segments of a master influenza virus, in combination with complementary segments derived from strains of interest (e.g., HA and/or NA antigenic variants herein). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. As explained elsewhere herein and, e.g., in U.S. patent application Ser. No. 10/423,828, etc., various embodiments of the invention utilize A/Ann Arbor (AA)/6/60 influenza strain as a "backbone" upon which to add HA and/or NA genes (e.g., such as those sequences listed herein, etc.) to create desired reassortant viruses. Thus, for example, in a 6:2 reassortant, 2 genes (i.e., NA and HA) would be from the influenza strain(s) against which an immunogenic reaction is desired, while the other 6 genes would be from the Ann Arbor strain, or other backbone strain, etc. The Ann Arbor virus is useful for its cold adapted, attenuated, temperature sensitive attributes. Of course, it will be appreciated that the HA and NA sequences herein are capable of reassortment with a number of other virus genes or virus types (e.g., a number of different "backbones" such as PR8, etc., containing the other influenza genes present in a reassortant, namely, the non-HA and non-NA genes Various embodiments herein can comprise live attenuated vaccines, having the HA and/or NA sequences herein, for pandemic influenza. Such vaccines typically comprise, e.g., the HA and/or NA sequences of SEQ ID NO: 11-20, 27-32, or 39-44, or their corresponding encoding nucleotides of SEQ ID NO: 1-10, 21-26, 33-38, or 45. One problem arising from growth of vaccine virus strains (e.g., reassortants) in eggs is that avian strains (which can be involved in pandemics) can kill the eggs in which the vaccines are to be produced and are, thus, hard to manipulate, produce, etc. through use of traditional (non-plasmid rescue) reassortant production. Such avian strains are of interest since evidence indicates they can result in influenza in humans and possible pandemics. Thus, use of plasmid-rescue systems to create/manipulate influenza reassortants with pandemic strains such as various avian sequences (e.g., the HA and NA sequences herein) are quite desirable and are features of the invention. It will be appreciated, however, that the current sequences are also capable of use with non-plasmid or traditional systems.

Aquatic birds (among others) can be infected by influenza A viruses of 15 hemagglutinin (HA) and 9 neuraminidase (NA) subtypes. Such birds can serve as a reservoir from which novel influenza subtypes can be introduced into human populations and cause pandemics. The observation that avian H7N7 influenza A viruses infected humans in The Netherlands in 2003 and avian H5N1 and H9N2 viruses infected humans in Hong Kong and China earlier, raise concerns that these (and other) subtypes have the potential to cause pandemics. Thus, vaccines are needed to prevent human infections with avian influenza A viruses. Live, attenuated influenza A virus vaccines against human influenza viruses were recently licensed in the United States. See above. Such vaccines are reassortant H1N1 and H3N2 viruses in which the internal protein genes of A/Ann Arbor (AA)/6/60 (H2N2) cold adapted (ca) virus confer the cold adapted, attenuation and temperature sensitive phenotypes of the AA ca virus on the reassortant viruses (i.e., the ones having the hemagglutinin and neuraminidase genes from the non-Ann Arbor strain). Classical genetic reassortment and plasmid-based reverse genetics techniques have been applied to generate reassortant viruses that contain the hemagglutinin and neuraminidase genes from avian influenza A viruses (H4-H14 subtypes) and six internal gene segments from the AA ca virus. Such reassortant viruses are features of the invention. See the HA and NA gene sequences below. These viruses bear biological properties that are desirable in candidate vaccines because the phenotypes associated with the AA ca virus are present in the reassortant viruses. The generation and evaluation of these reassortant viruses as seed viruses for vaccines are important steps in pandemic preparedness. It is contemplated that clinical trials can establish the safety, infectivity and immunogenicity of such live attenuated pandemic vaccines. Other embodiments of the invention include reassortant viruses (e.g., those used in vaccines) comprising pandemic antigenic genes HA and/or NA from, e.g., avian, porcine, etc., pandemic virus strains in addition to those listed herein, to produce pandemic vaccines which are created through plasmid-rescue reassortment (e.g., reassortment with A/Ann Arbor 6/60 (i.e., A/AA/6/60), PR8, etc. Methods of construction and use of such viruses and vaccines are also included. "Pandemic virus strains" as used herein is defined as an influenza strain A virus subtype that it is not circulating in the human population, that is declared to be a pandemic strain by the Centers for Disease Control or the World Health Organization or generally acknowledged as such within the scientific community.

In various embodiments herein, the antigenic sequences (e.g., the HA sequences) as well as viruses and vaccines from such viruses comprise modified polybasic cleavage sites. Some highly pathogenic avian pandemic influenza strains comprise multiple basic amino acid cleavage sites within hemagglutinin sequences. See, e.g., Li et al., *J. of Infectious Diseases,* 179:1132-8, 1999. Such cleavage sites, in typical embodiments herein, are, e.g., modified or altered in their sequences in comparison to the wild-type sequences from which the current sequences are derived (e.g., to disable the cleavage or reduce the cleavage there, etc.). Such modifications/alterations can be different in different strains due to the various sequences of the cleavage sites in the wild-type sequences. For example, 4 polybasic residues (RRKK) at 326-329 of mature H5 are typically removed in sequences herein (as compared to wt). See "SEQUENCES." In various embodiments, the polybasic cleavage sites can be modified in a number of ways (all of which are contained within the invention). For example, the polybasic cleavage site can be removed one amino acid at a time (e.g., one R removed, two Rs removed, RRK removed, or RRKK removed). Additionally, the amino acid residue directly upstream of the cleavage site can also be removed or altered (e.g., from an R to a T, etc.); also, the nucleotides encoding the amino acid residue directly after the cleavage site can also be modified. See, e.g., FIG. 1 for an illustration of cleavage site modification. In addition, hemagglutinin polypeptide sequences of influenza virus comprise amino terminal signal peptide sequences, thus, the hemagglutinin polypeptide sequences of the invention include both the mature (amino terminal signal peptide cleaved) form of the hemagglutinin polypeptides and the pre-cleaved form of hemagglutinin. The cleavage sites of any hemagglutinin polypeptide sequence of any influenza strain can be routinely measured or predicted using any number of methods in the art.

The terms "temperature sensitive," "cold adapted" and "attenuated" as applied to viruses (typically used as vaccines or for vaccine production) which optionally encompass the current sequences, are well known in the art. For example, the term "temperature sensitive" (ts) indicates, e.g., that the virus exhibits a 100 fold or greater reduction in titer at 39° C. relative to 33° C. for influenza A strains, or that the virus exhibits a 100 fold or greater reduction in titer at 37° C. relative to 33° C. for influenza B strains. The term "cold adapted" (ca) indicates that the virus exhibits growth at 25° C. within 100 fold of its growth at 33° C., while the term "attenuated" (au) indicates that the virus replicates in the upper airways of ferrets but is not detectable in their lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), or exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses and can be used in conjunction with the HA and NA sequences herein.

Again, the HA and NA sequences of the current invention are optionally utilized in the production of or in reassortment vaccines (and/or in other ts, cs, ca, and/or att viruses and vaccines). However, it should be noted that the HA and NA sequences, etc. of the invention are not limited to specific vaccine compositions or production methods, and can, thus, be utilized in substantially any vaccine type or vaccine production method which utilizes strain specific HA and NA antigens (e.g., any of SEQ ID NO: 11-20, 27-32, or 39-44 or the corresponding nucleotides encoding the specific HA and NA antigens, e.g., SEQ ID NO: 1-10, 21-26, 33-38, or 45).

FluMist™

As mentioned previously, numerous examples and types of influenza vaccine exist. An exemplary influenza vaccine is FluMist™ which is a live, attenuated vaccine that protects children and adults from influenza illness (Belshe et al. (1998) *The efficacy of live attenuated, cold-adapted, trivalent, intranasal influenza virus vaccine in children* N Engl J Med 338:1405-12; Nichol et al. (1999) *Effectiveness of live, attenuated intranasal influenza virus vaccine in healthy, working adults: a randomized controlled trial* JAMA 282: 137-44). In typical, and preferred, embodiments, the methods and compositions of the current invention are preferably adapted to/used with production of FluMist™ vaccine. However, it will be appreciated by those skilled in the art that the sequences, methods, compositions, etc. herein are also adaptable to production of similar or even different viral vaccines.

FluMist™ vaccine strains contain, e.g., HA and NA gene segments derived from the strains (e.g., wild-type strains) to which the vaccine is addressed along with six gene segments, FB1, PB2, PA, NP, M and NS, from a common master donor virus (MDV). The HA sequences herein, thus, are part of various FluMist™ formulations. The MDV for influenza A strains of FluMist™ (MDV-A), was created by serial passage of the wild-type A/Ann Arbor/6/60 (A/AA/6/60) strain in primary chicken kidney tissue culture at successively lower temperatures (Maassab (1967) *Adaptation and growth characteristics of influenza virus at 25 degrees C.* Nature 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A does not revert following passage through infected hamsters or in shed isolates from children (for a recent review, see Murphy & Coelingh (2002) *Principles underlying the development and use of live attenuated cold-adapted influenza A and B virus vaccines Viral Immunol* 15:295-323).

Clinical studies in over 20,000 adults and children involving 12 separate 6:2 reassortant strains have shown that these vaccines are attenuated, safe and efficacious (Belshe et al. (1998) *The efficacy of live attenuated, cold-adapted, trivalent, intranasal influenza virus vaccine in children* N Engl J Med 338:1405-12; Boyce et al. (2000) *Safety and immunogenicity of adjuvanted and unadjuvanted subunit influenza vaccines administered intranasally to healthy adults Vaccine* 19:217-26; Edwards et al. (1994) *A randomized controlled trial of cold adapted and inactivated vaccines for the prevention of influenza A disease J Infect Dis* 169:68-76; Nichol et al. (1999) *Effectiveness of live, attenuated intranasal influenza virus vaccine in healthy, working adults: a randomized controlled trial JAMA* 282:137-44). Reassortants carrying the six internal genes of MDV-A and the two HA and NA gene segments of a wild-type virus (i.e., a 6:2 reassortant) consistently maintain ca, ts and att phenotypes (Maassab et al. (1982) *Evaluation of a cold-recombinant influenza virus vaccine in ferrets J. Infect. Dis.* 146:780-900).

Production of such reassorted virus using B strains of influenza is more difficult, however, recent work (see, e.g., Multi-Plasmid System for the Production of Influenza Virus, U.S. Application No. 60/420,708, filed Oct. 23, 2002, U.S. application Ser. No. 10/423,828, filed Apr. 25, 2003, and U.S. Application No. 60/574,117, filed May 24, 2004) has shown an eight plasmid system for the generation of influenza B virus entirely from cloned cDNA. Methods for the production of attenuated live influenza A and B virus suitable for vaccine formulations, such as live virus vaccine formulations useful for intranasal administration were also shown.

The system and methods described previously are useful for the rapid production in cell culture of recombinant and reassortant influenza A and B viruses, including viruses suitable for use as vaccines, including live attenuated vaccines, such as vaccines suitable for intranasal administration. The sequences (e.g., nucleotide sequences SEQ ID NO: 1-10, 21-26, 33-38, or 45 and the corresponding amino acids encoded by the nucleotide sequences in SEQ ID NO: 11-20, 27-32, or 39-44), methods, etc. of the current invention, are optionally used in conjunction with, or in combination with, such previous work involving, e.g., reassorted influenza viruses for vaccine production to produce viruses for vaccines.

Methods and Compositions for Prophylactic Administration of Vaccines

As stated above, alternatively, or in addition to, use in production of FluMist™ vaccine, the current invention can be used in other vaccine formulations. In general, recombinant and reassortant viruses of the invention (e.g., those comprising polynucleotides of SEQ ID NO:1-10, 21, 23-26, 33-38, or 45 or polypeptides of SEQ ID NO:11-20, 27-32, or 39-44, or fragments thereof) can be administered prophylactically in an immunologically effective amount and in an appropriate carrier or excipient to stimulate an immune response specific for one or more strains of influenza virus as determined by the HA and/or NA sequence. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

A related aspect of the invention provides methods for stimulating the immune system of an individual to produce a protective immune response against influenza virus. In the methods, an immunologically effective amount of a recombinant influenza virus (e.g., comprising an HA and/or NA molecule of the invention), an immunologically effective amount of a polypeptide of the invention, and/or an immunologically effective amount of a nucleic acid of the invention is administered to the individual in a physiologically acceptable carrier.

Generally, the influenza viruses of the invention are administered in a quantity sufficient to stimulate an immune response specific for one or more strains of influenza virus (i.e., against the HA and/or NA strains of the invention). Preferably, administration of the influenza viruses elicits a protective immune response to such strains. Dosages and methods for eliciting a protective immune response against one or more influenza strains are known to those of skill in the art. See, e.g., U.S. Pat. No. 5,922,326; Wright et al., *Infect. Immun.* 37:397-400 (1982); Kim et al., *Pediatrics* 52:56-63 (1973); and Wright et al., *J. Pediatr.* 88:931-936 (1976). For example, influenza viruses are provided in the range of about 1-1000 $HID_{50}$ (human infectious dose), i.e., about $10^5$-$10^8$ pfu (plaque forming units) per dose administered. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. See above. While stimulation of a protective immune response with a single dose is preferred, additional dosages can be administered, by the same or different route, to achieve the desired prophylactic effect.

Typically, the attenuated recombinant influenza of this invention as used in a vaccine is sufficiently attenuated such that symptoms of infection, or at least symptoms of serious infection, will not occur in most individuals immunized (or otherwise infected) with the attenuated influenza virus. In some instances, the attenuated influenza virus can still be capable of producing symptoms of mild illness (e.g., mild upper respiratory illness) and/or of dissemination to unvaccinated individuals. However, its virulence is sufficiently abrogated such that severe lower respiratory tract infections do not occur in the vaccinated or incidental host.

Alternatively, an immune response can be stimulated by ex vivo or in vivo targeting of dendritic cells with influenza viruses comprising the sequences herein. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Optionally, the formulation for prophylactic administration of the influenza viruses also contains one or more adjuvants for enhancing the immune response to the influenza antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvant QS-21.

If desired, prophylactic vaccine administration of influenza viruses can be performed in conjunction with administration of one or more immunostimulatory molecules Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein (e.g., an HA and/or NA polypeptide of the invention, e.g., any of SEQ ID NO: 11-20, 27-32, or 39-44) or an expression vector comprising a nucleic acid (e.g., any of SEQ ID NO: 1-10, 21-26, 33-38, or 45) encoding the protein can be administered to produce an immunostimulatory effect.

The above described methods are useful for therapeutically and/or prophylactically treating a disease or disorder, typically influenza, by introducing a vector of the invention comprising a heterologous polynucleotide encoding a therapeutically or prophylactically effective HA and/or NA polypeptide (or peptide) or HA and/or NA RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences as described above in the sections entitled "Expression Vectors" and "Additional Expression Elements." Optionally, more than one heterologous coding sequence is incorporated into a single vector or virus. For example, in addition to a polynucleotide encoding a therapeutically or prophylactically active HA and/or NA polypeptide or RNA, the vector can also include additional therapeutic or prophylactic polypeptides, e.g., antigens, co-stimulatory molecules, cytokines, antibodies, etc., and/or markers, and the like.

Although vaccination of an individual with an attenuated influenza virus of a particular strain of a particular subgroup can induce cross-protection against influenza virus of different strains and/or subgroups, cross-protection can be enhanced, if desired, by vaccinating the individual with attenuated influenza virus from at least two strains, e.g., each of which represents a different subgroup. Additionally, vaccine combinations can optionally include mixes of pandemic vaccines (e.g., those against pandemic influenza strains such as various avian strains, see, e.g., the sequences herein, or other pandemic strains) and non-pandemic strains. Vaccine mixtures (or multiple vaccinations) can comprise components from human strains and/or non-human influenza strains (e.g., avian and human, etc.). Similarly, the attenuated influenza virus vaccines of this invention can optionally be combined with vaccines that induce protective immune responses against other infectious agents.

Polynucleotides of the Invention

It is well known in the art that the HA and NA polynucleotide segments of influenza viruses comprise both a coding region (encoding the ORF) and noncoding regions (NCRs), both 5' and 3' of the HA and NA coding sequence. An example of these NCRs are shown in SEQ ID NOS:1-9 (outside of the ORFs). It is also known that primers can be made to these NCRs to facilitate amplification of the entire HA and NA segments of influenza virus. (see, e.g., Hoffmann et al. Arch Virol. 2001 December; 146(12):2275-89). Further, it is known that the NCRs of the HA and NA of influenza may increase the efficiency of achieving reassortants. Therefore, the polynucleotide sequences of these NCRs (including fragments and variants (e.g., at least about 60%, or at least 70%, or at least 80%, or at least 90%, or at least about 91% or at least about 92%, or at least about 93%, or at least about 94%, or at least about 95%, or at least about 96%, or at least about 97%, or at least about 98%, or at least about 98.5%, or at least about 98.7%, or at least about 99%, or at least about 99.1%, or at least about 99.2%, or at least about 99.3%, or at least about 99.4%, or at least about 99.5%, or at least about 99.6%, or at least about 99.7%, or at least about 99.8%, or at least about 99.9% identity) thereof) are within the scope of this invention. When amplifying the HA and NA segments of any pandemic strain, one could make and use polynucleotide primers to bind conserved (e.g., among related strains) regions of the HA and NA NCRs for amplification (e.g., by RT-PCR). In one embodiment, HA and NA polynucleotides of the invention include both the NCR and ORF of the HA and NA sequences (including fragments and variants (e.g., at least about 60%, or at least 70%, or at least 80%, or at least 90%, or at least about 91% or at least about 92%, or at least about 93%, or at least about 94%, or at least about 95%, or at least about 96%, or at least about 97%, or at least about 98%, or at least about 98.5%, or at least about 98.7%, or at least about 99%, or at least about 99.1%, or at least about 99.2%, or at least about 99.3%, or at least about 99.4%, or at least about 99.5%, or at least about 99.6% or at least about 99.7%, or at least about 99.8%, or at least about 99.9%) thereof) of pandemic virus strains. In alternative embodiments, the HA and NA polynucleotides of the invention exclude the NCR, but include the ORF (including fragments and variants (e.g., at least about 60%, or at least 70%, or at least 80%, or at least 90%, or at least about 91% or at least about 92%, or at least about 93%, or at least about 94%, or at least about 95%, or at least about 96%, or at least about 97%, or at least about 98%, or at least about 98.5%, or at least about 98.7%, or at least about 99%, or at least about 99.1%, or at least about 99.2%, or at least about 99.3%, or at least about 99.4%, or at least about 99.5%, or at least about 99.6% or at least about 99.7%, or at least about 99.8%, or at least about 99.9% thereof)) of the HA and NA sequences of pandemic virus strains (e.g., SEQ ID NOS: 1-9).

The HA and NA polynucleotides of the invention, e.g., SEQ ID NO:1 through SEQ ID NO:10, SEQ ID NO:21 through SEQ ID NO:26, SEQ ID NO:33 through SEQ ID NO:38, SEQ ID NO:45, and fragments thereof, are optionally used in a number of different capacities alternative to, or in addition to, the vaccines described above. Other exemplary uses are described herein for illustrative purpose and not as limitations on the actual range of uses. Different methods of construction, purification, and characterization of the nucleotide sequences of the invention are also described herein. In some embodiments, nucleic acids including one or more polynucleotide sequence of the invention are favorably used as probes for the detection of corresponding or related nucleic acids in a variety of contexts, such as in nucleic hybridization experiments, e.g., to find and/or characterize homologous influenza variants (e.g., homologues to the sequences herein, etc.) infecting other species or in different influenza outbreaks, etc. The probes can be either DNA or RNA molecules, such as restriction fragments of genomic or cloned DNA, cDNAs, PCR amplification products, transcripts, and oligonucleotides, and can vary in length from oligonucleotides as short as about 10 nucleotides in length to full length sequences or cDNAs in excess of 1 kb or more. For example, in some embodiments, a probe of the invention includes a polynucleotide sequence or subsequence selected, e.g., from among SEQ ID NO: 1 through SEQ ID NO: 10, SEQ ID NO:21 through SEQ ID NO:26, SEQ ID NO:33 through SEQ ID NO:38, SEQ ID NO:45, or sequences complementary thereto. Alternatively, polynucleotide sequences that are variants of one of the above-designated sequences are used as probes. Most typically, such variants include one or a few conservative nucleotide variations. For example, pairs (or sets) of oligonucleotides can be selected, in which the two (or more) polynucleotide sequences are conservative variations of each other, wherein one polynucleotide sequence corresponds identically to a first variant or and the other(s) corresponds identically to additional variants. Such pairs of oligonucleotide probes are particularly useful, e.g., for specific hybridization experiments to detect polymorphic nucleotides or to, e.g., detect homologous influenza HA and NA variants, e.g., homologous to the current HA and NA sequences, infecting other species or present in different (e.g., either temporally and/or geographically different) influenza outbreaks. In other applications, probes are selected that are more divergent, that is probes that are at least about 91% (or about 92%, about 93%, about 94%, about 95%, about 96%, about 97%, about 98%, about 98.5%, about 98.7%, about 99%, about 99.1%, about 99.2%, about 99.3%, about 99.4%, about 99.5%, or about 99.6% or more about 99.7%, about 99.8%, about 99.9% or more) identical are selected.

The probes of the invention, e.g., as exemplified by sequences derived from the sequences herein, can also be used to identify additional useful polynucleotide sequences according to procedures routine in the art. In one set of embodiments, one or more probes, as described above, are utilized to screen libraries of expression products or chromosomal segments (e.g., expression libraries or genomic libraries) to identify clones that include sequences identical to, or with significant sequence similarity to, e.g., one or more probe of the sequences herein, i.e., variants, homologues, etc. It will be understood that in addition to such physical methods as library screening, computer assisted bioinformatic approaches, e.g., BLAST and other sequence homology search algorithms, and the like, can also be used for identifying related polynucleotide sequences. Polynucleotide sequences identified in this manner are also a feature of the invention.

Oligonucleotide probes are optionally produced via a variety of methods well known to those skilled in the art. Most typically, they are produced by well known synthetic methods, such as the solid phase phosphoramidite triester method described by Beaucage and Caruthers (1981) *Tetrahedron Letts* 22(20):1859-1862, e.g., using an automated synthesizer, or as described in Needham-Van Devanter et al. (1984) *Nucl Acids Res,* 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J Chrom* 255:137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560. Custom oligos can also easily be ordered from a variety of commercial sources known to persons of skill.

In other circumstances, e.g., relating to attributes of cells or organisms expressing the polynucleotides and polypeptides of the invention (e.g., those harboring virus comprising the sequences of the invention), probes that are polypeptides, peptides or antibodies are favorably utilized. For example, isolated or recombinant polypeptides, polypeptide fragments and peptides derived from any of the amino acid sequences of the invention (e.g., SEQ ID NO: 11-20, SEQ ID NO: 27-32, SEQ ID NO:39-44) and/or encoded by polynucleotide sequences of the invention, e.g., selected from SEQ ID NO: 1 through SEQ ID NO: 10, SEQ ID NO: 21 through SEQ ID NO: 26, SEQ ID NO:33 through SEQ ID NO:38, and SEQ ID NO:45 are favorably used to identify and isolate antibodies, e.g., from phage display libraries, combinatorial libraries, polyclonal sera, and the like. Polypeptide fragments of the inventions include a peptide or polypeptide comprising an amino acid sequence of at least 5 contiguous amino acid residues, or at least 10 contiguous amino acid residues, or at least 15 contiguous amino acid residues, or at least 20 contiguous amino acid residues, or at least 25 contiguous amino acid residues, or at least 40 contiguous amino acid residues, or at least 50 contiguous amino acid residues, or at least 60 contiguous amino residues, or at least 70 contiguous amino acid residues, or at least contiguous 80 amino acid residues, or at least contiguous 90 amino acid residues, or at least contiguous 100 amino acid residues, or at least contiguous 125 amino acid residues, or at least 150 contiguous amino acid residues, or at least contiguous 175 amino acid residues, or at least contiguous 200 amino acid residues, or at least contiguous 250 amino acid residues, or at least contiguous 350, or at least contiguous 400, or at least contiguous 450, or at least contiguous 500, or at least contiguous 550 amino acid residues of the amino acid sequence an HA or NA polypeptide of the invention (e.g., SEQ ID NOS: 11-20, SEQ ID NOS: 27-32, and SEQ ID NOS: 39-44). Polynucleotides encoding said polypeptide fragments and antibodies that specifically bind said polypeptides are also preferred embodiments of the invention.

Antibodies specific for any polypeptide sequence or subsequence, e.g., of SEQ ID NO: 11 through SEQ ID NO: 20, SEQ ID NO: 27 through SEQ ID NO: 32, and/or SEQ ID NO: 39 through SEQ ID NO: 44, and/or encoded by polynucleotide sequences of the invention, e.g., selected from SEQ ID NO: 1 through SEQ ID NO: 10, SEQ ID NO: 21 through SEQ ID NO: 26, SEQ ID NO: 33 through SEQ ID NO: 38, and SEQ ID NO:45 are likewise valuable as probes for evaluating expression products, e.g., from cells or tissues. In addition, antibodies are particularly suitable for evaluating expression of proteins comprising amino acid subsequences, e.g., of those given herein, or encoded by polynucleotides sequences of the invention, e.g., selected from those shown herein, in situ, in a tissue array, in a cell, tissue or organism, e.g., an organism infected by an unidentified influenza virus or the like. Antibodies can be directly labeled with a detectable reagent, or detected indirectly by labeling of a secondary antibody specific for the heavy chain constant region (i.e., isotype) of the specific antibody. Additional details regarding production of specific antibodies are provided below.

Diagnostic Assays

The nucleic acid sequences of the present invention can be used in diagnostic assays to detect influenza (and/or hemagglutinin and/or neuraminidase) in a sample, to detect hemagglutinin-like and/or neuraminidase-like sequences, and to detect strain differences in clinical isolates of influenza using either chemically synthesized or recombinant polynucleotide fragments, e.g., selected from the sequences herein. For example, fragments of the hemagglutinin and/or neuraminidase sequences comprising at least between 10 and 20 nucleotides can be used as primers to amplify nucleic acids using polymerase chain reaction (PCR) methods well known in the art (e.g., reverse transcription-PCR) and as probes in nucleic acid hybridization assays to detect target genetic material such as influenza RNA in clinical specimens.

The probes of the invention, e.g., as exemplified by unique subsequences selected from those given herein, can also be used to identify additional useful polynucleotide sequences (such as to characterize additional strains of influenza) according to procedures routine in the art. In one set of preferred embodiments, one or more probes, as described above, are utilized to screen libraries of expression products or cloned viral nucleic acids (i.e., expression libraries or genomic libraries) to identify clones that include sequences identical to, or with significant sequence identity to the sequences herein. In turn, each of these identified sequences can be used to make probes, including pairs or sets of variant probes as described above. It will be understood that in addition to such physical methods as library screening, computer assisted bioinformatic approaches, e.g., BLAST and other sequence homology search algorithms, and the like, can also be used for identifying related polynucleotide sequences.

The probes of the invention are particularly useful for detecting the presence and for determining the identity of influenza nucleic acids in cells, tissues or other biological samples (e.g., a nasal wash or bronchial lavage). For example, the probes of the invention are favorably utilized to determine whether a biological sample, such as a subject (e.g., a human subject) or model system (such as a cultured cell sample) has been exposed to, or become infected with influenza, or particular strain(s) of influenza. Detection of hybridization of the selected probe to nucleic acids originating in (e.g., isolated from) the biological sample or model system is indicative of exposure to or infection with the virus (or a related virus) from which the probe polynucleotide is selected.

It will be appreciated that probe design is influenced by the intended application. For example, where several allele-specific probe-target interactions are to be detected in a single assay, e.g., on a single DNA chip, it is desirable to have similar melting temperatures for all of the probes. Accordingly, the lengths of the probes are adjusted so that the melting temperatures for all of the probes on the array are closely similar (it will be appreciated that different lengths for different probes may be needed to achieve a particular $T_m$, where different probes have different GC contents). Although melting temperature is a primary consideration in probe design, other factors are optionally used to further adjust probe construction, such as selecting against primer self-complementarity and the like.

Vectors, Promoters and Expression Systems

The present invention includes recombinant constructs incorporating one or more of the nucleic acid sequences described herein. Such constructs optionally include a vector, for example, a plasmid, a cosmid, a phage, a virus, a bacterial artificial chromosome (BAC), a yeast artificial chromosome (YAC), etc., into which one or more of the polynucleotide sequences of the invention, e.g., comprising any of SEQ ID NO: 1 through SEQ ID NO:10, SEQ ID NO:21 through SEQ ID NO:26, SEQ ID NO:33 through SEQ ID NO:38, SEQ ID NO:45 or a subsequence thereof etc., has been inserted, in a forward or reverse orientation. For example, the inserted nucleic acid can include a viral chromosomal sequence or cDNA including all or part of at least one of the polynucleotide sequences of the invention. In one embodiment, the construct further comprises regulatory sequences, including, for example, a promoter, operably linked to the sequence. Large numbers of suitable vectors and promoters are known to those of skill in the art, and are commercially available.

The polynucleotides of the present invention can be included in any one of a variety of vectors suitable for generating sense or antisense RNA, and optionally, polypeptide (or peptide) expression products (e.g., a hemagglutinin and/or neuraminidase molecule of the invention, or fragments thereof). Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others (e.g., pCDL). Any vector that is capable of introducing genetic material into a cell, and, if replication is desired, which is replicable in the relevant host can be used.

In an expression vector, the HA and/or NA polynucleotide sequence of interest is physically arranged in proximity and orientation to an appropriate transcription control sequence (e.g., promoter, and optionally, one or more enhancers) to direct mRNA synthesis. That is, the polynucleotide sequence of interest is operably linked to an appropriate transcription control sequence. Examples of such promoters include: LTR or SV40 promoter, *E. coli* lac or trp promoter, phage lambda $P_L$ promoter, and other promoters known to control expression of genes in prokaryotic or eukaryotic cells or their viruses.

A variety of promoters are suitable for use in expression vectors for regulating transcription of influenza virus genome segments. In certain embodiments, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, immunoglobulin promoters, heat-shock promoters, and the like.

Transcription is optionally increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) *Heat stress promoters and transcription factors Results Probl Cell Differ* 20:125-62; Kriegler et al. (1990) *Assembly of enhancers, promoters, and splice signals to control expression of transferred genes Methods in Enzymol* 185: 512-27). Optionally, the amplicon can also contain a ribosome binding site or an internal ribosome entry site (IRES) for translation initiation.

The vectors of the invention also favorably include sequences necessary for the termination of transcription and for stabilizing the mRNA, such as a polyadenylation site or a terminator sequence. Such sequences are commonly available from the 5' and, occasionally 3', untranslated regions of eukaryotic or viral DNAs or cDNAs. In one embodiment, the SV40 polyadenylation signal sequences can provide a bi-directional polyadenylation site that insulates transcription of (+) strand mRNA molecules from the PolI promoter initiating replication of the (−) strand viral genome.

In addition, as described above, the expression vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The vector containing the appropriate nucleic acid sequence as described above, as well as an appropriate promoter or control sequence, can be employed to transform a host cell permitting expression of the protein. While the vectors of the invention can be replicated in bacterial cells, most frequently it will be desirable to introduce them into mammalian cells, e.g., Vero cells, BHK cells, MDCK cell, 293 cells, COS cells, or the like, for the purpose of expression.

As described elsewhere, the HA and NA sequences herein, in various embodiments, can be comprised within plasmids involved in plasmid-rescue reassortment. See, e.g., U.S. Application Nos. 60/420,708, filed Oct. 23, 2002; 60/574, 117, filed May 24, 2004; 10/423,828, filed Apr. 25, 2003; 60/578,962, filed Jun. 12, 2004; and 10/870,690 filed Jun. 16, 2004; and US20020164770, which are incorporated by reference herein. For example, preferred expression vectors of the invention include, but are not limited to, vectors comprising pol I promoter and terminator sequences or vectors using both the pol I and pol II promoters "the polI/polII promoter system" (e.g., Zobel et al., Nucl. Acids Res. 1993, 21:3607; US20020164770; Neumann et al., Proc. Natl. Acad. Sci. USA 1999, 96:9345; Fodor et al., J. Virol. 1999, 73:9679; and US20030035814). The reassortants produced can include the HA and NA genes arranged with the 6 other influenza genes from the A/Ann Arbor/6/60 donor strain (and/or derivatives and modifications thereof), the PR8 donor strain backbone, the A/Leningrad/17 donor strain backbone, etc. Other backbone strains are described, for example, in 20040137013 and 20030147916, which are incorporated by reference herein.

Additional Expression Elements

Most commonly, the genome segment encoding the influenza virus HA and/or NA protein includes any additional sequences necessary for its expression, including translation into a functional viral protein. In other situations, a minigene, or other artificial construct encoding the viral proteins, e.g., an HA and/or NA protein, can be employed. Again, in such case, it is often desirable to include specific initiation signals that aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually, in-frame with the polynucleotide sequence of interest, e.g., to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Where translation of a polypeptide encoded by a nucleic acid sequence of the invention is desired, additional translation specific initiation signals can improve the efficiency of translation. These signals can include, e.g., an ATG initiation codon and adjacent sequences, an IRES region, etc. In some cases, for example, full-length cDNA molecules or chromosomal segments including a coding sequence incorporating, e.g., a polynucleotide sequence of the invention (e.g., as in the sequences herein), a translation initiation codon and associated sequence elements are inserted into the appropriate expression vector simultaneously with the polynucleotide sequence of interest. In such cases, additional translational control signals frequently are not required. However, in cases where only a polypeptide coding sequence, or a portion thereof, is inserted, exogenous translational control signals, including, e.g., an ATG initiation codon is often provided for expression of the relevant sequence. The initiation codon is put in the correct reading frame to ensure transcription of the polynucleotide sequence of interest. Exogenous transcriptional elements and initiation codons can be of various origins, both natural and synthetic. The efficiency of expression can be enhanced by the inclusion of enhancers appropriate to the cell system in use (see, e.g., Scharf D. et al. (1994) *Results Probl Cell Differ* 20:125-62; Bittner et al. (1987) *Methods in Enzymol* 153:516-544).

Production of Recombinant Virus

Negative strand RNA viruses can be genetically engineered and recovered using a recombinant reverse genetics approach (see, e.g., U.S. Pat. No. 5,166,057 to Palese et al.). Such method was originally applied to engineer influenza viral genomes (Luytjes et al. (1989) Cell 59:1107-1113; Enami et al. (1990) *Proc. Natl. Acad. Sci. USA* 92:11563-11567), and has been successfully applied to a wide variety of segmented and nonsegmented negative strand RNA viruses, e.g., rabies (Schnell et al. (1994) *EMBO J.* 13: 4195-4203); VSV (Lawson et al. (1995) *Proc. Natl. Acad. Sci. USA* 92: 4477-4481); measles virus (Radecke et al. (1995) *EMBO J.* 14:5773-5784); rinderpest virus (Baron & Barrett (1997) *J. Virol.* 71: 1265-1271); human parainfluenza virus (Hoffman & Banerjee (1997) *J. Virol.* 71: 3272-3277; Dubin et al. (1997) *Virology* 235:323-332); SV5 (He et al. (1997) *Virology* 237:249-260); canine distemper virus (Gassen et al. (2000) *J. Virol.* 74:10737-44); and Sendai virus (Park et al. (1991) *Proc. Natl. Acad. Sci. USA* 88: 5537-5541; Kato et al. (1996) Genes to Cells 1:569-579). Those of skill in the art will be familiar with these and similar techniques to produce influenza virus comprising the HA and NA sequences of the invention. Recombinant influenza viruses produced according to such methods are also a feature of the invention, as are recombinant influenza virus comprising one or more nucleic acids and/or polypeptides of the invention.

Cell Culture and Expression Hosts

The present invention also relates to host cells that are introduced (transduced, transformed or transfected) with vectors of the invention, and the production of polypeptides of the invention by recombinant techniques. Host cells are genetically engineered (i.e., transduced, transformed or transfected) with a vector, such as an expression vector, of this invention. As described above, the vector can be in the form of a plasmid, a viral particle, a phage, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; or insect cells such as *Drosophila* and *Spodoptera frugiperda*.

Most commonly, mammalian cells are used to culture the HA and NA molecules of the invention. Suitable host cells for the replication of influenza virus include, e.g., Vero cells, BHK cells, MDCK cells, 293 cells and COS cells, including 293T cells, COS7 cells or the like. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

The engineered host cells can be cultured in conventional nutrient media modified as appropriate for activating promoters, selecting transformants, or amplifying the inserted polynucleotide sequences. The culture conditions, such as temperature, pH and the like, are typically those previously used with the particular host cell selected for expression, and will be apparent to those skilled in the art and in the references cited herein, including, e.g., Freshney (1994) *Culture of Animal Cells, a Manual of Basic Technique,* 3$^{rd}$ edition, Wiley-Liss, New York and the references cited therein. Other helpful references include, e.g., Paul (1975) *Cell and Tissue Culture,* 5$^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation*. in Cohen and Shafferman (eds.) *Novel Strategies in Design and Production of Vaccines*, which is incorporated herein in its entirety for all purposes. Additionally, variations in such procedures adapted to the present invention are readily determined through routine experimentation and will be familiar to those skilled in the art.

Cells for production of influenza virus (e.g., having the HA and/or NA sequences of the invention) can be cultured in serum-containing or serum free medium. In some cases, e.g., for the preparation of purified viruses, it is typically desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in many desired aspects of the current invention, it is important that the cultures be maintained at an appropriate temperature, to insure efficient recovery of recombinant and/or reassortant influenza virus using temperature dependent multi plasmid systems (see, e.g., Multi-Plasmid System for the Production of Influenza Virus, U.S. Application No. 60/420,708, filed Oct. 23, 2002, U.S. application Ser. No. 10/423,828, filed Apr. 25, 2003, and U.S. Application No. 60/574,117, filed May 24, 2004), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some embodiments herein (e.g., wherein reassorted viruses are to be produced from segments on vectors) vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reassorted viruses, etc. Thus, in one example, approximately 1 µg of each vector is introduced into a population of host cells with approximately 2 µl of TransIT-LT1 diluted in 160 µl medium, preferably serum-free medium, in a total volume of 200 µl. The DNA:transfection reagent mixtures are incubated at room temperature for 45 minutes followed by addition of 800 µl of medium. The transfection mixture is added to the host cells, and the cells are cultured as described via other methods well known to those skilled in the art. Accordingly, for the production of recombinant or reassortant viruses in cell culture, vectors incorporating each of the 8 genome segments, (PB2, PB1, PA, NP, M, NS, HA and NA, e.g., of the invention) are mixed with approximately 20 µl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce such vectors incorporating influenza genome segments into host cells. For example, plasmid vectors incorporating an influenza A or influenza B virus are favorably introduced into Vero cells using electroporation according to the following procedure. In brief, approximately $5 \times 10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 µl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

In mammalian host cells, a number of expression systems, such as viral-based systems, can be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing the polypeptides of interest in infected host cells (Logan and Shenk (1984) *Proc Natl Acad Sci* 81:3655-3659). In addition, transcription enhancers, such as the rous sarcoma virus (RSV) enhancer, can be used to increase expression in mammalian host cells.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing, which cleaves a precursor form into a mature form, of the protein is sometimes important for correct insertion, folding and/or function. Additionally proper location within a host cell (e.g., on the cell surface) is also important. Different host cells such as COS, CHO, BHK, MDCK, 293, 293T, COS7, etc. have specific cellular machinery and characteristic mechanisms for such post-translational activities and can be chosen to ensure the correct modification and processing of the current introduced, foreign protein.

For long-term, high-yield production of recombinant proteins encoded by, or having subsequences encoded by, the polynucleotides of the invention, stable expression systems are optionally used. For example, cell lines, stably expressing a polypeptide of the invention, are transfected using expression vectors that contain viral origins of replication or endogenous expression elements and a selectable marker gene. For example, following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Thus, resistant clumps of stably transformed cells, e.g., derived from single cell type, can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The cells expressing said protein can be sorted, isolated and/or purified. The protein or fragment thereof produced by a recombinant cell can be secreted, membrane-bound, or retained intracellularly, depending on the sequence (e.g., depending upon fusion proteins encoding a membrane retention signal or the like) and/or the vector used.

Expression products corresponding to the nucleic acids of the invention can also be produced in non-animal cells such as plants, yeast, fungi, bacteria and the like. In addition to Sambrook, Berger and Ausubel, all infra, details regarding cell culture can be found in Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors that direct high-level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., sequences comprising those found herein, etc., can be ligated into the vector in-frame with sequences for the amino-terminal translation initiating methionine and the subsequent 7 residues of beta-galactosidase producing a catalytically active beta galactosidase fusion protein; pIN vectors (Van Heeke & Schuster (1989) *J Biol Chem* 264:5503-5509); pET vectors (Novagen, Madison Wis.); and the like. Similarly, in the yeast *Saccharomyces cerevisiae* a number of vectors containing constitutive or inducible promoters such as alpha factor, alcohol oxidase and PGH can be used for production of the desired expression products. For reviews, see Ausubel, infra, and Grant et al., (1987); *Methods in Enzymology* 153: 516-544.

Nucleic Acid Hybridization

Comparative hybridization can be used to identify nucleic acids (e.g., SEQ ID NO: 1-10, SEQ ID NO: 21-26, SEQ ID NO:33-38, SEQ ID NO:45) of the invention, including conservative variations of nucleic acids of the invention. This comparative hybridization method is a preferred method of distinguishing nucleic acids of the invention. In addition, target nucleic acids which hybridize to the nucleic acids represented by, e.g., those shown herein under high, ultra-high and ultra-ultra-high stringency conditions are features of the invention. Examples of such nucleic acids include those with one or a few silent or conservative nucleic acid substitutions as compared to a given nucleic acid sequence.

A test target nucleic acid is said to specifically hybridize to a probe nucleic acid when it hybridizes at least one-half as well to the probe as to the perfectly matched complementary target, i.e., with a signal to noise ratio at least one-half as high as hybridization of the probe and target under conditions in which a perfectly matched probe binds to a perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well-characterized physico-chemical forces, such as hydrogen bonding, solvent exclusion, base stacking and the like. Numerous protocols for nucleic acid hybridization are well known in the art. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in Ausubel, Sambrook, and Berger and Kimmel, all below. Hames and Higgins (1995) *Gene Probes* 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions comprises a 0.2×SSC wash at 65° C. for 15 minutes (see, Sambrook, infra for a description of SSC buffer and other nucleic acid hybridization parameters). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

After hybridization, unhybridized nucleic acids can be removed by a series of washes, the stringency of which can be adjusted depending upon the desired results. Low stringency washing conditions (e.g., using higher salt and lower temperature) increase sensitivity, but can produce nonspecific hybridization signals and high background signals. Higher stringency conditions (e.g., using lower salt and higher temperature that is closer to the $T_m$) lower the background signal, typically with primarily the specific signal remaining. See, also, Rapley, R. and Walker, J. M. eds., *Molecular Biomethods Handbook* (Humana Press, Inc. 1998).

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra, and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the hybridization and wash conditions are gradually increased until a probe binds to a perfectly matched complementary target with a signal to noise ratio that is at least 5× as high as that observed for hybridization of the probe to an unmatched target.

In general, a signal to noise ratio of at least 2× (or higher, e.g., at least 5×, 10×, 20×, 50×, 100×, or more) than that observed for an unrelated probe in the particular hybridization assay indicates detection of a specific hybridization. Detection of at least stringent hybridization between two sequences in the context of the present invention indicates relatively strong structural similarity to, e.g., the nucleic acids of the present invention provided in the sequence listings herein.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH (as noted below, highly stringent conditions can also be referred to in comparative terms). Target sequences that are closely related or identical to the nucleotide sequence of interest (e.g., "probe") can be identified under stringent or highly stringent conditions. Lower stringency conditions are appropriate for sequences that are less complementary.

"Ultra high-stringency" hybridization and wash conditions are those in which the stringency of hybridization and wash conditions are increased until the signal to noise ratio for binding of a probe to a perfectly matched complementary target nucleic acid is at least 10× as high as that observed for hybridization to any unmatched target nucleic acids. A target nucleic acid which hybridizes to a probe under such conditions, with a signal to noise ratio of at least one-half that of the perfectly matched complementary target nucleic acid is said to bind to the probe under ultra-high stringency conditions.

In determining stringent or highly stringent hybridization (or even more stringent hybridization) and wash conditions, the hybridization and wash conditions are gradually increased (e.g., by increasing temperature, decreasing salt concentration, increasing detergent concentration and/or increasing the concentration of organic solvents, such as formamide, in the hybridization or wash), until a selected set of criteria are met. For example, the hybridization and wash conditions are gradually increased until a probe comprising one or more polynucleotide sequences of the invention, e.g., sequences or unique subsequences selected from those given herein (e.g., SEQ ID NO: 1-10, 21-26, 33-38, SEQ ID NO:45) and/or complementary polynucleotide sequences, binds to a perfectly matched complementary target (again, a nucleic acid comprising one or more nucleic acid sequences or subsequences selected from those given herein and/or complementary polynucleotide sequences thereof), with a signal to noise ratio that is at least 2× (and optionally 5×, 10×, or 100× or more) as high as that observed for hybridization of the probe to an unmatched target (e.g., a polynucleotide sequence comprising one or more sequences or subsequences selected from known influenza sequences present in public databases such as GenBank at the time of filing, and/or complementary polynucleotide sequences thereof), as desired.

Using the polynucleotides of the invention, or subsequences thereof, novel target nucleic acids can be obtained; such target nucleic acids are also a feature of the invention. For example, such target nucleic acids include sequences that hybridize under stringent conditions to a unique oligonucleotide probe corresponding to any of the polynucleotides of the invention, e.g., SEQ ID NO: 1-10, 21-26, 33-38, 45).

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any unmatched target nucleic acids. The particular signal will depend on the label used in the relevant assay, e.g., a fluorescent label, a colorimetric label, a radioactive label, or the like. A target nucleic acid which hybridizes to a probe under such conditions, with a signal to noise ratio of at least one-half that of the perfectly matched complementary target nucleic acid is said to bind to the probe under ultra-ultra-high stringency conditions and are also features of the invention.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Cloning, Mutagenesis and Expression of Biomolecules of Interest

General texts which describe molecular biological techniques, which are applicable to the present invention, such as cloning, mutation, cell culture and the like, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). These texts describe mutagenesis, the use of vectors, promoters and many other relevant topics related to, e.g., the generation of HA and/or NA molecules, etc.

Various types of mutagenesis are optionally used in the present invention, e.g., to produce and/or isolate, e.g., novel or newly isolated HA and/or NA molecules and/or to further modify/mutate the polypeptides (e.g., HA and NA molecules as in SEQ ID NO: 11-20 or 27-32 or 39-44) of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications (and references cited within): Sieber, et al., *Nature Biotechnology*, 19:456-460 (2001); Ling et al., *Approaches to DNA mutagenesis: an overview, Anal Biochem* 254(2): 157-178 (1997);

Dale et al., *Oligonucleotide-directed random mutagenesis using the phosphorothioate method*, Methods Mol Biol 57:369-374 (1996); I. A. Lorimer, I. Pastan, *Nucleic Acids Res* 23, 3067-8 (1995); W. P. C. Stemmer, *Nature* 370, 389-91 (1994); Arnold, *Protein engineering for unusual environments*, Current Opinion in Biotechnology 4:450-455 (1993); Bass et al., *Mutant Trp repressors with new DNA-binding specificities*, Science 242:240-245 (1988); Fritz et al., *Oligonucleotide-directed construction of mutations: a gapped duplex DNA procedure without enzymatic reactions in vitro*, Nucl Acids Res 16: 6987-6999 (1988); Kramer et al., *Improved enzymatic in vitro reactions in the gapped duplex DNA approach to oligonucleotide-directed construction of mutations*, Nucl Acids Res 16: 7207 (1988); Sakamar and Khorana, *Total synthesis and expression of a gene for the a-subunit of bovine rod outer segment guanine nucleotide-binding protein (transducin)*, Nucl Acids Res 14: 6361-6372 (1988); Sayers et al., *Y-T Exonucleases in phosphorothioate-based oligonucleotide-directed mutagenesis*, Nucl Acids Res 16:791-802 (1988); Sayers et al., *Strand specific cleavage of phosphorothioate-containing DNA by reaction with restriction endonucleases in the presence of ethidium bromide*, (1988) Nucl Acids Res 16: 803-814; Carter, *Improved oligonucleotide-directed mutagenesis using M13 vectors*, Methods in Enzymol 154: 382-403 (1987); Kramer & Fritz *Oligonucleotide-directed construction of mutations via gapped duplex DNA*, Methods in Enzymol 154:350-367 (1987); Kunkel, *The efficiency of oligonucleotide directed mutagenesis*, in Nucleic Acids & Molecular Biology (Eckstein, F. and Lilley, D. M. J. eds., Springer Verlag, Berlin)) (1987); Kunkel et al., *Rapid and efficient site-specific mutagenesis without phenotypic selection*, Methods in Enzymol 154, 367-382 (1987); Zoller & Smith, *Oligonucleotide-directed mutagenesis: a simple method using two oligonucleotide primers and a single-stranded DNA template*, Methods in Enzymol 154:329-350 (1987); Carter, *Site-directed mutagenesis*, Biochem J 237:1-7 (1986); Eghtedarzadeh & Henikoff, *Use of oligonucleotides to generate large deletions*, Nucl Acids Res 14: 5115 (1986); Mandecki, *Oligonucleotide-directed double-strand break repair in plasmids of Escherichia coli: a method for site-specific mutagenesis*, Proc Natl Acad Sci USA, 83:7177-7181 (1986); Nakamaye & Eckstein, *Inhibition of restriction endonuclease Nci I cleavage by phosphorothioate groups and its application to oligonucleotide-directed mutagenesis*, Nucl Acids Res 14: 9679-9698 (1986); Wells et al., *Importance of hydrogen-bond formation in stabilizing the transition state of subtilisin*, Phil Trans R Soc Lond A 317: 415-423 (1986); Botstein & Shortle, *Strategies and applications of in vitro mutagenesis*, Science 229:1193-1201 (1985); Carter et al., *Improved oligonucleotide site-directed mutagenesis using M13 vectors*, Nucl Acids Res 13: 4431-4443 (1985); Grundström et al., *Oligonucleotide-directed mutagenesis by microscale 'shot-gun' gene synthesis*, Nucl Acids Res 13: 3305-3316 (1985); Kunkel, *Rapid and efficient site-specific mutagenesis without phenotypic selection*, Proc Natl Acad Sci USA 82:488-492 (1985); Smith, *In vitro mutagenesis*, Ann Rev Genet 19:423-462 (1985); Taylor et al., *The use of phosphorothioate-modified DNA in restriction enzyme reactions to prepare nicked DNA*, Nucl Acids Res 13: 8749-8764 (1985); Taylor et al., *The rapid generation of oligonucleotide-directed mutations at high frequency using phosphorothioate-modified DNA*, Nucl Acids Res 13: 8765-8787 (1985); Wells et al., *Cassette mutagenesis: an efficient method for generation of multiple mutations at defined sites*, Gene 34:315-323 (1985); Kramer et al., *The gapped duplex DNA approach to oligonucleotide-directed mutation construction*, Nucl Acids Res 12: 9441-9456 (1984); Kramer et al., *Point Mismatch Repair*, Cell 38:879-887 (1984); Nambiar et al., *Total synthesis and cloning of a gene coding for the ribonuclease S protein*, Science 223: 1299-1301 (1984); Zoller & Smith, *Oligonucleotide-directed mutagenesis of DNA fragments cloned into M13 vectors*, Methods in Enzymol 100:468-500 (1983); and Zoller & Smith, *Oligonucleotide-directed mutagenesis using M13-derived vectors: an efficient and general procedure for the production of point mutations in any DNA fragment*, Nucl Acids Res 10:6487-6500 (1982). Additional details on many of the above methods can be found in *Methods in Enzymol* Volume 154, which also describes useful controls for trouble-shooting problems with various mutagenesis, gene isolation, expression, and other methods.

Oligonucleotides, e.g., for use in mutagenesis of the present invention, e.g., mutating libraries of the HA and/or NA molecules of the invention, or altering such, are typically synthesized chemically according to the solid phase phosphoramidite triester method described by Beaucage and Caruthers, *Tetrahedron Letts* 22(20):1859-1862, (1981) e.g., using an automated synthesizer, as described in Needham-VanDevanter et al., *Nucleic Acids Res*, 12:6159-6168 (1984).

In addition, essentially any nucleic acid can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, peptides and antibodies can be custom ordered from any of a variety of sources, such as PeptidoGenic (available at pkim@ccnet.com), HTI Bio-products, Inc. (www.htibio.com), BMA Biomedicals Ltd. (U.K.), Bio. Synthesis, Inc., and many others.

The present invention also relates to host cells and organisms comprising a HA and/or NA molecule or other polypeptide and/or nucleic acid of the invention, e.g., SEQ ID NOS: 1-45. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (see, From et al., *Proc Natl Acad Sci USA* 82, 5824 (1985), infection by viral vectors, high velocity ballistic penetration by small particles with the nucleic acid either within the matrix of small beads or particles, or on the surface (Klein et al., *Nature* 327, 70-73 (1987)). Berger, Sambrook, and Ausubel provide a variety of appropriate transformation methods. See, above.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or optionally both. See, Giliman & Smith, *Gene* 8:81 (1979); Roberts, et al., *Nature,* 328:731 (1987); Schneider, B., et al., *Protein Expr Purif* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds.) published by the ATCC. Additional basic procedures for sequencing, cloning and other aspects of molecular biology and underlying theoretical considerations are also found in Watson et al. (1992) *Recombinant DNA Second Edition* Scientific American Books, NY. See, above. Further vectors useful with the sequences herein are illustrated above in the section concerning production of influenza virus for vaccines and the references cited therein.

Polypeptide Production and Recovery

Following transduction of a suitable host cell line or strain and growth of the host cells to an appropriate cell density, the selected promoter is induced by appropriate means (e.g., temperature shift or chemical induction) and cells are cultured for an additional period. In some embodiments, a secreted polypeptide product, e.g., a HA and/or NA polypeptide as in a secreted fusion protein form, etc., is then recovered from the culture medium. In other embodiments, a virus particle containing a HA and/or a NA polypeptide of the invention is produced from the cell. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art. Additionally, cells expressing a HA and/or a NA polypeptide product of the invention can be utilized without separating the polypeptide from the cell. In such situations, the polypeptide of the invention is optionally expressed on the cell surface and is examined thus (e.g., by having HA and/or NA molecules (or fragments thereof, e.g., comprising fusion proteins or the like) on the cell surface bind antibodies, etc. Such cells are also features of the invention.

Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems known to those skilled in the art), hydroxylapatite chromatography, and lectin chromatography. Protein refolding steps can be used, as desired, in completing configuration of the mature protein. Also, high performance liquid chromatography (HPLC) can be employed in the final purification steps. In addition to the references noted herein, a variety of purification methods are well known in the art, including, e.g., those set forth in Sandana (1997) *Bioseparation of Proteins,* Academic Press, Inc.; and Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3$^{rd}$ Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ.

When the expressed polypeptides of the invention are produced in viruses, the viruses are typically recovered from the culture medium, in which infected (transfected) cells have been grown. Typically, crude medium is clarified prior to concentration of influenza viruses. Common methods include ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large-scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. *Vaccine Production,* in Nicholson et al. (eds.) *Textbook of Influenza* pp. 324-332; Merten et al. (1996) *Production of influenza virus in cell cultures for vaccine preparation,* in Cohen & Shafferman (eds.) *Novel Strategies in Design and Production of Vaccines* pp. 141-151, and U.S. Pat. No. 5,690,937. If desired, the recovered viruses can be stored at −80° C. in the presence of sucrose-phosphate-glutamate (SPG) as a stabilizer Alternatively, cell-free transcription/translation systems can be employed to produce polypeptides comprising an amino acid sequence or subsequence of, e.g., the sequences given herein such as SEQ ID NOS: 11-20 or 27-32 or 39-44, or encoded by the polynucleotide sequences of the invention, e.g., SEQ ID NOS: 1-10 or 21-26 or 33-38 or 45. A number of suitable in vitro transcription and translation systems are commercially available. A general guide to in vitro transcription and translation protocols is found in Tymms (1995) *In vitro Transcription and Translation Protocols: Methods in Molecular Biology* Volume 37, Garland Publishing, NY.

In addition, the polypeptides, or subsequences thereof, e.g., subsequences comprising antigenic peptides, can be produced manually or by using an automated system, by direct peptide synthesis using solid-phase techniques (see, Stewart et al. (1969) *Solid-Phase Peptide Synthesis,* WH Freeman Co, San Francisco; Merrifield J (1963) *J Am Chem Soc* 85:2149-2154). Exemplary automated systems include the Applied Biosystems 431A Peptide Synthesizer (Perkin Elmer, Foster City, Calif.). If desired, subsequences can be chemically synthesized separately, and combined using chemical methods to provide full-length polypeptides.

Modified Amino Acids

Expressed polypeptides of the invention can contain one or more modified amino acids. The presence of modified amino acids can be advantageous in, for example, (a) increasing polypeptide serum half-life, (b) reducing/increasing polypeptide antigenicity, (c) increasing polypeptide storage stability, etc Amino acid(s) are modified, for example, co-translationally or post-translationally during recombinant production (e.g., N-linked glycosylation at N-X-S/T motifs during expression in mammalian cells) or modified by synthetic means (e.g., via PEGylation).

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like, as well as amino acids modified by conjugation to, e.g., lipid moieties or other organic derivatizing agents. References adequate to guide one of skill in the modification of amino acids are replete throughout the literature. Example protocols are found in Walker (1998) *Protein Protocols on CD-ROM* Human Press, Towata, N.J.

Fusion Proteins

The present invention also provides fusion proteins comprising fusions of the sequences of the invention (e.g., encoding HA and/or NA polypeptides as exampled by SEQ ID NOS: 11-20, 27-32, and 39-44) or fragments thereof with, e.g., immunoglobulins (or portions thereof), sequences encoding, e.g., GFP (green fluorescent protein), or other similar markers, etc. Nucleotide sequences encoding such fusion proteins are another aspect of the invention. Fusion proteins of the invention are optionally used for, e.g., similar applications (including, e.g., therapeutic, prophylactic, diagnostic, experimental, etc. applications as described herein) as the non-fusion proteins of the invention. In addition to fusion with immunoglobulin sequences and marker sequences, the proteins of the invention are also optionally fused with, e.g., sequences which allow sorting of the fusion proteins and/or targeting of the fusion proteins to specific cell types, regions, etc.

Antibodies

The polypeptides of the invention can be used to produce antibodies specific for the polypeptides given herein and/or polypeptides encoded by the polynucleotides of the invention, e.g., those shown herein, and conservative variants thereof. Antibodies specific for the above mentioned polypeptides are useful, e.g., for diagnostic and therapeutic purposes, e.g., related to the activity, distribution, and expression of target polypeptides.

Antibodies specific for the polypeptides of the invention can be generated by methods well known in the art. Such antibodies can include, but are not limited to, polyclonal, monoclonal, chimeric, humanized, single chain, Fab fragments and fragments produced by an Fab expression library.

Polypeptides do not require biological activity for antibody production (e.g., full length functional hemagglutinin or neuraminidase is not required). However, the polypeptide or oligopeptide must be antigenic. Peptides used to induce specific antibodies typically have an amino acid sequence of at least about 4 amino acids, and often at least 5 or 10 amino acids. Short stretches of a polypeptide can be fused with another protein, such as keyhole limpet hemocyanin, and antibody produced against the chimeric molecule.

Numerous methods for producing polyclonal and monoclonal antibodies are known to those of skill in the art, and can be adapted to produce antibodies specific for the polypeptides of the invention, and/or encoded by the polynucleotide sequences of the invention, etc. See, e.g., Coligan (1991) *Current Protocols in Immunology* Wiley/Greene, NY; Paul (ed.) (1998) *Fundamental Immunology, Fourth Edition*, Lippincott-Raven, Lippincott Williams & Wilkins; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495-497. Other suitable techniques for antibody preparation include selection of libraries of recombinant antibodies in phage or similar vectors. See, Huse et al. (1989) *Science* 246: 1275-1281; and Ward, et al. (1989) *Nature* 341: 544-546. Specific monoclonal and polyclonal antibodies and antisera will usually bind with a $K_D$ of, e.g., at least about 0.1 μM, at least about 0.01 μM or better, and, typically and at least about 0.001 μM or better.

For certain therapeutic applications, humanized antibodies are desirable. Detailed methods for preparation of chimeric (humanized) antibodies can be found in U.S. Pat. No. 5,482,856. Additional details on humanization and other antibody production and engineering techniques can be found in Borrebaeck (ed.) (1995) *Antibody Engineering, $2^{nd}$ Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul). Additional details regarding specific procedures can be found, e.g., in Ostberg et al. (1983), *Hybridoma* 2: 361-367, Ostberg, U.S. Pat. No. 4,634,664, and Engelman et al., U.S. Pat. No. 4,634,666.

Defining Polypeptides by Immunoreactivity

Because the polypeptides of the invention provide a variety of new polypeptide sequences (e.g., comprising HA and NA molecules), the polypeptides also provide new structural features which can be recognized, e.g., in immunological assays. The generation of antisera which specifically bind the polypeptides of the invention, as well as the polypeptides which are bound by such antisera, are features of the invention.

For example, the invention includes polypeptides (e.g., HA and NA molecules) that specifically bind to or that are specifically immunoreactive with an antibody or antisera generated against an immunogen comprising an amino acid sequence selected from one or more of the sequences given herein (e.g., SEQ ID NOS: 11-20, 27-32, and 39-44), etc. To eliminate cross-reactivity with other homologues, the antibody or antisera is subtracted with the HA and/or NA molecules found in public databases at the time of filing, e.g., the "control" polypeptide(s). Where the other control sequences correspond to a nucleic acid, a polypeptide encoded by the nucleic acid is generated and used for antibody/antisera subtraction purposes.

In one typical format, the immunoassay uses a polyclonal antiserum which was raised against one or more polypeptide comprising one or more of the sequences corresponding to the sequences herein (e.g., SEQ ID NOS: 11-20, 27-32, and 39-44), etc. or a substantial subsequence thereof (i.e., at least about 30% of the full length sequence provided). The set of potential polypeptide immunogens derived from the present sequences are collectively referred to below as "the immunogenic polypeptides." The resulting antisera is optionally selected to have low cross-reactivity against the control hemagglutinin and/or neuraminidase homologues and any such cross-reactivity is removed, e.g., by immunoabsorbtion, with one or more of the control hemagglutinin and neuraminidase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity). Additional references and discussion of antibodies is also found herein and can be applied here to defining polypeptides by immunoreactivity. Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control hemagglutinin and/or neuraminidase polypeptide(s) to produce subtracted pooled titered polyclonal antisera.

The subtracted pooled titered polyclonal antisera are tested for cross reactivity against the control homologue(s) in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic polypeptides as compared to binding to the control homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control receptor homologues under discriminatory binding conditions, and at least about a ½ signal to noise ratio as compared to the immunogenic polypeptide(s), shares substantial structural similarity with the immunogenic polypeptide as compared to the known receptor, etc., and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control protein(s) to compete for binding to the pooled subtracted antisera is optionally determined as compared to the ability of the immunogenic polypeptide(s) to compete for binding to the antisera. Again, the percent cross-reactivity for the control polypeptide(s) is calculated, using standard calculations. Where the percent cross-reactivity is at least 5-10× as high for the test polypeptides as compared to the control polypeptide(s) and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptide(s)) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Nucleic Acid and Polypeptide Sequence Variants

As described herein, the invention provides for nucleic acid polynucleotide sequences and polypeptide amino acid sequences, e.g., hemagglutinin and neuraminidase sequences, and, e.g., compositions and methods comprising said sequences. Examples of said sequences are disclosed herein (e.g., SEQ ID NOS: 1-45). However, one of skill in the art will appreciate that the invention is not necessarily limited to those sequences disclosed herein and that the present invention also provides many related and unrelated sequences with the functions described herein, e.g., encoding a HA and/or a NA molecule.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Silent Variations

Due to the degeneracy of the genetic code, any of a variety of nucleic acid sequences encoding polypeptides and/or viruses of the invention are optionally produced, some which can bear lower levels of sequence identity to the HA and NA nucleic acid and polypeptide sequences herein. The following provides a typical codon table specifying the genetic code, found in many biology and biochemistry texts.

TABLE 1

Codon Table

| Amino acids | | | Codon | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations," discussed below. One of skill will recognize that each codon in a nucleic acid (except ATG, which is ordinarily the only codon for methionine, and TTG, which is ordinarily the only codon for tryptophan) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a hemagglutinin or a neuraminidase polypeptide of the invention. All such variations of every nucleic acid herein are specifically provided and described by consideration of the sequence in combination with the genetic code. One of skill is fully able to make these silent substitutions using the methods herein.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence of the invention which encodes an amino acid. Similarly, "conservative amino acid substitutions," in one or a few amino acids in an amino acid sequence are substituted with different amino acids with highly similar properties, are also readily identified as being highly similar to a disclosed construct such as those herein. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences, see, Table 2 below. One of skill will recognize that individual substitutions, deletions or additions which alter, add or delete a single amino acid or a small percentage of amino acids (typically less than 5%, more typically less than 4%, 3%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 4%, 3%, 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

TABLE 2

Conservative Substitution Groups

| | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Unique Polypeptide and Polynucleotide Subsequences

In one aspect, the invention provides a nucleic acid which comprises a unique subsequence in a nucleic acid selected from the sequence of HA and NA molecules disclosed herein, e.g., SEQ ID NOS: 1-10, 21-26, 33-38, and 45. The unique subsequence is unique as compared to a nucleic acids corresponding to nucleic acids such as, e.g., those found in GenBank or other similar public databases at the time of filing. Alignment can be performed using, e.g., BLAST set to default parameters. Any unique subsequence is useful, e.g., as a probe to identify the nucleic acids of the invention. See, above.

Similarly, the invention includes a polypeptide which comprises a unique subsequence in a polypeptide selected from the sequence of HA and NA molecules disclosed herein, e.g., SEQ ID NOS: 11-20, 27-32, and 39-44. Here, the unique subsequence is unique as compared to a polypeptide corresponding to, e.g., the amino acid corresponding to polynucleotide sequences found in, e.g., GenBank or other similar public databases at the time of filing.

The invention also provides for target nucleic acids which hybridize under stringent conditions to a unique coding oligonucleotide which encodes a unique subsequence in a polypeptide selected from the sequences of HA and NA molecules of the invention wherein the unique subsequence is unique as compared to a polypeptide corresponding to any of the control polypeptides (sequences of, e.g., the nucleic acids corresponding to those found in, e.g., GenBank or other similar public databases at the time of filing). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, "substantial identity" exists over a region of the amino acid sequences that is at least about 200 residues in length, at least about 250 residues, at least about 300 residues, 350 residues, 400 residues, 425 residues, 450 residues, 475 residues, 480 residues, 490 residues, 495 residues, 499 residues, 500 residues, 502 residues, 559 residues, 565 residues, or 566 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv Appl Math* 2:482 (1981), by the homology alignment algorithm of Needleman & Wunsch, *J Mol Biol* 48:443 (1970), by the search for similarity method of Pearson & Lipman, *Proc Natl Acad Sci USA* 85:2444 (1988), by computerized implementations of algorithms such as GAP, BESTFIT, FASTA, and TFASTA in the Wisconsin Genetics Software Package, Genetics Computer Group, 575 Science Dr., Madison, Wis., or by visual inspection (see generally, Ausubel et al., supra).

One example of an algorithm that is suitable for determining percent sequence identity and sequence similarity is the BLAST algorithm, which is described in Altschul et al., *J Mol Biol* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (see, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc Natl Acad Sci USA* 89:10915).

In addition to calculating percent sequence identity, the BLAST algorithm also performs a statistical analysis of the similarity between two sequences (see, e.g., Karlin & Altschul, *Proc Natl Acad Sci USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple DNA, or amino acid, sequence alignments is the CLUSTALW program (Thompson, J. D. et al. (1994) *Nucl. Acids. Res.* 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) *Proc. Natl. Acad. Sci. USA* 89: 10915-10919.

Digital Systems

The present invention provides digital systems, e.g., computers, computer readable media and integrated systems comprising character strings corresponding to the sequence information herein for the nucleic acids and isolated or recombinant polypeptides herein, including, e.g., the sequences shown herein, and the various silent substitutions and conservative substitutions thereof. Integrated systems can further include, e.g., gene synthesis equipment for making genes corresponding to the character strings.

Various methods known in the art can be used to detect homology or similarity between different character strings (see, above), or can be used to perform other desirable functions such as to control output files, provide the basis for making presentations of information including the sequences and the like. Examples include BLAST, discussed supra. Computer systems of the invention can include such programs, e.g., in conjunction with one or more data file or data base comprising a sequence as noted herein.

Thus, different types of homology and similarity of various stringency and length between various HA or NA sequences or fragments, etc. can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.).

Thus, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™, Paradox™, GeneWorks™, or MacVector™ or other similar programs) can be adapted to the present invention by inputting a character string corresponding to one or more polynucleotides and polypeptides of the invention (either nucleic acids or proteins, or both). For example, a system of the invention can include the foregoing software having the appropriate character string information, e.g., used in conjunction with a user interface (e.g., a GUI in a standard operating system such as a Windows, Macintosh or LINUX system) to manipulate strings of characters corresponding to the sequences herein. As noted, specialized alignment programs such as BLAST can also be incorporated into the systems of the invention for alignment of nucleic acids or proteins (or corresponding character strings).

Systems in the present invention typically include a digital computer with data sets entered into the software system comprising any of the sequences herein. The computer can be, e.g., a PC (Intel x86 or Pentium chip-compatible DOS™, OS2™ WINDOWS™ WINDOWSNT™, WINDOWS95™, WINDOWS2000™, WINDOWS98™, LINUX based machine, a MACINTOSH™, Power PC, or a UNIX based (e.g., SUN™ work station) machine) or other commercially available computer that is known to one of skill. Software for aligning or otherwise manipulating sequences is available, or can easily be constructed by one of skill using a standard programming language such as Visualbasic, PERL, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation, e.g., of appropriate mechanisms or transport controllers to carry out the desired operation. The software can also include output elements for controlling nucleic acid synthesis (e.g., based upon a sequence or an alignment of sequences herein), comparisons of samples for differential gene expression, or other operations.

Kits and Reagents

The present invention is optionally provided to a user as a kit. For example, a kit of the invention contains one or more nucleic acid, polypeptide, antibody, or cell line described herein (e.g., comprising, or with, a HA and/or NA molecule of the invention). The kit can contain a diagnostic nucleic acid or polypeptide, e.g., antibody, probe set, e.g., as a cDNA microarray packaged in a suitable container, or other nucleic acid such as one or more expression vector. The kit can also further comprise, one or more additional reagents, e.g., substrates, labels, primers, for labeling expression products, tubes and/or other accessories, reagents for collecting samples, buffers, hybridization chambers, cover slips, etc. The kit optionally further comprises an instruction set or user manual detailing preferred methods of using the kit components for discovery or application of diagnostic sets, etc.

When used according to the instructions, the kit can be used, e.g., for evaluating a disease state or condition, for evaluating effects of a pharmaceutical agent or other treatment intervention on progression of a disease state or condition in a cell or organism, or for use as a vaccine, etc.

In an additional aspect, the present invention provides system kits embodying the methods, composition, systems and apparatus herein. System kits of the invention optionally comprise one or more of the following: (1) an apparatus, system, system component or apparatus component; (2) instructions for practicing methods described herein, and/or for operating the apparatus or apparatus components herein and/or for using the compositions herein. In a further aspect, the present invention provides for the use of any apparatus, apparatus component, composition or kit herein, for the practice of any method or assay herein, and/or for the use of any apparatus or kit to practice any assay or method herein.

Additionally, the kits can include one or more translation system as noted above (e.g., a cell) with appropriate packaging material, containers for holding the components of the kit, instructional materials for practicing the methods herein and/or the like. Similarly, products of the translation systems (e.g., proteins such as HA and/or NA molecules) can be provided in kit form, e.g., with containers for holding the components of the kit, instructional materials for practicing the methods herein and/or the like.

To facilitate use of the methods and compositions of the invention, any of the vaccine components and/or compositions, e.g., reassorted virus in allantoic fluid, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

EXAMPLES

Example 1

Construction and Analysis of H5N1 ca Viruses and Vaccines

Various sequences herein comprising H5N1 HA/NA sequences were used to create influenza viruses and vaccines. The HA sequences in such vaccines were altered from wild-type by removal of the polybasic cleavage site within the HA. The HA/NA sequences were reassorted (in a 6:2 reassortment) with ca A/AA/6/60 (a ts, au, ca virus, see above).

Three strains of H5N1 influenza were used in this example: A/VN/1203/2004, A/HK/491/1997, and A/HK/213/2003. Such strains are also referred to within this example as the '97, '03, and '04 strains based on their year designations. The HA sequence homology of these three strains is 95-96%. FIG. 1 illustrates modification of the polybasic cleavage site of an exemplary HA sequence, the '04 HA sequences, used to construct the viruses/vaccines. As stated previously, various embodiments of the invention comprise sequences which have differing regions of the polybasic cleavage site removed. See above.

As stated, the modified H5N1 sequences (i.e., the modified '97, '03, and '04 genes) were used to construct 6:2 reassortant viruses with ca A/AA/6/60. It will be appreciated, and is pointed out elsewhere herein, that other desirable backbones could also have been used (e.g., PR8, etc.).

In the 6:2 reassortants of this example, the HA and NA gene sequences were derived from one or more wild type parent virus, i.e., the HA and NA gene sequences of the '03 virus were derived from A/HK/213/2003, the HA and NA gene sequences of the '04 virus were derived from A/VN/1203/2004, and the HA gene sequence of the '97 virus was derived from A/HK/491/1997 while the NA gene sequence was derived from A/HK/486/1997. The remaining genes of the 6:2 reassortants were characterized by sequence analysis as derived from the A/AA/6/60 ca parent virus. The reassorted viruses replicated to 8.0-8.5 $\log_{10}TCID_{50}$ in eggs. However, it will be appreciated that other embodiments wherein the $\log_{10}TCID_{50}$ comprises from about 7.0 to about 9.0, from about 7.5-8.5, or from about 8.0-8.5 are also within the scope of the invention. The cleavability of the modified HA in the constructed viruses by endogenous proteases was restricted in vitro and the viruses were dependent on trypsin (e.g., from about 0.1 ug/ml to about 1.0 ug/ml) for growth. The constructed viruses were temperature sensitive as assayed by an in vitro assay.

The H5N1 ca reassortant viruses (having the modified '97, '03, or '04 HA genes) were not lethal for chickens. For example, when 4-week-old SPF white Plymouth Rock chickens were inoculated intravenously with a 1:10 dilution of stock virus ($10^{8-8.75}$ $TCID_{50}$/ml) and observed for 10 days, it was observed that 8 out of 8 chickens died within 1-2 days when wild-type '97, '03, and '04 H5N1 were used, while 0 of 8 chickens died when the H5N1 ca reassortant viruses were used. As can be seen in FIG. 2, the intranasally administered H5N1 ca reassortant viruses did not replicate in chickens.

The H5N1/AA ca reassortants were also not lethal for mice. See FIG. 3, which also shows the $TCID_{50}$ for the H5N1 wild-type strains. FIG. 4 shows that the 1997 and 2004 H5N1 ca reassortant viruses were restricted in replication in mice. FIG. 5, shows that the H5N1 ca reassorted viruses are restricted in replication in lungs of mice.

A comparison of the serum HAI antibody titers elicited in mice following a single intranasal dose of vaccine (2003 ca as compared against 2003 wild-type), is shown in FIG. 6. FIGS. 7 and 15 show similar measurements, but using serum neutralizing antibody titers.

FIG. 8 displays that the H5N1 ca reassortant viruses protect mice from lethal challenge with 50, 500, or 5,000 $LD_{50}$ of wild-type H5N1 virus. FIG. 9 shows the efficacy of protection from pulmonary replication of homologous and heterologous H5N1 challenge viruses in mice. As can be seen, the ca reassortants replicated less well than the wild-type viruses did. FIG. 10 shows related data using upper respiratory tracts of mice. Those of skill in the art will be familiar with homologous and heterologous challenges (e.g., testing whether 2003 vaccine protects against a 2003 wild-type challenge (homologous) or whether a 2003 vaccine protects against a 1997 wild-type challenge (heterologous), etc.).

Figure 11:
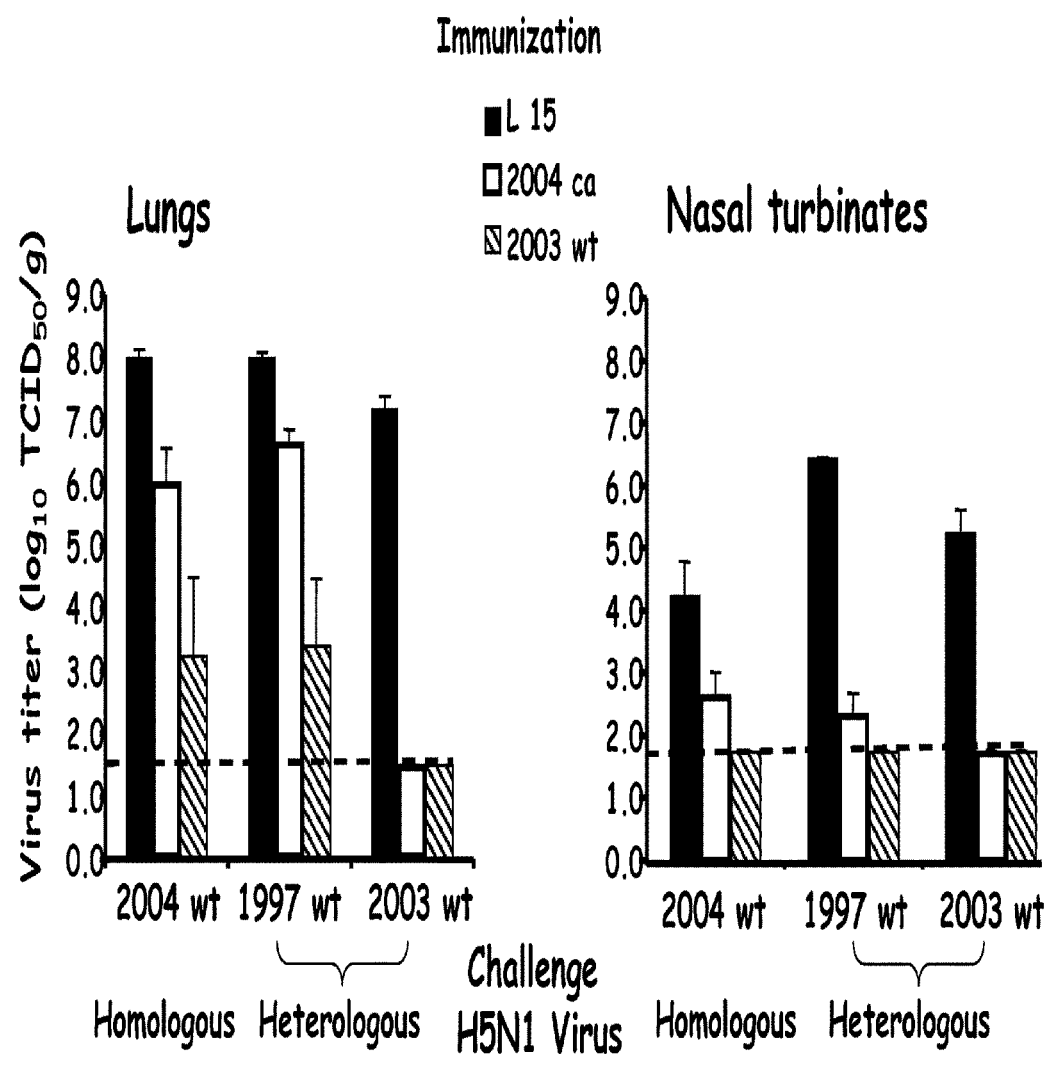
Figure 12:
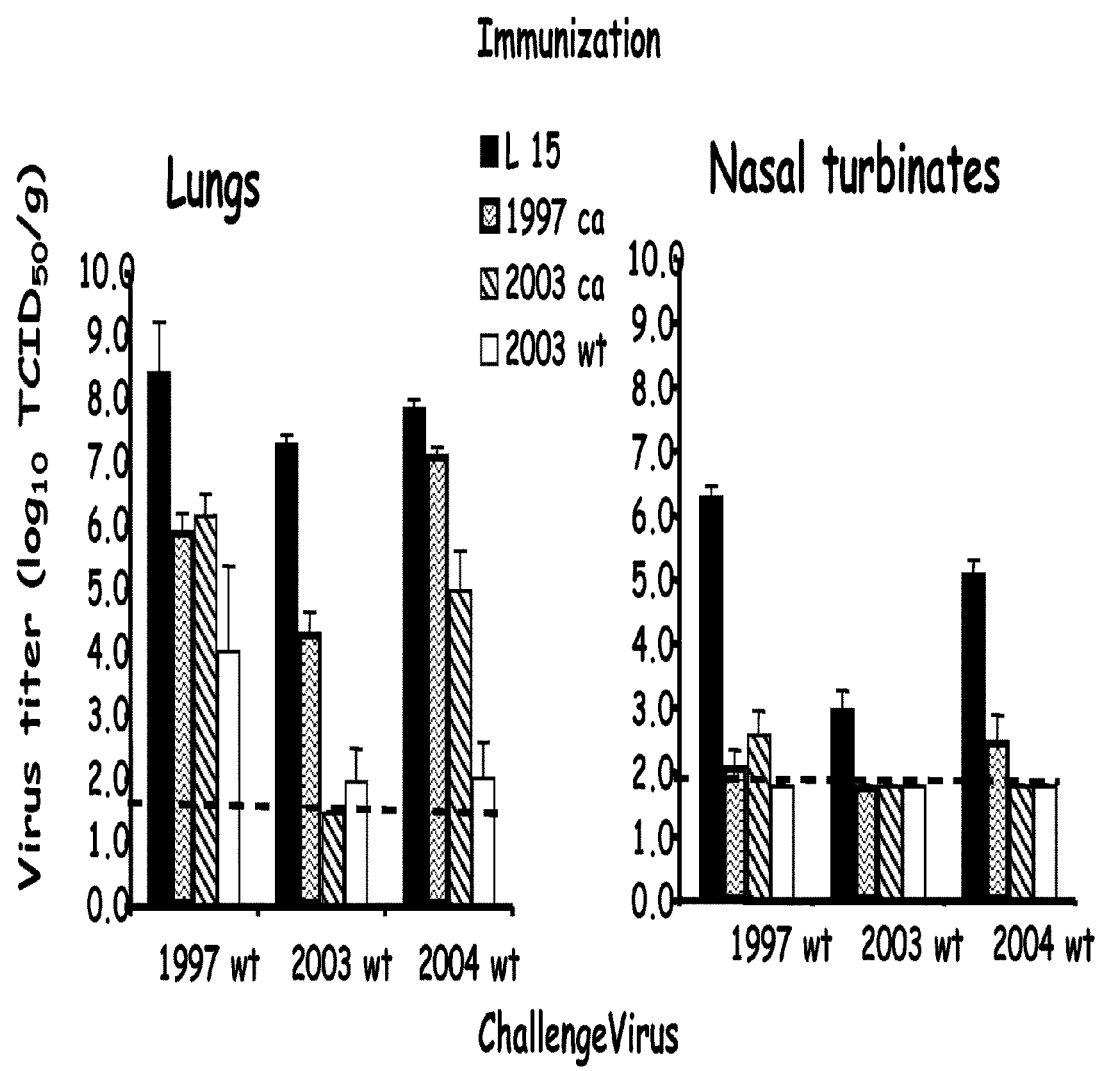
FIG. 12: Illustrates the efficacy of protection conferred by 1997 and 2003 H5N1 ca vaccines against high dose ($10_5 TCID_{50}$) challenges with homologous or heterologous H5N1 wild-type viruses in mice.
Figure 13:
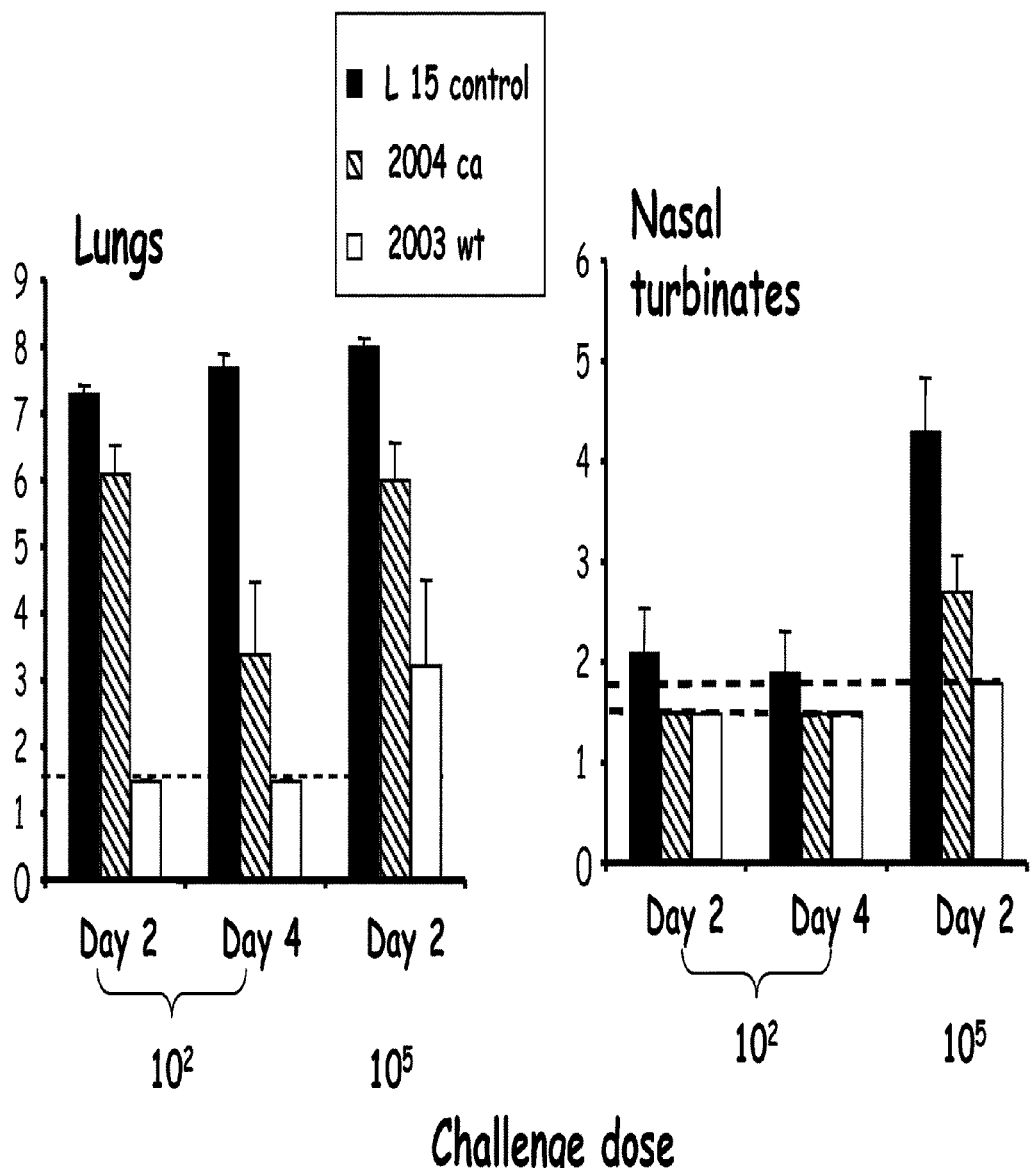
FIG. 13: Illustrates the efficacy of protection conferred by 2004 H5N1 ca vaccine against low or high doses of homologous H5N1 wild-type virus challenges in mice.

FIG. 11 shows efficacy of protection conferred by 2004 H5N1 ca vaccine against high dose ($10^5 TCID_{50}$) challenge with homologous or heterologous H5N1 wild-type viruses in mice. FIG. 12 shows efficacy of protection conferred by 1997 and 2003 H5N1 ca vaccines against high dose ($10^5 TCID_{50}$) challenge with homologous or heterologous H5N1 wild-type viruses in mice. FIG. 13 shows efficacy of protection conferred by 2004 H5N1 ca vaccine against low or high doses of homologous H5N1 wild-type virus challenge in mice. FIGS. 11-13 demonstrate that the tested vaccines could protect against other related viruses.

In healthy human adults nasal spray administration the '04 vaccine was well tolerated and its replication was highly restricted. See FIG. 27 for replication restriction of the vaccine in healthy adults. HI antibody responses to $10^{6.7}$ $TCID_{50}$ of the '04 vaccine were also observed in some of the healthy adults. See FIG. 28.

The current example demonstrates several points concerning exemplary H5N1 ca reassortant viruses/vaccines of the invention. The modified ca reassortant '97, '03, and '04 viruses were shown to have in vitro is phenotype, loss of pathogenicity in chickens and attenuation in mice. It is expected that attenuation is also present in ferrets. Efficacy of protection and cross-protection against lethal challenge and systemic spread with wild-type viruses in mice was also shown. Efficacy of protection and cross-protections against replication of wild-type challenge viruses in the respiratory tract of mice is also expected.

It is contemplated to use these (and similar) viruses/vaccines to determine whether immunogenicity and efficacy is improved following 2 doses of vaccine; to assess immunogenicity in non-human primates; to assess attenuation and vaccine efficacy in ferrets; to determine the contribution of humoral and cellular immunity to observed efficacy of the produced vaccines in mice; to determine which residues of the 2003 HA contribute to enhanced immunogenicity and introduce them into 1997 and 2004 HAs; and to determine the effects of deleting the multibasic amino acid cleavage site and of the gene constellation.

Example 2

Construction and Analysis of H6 ca Viruses and Vaccines

A set of three recombinant influenza viruses and vaccines comprising H6 HA sequences were prepared: (a) A/Duck, which comprised the H6 HA and N9 NA of A/Duck77; (b) A/Teal, which comprised the H6 HA and N1 NA of A/Teal97; and (c) A/Mallard, which comprised the H6 HA and N2 NA of A/Mallard85. The six internal genome segments of each recombinant virus were those of ca A/AA/6/60.

Figure 16:
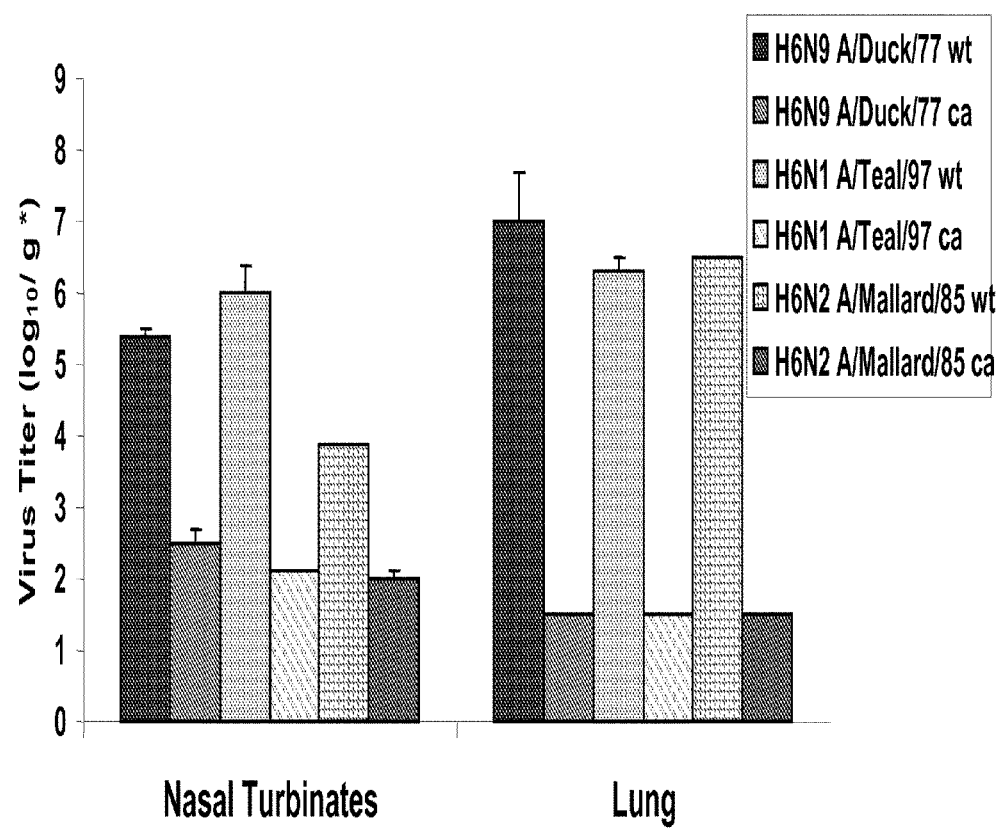
FIG. 16: H6 ca viruses are attenuated in ferrets. *$EID_{50}$/g for lungs; PFU/g for nasal turbinates. $10^7$ $TCID_{50}$ inoculated intranasally, tissues were harvested on day 3 post-infection.

Each of the A/Duck, A/Teal, and A/Mallard recombinant viruses was attenuated in nasal turbinates and lungs of ferrets. Ferrets were intranasally inoculated with $10^7$ TCID$_{50}$ recombinant (ca; see paragraph immediately above) or wild-type (wt) H6 influenza virus. Nasal turbinate and lung tissue was harvested from the ferrets three days post-infection for examination. FIG. 16 shows that the nasal turbinate and lung tissue of ferrets inoculated with recombinant virus (ca) exhibited lower virus titers than did the nasal turbinate and lung tissue of ferrets inoculated with the respective counterpart wt virus.

Each of the A/Duck, A/Teal, and A/Mallard recombinant (ca) viruses was also immunogenic in the ferrets. See FIG. 17.

Figure 18:
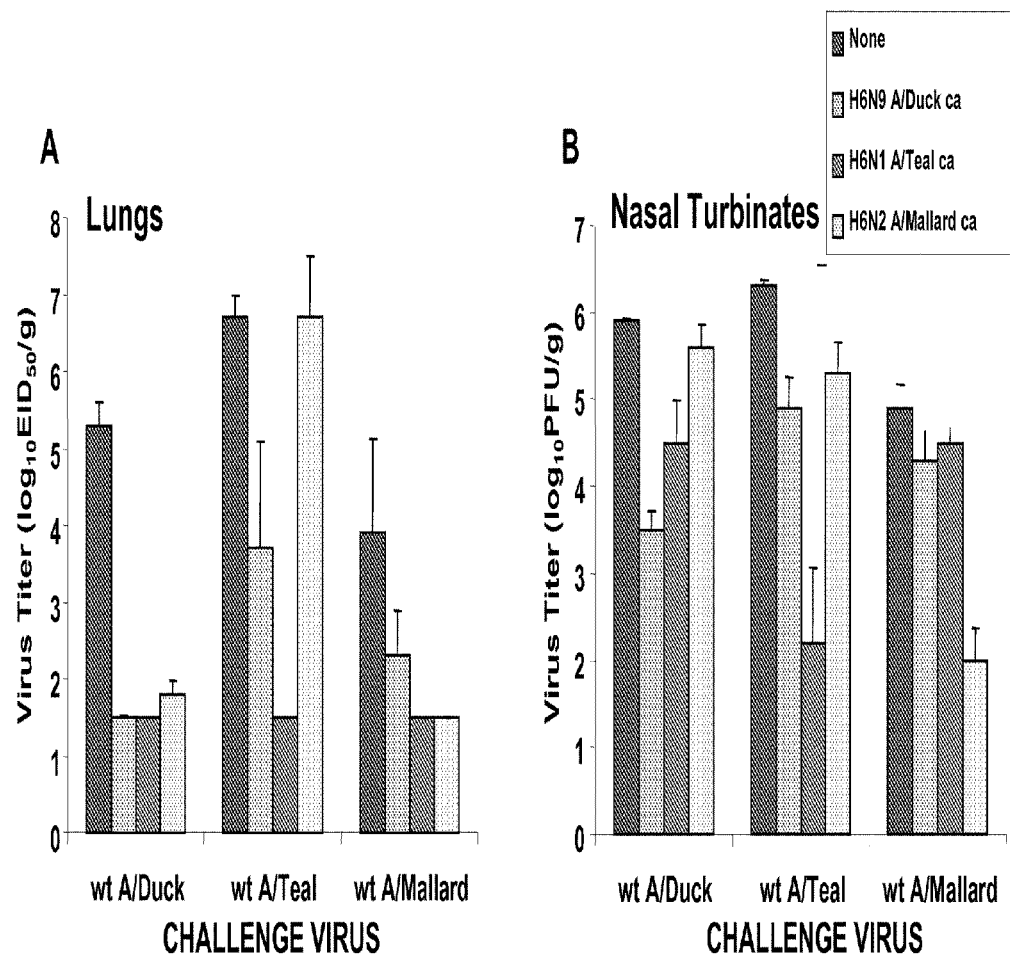
FIGS. 18(a) and 18(b): Efficacy of H6 ca vaccines in ferrets. Virus titer was measured in (a) lungs and (b) nasal turbinates. Vaccine: 1 dose of 7 $\log_{10}$ PFU. Challenge: 7 $\log_{10}$ PFU; 3 days post-challenge.

FIG. 18 shows the efficacy of protection conferred by the A/Duck, A/Teal, and A/Mallard vaccines. Ferrets were vaccinated with a single dose of 7 log$_{10}$ PFU recombinant A/Duck, A/Teal, or A/Mallard vaccine. The ferrets were then challenged with 7 log$_{10}$ PFU wt A/Duck, A/Teal, or A/Mallard virus. Three days post challenge lungs and nasal turbinates of the ferrets were harvested and virus titer in the tissues was determined. FIG. 18 shows efficacy of protection conferred by the recombinant (ca) H6 vaccines against homologous and heterologous wild-type H6 viruses in ferrets.

Example 3

Construction and Analysis of an H7N3, BC 04 ca, Virus and Vaccine

A further recombinant influenza virus and vaccine was prepared using the HA H7 and NA N3 sequences of A/ck/BC/CN-6/04 (BC 04 ca). These HA and NA sequences were combined with the six internal genome segments of ca A/AA/6/60.

Figure 19:
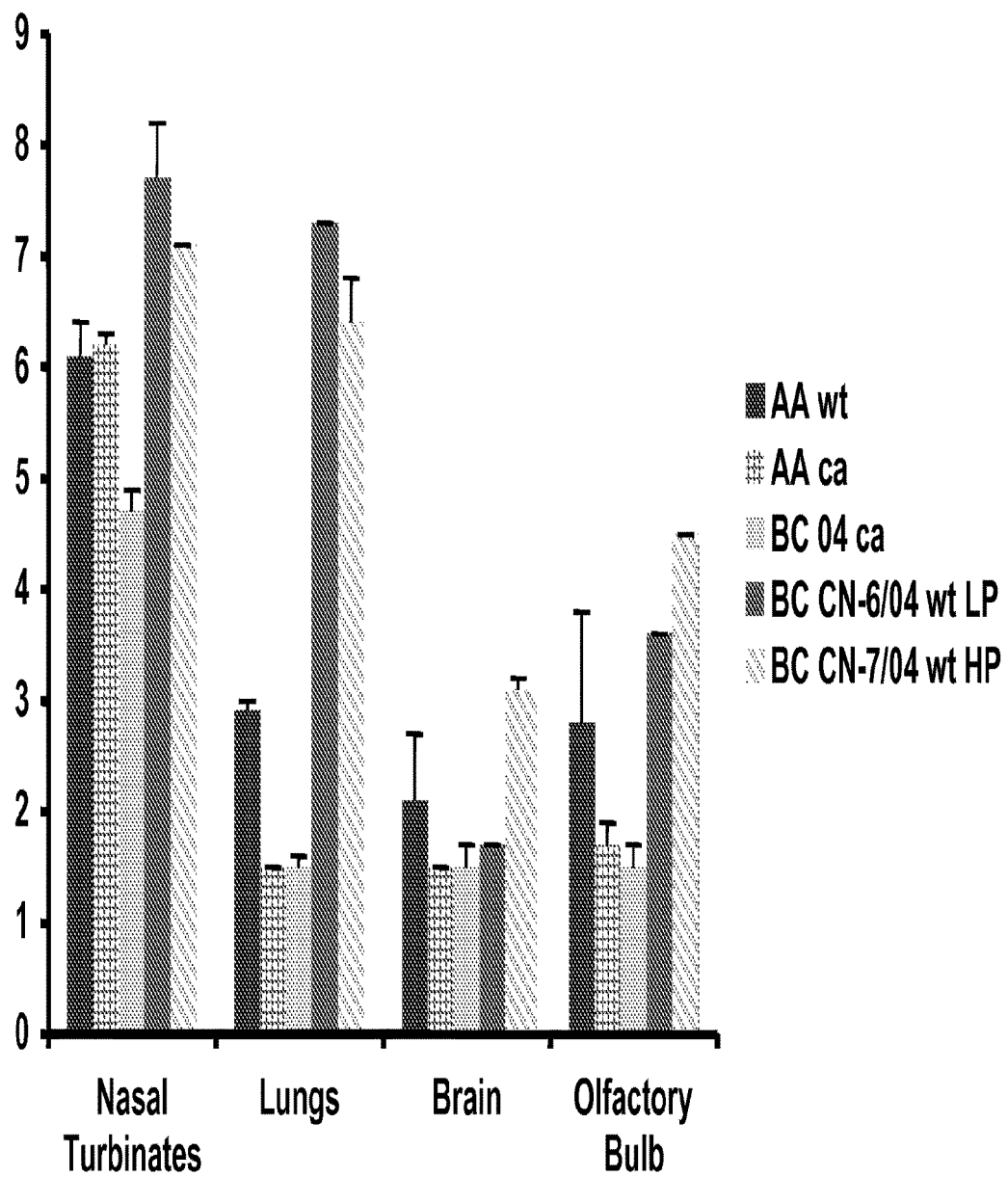
FIG. 19: H7N3 BC 04 ca is attenuated in ferrets. Inoculum: $10^7$ $TCID_{50}$ in 0.5 mL intranasally. Tissues were harvested on day 3 post-infection.

The BC 04 ca vaccine was attenuated in the ferrets. Ferrets were intranasally inoculated with $10^7$ TCID$_{50}$ vaccine in 0.5 mL. Three days following inoculation, ferret nasal turbinates, lungs, brain, and olfactory bulb were harvested. Virus titer in each of these tissues was diminished in ferrets inoculated with the vaccine virus relative to ferrets inoculated with wt viruses A/BC/CN-6/04 or A/BC/CN-7/04. See FIG. 19.

The BC 04 ca vaccine was immunogenic in mice. In mice receiving the BC 04 ca vaccine, neutralizing antibodies were detected at 4 weeks and these titers rose over 8 weeks. A second dose of vaccine boosted antibody titer but final titer achieved was similar to that following a single dose. See FIG. 20.

Figure 21:
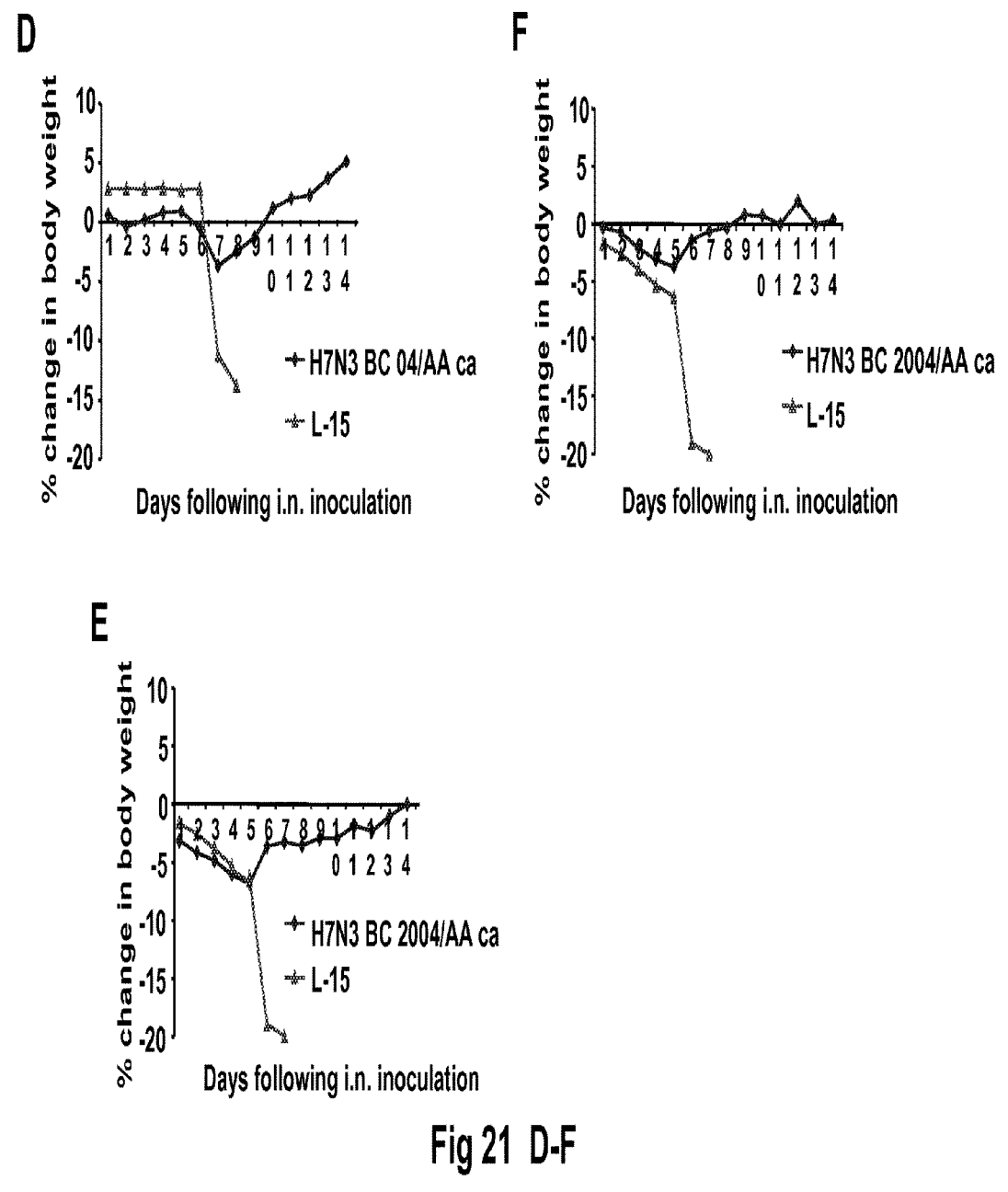
Figure 21:
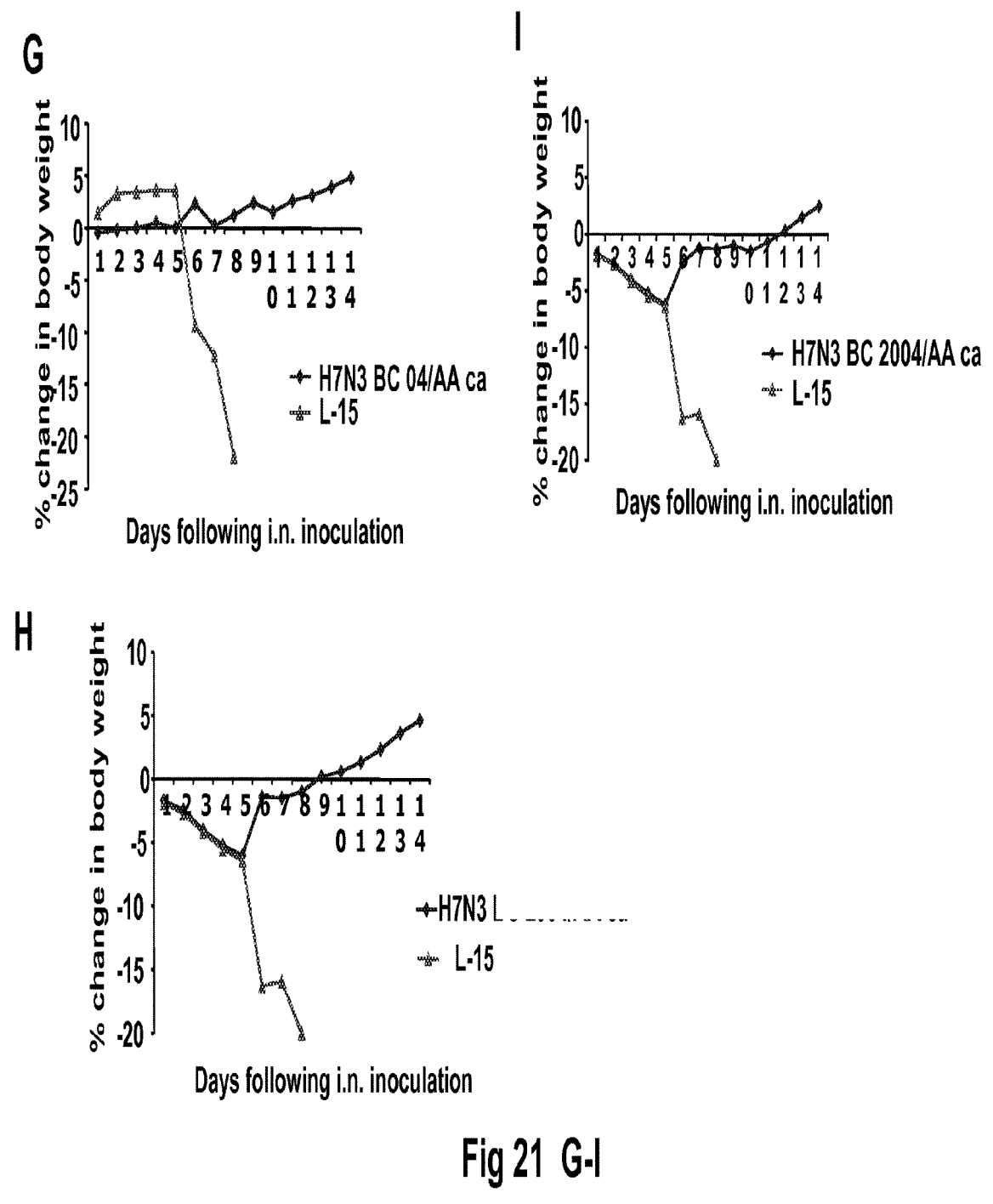
Figure 22A:
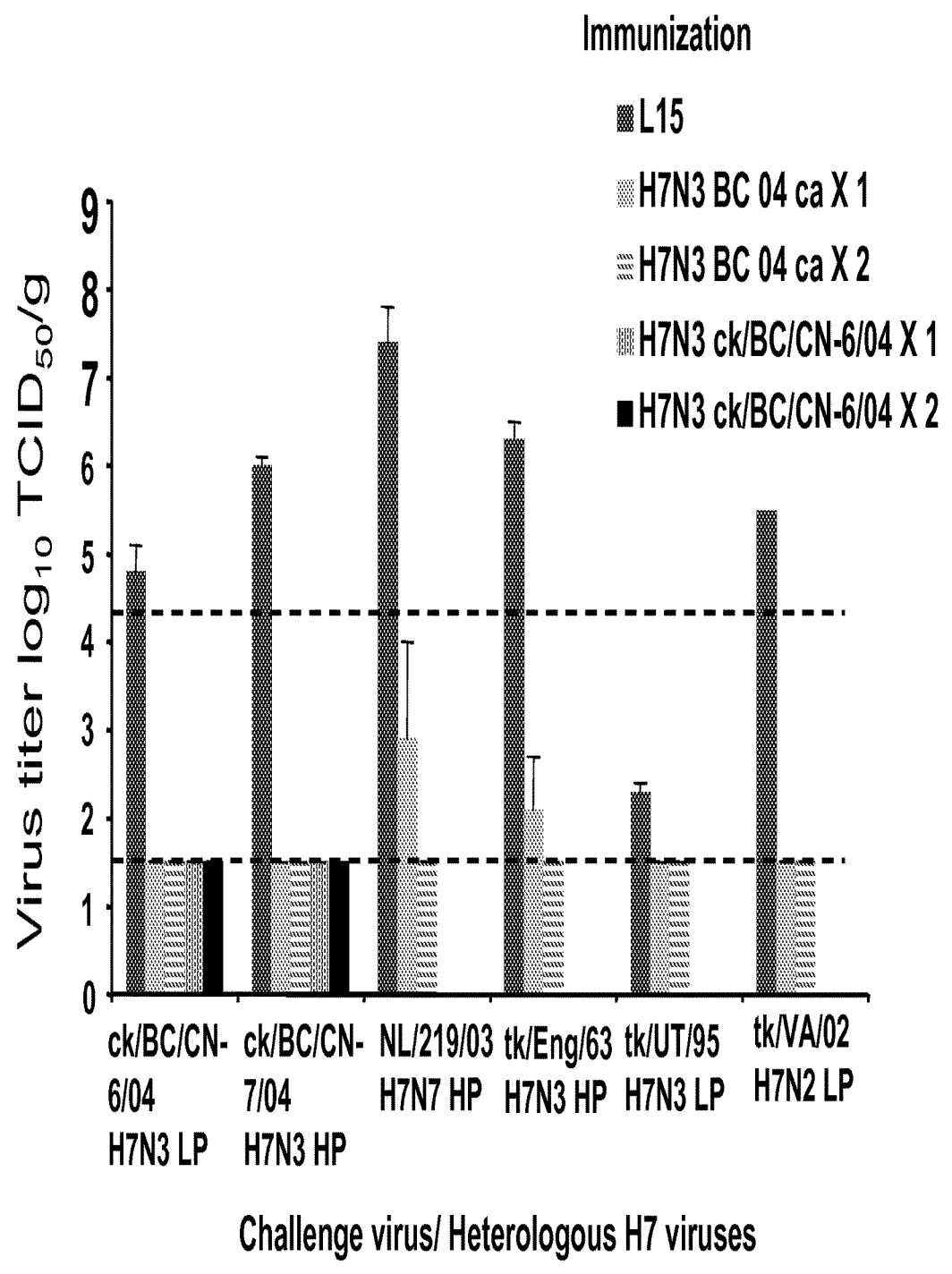
Figure 22B:
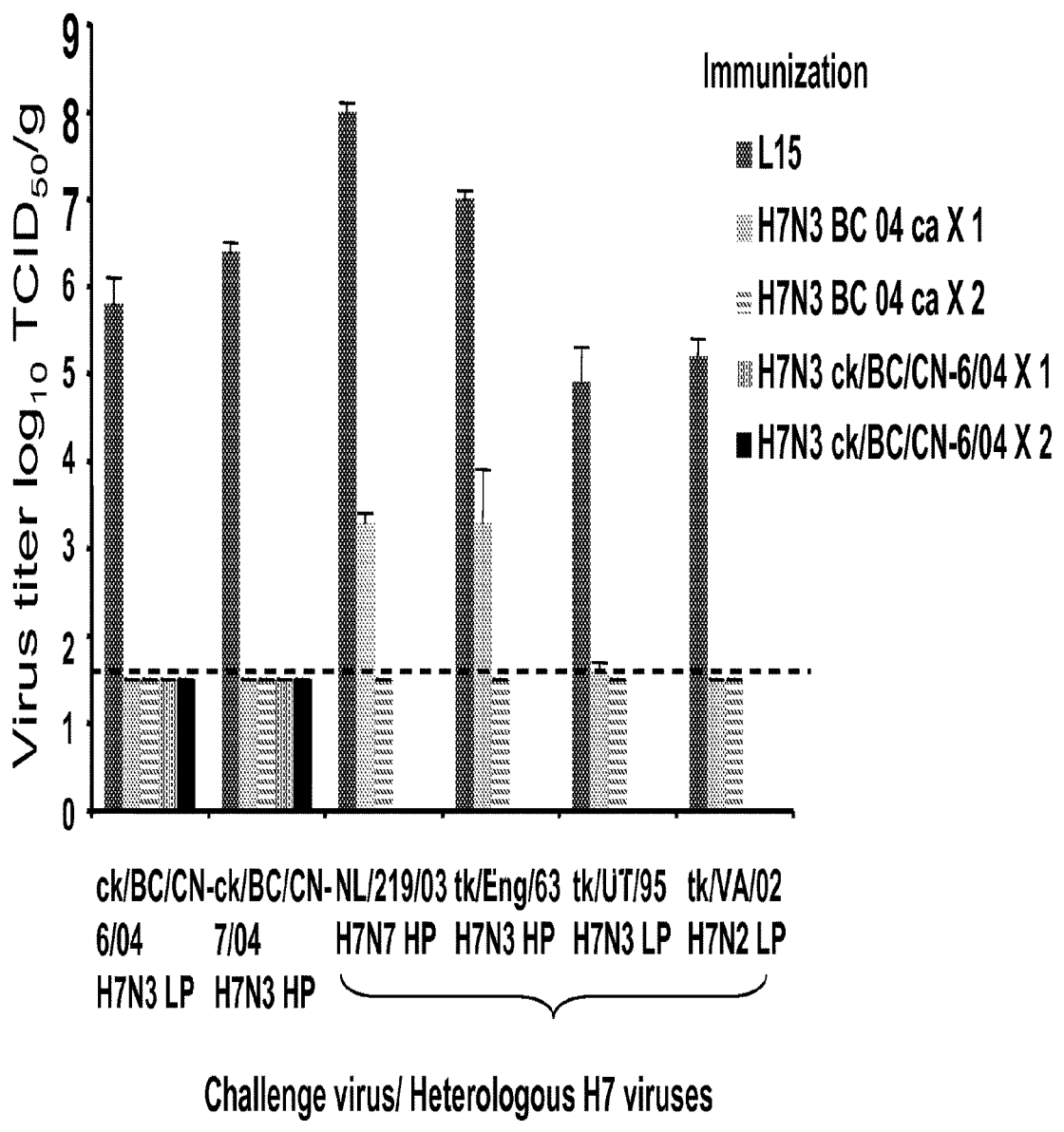

FIGS. 21 and 22 show the efficacy of protection conferred by the BC 04 ca vaccine against both homologous and heterologous H7 wt viruses. For FIG. 21, mice were intranasally inoculated with 1 dose vaccine four weeks before challenge, 1 dose vaccine 8 weeks before challenge, or 2 doses vaccine (administered 4 weeks apart) before lethal challenge with 50 LD$_{50}$ homologous (A/ck/BC/CN-7/04) and heterologous (A/NL/219/03 or A/tk/Eng/63) H7 wt viruses. Weight change of the mice following lethal challenged was monitored each day for fourteen days, to monitor morbidity associated with the wt influenza virus challenge.

For each of the mice lethally challenged with the homologous A/ck/BC/CN-7/04 virus little or no weight change was observed regardless of whether 1 dose of vaccine was administered 4 weeks prior to challenge (a), 1 dose of vaccine was administered 8 weeks prior to challenge (b) or 2 doses of vaccine were administered prior to challenge (c). Likewise, little to no weight loss occurred following challenge of the mice with either heterologous influenza virus, A/NL/2109/03 (d, e, f) or A/tk/Eng/63 (g, h, i). Again, the lack of weight loss was observed regardless of whether 1 dose of vaccine was administered 4 weeks prior to challenge (d or g), 1 dose of vaccine was administered 8 weeks prior to challenge (e, or h), or 2 doses of vaccine were administered prior to challenge (f or i).

FIG. 22 provides further evidence of the efficacy of the H7N3 BC 04 ca vaccine. In both nasal turbinates (a) and lungs (b) of mice receiving the H7N3 BC 04 ca vaccine, protection was observed against challenge using ck/BC/CN-6/04 (H7N3), ck/BC/CN-7/04 (H7N3), NL/219/03 (H7N7), tk/Eng/63 (H7N3), tk/UT/95 (H7N3), and tk/VA/02 (H7N2) viruses.

Example 4

Construction and Analysis of an H9N2 G9/AA ca, Virus and Vaccine

A further recombinant influenza virus and vaccine was prepared using the HA H9 and NA N2 sequences of A/ck/Hong Kong/G9/97 (G9/AA ca). These HA and NA sequences were combined with the six internal genome segments of ca A/AA/6/60.

Figure 23:
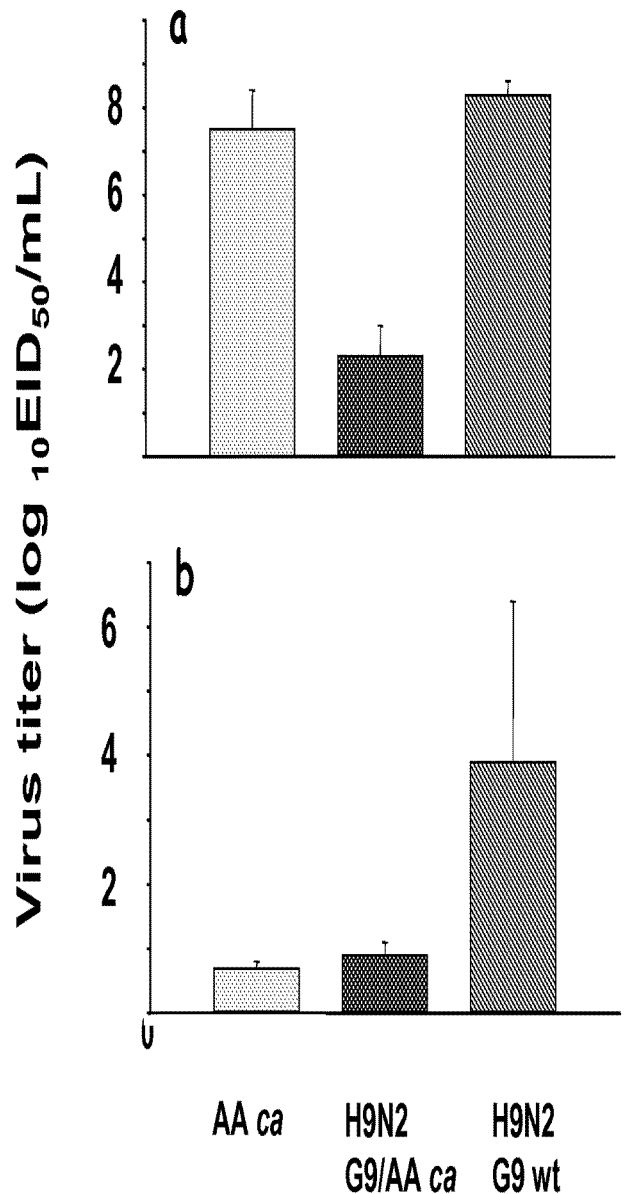
FIGS. 23(a) and (b): H9N2 G9/AA ca is attenuated in ferrets. Virus titer was measured in (a) nasal turbinates and (b) lungs.

The H9N2 G9/AA ca vaccine was attenuated in the ferrets. See FIG. 23, which shows reduced virus titers in nasal turbinates (a) and lungs (b) of ferrets following administration of the H9N2 G9/AA ca virus relative to the H9N2 G9 wt virus.

FIG. 24 provides evidence of the efficacy of the H9N2 G9 ca vaccine in mice. In the mice receiving the H9N2 G9 ca vaccine, protection was observed against challenge using H9N2 G9 wt and A/HK/1073/99 viruses.

The H9N2 G9/AA ca vaccine was also well tolerated in healthy adults in a clinical trial setting. Healthy adults were administered the H9N2 G9/AA ca vaccine by nose drop. In the healthy adults, the H9N2 G9/AA ca vaccine was highly restricted in replication. See FIG. 25. Furthermore, administration of $10^{7.0}$ TCID$_{50}$ of H9N2 G9/AA ca vaccine induced ≤4-fold increases in HI titer in 92% of healthy volunteers. See FIG. 26.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes. In particular, U.S. provisional application Nos. 60/821,832 filed Aug. 9, 2006 and 60/942,804, filed Jun. 8, 2007, are incorporated herein in their entirety for all purposes.

Specific Embodiments

Additional embodiments of the present invention are presented in Table 3 and 4.

TABLE 3

| | Specific embodiments |
|---|---|
| 1 | An isolated polypeptide, wherein said polypeptide is selected from the group consisting of:<br>a) a polypeptide encoded by a polynucleotide sequence as shown in any one of SEQ ID NOS: 21-26 or 33-38 or 45;<br>b) a polypeptide as shown in any one of SEQ ID NOS: 27-32 or 39-44;<br>c) the mature form of the polypeptide as shown in any one of SEQ ID NOS: 27-32 or 39-44;<br>d) a polypeptide encoded by a polynucleotide sequence which hybridizes under highly stringent conditions to a polynucleotide sequence encoding (a) (b) or (c); and<br>e) a polypeptide having at least 90% sequence identity to the polypeptide of (b). |
| 2 | An immunogenic composition comprising an immunologically effective amount of at least one polypeptide of embodiment 1. |
| 3 | An isolated antibody that specifically binds the polypeptide of embodiment 1. |
| 4 | A method for stimulating the immune system of an individual to produce a protective immune response against influenza virus, the method comprising administering to the individual an immunologically effective amount of the polypeptide of embodiment 1 in a physiologically acceptable carrier. |
| 5 | A recombinant influenza virus comprising the polypeptide of embodiment 1. |
| 6 | An immunogenic composition comprising an immunologically effective amount of the recombinant influenza virus of embodiment 5. |
| 7 | A method for stimulating the immune system of an individual to produce a protective immune response against influenza virus, the method comprising administering to the individual an immunologically effective amount of the recombinant influenza virus of embodiment 5 in a physiologically acceptable carrier. |
| 8 | An isolated nucleic acid, wherein said nucleic acid is selected from the group consisting of:<br>a) a polynucleotide sequence as shown in any one of SEQ ID NOS: 21-26 or 33-38 or 45, or a complementary sequence thereof;<br>b) a polynucleotide sequence encoding a polypeptide as shown in any one of SEQ ID NOS: 27-32 or 39-44, or a complementary polynucleotide sequence thereof;<br>c) a polynucleotide sequence which hybridizes under highly stringent conditions over substantially the entire length of polynucleotide sequence (a); and<br>d) a polynucleotide sequence having at least 98% sequence identity to the polynucleotide sequence of (a). |
| 9 | An immunogenic composition comprising at least one of the nucleic acids of embodiment 8. |
| 10 | A cell comprising at least one nucleic acid of embodiment 8. |
| 11 | A vector comprising the nucleic acid of embodiment 8. |
| 12 | The vector of embodiment 12, wherein the vector is a plasmid, a cosmid, a phage, a virus, or a fragment of a virus. |
| 13 | The vector of embodiment 12, wherein the vector is an expression vector. |
| 14 | A cell comprising the vector of embodiment 13. |
| 15 | An influenza virus comprising one or more nucleic acids of embodiment 8. |
| 16 | The virus of embodiment 15, wherein the virus is a reassortment virus. |
| 17 | A 6:2 reassortment influenza virus, wherein said virus comprises 6 gene encoding regions from A/Ann Arbor/6/60 and 2 gene encoding regions that encode polypeptides selected from the group consisting of: the polypeptides of SEQ ID NOS: 27-32, and 39-44. |
| 18 | A method of producing a recombinant influenza virus, the method comprising: culturing the cell of embodiment 14 in a suitable culture medium under conditions permitting expression of nucleic acid; and, isolating the recombinant influenza virus from a cell population comprising said cell or the medium. |
| 19 | An immunogenic composition comprising an immunologically effective amount of the recombinant influenza virus of embodiment 17. |
| 20 | A method for stimulating the immune system of an individual to produce a protective immune response against influenza virus, the method comprising administering to the individual an immunologically effective amount of the recombinant influenza virus of embodiment 17 in a physiologically effective carrier. |
| 21 | A method of producing an isolated or recombinant polypeptide, the method comprising: culturing the host cell of embodiment 10 in a suitable culture medium under conditions permitting expression of said nucleic acid; and, isolating the polypeptide from one or more of the host cells or the medium. |
| 22 | A method of prophylactic or therapeutic treatment of a viral infection in a subject, the method comprising: administering to the subject, a virus of embodiment 17 in an amount effective to produce an immunogenic response against the viral infection. |
| 23 | The method of embodiment 22, wherein the subject is a human. |
| 24 | The immunogenic composition of embodiment 19, wherein the hemagglutinin comprises a modified polybasic cleavage site. |
| 25 | A live attenuated influenza vaccine comprising the composition of embodiment 19. |

TABLE 3-continued

| Specific embodiments | |
|---|---|
| 26 | A split virus or killed virus vaccine comprising the composition of embodiment 19. |
| 27 | A live attenuated influenza vaccine comprising the composition of embodiment 24. |
| 28 | A split virus or killed virus vaccine comprising the composition of embodiment 24. |
| 29 | A method for producing influenza viruses in cell culture, the method comprising:<br>i) introducing into a population of host cells, which population of host cells is capable of supporting replication of influenza virus, a plurality of vectors comprising nucleic acid encoding at least 6 internal genome segments of a first influenza strain, wherein the first influenza strain is A/Ann Arbor/6/60; and, at least one genome segment encoding an immunogenic influenza surface antigen of a second influenza strain, wherein said second strain is a pandemic influenza strain,<br>ii) culturing the population of host cells at a temperature less than or equal to 35° C.; and,<br>iii) recovering a plurality of influenza viruses. |
| 30 | The method of embodiment 29, wherein the plurality of vectors comprise at least one isolated nucleic acid, wherein said nucleic acid is selected from the group consisting of:<br>a) a polynucleotide sequence of one of SEQ ID NOS: 21-26 or 33-38, or 45, or a complementary sequence thereof;<br>b) a polynucleotide sequence encoding a polypeptide of one of SEQ ID NOS: 27-32 or 39-44, or a complementary polynucleotide sequence thereof;<br>c) a polynucleotide sequence which hybridizes under highly stringent conditions over substantially the entire length of polynucleotide sequence (a); and<br>d) a polynucleotide sequence having at least 98% sequence identity to the polynucleotide sequence of (a). |
| 31 | An immunogenic composition comprising an immunologically effective amount of the influenza virus of embodiment 29. |
| 32 | An immunogenic composition comprising an immunologically effective amount of the influenza virus of embodiment 30. |
| 33 | A method for stimulating the immune system of an individual to produce a protective immune response against influenza virus, the method comprising administering to the individual an immunologically effective amount of the influenza virus of embodiment 29 in a physiologically effective carrier. |
| 34 | A method for stimulating the immune system of an individual to produce a protective immune response against influenza virus, the method comprising administering to the individual an immunologically effective amount of the influenza virus of embodiment 30 in a physiologically effective carrier. |
| 35 | A method for stimulating the immune system of an individual to produce a protective immune response against influenza virus, the method comprising administering to the individual the immunogenic composition of embodiment 31. |
| 36 | A method for stimulating the immune system of an individual to produce a protective immune response against influenza virus, the method comprising administering to the individual the immunogenic composition of embodiment 32. |
| 37 | A live attenuated influenza vaccine comprising the immunogenic composition of embodiment 31. |
| 38 | A split virus or killed virus vaccine comprising the immunogenic composition of embodiment 32. |

TABLE 4

| Specific embodiments. | |
|---|---|
| 1 | An isolated polypeptide, wherein said polypeptide is selected from the group consisting of:<br>a) a polypeptide comprising the amino acid sequence encoded by the nucleotide sequence as shown in any one of SEQ ID NOS: 21-26 or 33-38 or 45;<br>b) a polypeptide comprising the amino acid sequence as shown in any one of SEQ ID NOS: 27-32 or 39-44;<br>c) the mature form of a polypeptide comprising the amino acid sequence as shown in any one of SEQ ID NOS: 27-32 or 39-44;<br>d) a polypeptide comprising an amino acid sequence encoded by a polynucleotide which hybridizes under highly stringent conditions to a polynucleotide comprising a nucleotide sequence encoding (a) (b) or (c); and<br>e) a polypeptide comprising an amino acid sequence having at least 90% sequence identity to the polypeptide of (b). |
| 2 | An immunogenic composition comprising an immunologically effective amount of at least one polypeptide of embodiment 1. |
| 3 | An isolated antibody that specifically binds the polypeptide of embodiment 1. |
| 4 | A method for stimulating the immune system of an individual to produce a protective immune response against influenza virus, the method comprising administering to the individual an immunologically effective amount of the polypeptide of embodiment 1 in a physiologically acceptable carrier. |
| 5 | A recombinant influenza virus comprising the polypeptide of embodiment 1. |
| 6 | An immunogenic composition comprising an immunologically effective amount of the recombinant influenza virus of embodiment 5. |
| 7 | A method for stimulating the immune system of an individual to produce a protective immune response against influenza virus, the method comprising administering to the individual an immunologically effective amount of the recombinant influenza virus of embodiment 5 in a physiologically acceptable carrier. |

TABLE 4-continued

Specific embodiments.

8  An isolated polynucleotide, wherein said polynucleotide is selected from the group consisting of:
   a) a polynucleotide comprising the nucleotide sequence as shown in any one of SEQ ID NOS: 21-26 or 33-38 or 45, or a complementary sequence thereof;
   b) a polynucleotide comprising a nucleotide sequence encoding a polypeptide comprising the amino acid sequence as shown in any one of SEQ ID NOS: 27-32 or 39-44, or a complementary nucleotide sequence thereof;
   c) a polynucleotide which hybridizes under highly stringent conditions over substantially the entire length of the polynucleotide of (a); and
   d) a polynucleotide comprising a nucleotide sequence having at least 98% sequence identity to the polynucleotide of (a).
9  An immunogenic composition comprising at least one polynucleotide of embodiment 8.
10 A cell comprising at least one polynucleotide of embodiment 8.
11 A vector comprising the polynucleotide of embodiment 8.
12 The vector of embodiment 11, wherein the vector is a plasmid, a cosmid, a phage, a virus, or a fragment of a virus.
13 The vector of embodiment 12, wherein the vector is an expression vector.
14 A cell comprising the vector of embodiment 13.
15 An influenza virus comprising one or more polynucleotides of embodiment 8.
16 The virus of embodiment 15, wherein the virus is a reassortant virus.
17 A 6:2 reassortant influenza virus, wherein said virus comprises 6 internal genome segments from A/Ann Arbor/6/60 and 2 genome segments that encode an HA and/or a NA polypeptide selected from the group consisting of: the polypeptides of SEQ ID NOS: 27-32, and 39-44.
18 A method of producing a reassortant influenza virus, the method comprising: culturing the cell of embodiment 14 in a suitable culture medium under conditions permitting expression of said polynucleotide; and, isolating the reassortant influenza virus from a cell population comprising said cell or the medium.
19 An immunogenic composition comprising an immunologically effective amount of the reassortant influenza virus of embodiment 17.
20 A method for stimulating the immune system of an individual to produce a protective immune response against influenza virus, the method comprising administering to the individual an immunologically effective amount of the reassortant influenza virus of embodiment 17 in a physiologically effective carrier.
21 A method of producing an isolated or recombinant polypeptide, the method comprising: culturing the cell of embodiment 10 in a suitable culture medium under conditions permitting expression of said polynucleotide; and, isolating the polypeptide from the cell or the medium.
22 A method of prophylactic or therapeutic treatment of a viral infection in a subject, the method comprising: administering to the subject, the virus of embodiment 17 in an amount effective to produce an immunogenic response against the viral infection.
23 The method of embodiment 22, wherein the subject is a human.
24 The immunogenic composition of embodiment 19, wherein the hemagglutinin comprises a modified polybasic cleavage site.
25 A live attenuated influenza vaccine comprising the composition of embodiment 19.
26 A split virus or killed virus vaccine comprising the composition of embodiment 19.
27 A live attenuated influenza vaccine comprising the composition of embodiment 24.
28 A split virus or killed virus vaccine comprising the composition of embodiment 24.
29 A method for producing an influenza virus in cell culture, the method comprising:
   i) introducing into a population of host cells, which population of host cells is capable of supporting replication of influenza virus, a plurality of vectors comprising nucleotide sequences corresponding to at least 6 internal genome segments of A/Ann Arbor/6/60; and, at least one genome segment comprising a polynucleotide encoding an HA and/or a NA polypeptide selected from the group consisting of: the polypeptides of SEQ ID NOS: 27-32, and 39-44,
   ii) culturing the population of host cells at a temperature less than or equal to 35° C.; and,
   iii) recovering an influenza virus.
30 The method of embodiment 29, wherein the polynucleotide encoding the HA and/or NA polypeptide is selected from the group consisting of:
   a) a polynucleotide comprising the nucleotide sequence of any one of SEQ ID NOS: 21, 23-26 or 33-38, or 45, or a complementary nucleotide sequence thereof;
   b) a polynucleotide comprising a nucleotide sequence encoding a polypeptide comprising the amino acid sequence as shown in any one of SEQ ID NOS: 27-32 or 39-44, or a complementary nucleotide sequence thereof;
   c) a polynucleotide which hybridizes under highly stringent conditions over substantially the entire length of the polynucleotide of (a); and
   d) a polynucleotide comprising a nucleotide sequence having at least 98% sequence identity to the polynucleotide of (a).
31 An immunogenic composition comprising an immunologically effective amount of the influenza virus produced by the method of embodiment 29.
32 An immunogenic composition comprising an immunologically effective amount of the influenza virus produced by the method of embodiment 30.
33 A method for stimulating the immune system of an individual to produce a protective immune response against influenza virus, the method comprising administering to the individual an immunologically effective amount of the influenza virus produced by the method of embodiment 29 in a physiologically effective carrier.

TABLE 4-continued

Specific embodiments.

34  A method for stimulating the immune system of an individual to produce a protective immune response against influenza virus, the method comprising administering to the individual an immunologically effective amount of the influenza virus produced by the method of embodiment 30 in a physiologically effective carrier.
35  A method for stimulating the immune system of an individual to produce a protective immune response against influenza virus, the method comprising administering to the individual the immunogenic composition of embodiment 31.
36  A method for stimulating the immune system of an individual to produce a protective immune response against influenza virus, the method comprising administering to the individual the immunogenic composition of embodiment 32.
37  A live attenuated influenza vaccine comprising the immunogenic composition of embodiment 31.
38  A split virus or killed virus vaccine comprising the immunogenic composition of embodiment 32.
39  A 6:2 reassortant influenza virus, wherein said virus comprises 6 internal genome segments from one or more donor viruses other than A/Ann Arbor/6/60 and 2 genome segments that encode an HA and/or a NA polypeptide selected from the group consisting of: the polypeptides of SEQ ID NOS: 27-32, and 39-44.
40  The 6:2 reassortant influenza virus of embodiment 39, wherein said donor virus comprises one or more of the following phenotypes: temperature-sensitive, cold-adaped, or attenuated.
41  The 6:2 reassortant influenza virus of embodiment 39, wherein said donor virus is PR8.
42  The 6:2 reassortant influenza virus of embodiment 39, wherein said donor virus is A/Leningrad/17.
43  An immunogenic composition comprising an immunologically effective amount of the reassortant influenza virus of embodiment 39.
44  An immunogenic composition comprising an immunologically effective amount of the reassortant influenza virus of embodiment 40.
45  An immunogenic composition comprising an immunologically effective amount of the reassortant influenza virus of embodiment 41.
46  An immunogenic composition comprising an immunologically effective amount of the reassortant influenza virus of embodiment 42.
47  A method for stimulating the immune system of an individual to produce a protective immune response against influenza virus, the method comprising administering to the individual an immunologically effective amount of the reassortant influenza virus of embodiment 39 in a physiologically effective carrier.
48  A method for stimulating the immune system of an individual to produce a protective immune response against influenza virus, the method comprising administering to the individual an immunologically effective amount of the reassortant influenza virus of embodiment 40 in a physiologically effective carrier.
49  A method for stimulating the immune system of an individual to produce a protective immune response against influenza virus, the method comprising administering to the individual an immunologically effective amount of the reassortant influenza virus of embodiment 41 in a physiologically effective carrier.
50  A method for stimulating the immune system of an individual to produce a protective immune response against influenza virus, the method comprising administering to the individual an immunologically effective amount of the reassortant influenza virus of embodiment 42 in a physiologically effective carrier.
51  A method of prophylactic or therapeutic treatment of a viral infection in a subject, the method comprising: administering to the subject, the virus of embodiment 39 in an amount effective to produce an immunogenic response against the viral infection.
52  A method of prophylactic or therapeutic treatment of a viral infection in a subject, the method comprising: administering to the subject, the virus of embodiment 41 in an amount effective to produce an immunogenic response against the viral infection.
53  A method of prophylactic or therapeutic treatment of a viral infection in a subject, the method comprising: administering to the subject, the virus of embodiment 42 in an amount effective to produce an immunogenic response against the viral infection.
54  The method of embodiment 51, wherein said virus is killed or inactivated.
55  The method of embodiment 52, wherein said virus is killed or inactivated.
56  The method of embodiment 53, wherein said virus is killed or inactivated.
57  The immunogenic composition of embodiment 43, wherein the hemagglutinin comprises a modified polybasic cleavage site.
58  The immunogenic composition of embodiment 44, wherein the hemagglutinin comprises a modified polybasic cleavage site.
59  The immunogenic composition of embodiment 45, wherein the hemagglutinin comprises a modified polybasic cleavage site
60  The immunogenic composition of embodiment 46, wherein the hemagglutinin comprises a modified polybasic cleavage site.
61  The method of embodiment 47, wherein the subject is a human.
62  The method of embodiment 48, wherein the subject is a human.
63  The method of embodiment 49, wherein the subject is a human.
64  A live attenuated influenza vaccine comprising the composition of embodiment 45.
65  A live attenuated influenza vaccine comprising the composition of embodiment 46.
66  A method for producing an influenza virus in cell culture, the method comprising:
    i) introducing into a population of host cells, which population of host cells is capable of supporting replication of influenza virus, a plurality of vectors comprising nucleotide sequences corresponding to:

TABLE 4-continued

Specific embodiments.

(a) at least 6 internal genome segments of a first influenza strain, wherein the first influenza strain is not A/Ann Arbor/6/60; and, at least one genome segment encoding an HA or an NA polypeptide selected from the group consisting of: the polypeptides of SEQ ID NOS: 27-32, and 39-44; or
(b) at least 6 internal genome segments of a first influenza strain, wherein the first influenza strain is not A/Ann Arbor/6/60 and which influenza strain comprises one or more phenotypic attributes selected from the group consisting of: attenuated, cold adapted and temperature sensitive; and, at least one genome segment encoding an HA or an NA polypeptide selected from the group consisting of: the polypeptides of SEQ ID NOS: 27-32, and 39-44,
ii) culturing the population of host cells at a temperature less than or equal to 35° C.; and,
iii) recovering an influenza virus.
67 An immunogenic composition comprising an immunologically effective amount of the influenza virus produced by the method of embodiment 66.
68 A method for stimulating the immune system of an individual to produce a protective immune response against influenza virus, the method comprising administering to the individual an immunologically effective amount of the influenza virus produced by the method of embodiment 66 in a physiologically effective carrier.
69 A method for stimulating the immune system of an individual to produce a protective immune response against influenza virus, the method comprising administering to the individual the immunogenic composition of embodiment 67.
70 A live attenuated influenza vaccine comprising the immunogenic composition of embodiment 67.
71 A split virus or killed virus vaccine comprising the immunogenic composition of embodiment 67.

Sequences
ca A/Vietnam/1203/04
Nucleotide Sequence of ca A/Vietnam/1203/04 H5 (SEQ ID NO:1)
Entire molecule length: 1767 nt

```
   1 agcaaaagca ggggttcaat ctgtcaaaat ggagaaaata gtgcttcttt 51 ttgcaatagt cagtcttgtt aaaagtgatc agatttgcat tggttaccat 101 gcaaacaact cgacagagca ggttgacaca ataatggaaa agaacgttac 151 tgttacacat gcccaagaca tactggaaaa gaaacacaac gggaagctct 201 gcgatctaga tggagtgaag cctctaattt tgagagattg tagcgtagct 251 ggatggctcc tcggaaaccc aatgtgtgac gaattcatca atgtgccgga 301 atggtcttac atagtggaga aggccaatcc agtcaatgac ctctgttacc 351 caggggattt caatgactat gaagaattga aacacctatt gagcagaata 401 aaccattttg agaaaattca gatcatcccc aaaagttctt ggtccagtca 451 tgaagcctca ttagggtga gctcagcatg tccataccag ggaaagtcct 501 ccttttcag aaatgtggta tggcttatca aaaagaacag tacatacca 551 acaataaaga ggagctacaa taataccaac caagaagatc ttttggtact 601 gtggggatt caccatccta atgatgcggc agagcagaca aagctctatc 651 aaaacccaac cacctatatt tccgttggga catcaacact aaaccagaga 701 ttggtaccaa gaatagctac tagatccaaa gtaaacgggc aaagtggaag 751 gatggagttc ttctggacaa ttttaaagcc gaatgatgca atcaacttcg 801 agagtaatgg aaatttcatt gctccagaat atgcatacaa aattgtcaag 851 aaaggggact caacaattat gaaaagtgaa ttggaatatg gtaactgcaa 901 caccaagtgt caaactccaa tgggggcgat aaactctagc atgccattcc 951 acaatataca ccctctcacc attggggaat gccccaaata tgtgaaatca 1001 aacagattag tccttgcgac tgggctcaga aatagccctc aaagagagac
```

-continued

```
1051 tcgaggatta tttggagcta tagcaggttt tatagaggga ggatggcagg 1101 gaatggtaga tggttggtat gggtaccacc atagcaatga gcaggggagt 1151 gggtacgctg cagacaaaga atccactcaa aaggcaatag atggagtcac 1201 caataaggtc aactcgatca ttgacaaaat gaacactcag tttgaggccg 1251 ttggaaggga atttaacaac ttagaaagga gaatagagaa tttaaacaag 1301 aagatggaag acgggttcct agatgtctgg acttataatg ctgaacttct 1351 ggttctcatg gaaaatgaga gaactctaga ctttcatgac tcaaatgtca 1401 agaacctta cgacaaggtc cgactacagc ttagggataa tgcaaaggag 1451 ctgggtaacg gttgtttcga gttctatcat aaatgtgata atgaatgtat 1501 ggaaagtgta agaaatggaa cgtatgacta cccgcagtat tcagaagaag 1551 cgagactaaa aagagaggaa ataagtggag taaaattgga atcaatagga 1601 atttaccaaa tactgtcaat ttattctaca gtggcgagtt ccctagcact 1651 ggcaatcatg gtagctggtc tatccttatg gatgtgctcc aatgggtcgt 1701 tacaatgcag aatttgcatt taaatttgtg agttcagatt gtagttaaaa 1751 acaccttgt ttctact
```

Amino acid sequence of ca A/Vietnam/1203/04 H5 (SEQ ID NO: 11)
Entire molecule length: 564 aa

```
  1 mekivllfai vslvksdqic igyhannste qvdtimeknv tvthaqdile 51 kkhngklcdl dgvkplilrd csvagwllgn pmcdefinvp ewsyivekan 101 pvndlcypgd fndyeelkhl lsrinhfeki qiipksswss heaslgvssa 151 cpyqgkssff rnvvwlikkn styptikrsy nntnqedllv lwgihhpnda 201 aeqtklyqnp ttyisvgtst lnqrlvpria trskvngqsg rmeffwtilk 251 pndainfesn gnfiapeyay kivkkgdsti mkseleygnc ntkcqtpmga 301 inssmpfhni hpltigecpk yvksnrlvla tglrnspqre trglfgaiag 351 fieggwqgmv dgwygyhhsn eqgsgyaadk estqkaidgv tnkvnsiidk 401 mntqfeavgr efnnlerrie nlnkkmedgf ldvwtynael lvlmenertl 451 dfhdsnvknl ydkvrlqlrd nakelgngcf efyhkcdnec mesvrngtyd 501 ypqyseearl kreeisgvkl esigiyqils iystvassla laimvaglsl 551 wmcsngslqc rici
```

Nucleotide Sequence of ca A/Vietnam/1203/04 N1 (SEQ ID NO: 2)
Entire molecule length: 1398 nt

```
  1 agcaaaagca ggagttcaaa atgaatccaa atcagaagat aataaccatc 51 gggtcaatct gtatggtaac tggaatagtt agcttaatgt tacaaattgg 101 gaacatgatc tcaatatggg tcagtcattc aattcacaca gggaatcaac 151 accaatctga accaatcagc aatactaatt ttcttactga gaaagctgtg 201 gcttcagtaa aattagcggg caattcatct ctttgcccca ttaacggatg 251 ggctgtatac agtaaggaca acagtataag gatcggttcc aagggggatg 301 tgtttgttat aagagagccg ttcatctcat gctcccactt ggaatgcaga
```

-continued

```
 351 actttcttttt tgactcaggg agccttgctg aatgacaagc actccaatgg 401 gactgtcaaa gacagaagcc ctcacagaac attaatgagt tgtcctgtgg 451 gtgaggctcc ctccccatat aactcaaggt ttgagtctgt tgcttggtca 501 gcaagtgctt gccatgatgg caccagttgg ttgacgattg gaatttctgg 551 cccagacaat ggggctgtgg ctgtattgaa atacaatggc ataataacag 601 acactatcaa gagttggagg aacaacatac tgagaactca agagtctgaa 651 tgtgcatgtg taaatggctc ttgctttact gtaatgactg acggaccaag 701 taatggtcag gcatcacata agatcttcaa aatggaaaaa gggaaagtgg 751 ttaaatcagt cgaattggat gctcctaatt atcactatga ggaatgctcc 801 tgttatccta atgccggaga aatcacatgt gtgtgcaggg ataattggca 851 tggctcaaat cggccatggg tatctttcaa tcaaaatttg gagtatcaaa 901 taggatatat atgcagtgga gttttcggag acaatccacg ccccaatgat 951 ggaacaggta gttgtggtcc ggtgtcctct aacggggcat atggggtaaa 1001 agggttttca tttaaatacg gcaatggtgt ctggatcggg agaaccaaaa 1051 gcactaattc caggagcggc tttgaaatga tttgggatcc aaatgggtgg 1101 actgaaacgg acagtagctt ttcagtgaaa caagatatcg tagcaataac 1151 tgattggtca ggatatagcg ggagttttgt ccagcatcca gaactgacag 1201 gactagattg cataagacct tgtttctggg ttgagttgat cagagggcgg 1251 cccaaagaga gcacaatttg gactagtggg agcagcatat cttttttgtgg 1301 tgtaaatagt gacactgtgg gttggtcttg gccagacggt gctgagttgc 1351 cattcaccat tgacaagtag tttgttcaaa aaactccttg tttctact
```

Amino acid sequence of ca A/Vietnam/1203/04 N1 (SEQ ID NO: 12)
Entire molecule length: 449 aa

```
  1 mnpnqkiiti gsicmvtgiv slmlqignmi siwvshsiht gnqhqsepis 51 ntnfltekav asvklagnss lcpingwavy skdnsirigs kgdvfvirep 101 fiscshlecr tffltqgall ndkhsngtvk drsphrtlms cpvgeapspy 151 nsrfesvaws asachdgtsw ltigisgpdn gavavlkyng iitdtikswr 201 nnilrtqese cacvngscft vmtdgpsngq ashkifkmek gkvvksveld 251 apnyhyeecs cypnageitc vcrdnwhgsn rpwvsfnqnl eyqigyicsg 301 vfgdnprpnd gtgscgpvss ngaygvkgfs fkygngvwig rtkstnsrsg 351 femiwdpngw tetdssfsvk qdivaitdws gysgsfvqhp eltgldcirp 401 cfwvelirgr pkestiwtsg ssisfcgvns dtvgwswpdg aelpftidk
``` ca A/Hong Kong/213/03
Nucleotide Sequence of ca A/Hong Kong/213/03 H5 (SEQ ID NO: 3)
Entire molecule length: 1767 nt

```
  1 agcaaaagca ggggttcaat ctgtcaaaat ggagaaaata gtgcttcttt 51 ttgcaatagt cagtcttgtt aaaagtgatc agatttgcat tggttaccat 101 gcaaacaact cgacagagca ggttgacaca ataatggaaa agaacgttac
```

```
 151 tgttacacat gcccaagaca tactggaaaa gacacacaac gggaagctct
 201 gcgatctaga tggagtgaag cctctaattt tgagagattg tagtgtagct
 251 ggatggctcc tcggaaaccc aatgtgtgac gaattcatca atgtgccgga
 301 atggtcttac atagtggaga aggccaatcc agccaatgac ctctgttacc
 351 caggggattt caacgactat gaagaattga acacctatt gagcagaata
 401 aaccattttg agaaaattca gatcatcccc aaaaattctt ggtccagtca
 451 tgaagcctca ttaggggtga gctcagcatg tccataccaa ggaaagtcct
 501 ccttttcag gaatgtggta tggcttatca aaagaacaa tgcataccca
 551 acaataaaga ggagctacaa taataccaac caagaagatc ttttggtatt
 601 gtggggatt caccatccta atgatgcggc agagcagact aggctctatc
 651 aaaacccaac cacctacatt tccgttggga catcaacact aaaccagaga
 701 ttggtaccaa aaatagctac tagatccaaa gtaaacgggc aaaatggaag
 751 gatggagttc ttctggacaa ttttaaaacc gaatgatgca atcaacttcg
 801 agagcaatgg aaatttcatt gctccagaat atgcatacaa aattgtcaag
 851 aaaggggact cagcaattat gaaaagtgaa ttggaatatg gtaactgcaa
 901 caccaagtgt caaactccaa tggggcgat aaactctagt atgccattcc
 951 acaatataca ccctctcacc atcggggaat gccccaaata tgtgaaatca
1001 aacagattag tccttgcgac tgggctcaga aatagccctc aaagagagac
1051 tcgaggatta tttggagcta tagcaggttt tatagaggga ggatggcagg
1101 gaatggtaga tggttggtat gggtaccacc atagcaatga gcaggggagt
1151 gggtacgctg cagacaaaga atccactcaa aaggcaatag atggagtcac
1201 caataaggtc aactcgatca ttgacaaaat gaacactcag tttgaggccg
1251 ttggaaggga atttaataac ttagaaagga gaatagagaa tttaaacaag
1301 aagatggaag acggattcct agatgtctgg acttataatg ctgaacttct
1351 ggttctcatg gaaaatgaga gaactctaga ctttcatgac tcaaatgtca
1401 agaaccttta cgacaaggtc cgactacagc ttagggataa tgcaaggag
1451 ctgggtaacg gttgtttcga gttctatcac aaatgtgata tgaatgtat
1501 ggaaagtgta agaaacggaa cgtatgacta cccgcagtat tcagaagaag
1551 caagactaaa aagagaggaa ataagtggag taaaattgga gtcaatagga
1601 acttaccaaa tactgtcaat ttattctaca gtggcgagtt ccctagcact
1651 ggcaatcatg gtagctggtc tatctttatg gatgtgctcc aatgggtcgt
1701 tacaatgcag aatttgcatt taaatttgtg agttcagatt gtagttaaaa
1751 acacccttgt ttctact
```

Amino acid sequence of ca A/Hong Kong/213/03 H5 (SEQ ID NO: 13)
Entire molecule length: 564 aa

```
  1 mekivllfai vslvksdqic igyhannste qvdtimeknv tvthaqdile 51 kthngklcdl dgvkplilrd csvagwllgn pmcdefinvp ewsyivekan 101 pandlcypgd fndyeelkhl lsrinhfeki qiipknswss heaslgvssa 151 cpyqgkssff rnvvwlikkn nayptikrsy nntnqedllv lwgihhpnda
```

-continued

```
201 aeqtrlyqnp ttyisvgtst lnqrlvpkia trskvngqng rmeffwtilk
251 pndainfesn gnfiapeyay kivkkgdsai mkseleygnc ntkcqtpmga
301 inssmpfhni hpltigecpk yvksnrlvla tglrnspqre trglfgaiag
351 fieggwqgmv dgwygyhhsn eqgsgyaadk estqkaidgv tnkvnsiidk
401 mntqfeavgr efnnlerrie nlnkkmedgf ldvwtynael lvlmenertl
451 dfhdsnvknl ydkvrlqlrd nakelgngcf efyhkcdnec mesvrngtyd
501 ypqyseearl kreeisgvkl esigtyqils iystvassla laimvaglsl
551 wmcsngslqc rici
```

Nucleotide Sequence of ca A/Hong Kong/213/03 N1 (SEQ ID NO: 4)
Entire molecule length: 1458 nt

```
   1 agcaaaagca ggagttcaaa atgaatccaa atcagaagat aacaaccatt
  51 ggatcaatct gtatggtaat tggaatagtt agcttgatgt tacaaattgg
 101 gaacataatc tcaatatggg ttagtcattc aattcaaaca gggaatcaac
 151 accaggctga accatgcaat caaagcatta ttacttatga aaacaacacc
 201 tgggtaaacc agacatatgt caacatcagc aataccaatt ttcttactga
 251 gaaagctgtg gcttcagtaa cattagcggg caattcatct ctttgcccca
 301 ttagtggatg ggctgtatac agtaaggaca acggtataag aatcggttcc
 351 aagggggatg tgtttgttat aagagagccg ttcatctcat gctcccactt
 401 ggaatgcaga actttctttt tgactcaggg agccttgctg aatgacaagc
 451 attctaatgg gaccgtcaaa gacagaagcc ctcacagaac attaatgagt
 501 tgtcccgtgg gtgaggctcc ttccccatac aactcgaggt ttgagtctgt
 551 tgcttggtcg gcaagtgctt gtcatgatgg cactagttgg ttgacaattg
 601 gaatttctgg cccagacaat ggggctgtgg ctgtattgaa atacaatggc
 651 ataataacag acactatcaa gagttggagg aacaacataa tgagaactca
 701 agagtctgaa tgtgcatgtg taaatggctc ttgctttact gttatgactg
 751 atggaccaag taatgggcag gcttcataca aaatcttcag aatagaaaaa
 801 gggaaagtag ttaaatcagc cgaattaaat gcccctaatt atcactatga
 851 ggagtgctcc tgttatcctg atgctggaga aatcacatgt gtgtgcaggg
 901 ataactggca tggctcaaat cggccatggg tatctttcaa tcaaaatttg
 951 gagtatcgaa taggatatat atgcagtgga gttttcggag acaatccacg
1001 ccccaatgat gggacaggca gttgtggtcc ggtgtcccct aaaggggcat
1051 atggaataaa agggttctca tttaaatacg gcaatggtgt ttggatcggg
1101 agaaccaaaa gcactaattc caggagcggc tttgaaatga tttgggatcc
1151 aaatggatgg actggtacgg acagtaattt ttcagtaaag caagatattg
1201 tagctataac cgattggtca ggatatagcg ggagttttgt ccagcatcca
1251 gaactgacag gattagattg cataagacct tgtttctggg ttgagctaat
1301 cagagggcgg cccaaagaga gcacaatttg gactagtggg agcagcatat
1351 ccttttgtgg tgtaaatagt gacactgtgg gttggtcttg gccagacggt
```

-continued

```
1401 gctgagttgc cattcaccat tgacaagtag tttgttcaaa aaactccttg 1451 tttctact
```

Amino acid sequence of ca A/Hong Kong/213/03 N1 (SEQ ID NO: 14)
Entire molecule length: 469 aa

```
  1 mnpnqkitti gsicmvigiv slmlqignii siwvshsiqt gnqhqaepcn 51 qsiityennt wvnqtyvnis ntnfltekav asvtlagnss lcpisgwavy 101 skdngirigs kgdvfvirep fiscshlecr tffltqgall ndkhsngtvk 151 drsphrtlms cpvgeapspy nsrfesvaws asachdgtsw ltigisgpdn 201 gavavlkyng iitdtikswr nnimrtqese cacvngscft vmtdgpsngq 251 asykifriek gkvvksaeln apnyhyeecs cypdageitc vcrdnwhgsn 301 rpwvsfnqnl eyrigyicsg vfgdnprpnd gtgscgpvsp kgaygikgfs 351 fkygngvwig rtkstnsrsg femiwdpngw tgtdsnfsvk qdivaitdws 401 gysgsfvqhp eltgldcirp cfwvelirgr pkestiwtsg ssisfcgvns 451 dtvgwswpdg aelpftidk
``` ca A/Hong Kong/491/97 (HA)+A/Hong Kong/486/97 (NA)
Nucleotide Sequence of ca A/Hong Kong/491/97 H5 (SEQ ID NO: 5)
Entire molecule length: 1767 nt

```
   1 agcaaaagca ggggtataat ctgtcaaaat ggagaaaata gtgcttcttc 51 ttgcaacagt cagccttgtt aaaagtgacc agatttgcat tggttaccat 101 gcaaacaact cgacagagca agttgacaca ataatggaaa agaatgttac 151 tgttacacat gcccaagaca tactggaaag gacacacaac gggaagctct 201 gcgatctaaa tggagtgaag cctctgattt tgagggattg tagtgtagct 251 ggatggctcc tcggaaaccc tatgtgtgac gaattcatca atgtgccgga 301 atggtcttac atagtggaga aggccagtcc agccaatgac ctctgttatc 351 cagggaattt caacgactat gaagaactga aacacctatt gagcagaata 401 aaccattttg agaaaattca gataatcccc aaaagttctt ggtccaatca 451 tgatgcctca tcaggggtga gctcagcatg tccataccct gggaggtcct 501 cctttttcag aaatgtggta tggcttatca aaagaacag tagctaccca 551 acaataaaga ggagctacaa taataccaac caagaagatc ttttggtact 601 gtgggggatt caccatccta atgatgcggc agagcagaca aggctctatc 651 aaaacccaac cacctacatt tccgttggaa catcaacact gaaccagaga 701 ttggttccag aaatagctac tagacccaaa gtaaacgggc aaagtggaag 751 aatggagttc ttctggacaa ttttaaagcc gaatgatgcc atcaatttcg 801 agagtaatgg aaatttcatt gctccagaat atgcatacaa aattgtcaag 851 aaaggggact caacaattat gaaaagtgaa ttggaatatg gtaactgcaa 901 caccaagtgt caaactccaa tggggcaat aaactctagt atgccattcc 951 acaacataca cccctcacc atcggggaat gccccaaata tgtgaaatca 1001 aacagattag tccttgcaac tggactcaga aatacccctc aacgagagac
```

-continued

```
1051 gcgaggacta tttggagcta tagcaggttt tatagaggga ggatggcagg 1101 gaatggtaga tggttggtat gggtaccacc atagcaatga gcaggggagt 1151 ggatacgctg cagaccaaga atccacacaa aaggcaatag atggagtcac 1201 caataaggtc aactcgatca ttaacaaaat gaacactcag tttgaggccg 1251 ttggaaggga atttaataac ttggaaagga ggatagagaa tttaaacaag 1301 aaaatggaag acggattcct agatgtctgg acttacaatg ccgaacttct 1351 ggttctcatg gaaaatgaga gaactctaga ctttcatgac tcaaatgtca 1401 agaacctta cgacaaggtc cgactacagc ttagggataa tgcaaaggag 1451 ctgggtaatg gttgtttcga attctatcac aaatgtgata cgaatgtat 1501 ggaaagtgta aaaaacggaa cgtatgacta cccgcagtat tcagaagaag 1551 caagactaaa cagagaggaa ataagtggag taaaattgga atcaatggga 1601 acttaccaaa tactgtcaat ttattcaaca gtggcgagtt ccctagcact 1651 ggcaatcatg gtagctggtc tatctttatg gatgtgctcc aatggatcgt 1701 tacaatgcag aatttgcatt taaatttgtg agttcagatt gtagttaaaa 1751 acacccttgt ttctact
```

Amino acid sequence of ca A/Hong Kong/491/97 H5 (SEQ ID NO: 15)
Entire molecule length: 564 aa

```
  1 mekivlllat vslvksdqic igyhannste qvdtimeknv tvthaqdile
 51 rthngklcdl ngvkplilrd csvagwllgn pmcdefinvp ewsyivekas
101 pandlcypgn fndyeelkhl lsrinhfeki qiipksswsn hdassgvssa
151 cpylgrssff rnvvwlikkn ssyptikrsy nntnqedllv lwgihhpnda
201 aeqtrlyqnp ttyisvgtst lnqrlvpeia trpkvngqsg rmeffwtilk
251 pndainfesn gnfiapeyay kivkkgdsti mkseleygnc ntkcqtpmga
301 inssmpfhni hpltigecpk yvksnrlvla tglrntpqre trglfgaiag
351 fieggwqgmv dgwygyhhsn eqgsgyaadq estqkaidgv tnkvnsiink
401 mntqfeavgr efnnlerrie nlnkkmedgf ldvwtynael lvlmenertl
451 dfhdsnvknl ydkvrlqlrd nakelgngcf efyhkcdnec mesvkngtyd
501 ypqyseearl nreeisgvkl esmgtyqils iystvassla laimvaglsl
551 wmcsngslqc rici
```

Nucleotide Sequence of ca A/Hong Kong/486/97 N1 (SEQ ID NO: 6)
Entire molecule length: 1401 nt

```
  1 agcaaaagca ggagtttaaa atgaatccaa atcagaagat aataaccatt
 51 ggatcaatct gcatggtagt tgggataatc agcttgatgt tacaaattgg
101 aaacacaata tcagtatggg tcagccacat aattaaaact tggcacccaa
151 accagcctga accatgcaac caaagcatca atttttacac tgagcaggct
201 gcagcttcag tgacattagc gggcaattcc tctctctgcc ctattagtgg
251 atgggctata tacagcaagg acaatagtat aagaattggt tccaaagggg
301 atgtgtttgt tataagagaa ccattcatct catgctccca tttggaatgc
```

-continued

```
 351 agaaccttttt tcttgaccca aggagcccta ttgaatgaca agcattctaa
 401 tgggaccgtc aaagacagga gcccctatag aactttaatg agctgtcctg
 451 ttggtgaggc cccttcccca tacaactcaa ggtttgagtc tgttgcttgg
 501 tcagcaagtg cttgccatga tggcattagt tggctaacaa ttggaatttc
 551 cggtccggat aatggggctg tggctgtgtt gaaatacaat ggcataataa
 601 cagacaccat caagagttgg aggaacaaca cactgaggac gcaagagtct
 651 gaatgtgcat gtgtgaatgg ttcttgtttt actgtaatga cagatggacc
 701 gagtaatgaa caggcctcat acaagatttt caagatagaa aaggggaggg
 751 tagtcaaatc agttgagttg aacgcccta attatcatta cgaggaatgc
 801 tcctgttatc ctgatgctgg cgaaatcaca tgtgtgtgca gggataattg
 851 gcatggctcg aaccgaccat gggtgtcttt caatcagaat ctggagtatc
 901 aaataggata tatatgcagt ggggttttcg gagacagtcc acgccccaat
 951 gatgggacag gcagttgtgg tccagtgtct cttaacggag cgtatggagt
1001 aaaagggttt tcatttaaat acggcaatgg tgtttggatc gggagaacca
1051 aaagcactag ttccaggagc ggttttgaaa tgatttggga tccaaatggg
1101 tggaccgaaa cagacagtag cttctcgttg aagcaagaca tcatagcgat
1151 aactgattgg tcaggataca gcgggagttt tattcaacat ccagaactga
1201 caggattaaa ttgcatgaga ccttgcttct gggttgaact aatcagaggg
1251 aggcccaaag agaaaacaat ctggactagt gggagcagta tatctttctg
1301 tggtgtaaat agtgacactg tggggttggtc ttggccagac ggtgctgagt
1351 tgccatacac cattgacaag tagtttgttc aaaaaactcc ttgtttctac
1401 t
```

Amino acid sequence of ca A/Hong Kong/486/97 N1 (SEQ ID NO: 16)
Entire molecule length: 450 aa

```
  1 mnpnqkiiti gsicmvvgii slmlqignti svwvshiikt whpnqpepcn
 51 qsinfyteqa aasvtlagns slcpisgwai yskdnsirig skgdvfvire
101 pfiscshlec rtffltqgal lndkhsngtv kdrspyrtlm scpvgeapsp
151 ynsrfesvaw sasachdgis wltigisgpd ngavavlkyn giitdtiksw
201 rnntlrtqes ecacvngscf tvmtdgpsne qasykifkie kgrvvksvel
251 napnyhyeec scypdageit cvcrdnwhgs nrpwvsfnqn leyqigyics
301 gvfgdsprpn dgtgscgpvs lngaygvkgf sfkygngvwi grtkstssrs
351 gfemiwdpng wtetdssfsl kqdiiaitdw sgysgsfiqh peltglncmr
401 pcfwvelirg rpkektiwts gssisfcgvn sdtvgwswpd gaelpytidk
``` ca A/Hong Kong/491/97 (Ser211) (HA)+ca A/Hong Kong/486/97 (NA)
Nucleotide Sequence of ca A/Hong Kong/491/97 (Ser211) H5 (SEQ ID NO: 7)
Entire molecule length: 1767 nt

```
  1 agcaaaagca ggggtataat ctgtcaaaat ggagaaaata gtgcttcttc
 51 ttgcaacagt cagccttgtt aaaagtgacc agatttgcat tggttaccat
```

```
-continued
 101 gcaaacaact cgacagagca agttgacaca ataatggaaa agaatgttac
 151 tgttacacat gcccaagaca tactggaaag gacacacaac gggaagctct
 201 gcgatctaaa tggagtgaag cctctgattt tgagggattg tagtgtagct
 251 ggatggctcc tcggaaaccc tatgtgtgac gaattcatca atgtgccgga
 301 atggtcttac atagtggaga aggccagtcc agccaatgac ctctgttatc
 351 cagggaattt caacgactat gaagaactga acacctatt gagcagaata
 401 aaccattttg agaaaattca gataatcccc aaaagttctt ggtccaatca
 451 tgatgcctca tcaggggtga gctcagcatg tccatacctt gggaggtcct
 501 cctttttcag aaatgtggta tggcttatca aaaagaacag tagctaccca
 551 acaataaaga ggagctacaa taataccaac caagaagatc ttttggtact
 601 gtgggggatt caccatccta atgatgcggc agagcagaca aggctctatc
 651 aaaacccaac cacctacatt tccgttggaa catcaacact gaaccagaga
 701 ttggtttcag aaatagctac tagacccaaa gtaaacgggc aaagtggaag
 751 aatggagttc ttctggacaa ttttaaagcc gaatgatgcc atcaatttcg
 801 agagtaatgg aaatttcatt gctccagaat atgcatacaa aattgtcaag
 851 aaagggact caacaattat gaaaagtgaa ttggaatatg gtaactgcaa
 901 caccaagtgt caaactccaa tgggggcaat aaactctagt atgccattcc
 951 acaacataca cccctcacc atcggggaat gccccaaata tgtgaaatca
1001 aacagattag tccttgcaac tggactcaga atacccctc aacgagagac
1051 gcgaggacta tttggagcta tagcaggttt tatagaggga ggatggcagg
1101 gaatggtaga tggttggtat gggtaccacc atagcaatga gcaggggagt
1151 ggatacgctg cagaccaaga atccacacaa aaggcaatag atggagtcac
1201 caataaggtc aactcgatca ttaacaaaat gaacactcag tttgaggccg
1251 ttggaaggga atttaataac ttggaaagga ggatagagaa tttaaacaag
1301 aaaatggaag acggattcct agatgtctgg acttacaatg ccgaacttct
1351 ggttctcatg gaaaatgaga gaactctaga ctttcatgac tcaaatgtca
1401 agaacctta cgacaaggtc cgactacagc ttagggataa tgcaaaggag
1451 ctgggtaatg gttgtttcga attctatcac aaatgtgata acgaatgtat
1501 ggaaagtgta aaaaacggaa cgtatgacta cccgcagtat tcagaagaag
1551 caagactaaa cagagaggaa ataagtggag taaaattgga atcaatggga
1601 acttaccaaa tactgtcaat ttattcaaca gtggcgagtt ccctagcact
1651 ggcaatcatg gtagctggtc tatctttatg gatgtgctcc aatggatcgt
1701 tacaatgcag aatttgcatt taaatttgtg agttcagatt gtagttaaaa
1751 acacccttgt ttctact
```

Amino acid sequence of ca A/Hong Kong/491/97 (Ser211)
H5 (SEQ ID NO: 17)
Entire molecule length: 564 aa

```
  1 mekivlllat vslvksdqic igyhannste qvdtimeknv tvthaqdile
 51 rthngklcdl ngvkplilrd csvagwllgn pmcdefinvp ewsyivekas
101 pandlcypgn fndyeelkhl lsrinhfeki qiipksswsn hdassgvssa
```

-continued

```
151 cpylgrssff rnvvwlikkn ssyptikrsy nntnqedllv lwgihhpnda 201 aeqtrlyqnp ttyisvgtst lnqrlvseia trpkvngqsg rmeffwtilk 251 pndainfesn gnfiapeyay kivkkgdsti mkseleygnc ntkcqtpmga 301 inssmpfhni hpltigecpk yvksnrlvla tglrntpqre trglfgaiag 351 fieggwqgmv dgwygyhhsn eqgsgyaadq estqkaidgv tnkvnsiink 401 mntqfeavgr efnnlerrie nlnkkmedgf ldvwtynael lvlmenertl 451 dfhdsnvknl ydkvrlqlrd nakelgngcf efyhkcdnec mesvkngtyd 501 ypqyseearl nreeisgvkl esmgtyqils iystvassla laimvaglsl 551 wmcsngslqc rici
```

Nucleotide Sequence of ca A/Hong Kong/486/97 N1 (SEQ ID NO: 8)
Entire molecule length: 1401 nt

```
   1 agcaaaagca ggagtttaaa atgaatccaa atcagaagat aataaccatt 51 ggatcaatct gcatggtagt tgggataatc agcttgatgt tacaaattgg 101 aaacacaata tcagtatggg tcagccacat aattaaaact tggcacccaa 151 accagcctga accatgcaac caaagcatca atttttacac tgagcaggct 201 gcagcttcag tgacattagc gggcaattcc tctctctgcc ctattagtgg 251 atgggctata tacagcaagg acaatagtat aagaattggt tccaaagggg 301 atgtgtttgt tataagagaa ccattcatct catgctccca tttggaatgc 351 agaacctttt tcttgaccca aggagcccta ttgaatgaca agcattctaa 401 tgggaccgtc aaagacagga gcccctatag aactttaatg agctgtcctg 451 ttggtgaggc cccttcccca tacaactcaa ggtttgagtc tgttgcttgg 501 tcagcaagtg cttgccatga tggcattagt tggctaacaa ttggaatttc 551 cggtccggat aatggggctg tggctgtgtt gaaatacaat ggcataataa 601 cagacaccat caagagttgg aggaacaaca cactgaggac gcaagagtct 651 gaatgtgcat gtgtgaatgg ttcttgtttt actgtaatga cagatggacc 701 gagtaatgaa caggcctcat acaagatttt caagatagaa aaggggaggg 751 tagtcaaatc agttgagttg aacgccccta attatcatta cgaggaatgc 801 tcctgttatc ctgatgctgg cgaaatcaca tgtgtgtgca gggataattg 851 gcatggctcg aaccgaccat gggtgtcttt caatcagaat ctggagtatc 901 aaataggata tatatgcagt ggggttttcg gagacagtcc acgccccaat 951 gatgggacag gcagttgtgg tccagtgtct cttaacggag cgtatggagt 1001 aaaagggttt tcatttaaat acggcaatgg tgtttggatc gggagaacca 1051 aaagcactag ttccaggagc ggttttgaaa tgatttggga tccaaatggg 1101 tggaccgaaa cagacagtag cttctcgttg aagcaagaca tcatagcgat 1151 aactgattgg tcaggataca gcgggagttt tattcaacat ccagaactga 1201 caggattaaa ttgcatgaga ccttgcttct gggttgaact aatcagaggg 1251 aggcccaaag agaaaacaat ctggactagt gggagcagta tatctttctg 1301 tggtgtaaat agtgacactg tgggttggtc ttggccagac ggtgctgagt
```

```
1351  tgccatacac cattgacaag tagtttgttc aaaaaactcc ttgtttctac 1401  t
```

Amino acid sequence of ca A/Hong Kong/486/97 N1 (SEQ ID NO: 18)
Entire molecule length: 450 aa

```
  1  mnpnqkiiti gsicmvvgii slmlqignti svwvshiikt whpnqpepcn
 51  qsinfyteqa aasvtlagns slcpisgwai yskdnsirig skgdvfvire
101  pfiscshlec rtffltqgal lndkhsngtv kdrspyrtlm scpvgeapsp
151  ynsrfesvaw sasachdgis wltigisgpd ngavavlkyn giitdtiksw
201  rnntlrtqes ecacvngscf tvmtdgpsne qasykifkie kgrvvksvel
251  napnyhyeec scypdageit cvcrdnwhgs nrpwvsfnqn leyqigyics
301  gvfgdsprpn dgtgscgpvs lngaygvkgf sfkygngvwi grtkstssrs
351  gfemiwdpng wtetdssfsl kqdiiaitdw sgysgsfiqh peltglncmr
401  pcfwvelirg rpkektiwts gssisfcgvn sdtvgwswpd gaelpytidk
                                                         25
``` ca A/ck/Hong Kong/G9/97
Nucleotide sequence of ca A/ck/Hong Kong/G9/97 (SEQ ID NO: 9)
Entire molecule length: 1690 bp

```
   1  ttaaccactc aagatggaag caataccact aataactata ctactagtag
  51  taacagcaag caatgcagac aaaatctgca tcggctacca atcaacaaac
 101  tccacagaaa ccgtagacac gctaacagaa acaatgttc ctgtgacaca
 151  tgccaaagaa ttgctccaca cagagcacaa tgggatgctg tgtgcaacaa
 201  atctgggacg tcctcttatt ctagacactt gcaccattga aggactgatc
 251  tatggcaacc cttcttgtga tctactgttg ggaggaagag aatggtccta
 301  catcgtcgaa agaccatcgg ctgttaatgg aatgtgttac cccgggaatg
 351  tagaaaacct agaggaacta aggtcatttt ttagttctgc tagttcctac
 401  caaagaatcc agatctttcc agacacaatc tggaatgtgt cttacagtgg
 451  aacaagcaaa gcatgttcag attcattcta caggagcatg agatggttga
 501  ctcaaaagaa caacgcttac cctattcaag acgcccaata cacaaataat
 551  agaggaaaga gcattctttt catgtgggc ataaatcacc cacctaccga
 601  tactgcacag acaaatctgt acacaaggac tgacacaaca caagtgtgg
 651  caacagaaga tataaatagg accttcaaac cagtgatagg gccaaggccc
 701  cttgtcaatg gtctgcaggg aagaattgat tattattggt cggtattgaa
 751  accaggtcag acattgcgag taagatccaa tgggaatcta atcgctccat
 801  ggtatgggca cattctttca ggagagagcc acggaagaat cctgaagact
 851  gatttaaaca gtggtagctg tgtagtgcaa tgtcaaacag aaagaggtgg
 901  cttaaatact actttgccat tccacaatgt cagtaaatat gcatttggaa
 951  actgcccaaa atatgttgga gtaaagagtc tcaaactggc agttggtctg
1001  aggaatgtgc ctgctagatc aagtagagga ctatttgggg ccatagctgg
1051  attcatagag ggaggttggt cagggctggt cgctggttgg tatgggttcc
```

-continued

```
1101  agcattcaaa tgatcaaggg gttggtatag ctgcagatag agactcaact
1151  caaagggcaa ttgacaaaat aacgtccaaa gtgaataata tagtcgataa
1201  aatgaacaag caatatgaaa ttattgatca tgaattcagc gaggttgaaa
1251  atagactcaa tatgatcaat aataagattg atgaccagat acaagacata
1301  tgggcatata acgctgaatt gctagtgctg cttgaaaacc agaaaacact
1351  cgatgagcat gatgcgaatg taaacaatct atataacaaa gtgaagaggg
1401  cactgggttc caatgcaatg aagatggga aaggatgttt cgagctatac
1451  cataaatgtg atgatcagtg catggagaca attcggaacg ggacctataa
1501  caggaggaag tataaagagg aatcaagact agaaagacag aaaatagaag
1551  gggtcaagct ggaatctgaa ggaacttaca aaatcctcac catttattcg
1601  actgtcgcct catctcttgt gattgcaatg gggtttgctg ccttcttgtt
1651  ctgggccatg tccaatggat cttgcagatg caacatttga
```

Amino acid sequence of ca A/ck/Hong Kong/G9/97 H9 (SEQ ID NO: 19)
Entire molecule length: 558 aa

```
  1  meaiplitil lvvtasnadk icigyqstns tetvdtlten nvpvthakel
 51  lhtehngmlc atnlgrplil dtctiegliy gnpscdlllg grewsyiver
101  psavngmcyp gnvenleelr sffssassyq riqifpdtiw nvsysgtska
151  csdsfyrsmr wltqknnayp iqdaqytnnr gksilfmwgi nhpptdtaqt
201  nlytrtdttt svatedinrt fkpvigprpl vnglqgridy ywsvlkpgqt
251  lrvrsngnli apwyghilsg eshgrilktd lnsgscvvqc gterggglntt
301  lpfhnvskya fgncpkyvgv kslklavglr nvparssrgl fgaiagfieg
351  gwsglvagwy gfqhsndqgv giaadrdstq raidkitskv nnivdkmnkq
401  yeiidhefse venrlnminn kiddqiqdiw aynaellvll enqktldehd
451  anvnnlynkv kralgsname dgkgcfelyh kcddqcmeti rngtynrrky
501  keesrlerqk iegvkleseg tykiltiyst vasslviamg faaflfwams
551  ngscrcni
```

Nucleotide sequence of ca A/ck/Hong Kong/G9/97 N2 (SEQ ID NO: 10)
Entire molecule length: 1428 bp

```
  1  aaatgaatcc aaatcagaag ataatagcaa ttggctctgt ttctctaact
 51  attgcgacaa tatgcctcct catgcagatt gctatcttag caacgactat
101  gacactacat ttcaagcaga atgaatgcat caactcctcg aataatcaag
151  tagtgccatg tgaaccaatc ataatagaaa ggaacataac agagatagtg
201  catttgaata gtactacctt agagaaggaa atttgtccta agtagcaga
251  ctacaggaat tggtcaaaac cacaatgtca aatcacaggg ttcgctcctt
301  tctccaagga caattcaatt aggctctccg caggtggaga tatttgggtg
351  acaagagaac cttatgtatc gtgcggtctt ggtaaatgtt atcaatttgc
401  acttgggcag ggaaccactt tggagaacaa cactcaaac ggcacagcac
451  atgatagaac tcctcataga acccttttaa tgaatgagtt gggtgttccg
```

-continued

```
 501  tttcatttgg caaccaaaca agtgtgcata gcatggtcca gctcaagctg 551  ccatgatggg aaagcatggt tacatgtttg tgtcactggg gatgatagaa 601  atgcaacggc tagcatcatt tatgatggga tacttgttga cagtattggt 651  tcatggtcta aaaacatcct cagaactcag gagtcagaat gcgtttgcat 701  caatggaacc tgtgcagtag taatgactga tggaagtgca tcaggaaggg 751  ctgacactag aatactattt attagagagg ggaaaattgc acacattagc 801  ccattgtcag gaagtgctca gcatgtggag gaatgctcct gttaccccccg 851  atatccagaa gttagatgtg tttgcagaga caattggaag ggatccaata 901  ggcccgttct atatataaat atggcaaatt atagtattga ttccagttat 951  gtgtgctcag gacttgttgg cgacacacca agaaatgatg ataggtctag 1001  cagcagcaac tgcagagatc ctaataacga gagggggcc ccaggagtaa 1051  aagggtgggc ctttgacaat ggaaatgaca tttggatggg aagaacaatc 1101  aaaaaggatt cgcgctcagg ttatgagact ttcagggtca ttggtggttg 1151  gaccactgct aattccaagt cacagataaa tagacaagtc atagttgaca 1201  gtgataactc gtctgggtat tctggtatct tctctgttga aggcaaaagc 1251  tgcatcaaca ggtgttttta cgtggagttg ataagaggaa gaccaaagga 1301  gactagggtg tggtggactt caaatagcat cattgtatttt gtggaactt 1351  caggtaccta tggaacaggc tcatggcctg atggggcgaa tatcaatttc 1401  atgcctatat aagctttcgc aattttag
```

Amino acid sequence of ca A/ck/Hong Kong/G9/97 N2 (SEQ ID NO: 20)
Entire molecule length: 469 aa

```
   1  mnpnqkiiai gsvsltiati cllmqiaila ttmtlhfkqn ecinssnnqv 51  vpcepiiier niteivhlns ttlekeicpk vadyrnwskp qcqitgfapf 101  skdnsirlsa ggdiwvtrep yvscglgkcy qfalgqgttl enkhsngtah 151  drtphrtllm nelgvpfhla tkqvciawss sschdgkawl hvcvtgddrn 201  atasiiydgi lvdsigswsk nilrtqesec vcingtcavv mtdgsasgra 251  dtrilfireg kiahisplsg saqhveecsc yprypevrcv crdnwkgsnr 301  pvlyinmany sidssyvcsg lvgdtprndd rssssncrdp nnergapgvk 351  gwafdngndi wmgrtikkds rsgyetfrvi ggwttansks qinrqvivds 401  dnssgysgif svegkscinr cfyvelirgr pketrvwwts nsiivfcgts 451  gtygtgswpd ganinfmpi
```

A/Netherlands/219/03
Nucleotide sequence of A/Netherlands/219/03 H7 (SEQ ID NO: 21)
Entire molecule length: 1737 bp

```
   1  agcaaaagca ggggatacaa aatgaacact caaatcctgg tattcgctct 51  ggtggcgagc attccgacaa atgcagacaa gatctgcctt ggcatcatg 101  ccgtgtcaaa cgggactaaa gtaaacacat taactgagag aggagtggaa 151  gtcgttaatg caactgaaac ggtggaacga acaaacgttc ccaggatctg
```

```
 201   ctcaaaaggg aaaaggacag ttgacctcgg tcaatgtgga cttctgggaa
 251   caatcactgg gccaccccaa tgtgaccaat tcctagaatt ttcggccgac
 301   ttaattattg agaggcgaga aggaagtgat gtctgttatc ctgggaaatt
 351   cgtgaatgaa gaagctctga ggcaaattct cagagagtca ggcggaattg
 401   acaaggagac aatgggattc acctacagcg gaataagaac taatggaaca
 451   accagtgcat gtaggagatc aggatcttca ttctatgcag agatgaaatg
 501   gctcctgtca aacacagaca atgctgcttt cccgcaaatg actaagtcat
 551   acaagaacac aaggaaagac ccagctctga taatatgggg gatccaccat
 601   tccggatcaa ctacagaaca gaccaagcta tatgggagtg aaacaaaact
 651   gataacagtt gggagttcta attaccaaca gtcctttgta ccgagtccag
 701   gagcgagacc acaagtgaat ggccaatctg gaagaattga ctttcattgg
 751   ctgatactaa accctaatga cacggtcact ttcagtttca atggggcctt
 801   catagctcca gaccgtgcaa gctttctgag agggaagtcc atgggaattc
 851   agagtgaagt acaggttgat gccaattgtg aaggagattg ctatcatagt
 901   ggagggacaa taataagtaa tttgcccttt cagaacataa atagcagggc
 951   agtaggaaaa tgtccgagat atgttaagca agagagtctg ctgttggcaa
1001   caggaatgaa gaatgttccc gaaatcccaa agaggaggag gagaggccta
1051   tttggtgcta tagcgggttt cattgaaaat ggatgggaag tttgattga
1101   tgggtggtat ggcttcaggc atcaaaatgc acaaggggag ggaactgctg
1151   cagattacaa aagcacccaa tcagcaattg atcaaataac agggaaatta
1201   aatcggctta tagaaaaaac taaccaacag tttgagttaa tagacaacga
1251   attcactgag gttgaaaggc aaattggcaa tgtgataaac tggaccagag
1301   attccatgac agaagtgtgg tcctataacg ctgaactctt agtagcaatg
1351   gagaatcagc acacaattga tctggccgac tcagaaatga acaaactgta
1401   cgaacgagtg aagagacaac tgagagagaa tgccgaagaa gatggcactg
1451   gttgcttcga atatttcac aagtgtgatg acgactgcat ggccagtatt
1501   agaaacaaca cctatgatca gcaagtac agggaagaag caatacaaaa
1551   tagaatacag attgacccag tcaaactaag cagcggctac aaagatgtga
1601   tactttggtt tagcttcggg gcatcatgtt tcatacttct ggccattgca
1651   atgggccttg tcttcatatg tgtgaagaat ggaaacatgc ggtgcactat
1701   ttgtatataa gtttggaaaa acacccttgt ttctact
```

Amino acid sequence of A/Netherlands/219/03 H7 (SEQ ID NO: 27)
Entire molecule length: 562 aa

```
  1   mntqilvfal vasiptnadk iclghhavsn gtkvntlter gvevvnatet
 51   vertnvpric skgkrtvdlg qcgllgtitg ppqcdqflef sadliierre
101   gsdvcypgkf vneealrqil resggidket mgftysgirt ngttsacrrs
151   gssfyaemkw llsntdnaaf pqmtksyknt rkdpaliiwg ihhsgstteq
201   tklygsgnkl itvgssnyqq sfvpspgarp qvngqsgrid fhwlilnpnd
251   tvtfsfngaf iapdrasflr gksmgiqsev qvdancegdc yhsggtiisn
```

```
301  lpfqninsra  vgkcpryvkq  eslllatgmk  nvpeipkrrr  rglfgaiagf
351  iengweglid  gwygfrhqna  qgegtaadyk  stqsaidqit  gklnrliekt
401  nqqfelidne  fteverqign  vinwtrdsmt  evwsynaell  vamenqhtid
451  ladsemnkly  ervkrqlren  aeedgtgcfe  ifhkcdddcm  asirnntydh
501  skyreeaiqn  riqidpvkls  sgykdvilwf  sfgascfill  aiamglvfic
551  vkngnmrcti  ci
```

Nucleotide Sequence of A/Netherlands/219/03 N7 (SEQ ID NO: 22)
Entire molecule length: 1465 nt

```
   1  agcaaaagca  gggtgatcga  gaatgaatcc  aaatcagaaa  ctatttgcat
  51  tatctggagt  ggcaatagca  cttagtgtac  tgaacttatt  gataggaatc
 101  tcaaacgtcg  gattgaacgt  atctctacat  ctaaaggaaa  aaggacccaa
 151  acaggaggag  aatttaacat  gcacgaccat  aatcaaaac   aacactactg
 201  tagtagaaaa  cacatatgta  aataatacaa  caataattac  caagggaact
 251  gatttgaaaa  caccaagcta  tctgctgttg  aacaagagcc  tgtgcaatgt
 301  tgaagggtgg  gtcgtgatag  caaaagacaa  tgcagtaaga  tttggggaaa
 351  gtgaacaaat  cattgttacc  agggagccat  atgtatcatg  cgacccaaca
 401  ggatgcaaaa  tgtatgcctt  gcaccaaggg  actaccatta  ggaacaaaca
 451  ttcaaatgga  acgattcatg  acagaacagc  tttcagaggt  ctcatctcca
 501  ctccattggg  cactccacca  accgtaagta  acagtgactt  tatgtgtgtt
 551  ggatggtcaa  gcacaacttg  ccatgatggg  attgctagga  tgactatctg
 601  tatacaagga  ataatgaca   atgctacagc  aacggtttat  acaacagaa
 651  ggctgaccac  taccattaag  acctgggcca  gaaacattct  gaggactcaa
 701  gaatcagaat  gtgtgtgcca  aatggcaca   tgtgcagttg  taatgaccga
 751  cggatcggct  agtagtcaag  cctatacaaa  agtaatgtat  ttccacaagg
 801  gattagtagt  taaggaggag  gagttaaggg  gatcagccag  acatattgag
 851  gaatgctcct  gttatggaca  caatcaaaag  gtgacctgtg  tgtgcagaga
 901  taactggcag  ggagcaaaca  ggcctattat  agaaattgat  atgagcacat
 951  tggagcacac  aagtagatac  gtgtgcactg  gaattctcac  agacaccagc
1001  agacctgggg  acaaatctag  tggtgattgt  tccaatccaa  taactgggag
1051  tcccggcgtt  ccgggagtga  agggattcgg  gtttctaaat  ggggataaca
1101  catggcttgg  taggaccatc  agccccagat  caagaagtgg  attcgaaatg
1151  ttgaaaatac  ctaatgcagg  tactgatccc  aattctagaa  tagcagaacg
1201  acaggaaatt  gtcgacaata  caattggtc   aggctattcc  ggaagcttta
1251  ttgactattg  gaatgataac  agtgaatgct  acaatccatg  cttttacgta
1301  gagttaatta  gaggaagacc  cgaagaggct  aaatacgtat  ggtgggcaag
1351  taacagtcta  attgccctat  gtggaagccc  attcccagtt  gggtctggtt
1401  ccttccccga  tggggcacaa  atccaatact  tttcgtaaaa  tgcaaaaaaa
1451  ctccttgttt  ctact
```

Nucleotide Sequence of A/Netherlands/219/03 N7 (SEQ ID NO: 45)
Entire molecule length: 1464 nt

```
   1 agcaaaagca gggtgatcga gaatgaatcc aaatcagaaa ctatttgcat tatctggagt
  61 ggcaatagca cttagtgtac tgaacttatt gataggaatc tcaaacgtcg gattgaacgt
 121 atctctacat ctaaaggaaa aaggacccaa acaggaggag aatttaacat gcacgaccat
 181 taatcaaaac aacactactg tagtagaaaa cacatatgta aataatacaa caataattac
 241 caagggaact gatttgaaaa caccaagcta tctgctgttg aacaagagcc tgtgcaatgt
 301 tgaagggtgg gtcgtgatag caaaagacaa tgcagtaaga tttggggaaa gtgaacaaat
 361 cattgttacc agggagccat atgtatcatg cgacccaaca ggatgcaaaa tgtatgcctt
 421 gcaccaaggg actaccatta ggaacaaaca ttcaaatgga acgattcatg acagaacagc
 481 tttcagaggt ctcatctcca ctccattggg cactccacca accgtaagta acagtgactt
 541 tatgtgtgtt ggatggtcaa gcacaacttg ccatgatggg attgctagga tgactatctg
 601 tatacaagga aataatgaca atgctacagc aacggtttat tacaacagaa ggctgaccac
 661 taccattaag acctgggcca gaaacattct gaggactcaa gaatcagaat gtgtgtgcca
 721 caatggcaca tgtgcagttg taatgaccga cggatcggct agtagtcaag cctatacaaa
 781 agtaatgtat ttccacaagg gattagtagt taaggaggag gagttaaggg gatcagccag
 841 acatattgag gaatgctcct gttatggaca caatcaaaag gtgacctgtg tgtgcagaga
 901 taactggcag ggagcaaaca ggcctattat agaaattgat atgagcacat tggagcacac
 961 aagtagatac gtgtgcactg gaattctcac agacaccagc agacctgggg acaaatctag
1021 tggtgattgt tccaatccaa taactgggag tcccggcgtt ccgggagtga agggattcgg
1081 gtttctaaat ggggataaca catggcttgg taggaccatc agccccagat caagaagtgg
1141 attcgaaatg ttgaaaatac ctaatgcagg tactgatccc aattctagaa tagcagaacg
1201 acaggaaatt gtcgacaata acaattggtc aggctattcc ggaagcttta ttgactattg
1261 gaatgataac agtgaatgct acaatccatg cttttacgta gagttaatta gaggaagacc
1321 cgaagaggct aaatacgtat ggtgggcaag taacagtcta attgccctat gtggaagccc
1381 attcccagtt gggtctggtt ccttccccga tggggcacaa atccaatact tttcgtaaaa
1441 tgcaaaaaca cccttgtttc tact
```

Amino acid sequence of A/Netherlands/219/03 N7 (SEQ ID NO: 28)

Entire molecule length: 471 aa

```
  1  mnpnqklfal sgvaialsvl nlligisnvg lnvslhlkek gpkqeenltc
 51  ttinqnnttv ventyvnntt iitkgtdlkt psylllnksl cnvegwvvia
101  kdnavrfges eqiivtrepy vscdptgckm yalhqgttir nkhsngtihd
151  rtafrglist plgtpptvsn sdfmcvgwss ttchdgiarm ticiqgnndn
201  atatvyynrr ltttiktwar nilrtqesec vchngtcavv mtdgsassqa
251  ytkvmyfhkg lvvkeeelrg sarhieecsc yghnqkvtcv crdnwqganr
301  piieidmstl ehtsryvctg iltdtsrpgd kssgdcsnpi tgspgvpgvk
351  gfgflngdnt wlgrtisprs rsgfemlkip nagtdpnsri aerqeivdnn
401  nwsgysgsfi dywndnsecy npcfyvelir grpeeakyvw wasnslialc
451  gspfpvgsgs fpdgaqiqyf s
```

A/ck/BC/CN-7/04
Nucleotide sequence of A/ck/BC/CN-7/04 H7 (SEQ ID NO: 23)
Entire molecule length: 1754 bp

```
   1 agcaaaagca ggggatacaa aatgaatact caaattttgg cattcattgc
  51 ttgtatgctg attggaacta aaggagacaa aatatgtctt gggcaccatg
 101 ctgtggcaaa tgggacaaaa gtgaacacac taacagagag gggaattgaa
 151 gtagtcaatg ccacggagac ggtggaaact gtaaatatta aaaaaatatg
 201 cactcaagga aaaaggccaa cagatctggg acaatgtgga cttctaggaa
 251 ccctaatagg acctccccaa tgcgatcaat ttctggagtt tgacgctaat
 301 ttgataattg aacgaagaga aggaaccgat gtgtgctatc ccgggaagtt
 351 cacaaatgaa gaatcactga ggcagatcct tcgagggtca ggaggaattg
 401 ataaagagtc aatgggtttc acctatagtg aataagaac caatggggcg
 451 acgagtgcct gcagaagatc aggttcttct ttctatgcgg agatgaagtg
 501 gttactgtcg aattcagaca atgcggcatt tccccaaatg actaagtcgt
 551 ataggaatcc caggaacaaa ccagctctga taatctgggg agtgcatcac
 601 tctggatcag ctactgagca gaccaaactc tatggaagtg gaaacaagtt
 651 gataacagta ggaagctcga ataccagca atcattcact ccaagtccgg
 701 gagcacggcc acaagtgaat ggacaatcag gaaggattga ttttcattgg
 751 ctactccttg accccaatga cacagtgacc ttcactttca tggggcatt
 801 catagcccct gacagggcaa gtttctttag aggagaatcg ctaggagtcc
 851 agagtgatgt tcctttggat tctggttgtg aaggggattg cttccacagt
 901 gggggtacga tagtcagttc cctgccattc aaaacatca accctagaac
 951 agtggggaaa tgccctcgat atgtcaaaca gacaagcctc cttttggcta
1001 caggaatgag aaacgtccca gagaccccca gcaggccta ccggaaacgg
1051 atgaccagag gcctttttgg agcgattgct ggattcatag agaatggatg
1101 ggaaggtctc atcgatggat ggtatggttt cagacatcaa aatgcacaag
1151 gagaaggaac tgcagctgac tacaaaagca cccaatctgc aatagatcag
1201 atcacaggca aattgaatcg tctgattgac aaaacaaacc agcagtttga
1251 actgatagac aatgaattca gtgagataga caacaaatc gggaatgtca
1301 ttaactggac acgagactca atgactgagg tatggtcgta taatgctgag
1351 ctgttggtgg caatggagaa tcagcataca atagatcttg cagactcaga
1401 aatgaacaaa ctttacgaac gcgtcagaaa acaactaagg gaaaatgctg
1451 aagaagatgg aactggatgc tttgagatat tccataagtg tgatgatcag
1501 tgtatggaga gcataaggaa caacacttat gaccataccc aatacaggac
1551 agagtcattg cagaatagaa tacagataga cccagtgaaa ttgagtagtg
1601 gatacaaaga cataatctta tggtttagct cggggcatc atgttttctt
1651 cttctagcca ttgcaatggg attggttttc atttgcataa agaatggaaa
1701 catgcggtgc actatttgta tatagtttga gaaaaaaaca cccttgtttc
1751 tact
```

Amino acid sequence of A/ck/BC/CN-7/04 H7 (SEQ ID NO: 29)
Entire molecule length: 567 aa

```
  1  mntqilafia cmligtkgdk iclghhavan gtkvntlter gievvnatet
 51  vetvnikkic tqgkrptdlg qcgllgtlig ppqcdqflef danliierre
101  gtdvcypgkf tneeslrqil rgsggidkes mgftysgirt ngatsacrrs
151  gssfyaemkw llsnsdnaaf pqmtksyrnp rnkpaliiwg vhhsgsateq
201  tklygsgnkl itvgsskyqq sftpspgarp qvngqsgrid fhwllldpnd
251  tvtftfngaf iapdrasffr geslgvqsdv pldsgcegdc fhsggtivss
301  lpfqninprt vgkcpryvkq tslllatgmr nvpenpkqay rkrmtrglfg
351  aiagfiengw eglidgwygf rhqnaqgegt aadykstqsa idqitgklnr
401  lidktnqqfe lidnefseie qqignvinwt rdsmtevwsy naellvamen
451  qhtidladse mnklyervrk qlrenaeedg tgcfeifhkc ddqcmesirn
501  ntydhtqyrt eslqnriqid pvklssgykd iilwfsfgas cflllaiamg
551  lvficikngn mrctici
```

Nucleotide Sequence of A/ck/BC/CN-7/04 N3 (SEQ ID NO: 24)
Entire molecule length: 1453 nt

```
   1  agcaaaagca ggtgcgagat gaatccgaat cagaagataa taacaatcgg
  51  ggtagtgaat accactctgt caacaatagc ccttctcatt ggagtgggaa
 101  acttagtttt caacacagtc atacatgaga aaataggaga ccatcaaata
 151  gtgacccatc aacaataat gacccctgaa gtaccgaact gcagtgacac
 201  tataataaca tacaataaca ctgttataaa caacataaca acaacaataa
 251  taactgaagc agaaaggcct ttcaagtctc cactaccgct gtgcccctto
 301  agaggattct tccctttca caaggacaat gcaatacgac tgggtgaaaa
 351  caaagacgtc atagtcacaa gggagcctta tgttagctgc gataatgaca
 401  actgctggtc ctttgctctc gcacaaggag cattgctagg gactaaacat
 451  agcaatggga ccattaaaga cagaacacca tataggtctc taattcgttt
 501  cccaatagga acagctccag tactaggaaa ttacaaagag atatgcattg
 551  cttggtcgag cagcagttgc tttgacggga agagtggat gcatgtgtgc
 601  atgacaggga atgataatga tgcaagtgcc cagataatat atggaggaag
 651  aatgacagac tccattaaat catggaggaa ggacatacta agaacccagg
 701  agtctgaatg tcaatgcatt gacgggactt gtgttgttgc tgtcacagat
 751  ggccctgctg ctaatagtgc agatcacagg gtttactgga tacgggaggg
 801  aagaataata agtatgaaa atgttcccaa acaaagata caacacttag
 851  aagaatgttc ctgctatgtg gacattgatg tttactgtat atgtagggac
 901  aattggaagg gctctaacag accttggatg agaatcaaca acgagactat
 951  actggaaaca ggatatgtat gtagtaaatt tcactcagac accccaggc
1001  cagctgaccc ttcaataatg tcatgtgact ccccaagcaa tgtcaatgga
1051  ggacccggag tgaaggggtt tggtttcaaa gctggcaatg atgtatggtt
1101  aggtagaaca gtgtcaacta gtggtagatc gggctttgaa attatcaaag
```

```
-continued
1151  ttacagaagg gtggatcaac tctcctaacc atgtcaaatc aattacacaa
1201  acactagtgt ccaacaatga ctggtcaggc tattcaggta gcttcattgt
1251  caaagccaag gactgttttc agccctgttt ttatgttgag cttatacgag
1301  ggaggcccaa caagaatgat gacgtctctt ggacaagtaa tagtatagtt
1351  actttctgtg gactagacaa tgaacctgga tcgggaaatt ggccagatgg
1401  ttctaacatt gggtttatgc ccaagtaata gaaaaagca ccttgtttct
1451  act
```

Amino acid sequence of A/ck/BC/CN-7/04 N3 (SEQ ID NO: 30)
Entire molecule length: 469 aa

```
  1   mnpnqkiiti gvvnttlsti alligvgnlv fntvihekig dhqivthpti
 51   mtpevpncsd tiitynntvi nnitttiite aerpfksplp lcpfrgffpf
101   hkdnairlge nkdvivtrep yvscdndncw sfalaqgall gtkhsngtik
151   drtpyrslir fpigtapvlg nykeiciaws ssscfdgkew mhvcmtgndn
201   dasaqiiygg rmtdsikswr kdilrtqese cqcidgtcvv avtdgpaans
251   adhrvywire griikyenvp ktkiqhleec scyvdidvyc icrdnwkgsn
301   rpwmrinnet iletgyvcsk fhsdtprpad psimscdsps nvnggpgvkg
351   fgfkagndvw lgrtvstsgr sgfeiikvte gwinspnhvk sitqtivsnn
401   dwsgysgsfi vkakdcfqpc fyvelirgrp nknddvswts nsivtfcgld
451   nepgsgnwpd gsnigfmpk
``` ca A/ck/BC/CN-6/04
Nucleotide sequence of ca A/ck/BC/CN-6/04 H7 (SEQ ID NO: 25)
Entire molecule length: 1734 bp

```
  1   agcgaaagca ggggatacaa aatgaatact caaattttgg cattcattgc
 51   ttgtatgctg attggaacta aaggagacaa atatgtctct gggcaccatg
101   ctgtggcaaa tgggacaaaa gtgaacacac taacagagag gggaattgaa
151   gtagtcaatg ccacggagac ggtggaaact gtaaatatta gaaaaatatg
201   cactcaagga aaaaggccaa cagatctggg acaatgtgga cttctaggaa
251   ccctaatagg acctccccaa tgcgatcaat ttctggagtt tgacgctaat
301   ttgataattg aacgaagaga aggaaccgat gtgtgctatc ccgggaagtt
351   cacaaatgaa gaatcactga ggcagatcct tcgagggtca ggaggaattg
401   ataaagagtc aatgggtttc acctatagtg aataagaac caatggggcg
451   acgagtgcct gcagaagatc aggttcttct ttctatgcgg agatgaagtg
501   gttactgtcg aattcagaca atgcggcatt tccccaaatg actaagtcgt
551   ataggaatcc caggaacaaa ccagctctga taatctgggg agtgcatcac
601   tctggatcag ctactgagca gaccaaactc tatggaagtg gaaacaagtt
651   gataacagta ggaagctcga ataccagca atcattcact ccaagtccgg
701   gagcacggcc acaagtgaat ggacaatcag gaaggattga ttttcattgg
751   ctactccttg accccaatga cacagtgacc ttcactttca atggggcatt
```

```
 801  catagcccct gacagggcaa gtttctttag aggagaatcg ctaggagtcc
 851  agagtgatgt tcctttggat tctggttgtg aaggggattg cttccacagt
 901  gggggtacga tagtcagttc cctgccattc aaaacatca accctagaac
 951  agtggggaaa tgccctcgat atgtcaaaca gacaagcctc cttttggcta
1001  caggaatgag aaacgtccca gagaacccca agaccagagg ccttttttgga
1051  gcgattgctg gattcataga gaatggatgg gaaggtctca tcgatggatg
1101  gtatggtttc agacatcaaa atgcacaagg agaaggaact gcagctgact
1151  acaaaagcac ccaatctgca atagatcaga tcacaggcaa attgaatcgt
1201  ctgattgaca aaacaaacca gcagtttgaa ctgatagaca atgaattcag
1251  tgagataaaa caacaaatcg gaatgtcat taactggaca cgagactcaa
1301  tgactgaggt atggtcgtat aatgctgagc tgttggtggc aatggagaat
1351  cagcatacaa tagatcttgc agactcagaa atgaacaaac tttacgaacg
1401  cgtcagaaaa caactaaggg aaaatgctga agaagatgga actggatgct
1451  ttgagatatt ccataagtgt gatgatcagt gtatggagag cataaggaac
1501  aacacttatg accatacca atacaggaca gagtcattgc agaatagaat
1551  acagatagac ccagtgaaat tgagtagtgg atacaaagac ataatcttat
1601  ggtttagctt cggggcatca tgttttcttc ttctagccat tgcaatggga
1651  ttggttttca tttgcataaa gaatggaaac atgcggtgca ctatttgtat
1701  atagtttgag aaaaaaacac ccttgttct act
```

Amino acid sequence of ca A/ck/BC/CN-6/04 H7 (SEQ ID NO: 31)  
Entire molecule length: 560 aa

```
  1  mntqilafia cmligtkgdk iclghhavan gtkvntlter gievvnatet
 51  vetvnikkic tqgkrptdlg qcgllgtlig ppqcdqflef danliierre
101  gtdvcypgkf tneeslrqil rgsggidkes mgftysgirt ngatsacrrs
151  gssfyaemkw llsnsdnaaf pqmtksyrnp rnkpaliiwg vhhsgsateq
201  tklygsgnkl itvgsskyqq sftpspgarp qvngqsgrid fhwllldpnd
251  tvtftfngaf iapdrasffr geslgvqsdv pldsgcegdc fhsggtivss
301  lpfqninprt vgkcpryvkq tslllatgmr nvpenpktrg lfgaiagfie
351  ngweglidgw ygfrhqnaqg egtaadykst qsaidqitgk lnrlidktnq
401  qfelidnefs eieqqignvi nwtrdsmtev wsynaellva menqhtidla
451  dsemnklyer vrkqlrenae edgtgcfeif hkcddqcmes irnntydhtq
501  yrteslqnri qidpvklssg ykdiilwfsf gascflllai amglvficik
551  ngnmrctici
```

Nucleotide sequence of ca A/ck/BC/CN-6/04 N3 (SEQ ID NO: 26)  
Entire molecule length: 1453 nt

```
  1  agcaaaagca ggtgcgagat gaatccgaat cagaagataa taacaatcgg
 51  ggtagtgaat accactctgt caacaatagc ccttctcatt ggagtgggaa
101  acttagtttt caacacagtc atacatgaga aaataggaga ccatcaaata
```

-continued

```
 151 gtgacccatc caacaataat gacccctgaa gtaccgaact gcagtgacac
 201 tataataaca tacaataaca ctgttataaa caacataaca acaacaataa
 251 taactgaagc agaaaggcct ttcaagtctc cactaccgct gtgcccttc
 301 agaggattct tcccttttca caaggacaat gcaatacgac tgggtgaaaa
 351 caaagacgtc atagtcacaa gggagcctta tgttagctgc gataatgaca
 401 actgctggtc ctttgctctc gcacaaggag cattgctagg gactaaacat
 451 agcaatggga ccattaaaga cagaacacca tataggtctc taattcgttt
 501 cccaatagga acagctccag tactaggaaa ttacaaagag atatgcattg
 551 cttggtcgag cagcagttgc tttgacggga agagtggat gcatgtgtgc
 601 atgacaggga atgataatga tgcaagtgcc cagataatat atggaggaag
 651 aatgacagac tccattaaat catggaggaa ggacatacta agaacccagg
 701 agtctgaatg tcaatgcatt gacgggactt gtgttgttgc tgtcacagat
 751 ggccctgctg ctaatagtgc agatcacagg gtttactgga tacgggaggg
 801 aagaataata aagtatgaaa atgttcccaa aacaaagata caacacttag
 851 aagaatgttc ctgctatgtg gacattgatg tttactgtat atgtagggac
 901 aattggaagg gctctaacag accttggatg agaatcaaca acgagactat
 951 actggaaaca ggatatgtat gtagtaaatt tcactcagac accccccaggc
1001 cagctgaccc ttcaataatg tcatgtgact ccccaagcaa tgtcaatgga
1051 ggacccggag tgaaggggtt tggtttcaaa gctgcaatg atgtatggtt
1101 aggtagaaca gtgtcaacta gtggtagatc gggctttgaa attatcaaag
1151 ttacagaagg gtggatcaac tctcctaacc atgtcaaatc aattacacaa
1201 acactagtgt ccaacaatga ctggtcaggc tattcaggta gcttcattgt
1251 caaagccaag gactgttttc agccctgttt ttatgttgag cttatacgag
1301 ggaggcccaa caagaatgat gacgtctctt ggacaagtaa tagtatagtt
1351 actttctgtg gactagacaa tgaacctgga tcgggaaatt ggccagatgg
1401 ttctaacatt gggtttatgc ccaagtaata gaaaaaagca ccttgtttct
1451 act
```

Amino acid sequence of ca A/ck/BC/CN-6/04 N3 (SEQ ID NO: 32)
Entire molecule length: 469 aa

```
  1 mnpnqkiiti gvvnttlsti alligvgnlv fntvihekig dhqivthpti
 51 mtpevpncsd tiitynntvi nnitttiite aerpfksplp lcpfrgffpf
101 hkdnairlge nkdvivtrep yvscdndncw sfalaqgall gtkhsngtik
151 drtpyrslir fpigtapvlg nykeiciaws ssscfdgkew mhvcmtgndn
201 dasaqiiygg rmtdsikswr kdilrtqese cqcidgtcvv avtdgpaans
251 adhrvywire griikyenvp ktkiqhleec scyvdidvyc icrdnwkgsn
301 rpwmrinnet iletgyvcsk fhsdtprpad psimscdsps nvnggpgvkg
351 fgfkagndvw lgrtvstsgr sgfeiikvte gwinspnhvk sitqtlvsnn
401 dwsgysgsfi vkakdcfqpc fyvelirgrp nknddvswts nsivtfcgld
451 nepgsgnwpd gsnigfmpk
``` ca A/Duck
Nucleotide sequence of ca A/Duck H6 (SEQ ID NO: 33)
Entire molecule length: 1743 bp

```
   1 agcaaaagca ggggaaaatg attgcagtca ttataatagc ggtactggca acggccggaa
  61 aatcagacaa gatctgcatt gggtatcatg ccaacaattc aacaacacaa gtggatacga
 121 tacttgagaa gaatgtaacc gtcacacact cagttgaatt gctggagaac caaaaagaag
 181 aaagattctg caagatcttg aacaaggccc ctctcgattt aagaggatgt accatagagg
 241 gttggatctt ggggaatccc aatgcgacc tattgcttgg tgatcaaagc tggtcatata
 301 tagtggaaag acctacagct caaaatggga tctgctaccc aggaattttg aatgaagtag
 361 aagaactgaa ggcacttatt ggatcaggag aaagagtgga gagatttgaa atgtttccca
 421 aaagtacatg gcaggagta gacaccagca gtggggtaac aaaggcttgc ccttatacta
 481 gtggttcgtc tttctacaga aacctcctat ggataataaa accaagtcc gcagcatatc
 541 cagtaattaa gggaacctac aataacactg aagccagcc aatcctctat ttctggggtg
 601 tgcaccatcc tcctgacacc aatgagcaaa acactttgta tggctctggt gatcgatatg
 661 tcaggatggg aactgaaagc atgaattttg ccaagagccc agaaattgcg gcaaggcctg
 721 ctgtgaatgg tcaaagaggc agaattgatt attactggtc tgttttaaag ccgggggaaa
 781 ccttgaatgt ggaatctaat ggaaatctaa tcgcccttg gtatgcatac aaatttgtca
 841 gcaccaatag taaaggagcc gtcttcaagt caaatttacc aatcgagaac tgtgatgcca
 901 catgccagac tattgcagga gtcttaagaa ccaataaaac atttcagaat gtaagccctc
 961 tgtggatagg agaatgcccc aaatatgtga aaagtgaaag tttgaggctt gcaactggac
1021 taagaaatat tccacagatt gagactagag gacttttcgg agctatcgca gggtttattg
1081 aaggaggatg gactggaatg atagatgggt ggtatggcta tcaccatgaa aattctcaag
1141 gctcagggta tgcggcagac agagaaagca ctcaaaggc tatagacgga attacaaata
1201 aggtcaattc cattatagac aaaatgaaca cacaattcga agctatagac cacgaattct
1261 caaatttgga gagaagaatt gacagtctga acaaaagaat ggaagatgga tttctggacg
1321 tttggacata caatgctgaa ctgttggttc ttcttgaaaa cgaaaggaca ctagacctac
1381 atgacgcgaa tgtgaagaac ctgtatgaaa aggtcaaatc acaactacgg acaatgcta
1441 atgatctagg aaatggatgc tttgaatttt ggcataagtg tgacaatgaa tgcatagagt
1501 ctgtcaaaaa tggtacctat gactatccca aatatcagga tgaaagcaaa ttgaacaggc
1561 aggaaataga atcggtgaag ctggagaacc ttggtgtgta tcaaatcctc gccatttata
1621 gtacggtatc gagcagtcta gtcttggtag ggctgattat agcaatgggc cttggatgt
1681 gttcaaatgg ttcaatgcaa tgcaggatat gtatataatt aagaaaaaca cccttgttct
1741 act
```

Amino acid sequence of ca A/Duck H6 (SEQ ID NO: 39)
Entire molecule length: 566 aa

```
  1 miaviiiavl atagksdkic igyhannstt qvdtileknv tvthsvelle nqkeerfcki
 61 lnkapldlrg ctiegwilgn pqcdlllgdq swsyiverpt aqngicypgi lneveelkal
121 igsgerverf emfpkstwag vdtssgvtka cpytsgssfy rnllwiiktk saaypvikgt
181 ynntgsqpil yfwgvhhppd tneqntlygs gdryvrmgte smnfakspei aarpavngqr
241 gridyywsvl kpgetlnves ngnliapwya ykfvstnskg avfksnlpie ncdatcqtia
301 gvlrtnktfq nvsplwigec pkyvkseslr latglrnipq ietrglfgai agfieggwtg
```

-continued

```
361 midgwygyhh ensqgsgyaa drestqraid gitnkvnsii dkmntqfeai dhefsnlerr
421 idslnkrmed gfldvwtyna ellvllener tldlhdanvk nlyekvksql rdnandlgng
481 cfefwhkcdn eciesvkngt ydypkyqdes klnrqeiesv klenlgvyqi laiystvsss
541 lvlvgliiam glwmcsngsm qcrici
```

Nucleotide sequence of ca A/Duck N9 (SEQ ID NO: 34)
Entire molecule length: 1460 nt

```
   1 agcaaaagca gggtcaagat gaatccaaat cagaagattc tatgcacatc tgctactgcc
  61 attgcaatag gcacaattgc tgtattaata ggaatagcaa acctgggttt gaacatagga
 121 ctacacctga aaccgagctg caactgctcc aaccctcctc ctgaaacaac aaatgtaagc
 181 caaacaataa taaacaatta ctacaatgaa acaaatgtta cccaaataag taacacaaac
 241 attcaacata tgggggggaac cgaaaaggac ttcaacaatc tgactaaagg gctctgcaca
 301 ataaattcat ggcatatatt cggaaaggac aatgctataa gaatagggga gaactctgat
 361 gttttagtca caagagagcc atatgtttct tgtgatccag atgaatgcag attctatgct
 421 ctcagccaag gaacaacaat acggggaaag cactcaaatg gaacaataca cgatagatcc
 481 caataccgtg ctttagtgag ctggccttta tcatcaccac ccactgtgta caataccaga
 541 gtagaatgca ttggatggtc cagtacaagc tgccatgatg ggaaagcacg aatgtctata
 601 tgtgtctcag gtcccaacaa caatgcatca gcagtgattt ggtacaaagg gcggcctatc
 661 acggaaatca atacgtgggc ccgaaacata ttgagaaccc aagaatctga gtgtgtatgc
 721 cacaatggaa tatgtccagt agtgttcact gacggttctg ccaccggtcc agcagaaact
 781 aggatatact atttcaaaga ggggaaaatc ctcaaatggg agccactaac tggaaccgcc
 841 aagcacattg aagaatgctc ttgctatggg aaagactcag aaataacgtg cacatgtaga
 901 gacaattggc aaggctcgaa tagaccagta atacaaataa accccacaat gatgactcac
 961 actagtcaat acatatgcag ccctgtcctc acagacaatc cacgccccaa tgaccccacg
1021 gtaggcaagt gtaatgatcc ttatccagga aacaacaata atggagtcaa aggattctca
1081 tatttagatg gtgacaatac atggctagga agaacgataa gcacagcctc taggtctggg
1141 tatgaaatgc tgaaagtgcc taatgcattg acagatgata gatcaaaacc tactcaaggt
1201 cagacaattg tattaaacac agactggagt ggttacagtg ggtctttcat tgattactgg
1261 gcaaaagggg agtgctatag agcatgcttc tacgttgagc tgatccgtgg aaggccaaaa
1321 gaggacaaag tgtggtggac cagtaatagt atagtgtcga tgtgttccag cacagagttc
1381 cttggacaat ggaactggcc agatggggct aaaatagagt acttcctcta agatgtagaa
1441 aaaagaccct tgtttctact
```

Amino acid sequence of ca A/Duck N9 (SEQ ID NO: 40)
Entire molecule length: 470 aa

```
  1 mnpnqkilct satalaigti avligianlg lniglhlkps cncsnpppet tnvsqtiinn
 61 yynetnvtqi sntniqhmgg tekdfnnltk glctinswhi fgkdnairig ensdvlvtre
121 pyvscdpdec rfyalsqgtt irgkhsngti hdrsqyralv swplsspptv yntrvecigw
181 sstschdgka rmsicvsgpn nnasaviwyk grpiteintw arnilrtqes ecvchngicp
241 vvftdgsatg paetriyyfk egkilkwepl tgtakhieec scygkdseit ctcrdnwqgs
301 nrpviqinpt mmthtsqyic spvltdnprp ndptvgkcnd pypgnnnngv kgfsyldgdn
```

-continued

```
361 twlgrtista srsgyemlkv pnaltddrsk ptqgqtivln tdwsgysgsf idywakgecy
421 racfyvelir grpkedkvww tsnsivsmcs steflgqwnw pdgakieyfl
``` ca A/Teal
Nucleotide sequence of ca A/Teal H6 (SEQ ID NO: 35)
Entire molecule length: 1747 bp

```
   1 agcaaaagca ggggaaaatg attgcaatca ttgtaatagc aatactggca gcagccggaa
  61 aatcagacaa gatctgcatt gggtatcatg ccaacaattc aacaacacag gtagatacga
 121 tacttgagaa gaatgtgact gtcacacact caattgaatt gctggaaaat cagaaggaag
 181 aaagattctg caagatattg aacaaggccc ctctcgactt aagggaatgt accatagagg
 241 gttggatctt ggggaatccc caatgcgacc tattgcttgg tgatcaaagc tggtcataca
 301 ttgtggaaag acctactgct caaaacggga tctgctaccc aggaacctta aatgaggtag
 361 aagaactgag ggcacttatt ggatcaggag aaagggtaga gagatttgag atgtttcccc
 421 aaagcacctg gcaaggagtt gacaccaaca gtggaacaac aagatcctgc ccttattcta
 481 ctggtgatcc gtctttctac agaaacctcc tatggataat aaaaaccaag acagcagaat
 541 atccagtaat taagggaatt tacaacaaca ctggaaccca gccaatcctc tatttctggg
 601 gtgtgcatca tcctcctaac accgacgagc aagatactct gtatggctct ggtgatcgat
 661 acgttagaat gggaactgaa agcatgaatt ttgccaagag tccggaaatt gcggcaaggc
 721 ctgctgtgaa tggacaaaga ggcagaattg attattattg gtcggtttta aaaccagggg
 781 aaaccttgaa tgtggaatct aatggaaatc taatcgcccc ttggtatgca tacaaatttg
 841 tcaacacaaa tagtaaagga gccgtcttca ggtcagattt accaatcgag aactgcgatg
 901 ccacatgcca gactattgca ggggttctaa ggaccaataa aacatttcag aatgtgagtc
 961 ccctgtggat aggagaatgt cccaaatacg tgaaaagtga aagtctgagg cttgcaactg
1021 gactaagaaa tgttccacag attgaaacta gaggactctt cggagctatt gcagggttta
1081 ttgaaggagg atggactggg atgatagatg ggtggtatgg ctatcaccat gaaaattctc
1141 aagggtcagg atatgcagcg gacagagaaa gcactcaaaa ggctgtaaac agaattacaa
1201 ataaggtcaa ttccatcatc aacaaaatga acacacaatt tgaagctgtc gatcacgaat
1261 tttcaaatct ggagaggaga atcgacaatc tgaacaaaag aatgcaagat ggatttctgg
1321 atgtttggac atacaatgct gaactgttgg ttcttcttga aaacgaaaga acactagaca
1381 tgcatgacgc aaatgtgaag aacctacatg aaaaggtcaa atcacaacta agggacaatg
1441 ctaacgatct agggaatggt tgctttgaat tttggcataa gtgtgacaat gaatgcatag
1501 agtctgtcaa aaatggtaca tatgactatc ccaaatacca gactgaaagc aaattaaaca
1561 ggctaaaaat agaatcagta aagctagaga accttggtgt gtatcaaatt cttgccattt
1621 atagtacggt atcgagcagc ctagtgttgg tagggctgat catggcaatg ggtctttgga
1681 tgtgttcaaa tggttcaatg cagtgcaatg tgtgtatatg attaagaaaa acacccttgt
1741 ttctact
```

Amino acid sequence of ca A/Teal H6 (SEQ ID NO: 41)
Entire molecule length: 567 aa

```
 1 miaiiviail aaagksdkic igyhannstt qvdtileknv tvthsielle nqkeerfcki
61 lnkapldlre ctiegwilgn pqcdlllgdq swsyiverpt aqngicypgt lneveelral
```

-continued

```
121 igsgerverf emfpqstwqg vdtnsgttrs cpystgdpsf yrnllwiikt ktaeypvikg 181 iynntgtqpi lyfwgvhhpp ntdeqdtlyg sgdryvrmgt esmnfakspe iaarpavngq 241 rgridyywsv lkpgetlnve sngnliapwy aykfvntnsk gavfrsdlpi encdatcqti 301 agvlrtnktf qnvsplwige cpkyvksesl rlatglrnvp qietrglfga iagfieggwt 361 gmidgwygyh hensqgsgya adrestqkav nritnkvnsi inkmntqfea vdhefsnler 421 ridnlnkrmq dgfldvwtyn aellvllene rtldmhdanv knlhekvksq lrdnandlgn 481 gcfefwhkcd neciesvkng tydypkyqte sklnrlkies vklenlgvyq ilaiystvss 541 slvlvglima mglwmcsngs mqcnvci
```

Nucleotide sequence of ca A/Teal N1 (SEQ ID NO: 36)
Entire molecule length: 1401 nt

```
   1 agcaaaagca ggagtttaac atgaatccaa atcagaagat aataaccatt gggtcaatct 61 gtatggtagt tggaataatc agcttgatgt tacaaattgg aaacataata tcaatatggg 121 ttagccacat aattcagact gggcatccaa accagcctgg gccatgcaat caaagcatca 181 attttttacac tgagcaggct gcagcttcag tgacattagc gggtaattcc tctctctgcc 241 ctattagtgg atgggctata tacagtaaag acaatagtat aagaattggt tccaaagggg 301 atgtgtttgt tatgagagaa ccattcgttt catgctccca tttggaatgc agaaccttt 361 tcttgactca aggagcccta ttgaatgaca agcattctaa tgggaccgtt aaagacagaa 421 gccccttatag aactttaatg agctgtcctg ttggtgaggc tccttcccca tacaactcaa 481 ggtttgagtc tgttgcttgg tcagcaagtg cttgccatga tggcattagt ggctaacaa 541 ttggaattc cggtccggat aatggggctg tggctgtgtt gaaatacaat ggcataataa 601 cagacaccat caagagttgg aggaacaaca tactgaggac acaagagtct gaatgtgcat 661 gtgtgaatgg ttcttgtttt actgtaatga cagatggacc gagtaatgaa caggcctcat 721 acaagatttt caagatagag aaggggaaag tagtcaaatc agttgagttg aacgcccta 781 attatcatta cgaggaatgc tcctgttatc ctgatgctgg cgaaatcaca tgtgtgtgca 841 gggataattg gcatggctcg aaccgaccgt gggtgtcttt caatcagaat ctggagtatc 901 aaataggata tatatgcagt ggggttttcg gagacagtcc acgccccaat gatggaacag 961 gcagttgcgg tccagtgtct cttaacggag agtatgagt aaaagggttt tcatttaagt 1021 acggtgatgg tgtttggatc gggagaacca aaagcactag ttccaggagc gggtttgaaa 1081 tgatttggga tccaaatggg tggaccgaaa cagatagtaa cttctcattg aagcaagaca 1141 tcatagcaat aactgattgg tcaggataca gcgggagttt tgtccaacat ccagaactga 1201 caggattaaa ttgcatgagg ccttgcttct gggttgaact aatcagaggg aggcccaaag 1261 agaaaacaat ctggactagt gggagcagta tatctttctg tggtgtaaat agtgacactg 1321 tgggttggtc ttggccagac ggtgctgagg tgccattcac cattgacaag tagtttgttc 1381 aaaaactcc ttgtttctac t
```

Amino acid sequence of ca A/Teal N1 (SEQ ID NO: 42)
Entire molecule length: 450 aa

```
   1 mnpnqkiiti gsicmvvgii slmlqignii siwvshiiqt ghpnqpgpcn qsinfyteqa 61 aasvtlagns slcpisgwai yskdnsirig skgdvfvmre pfvscshlec rtffltqgal 121 lndkhsngtv kdrspyrtlm scpvgeapsp ynsrfesvaw sasachdgis wltigisgpd
```

-continued

```
181 ngavavlkyn giitdtiksw rnnilrtqes ecacvngscf tvmtdgpsne qasykifkie
241 kgkvvksvel napnyhyeec scypdageit cvcrdnwhgs nrpwvsfnqn leyqigyics
301 gvfgdsprpn dgtgscgpvs lngeygvkgf sfkygdgvwi grtkstssrs gfemiwdpng
361 wtetdsnfsl kqdiiaitdw sgysgsfvqh peltglncmr pcfwvelirg rpkektiwts
421 gssisfcgvn sdtvgwswpd gaevpftidk
``` ca A/Mallard
Nucleotide sequence of ca A/Mallard H6 (SEQ ID NO: 37)
Entire molecule length: 1745 bp

```
   1 agcaaaagca ggggaaaatg attgcaatca taatacttgc aatagtggtc tctaccagca
  61 agtcagacag gatctgcatt ggttaccatg caaacaactc gacaacacaa gtggacacaa
 121 tattagagaa gaatgtgaca gtgacacact cagtggagct cctagaaaac cagaaggaga
 181 atagattctg cagagtcttg aataaagcgc cactggatct aatggactgc accactgagg
 241 gttggatcct tggaaacccc cgatgtgata acttactcgg tgatcaaagt tggtcataca
 301 tagtagagag gcctgatgcc caaaatggga tatgttaccc aggggtattg aaggagacgg
 361 aagagctgaa agcactcatt gggtctatag atagcataca aagatttgaa atgtttccca
 421 agagcacgtg gaccggggta gatactaata gcggagttac gagcgcttgc ccctacaatg
 481 gtgaatcttc cttttacagg aatctgttgt ggataataaa aataagatct gatccgtact
 541 cattgatcaa ggggacatat accaatacag gctctcagcc aatcttatat ttctggggtg
 601 tgcaccatcc tccagatgaa gttgagcaag ctaacttgta tggaattggt acccggtatg
 661 ttaggatggg aactgaaagt atgaattttg ccaaaggtcc tgaaatagca ggcagaccac
 721 ctgcgaatgg gcaacgagga agaattgatt attattggtc tgtgttgaag ccaggagaaa
 781 ccttgaatgt ggaatccaat ggaaatttaa tagctccttg gtatgcttac aagttcacta
 841 gttccagaaa caagggagct atttttcaaat cagaccttcc aattgagaat tgtgatgctg
 901 tctgtcaaac tttagctgga gcaataaata aaacaaaac cttccaaaat attagtccag
 961 tctggattgg agaatgcccc aaatatgtta aagtaagag cctaaaacta gcaactggtc
1021 tgagaaatgt tccacaggca gaaacaagag gattgtttgg agcaatagct gggtttatag
1081 aaggaggatg gacaggtatg gtagacggat ggtacggata ccaccatgaa aattcacagg
1141 ggtctggtta tgcagcagat aaagaaagca ctcagaaagc aatagacggg atcaccaata
1201 aagtcaattc aatcattgac aaaatgaaca cacaatttga ggcagtagag catgagttct
1261 caagtctcga aggagaata ggcaatctga acaaaagaat ggaagatgga ttttttagacg
1321 tgtggacata caatgctgaa cttctggttc tactggaaaa tgagaggact ttggacatgc
1381 atgatgctaa tgtaaagaat ctacatgaaa aggtgaaatc acaattaagg gataatgcaa
1441 aggatttggg taatgggtgt tttgaatttt ggcacaaatg cgacaatgaa tgcatcaact
1501 cagttaaaaa tggcacatat gactacccaa agtaccagga agagagcaga cttaataggc
1561 aggaaataaa atcagtgatg ctggaaaatc tgggagtata ccaaatcctt gctatttata
1621 gtacggtatc gagcagtctg gttttggtgg gactgatcat tgccatgggt ctttggatgt
1681 gctcaaatgg ctcaatgcaa tgcaagatat gtatataatt agaaaaaaac accctttgttt
1741 ctact
```

Amino acid sequence of ca A/Mallard H6 (SEQ ID NO: 43)
Entire molecule length: 566 aa

```
  1 miaiiilaiv vstsksdric igyhannstt qvdtileknv tvthsvelle nqkenrfcrv
 61 lnkapldlmd cttegwilgn prcdnllgdq swsyiverpd aqngicypgv lketeelkal
121 igsidsiqrf emfpkstwtg vdtnsgvtsa cpyngessfy rnllwiikir sdpyslikgt
181 ytntgsqpil yfwgvhhppd eveqanlygi gtryvrmgte smnfakgpei agrppangqr
241 gridyywsvl kpgetlnves ngnliapwya ykftssrnkg aifksdlpie ncdavcqtla
301 gaintnktfq nispvwigec pkyvkskslk latglrnvpq aetrglfgai agfieggwtg
361 mvdgwygyhh ensqgsgyaa dkestqkaid gitnkvnsii dkmntqfeav ehefsslerr
421 ignlnkrmed gfldvwtyna ellvllener tldmhdanvk nlhekvksql rdnakdlgng
481 cfefwhkcdn ecinsvkngt ydypkyqees rlnrqeiksv mlenlgvyqi laiystvsss
541 lvlvgliiam glwmcsngsm qckici
```

20

Nucleotide sequence of ca A/Mallard N2 (SEQ ID NO: 38)
Entire molecule length: 1467 nt

```
   1 agcaaaagca ggagtgaaaa tgaatccaaa tcagaggata ataacaattg gatccgtctc
  61 tctaactatt gcaacagtgt gtttcctcat gcagattgcc atcctagcaa cgactgtgac
 121 actgcatttc aaacaaaatg aatgcagcat tcccgcaaac aaccaagtaa cgccatgtga
 181 accaatagta atagagagga acataacaga gatagtgtat ttgaataata ctaccataga
 241 aaaagagatt tgtcctgaag tagtagaata caggaattgg tcaaaaccgc aatgtcaaat
 301 tacagggttt gctcctttct ccaaggacaa ctcaattcgg ctttctgctg gtgggacat
 361 ttggataaca agagaacctt atgtgtcatg cgaccccagt aaatgttatc aatttgcact
 421 cgggcagggg accacgctgg acaacaaaca ctcaaatggc acaatacatg atagaatccc
 481 tcatcggacc cttttgatga atgaattggg tgttccgttt catttgggaa ccaaacaagt
 541 gtgcatagca tggtccagct caagctgtca tgatgggaaa gcatggttgc acgtttgtgt
 601 cactggggat gatagaaatg caactgctag tttcatttat gatgggatgc ttattgacag
 661 tattggttcc tggtctcaaa atatcctcag gactcaggag tcagaatgcg tttgtatcag
 721 tggaacttgt acagtagtaa tgactgatgg aagtgcatca ggaagggcag acactagaat
 781 actattcatt agagaggga aaattgtcca cattagtcca ttgtcaggaa gtgctcagca
 841 tgtagaggaa tgttcttgtt atccccggta cccaaacgtc agatgtgtct gcagagacaa
 901 ctggaagggc tctaataggc ccgttataga tataaatatg gcagattata gcattgactc
 961 aagttatgtg tgctcaggac ttgttggaga cacaccaagg aacgatgata gctctagcag
1021 cagcaactgc agggatccta ataatgagag agggaaccca ggagtgaaag ggtgggcctt
1081 tgataatgga aatgatgtgt ggatgggaag aacaatcagt aaagattcgc gctcaggcta
1141 tgagaccttc aaggtcattg gtggttgggc cattgctaat tccaagtcac agaccaatag
1201 acaagtcata gttgataata caactggtc tggttattct ggtatttctc tgttgaaag
1261 caaaggctgc atcaataggt gttttttatgt ggagttgata agaggaaggc cacaggagac
1321 tagagtatgg tggacctcaa acagtattgt cgtattttgt ggcacttcag ggacatatgg
1381 aacaggctca tggcctgatg gggcgaatat cgatttcatg cctatataag ctttcgcaat
1441 tttagaaaaa aactccttgt ttctact
```

Amino acid sequence of ca A/Mallard N2 (SEQ ID NO: 44)
Entire molecule length: 469 aa

```
  1 mnpnqriiti gsvsltiatv cflmqiaila ttvtlhfkqn ecsipannqv tpcepivier 61 niteivylnn ttiekeicpe vveyrnwskp qcqitgfapf skdnsirlsa ggdiwitrep 121 yvscdpskcy qfalgqgttl dnkhsngtih driphrtllm nelgvpfhlg tkqvciawss 181 sschdgkawl hvcvtgddrn atasfiydgm lidsigswsq nilrtqesec vcisgtctvv 241 mtdgsasgra dtrilfireg kivhisplsg saqhveecsc yprypnvrcv crdnwkgsnr 301 pvidinmady sidssyvcsg lvgdtprndd sssssncrdp nnergnpgvk gwafdngndv 361 wmgrtiskds rsgyetfkvi ggwaiansks qtnrqvivdn nnwsgysgif sveskgcinr 421 cfyvelirgr pqetrvwwts nsivvfcgts gtygtgswpd ganidfmpi
```

SUMMARY OF SEQ ID NO DESIGNATIONS

| SEQ ID NO | HA or NA | STRAIN NAME | Amino Acid or Nucleotide |
|---|---|---|---|
| SEQ ID NO: 1 | HA (H5) | ca A/Vietnam/1203/04 | Nucleotide |
| SEQ ID NO: 2 | NA (N1) | ca A/Vietnam/1203/04 | Nucleotide |
| SEQ ID NO: 3 | HA (H5) | ca A/Hong Kong/213/03 | Nucleotide |
| SEQ ID NO: 4 | NA (N1) | ca A/Hong Kong/213/03 | Nucleotide |
| SEQ ID NO: 5 | HA (H5) | ca A/Hong Kong/491/97 | Nucleotide |
| SEQ ID NO: 6 | NA (N1) | ca A/Hong Kong/486/97 | Nucleotide |
| SEQ ID NO: 7 | HA (H5) | ca A/Hong Kong/491/97 (Ser211) | Nucleotide |
| SEQ ID NO: 8 | NA (N1) | ca A/Hong Kong/486/97 | Nucleotide |
| SEQ ID NO: 9 | HA (H9) | ca A/ck/Hong Kong/G9/97 | Nucleotide |
| SEQ ID NO: 10 | NA (N2) | ca A/ck/Hong Kong/G9/97 | Nucleotide |
| SEQ ID NO: 21 | HA (H7) | A/Netherlands/219/03 | Nucleotide |
| SEQ ID NOs: 22 & 45 | NA (N7) | A/Netherlands/219/03 | Nucleotide |
| SEQ ID NO: 23 | HA (H7) | A/ck/BC/CN-7/04 | Nucleotide |
| SEQ ID NO: 24 | NA (N3) | A/ck/BC/CN-7/04 | Nucleotide |
| SEQ ID NO: 25 | HA (H7) | ca A/ck/BC/CN-6/04 | Nucleotide |
| SEQ ID NO: 26 | NA (N3) | ca A/ck/BC/CN-6/04 | Nucleotide |
| SEQ ID NO: 33 | HA (H6) | ca A/Duck | Nucleotide |
| SEQ ID NO: 34 | NA (N9) | ca A/Duck | Nucleotide |
| SEQ ID NO: 35 | HA (H6) | ca A/Teal | Nucleotide |
| SEQ ID NO: 36 | NA (N1) | ca A/Teal | Nucleotide |
| SEQ ID NO: 37 | HA (H6) | ca A/Mallard | Nucleotide |
| SEQ ID NO: 38 | NA (N2) | ca A/Mallard | Nucleotide |
| SEQ ID NO: 11 | HA (H5) | ca A/Vietnam/1203/04 | Amino Acid |
| SEQ ID NO: 12 | NA (N1) | ca A/Vietnam/1203/04 | Amino Acid |
| SEQ ID NO: 13 | HA (H5) | ca A/Hong Kong/213/03 | Amino Acid |
| SEQ ID NO: 14 | NA (N1) | ca A/Hong Kong/213/03 | Amino Acid |
| SEQ ID NO: 15 | HA (H5) | ca A/Hong Kong/491/97 | Amino Acid |
| SEQ ID NO: 16 | NA (N1) | ca A/Hong Kong/486/97 | Amino Acid |
| SEQ ID NO: 17 | HA (H5) | ca A/Hong Kong/491/97 (Ser211) | Amino Acid |
| SEQ ID NO: 18 | NA (N1) | ca A/Hong Kong/486/97 | Amino Acid |
| SEQ ID NO: 19 | HA (H9) | ca A/ck/Hong Kong/G9/97 | Amino Acid |
| SEQ ID NO: 20 | NA (N2) | ca A/ck/Hong Kong/G9/97 | Amino Acid |
| SEQ ID NO: 27 | HA (H7) | A/Netherlands/219/03 | Amino Acid |
| SEQ ID NO: 28 | NA (N7) | A/Netherlands/219/03 | Amino Acid |
| SEQ ID NO: 29 | HA (H7) | A/ck/BC/CN-7/04 | Amino Acid |
| SEQ ID NO: 30 | NA (N3) | A/ck/BC/CN-7/04 | Amino Acid |
| SEQ ID NO: 31 | HA (H7) | ca A/ck/BC/CN-6/04 | Amino Acid |
| SEQ ID NO: 32 | NA (N3) | ca A/ck/BC/CN-6/04 | Amino Acid |
| SEQ ID NO: 39 | HA (H6) | ca A/Duck | Amino Acid |
| SEQ ID NO: 40 | NA (N9) | ca A/Duck | Amino Acid |
| SEQ ID NO: 41 | HA (H6) | ca A/Teal | Amino Acid |
| SEQ ID NO: 42 | NA (N1) | ca A/Teal | Amino Acid |
| SEQ ID NO: 43 | HA (H6) | ca A/Mallard | Amino Acid |
| SEQ ID NO: 44 | NA (N2) | ca A/Mallard | Amino Acid |

What is claimed is:

1. A reassortant influenza virus comprising a genome segment encoding a polypeptide comprising the amino acid sequence of SEQ ID NO: 39.

2. The reassortant influenza virus of claim 1, wherein the genome segment comprises a polynucleotide comprising the nucleotide sequence of SEQ ID NO: 33.

3. The reassortant influenza virus of claim 1, which is a 6:2 reassortant virus comprising 6 internal genome segments from one or more donor viruses and 2 genome segments encoding surface antigens of an influenza virus.

4. The reassortant influenza virus of claim 3, wherein the one or more donor viruses are A/Ann Arbor/6/60.

5. The reassortant influenza virus of claim 3, wherein the one or more donor viruses are selected for one or more phenotypic attributes chosen from attenuated, cold adapted and temperature sensitive.

6. An immunogenic composition comprising an immunologically effective amount of the reassortant influenza virus of claim 1.

7. A live attenuated influenza vaccine comprising the immunogenic composition of claim 6.

8. An immunogenic composition comprising an immunologically effective amount of the reassortant influenza virus of claim 3.

9. A live attenuated influenza vaccine comprising the immunogenic composition of claim 8.

10. A method for producing reassortant influenza viruses in cell culture, the method comprising:
   i) introducing a plurality of vectors comprising polynucleotides corresponding to an influenza virus genome into a population of host cells capable of supporting replication of influenza virus, which plurality of vectors comprises polynucleotides corresponding to at least 6 internal genome segments of a first influenza strain, and at least one genome segment of a second influenza strain, wherein the at least one genome segment of the second influenza strain comprises a polynucleotide comprising a nucleotide sequence encoding the amino acid sequence of SEQ ID NO: 39;
   ii) culturing the population of host cells; and
   iii) recovering a plurality of influenza viruses.

11. The method of claim 10, wherein the at least one genome segment of the second influenza strain comprises a polynucleotide comprising the nucleotide sequence of SEQ ID NO: 33.

12. The method of claim 10, wherein the first influenza strain is an attenuated influenza virus strain, a cold-adapted influenza virus strain, or a temperature-sensitive influenza virus strain.

13. The method of claim 10, wherein the plurality of vectors is eight vectors.

14. The reassortant influenza virus of claim 3, wherein the one or more donor viruses are other than A/Ann Arbor/6/60.

15. The reassortant influenza virus of claim 14, wherein the one or more donor viruses are PR8.

16. The reassortant influenza virus of claim 14, wherein the one or more donor viruses are A/Leningrad/17.

17. The method of claim 10, wherein the first influenza strain is A/Ann Arbor/6/60.

18. The method of claim 10, wherein the first influenza strain is other than is A/Ann Arbor/6/60.

19. The method of claim 18, wherein the first influenza strain is PR8.

20. The method of claim 18, wherein the first influenza strain is A/Leningrad/17.

* * * * *